(12) United States Patent
Satomaa et al.

(10) Patent No.: US 10,973,922 B2
(45) Date of Patent: Apr. 13, 2021

(54) GLYCOPROTEIN-TOXIC PAYLOAD CONJUGATES

(71) Applicant: GLYKOS FINLAND OY, Helsinki (FI)

(72) Inventors: Tero Satomaa, Helsinki (FI); Jari Helin, Rajamäki (FI); Filip S. Ekholm, Porvoo (FI)

(73) Assignee: Glykos Finland OY, Helsinki (FI)

( * ) Notice: Subject to any disclaimer, the term of this patent is extended or adjusted under 35 U.S.C. 154(b) by 0 days.

(21) Appl. No.: 15/704,026

(22) Filed: Sep. 14, 2017

(65) Prior Publication Data

US 2018/0256732 A1 Sep. 13, 2018

Related U.S. Application Data

(63) Continuation of application No. 14/888,545, filed as application No. PCT/FI2014/050322 on May 2, 2014, now abandoned.

(30) Foreign Application Priority Data

May 2, 2013 (FI) ...................................... 20135451
Oct. 14, 2013 (FI) ...................................... 20136020

(51) Int. Cl.
| | | |
|---|---|---|
| *A61K 47/61* | (2017.01) | |
| *A61K 31/704* | (2006.01) | |
| *A61K 31/404* | (2006.01) | |
| *A61K 38/08* | (2019.01) | |
| *A61K 47/54* | (2017.01) | |
| *A61K 47/64* | (2017.01) | |
| *A61K 47/68* | (2017.01) | |
| *C07K 16/28* | (2006.01) | |
| *C07K 16/30* | (2006.01) | |
| *C07K 9/00* | (2006.01) | |
| *C07K 16/32* | (2006.01) | |

(52) U.S. Cl.
CPC ............ *A61K 47/61* (2017.08); *A61K 31/404* (2013.01); *A61K 31/704* (2013.01); *A61K 38/08* (2013.01); *A61K 47/549* (2017.08); *A61K 47/64* (2017.08); *A61K 47/6803* (2017.08); *A61K 47/6807* (2017.08); *A61K 47/6817* (2017.08); *A61K 47/6849* (2017.08); *A61K 47/6851* (2017.08); *A61K 47/6869* (2017.08); *A61K 47/6889* (2017.08); *C07K 9/001* (2013.01); *C07K 16/2863* (2013.01); *C07K 16/3069* (2013.01); *C07K 16/32* (2013.01); *C07K 2317/24* (2013.01); *C07K 2317/90* (2013.01); *Y02A 50/30* (2018.01)

(58) Field of Classification Search
CPC .... A61K 47/61; A61K 47/6869; A61K 38/08; A61K 31/704; A61K 31/404; A61K 47/6889; A61K 47/6849; A61K 47/6817; A61K 47/6803; A61K 47/549; A61K 47/64; A61K 47/6851; A61K 47/6807; C07K 16/32; C07K 16/3069; C07K 16/2863; C07K 9/001; C07K 2317/24; C07K 2317/90

See application file for complete search history.

(56) References Cited

U.S. PATENT DOCUMENTS

| | | |
|---|---|---|
| 5,278,299 A | 1/1994 | Wong et al. |
| 5,334,514 A | 8/1994 | Kittlemann et al. |
| 5,461,143 A | 10/1995 | Wong et al. |
| 5,635,483 A | 6/1997 | Pettit et al. |
| 7,691,962 B2 | 4/2010 | Boyd et al. |
| 7,820,714 B2 | 10/2010 | Kelm et al. |
| 8,008,252 B2 | 8/2011 | Defrees et al. |
| 8,357,671 B2 | 1/2013 | Paulson et al. |
| 8,398,956 B2 | 3/2013 | McBride et al. |
| 8,557,984 B2 | 10/2013 | Bouillot et al. |
| 8,716,033 B2 | 5/2014 | Agnew et al. |
| 8,765,920 B2 | 7/2014 | Barbas, III et al. |
| 8,815,580 B2 | 8/2014 | Callewaert et al. |
| 8,859,629 B2 | 10/2014 | van Delft et al. |
| 9,260,467 B2 | 2/2016 | Brossmer et al. |
| 9,326,939 B2 | 5/2016 | Paulson et al. |
| 9,504,758 B2 | 11/2016 | van Delft et al. |
| 2004/0142856 A1 | 7/2004 | Defrees et al. |
| 2005/0130235 A1 | 6/2005 | Hsieh-Wilson et al. |
| 2005/0256030 A1 | 11/2005 | Feng |
| 2006/0034828 A1 | 2/2006 | Gerngross et al. |

(Continued)

FOREIGN PATENT DOCUMENTS

| | | |
|---|---|---|
| EP | 1 577 316 A1 | 9/2005 |
| EP | 2305314 A2 | 6/2011 |

(Continued)

OTHER PUBLICATIONS

Garbe et al. Bacterial Hydrolysis of Host Glycoproteins—Powerful Protein Modification and Efficient Nutrient Acquisition. J Innate Immun 2012;4:121-131. (Year: 2012).*

(Continued)

*Primary Examiner* — Yih-Horng Shiao

(74) *Attorney, Agent, or Firm* — Patrick J. Halloran

(57) ABSTRACT

The invention relates to a glycoprotein-toxic payload molecule conjugate, a toxic payload molecule-glycan conjugate, and a pharmaceutical composition. The invention further relates to a method for preparing the glycoprotein-toxic payload molecule conjugate, the method for modulating growth of a cell population and a method of treating tumour cells.

5 Claims, 12 Drawing Sheets

Specification includes a Sequence Listing.

(56) References Cited

U.S. PATENT DOCUMENTS

| | | |
|---|---|---|
| 2006/0074008 A1 | 4/2006 | Senter et al. |
| 2006/0110782 A1 | 5/2006 | Bertozzi et al. |
| 2007/0027068 A1 | 2/2007 | DeFrees et al. |
| 2007/0059275 A1 | 3/2007 | Defrees |
| 2007/0190597 A1 | 8/2007 | Agnew et al. |
| 2007/0249014 A1* | 10/2007 | Agnew ............... A61K 47/549 435/68.1 |
| 2009/0068738 A1 | 3/2009 | Bertozzi et al. |
| 2009/0312335 A1 | 12/2009 | Wai et al. |
| 2011/0207147 A1 | 8/2011 | Jewett et al. |
| 2012/0029186 A1 | 2/2012 | Vladimir et al. |
| 2012/0076727 A1 | 3/2012 | McBride et al. |
| 2012/0195831 A1 | 8/2012 | Zhang et al. |
| 2013/0137763 A1 | 5/2013 | van Delft et al. |
| 2014/0227295 A1 | 8/2014 | Cong et al. |
| 2014/0249296 A1 | 9/2014 | Ploegh et al. |
| 2014/0275009 A1 | 9/2014 | Brenchley et al. |
| 2015/0174262 A1 | 6/2015 | Brossmer et al. |
| 2015/0202314 A1 | 7/2015 | Krantz et al. |
| 2015/0258210 A1* | 9/2015 | Van Delft .......... A61K 47/6869 530/391.9 |

FOREIGN PATENT DOCUMENTS

| | | |
|---|---|---|
| EP | 2610263 A1 | 7/2013 |
| EP | 2910561 A1 | 8/2015 |
| GB | 2511137 A1 | 8/2014 |
| WO | WO 88/04323 A1 | 6/1988 |
| WO | 1992016640 A1 | 10/1992 |
| WO | WO 95/15769 A1 | 6/1995 |
| WO | WO 97/34632 A1 | 9/1997 |
| WO | 2001062912 A2 | 8/2001 |
| WO | WO 02/26262 A2 | 4/2002 |
| WO | 2003000709 A2 | 1/2003 |
| WO | WO 03/031464 A2 | 4/2003 |
| WO | WO 03/086312 A2 | 10/2003 |
| WO | WO 03/102583 A1 | 12/2003 |
| WO | 2004063344 A2 | 7/2004 |
| WO | WO 2007/011968 A2 | 1/2005 |
| WO | WO 2005/012484 * | 2/2005 |
| WO | WO 2005/012484 A2 | 2/2005 |
| WO | 2007050510 A2 | 5/2005 |
| WO | 2005051429 A2 | 6/2005 |
| WO | 2005056783 A1 | 6/2005 |
| WO | 2005082023 A2 | 9/2005 |
| WO | 2006102652 A2 | 9/2006 |
| WO | 2007048077 A2 | 4/2007 |
| WO | 2007056525 A2 | 5/2007 |
| WO | 2007095506 A2 | 8/2007 |
| WO | 2007133855 A2 | 11/2007 |
| WO | 2007140371 A2 | 12/2007 |
| WO | 2008029281 A2 | 3/2008 |
| WO | 2008060705 A2 | 5/2008 |
| WO | 2008083312 A2 | 7/2008 |
| WO | WO 2008/090151 A1 | 7/2008 |
| WO | 2008143944 A2 | 11/2008 |
| WO | 2009013359 A2 | 1/2009 |
| WO | WO 2009/006620 A1 | 1/2009 |
| WO | 2009025645 A1 | 2/2009 |
| WO | 2009025646 A1 | 2/2009 |
| WO | WO 2009/033670 A2 | 3/2009 |
| WO | 2009067663 A1 | 5/2009 |
| WO | 2009089396 A2 | 7/2009 |
| WO | 2009102820 A2 | 8/2009 |
| WO | 2008120107 A2 | 10/2009 |
| WO | WO 2010/015722 A1 | 2/2010 |
| WO | 2010120561 A1 | 10/2010 |
| WO | 2010124833 A1 | 11/2010 |
| WO | 2011028507 A2 | 3/2011 |
| WO | 2011136645 A1 | 3/2011 |
| WO | 2011051733 A2 | 5/2011 |
| WO | 2011054846 A1 | 5/2011 |
| WO | 2011061629 A2 | 5/2011 |
| WO | 2011079315 A1 | 6/2011 |
| WO | WO 2011/064303 A1 | 6/2011 |
| WO | 2011140393 A1 | 11/2011 |
| WO | 2012018377 A2 | 2/2012 |
| WO | 2012020038 A1 | 2/2012 |
| WO | 2012044612 A2 | 4/2012 |
| WO | 2012059882 A2 | 5/2012 |
| WO | 2012064733 A2 | 5/2012 |
| WO | 2012075361 A2 | 6/2012 |
| WO | 2012121973 A1 | 9/2012 |
| WO | 2012131527 A1 | 10/2012 |
| WO | 2012134925 A1 | 10/2012 |
| WO | 2012143523 A1 | 10/2012 |
| WO | 2012162482 A1 | 11/2012 |
| WO | WO 2012/153193 A1 | 11/2012 |
| WO | WO 2012/166559 A1 | 12/2012 |
| WO | WO 2012/166560 A1 | 12/2012 |
| WO | WO 2013/012961 A2 | 1/2013 |
| WO | 2013036748 A1 | 3/2013 |
| WO | 2013037824 A1 | 3/2013 |
| WO | WO 2013/037824 A1 | 3/2013 |
| WO | WO 2013/087992 A1 | 6/2013 |
| WO | WO 20131087993 A1 | 6/2013 |
| WO | 2013097942 A1 | 7/2013 |
| WO | 2013120066 A1 | 8/2013 |
| WO | 2013170272 A2 | 11/2013 |
| WO | 2013185115 A1 | 12/2013 |
| WO | 2013190103 A1 | 12/2013 |
| WO | 2014004639 A1 | 1/2014 |
| WO | 2014036492 A1 | 3/2014 |
| WO | 2014065661 A1 | 5/2014 |
| WO | 2014066733 A2 | 5/2014 |
| WO | WO 2014/065661 A1 | 5/2014 |
| WO | WO 2014/096551 A1 | 6/2014 |
| WO | 2014143241 A1 | 9/2014 |
| WO | 2014189370 A1 | 11/2014 |
| WO | 2014202775 A1 | 12/2014 |
| WO | 2015057063 A1 | 4/2015 |
| WO | 2015057064 A1 | 4/2015 |
| WO | 2015057065 A1 | 4/2015 |
| WO | 2015057066 A1 | 4/2015 |
| WO | 2015128344 A1 | 9/2015 |
| WO | 2017137423 A1 | 8/2017 |
| WO | 2017137458 A1 | 8/2017 |
| WO | 2017137459 A1 | 8/2017 |

OTHER PUBLICATIONS

Sjogren et al. EndoS2 is a unique and conserved enzyme of serotype M49 group A *Streptococcus* that hydrolyses N-linked glycans on IgG and α1-acid glycoprotein. Biochem. J. (2013) 455, 107-118. (Year: 2013).*

International Search Report for International Patent Application No. PCT/2014/050322 dated Aug. 21, 2014.

Finnish Search Report for Finnish Patent Application No. 20135451 dated Feb. 28, 2014.

Afar, D. et al., "Preclinical validation of and-TMEFF2-auristatin E-conjugated antibodies in the treatment of prostate cancer", *Mol. Cancer Ther.*, 3(8): 921-932 (2004).

Bai, R. et al., "Intracellular Activation and Deactivation of Tasidotin, an Analog of Dolastatin 15: Correlation with Cytotoxicity", *Mol. Pharmacol.*, 75(1): 218-226 (2009).

Dosio, F. et al., "Immunotoxins and Anticancer Drug Conjugate assemblies: The Role of the Linkage between Components", *Toxins*, 3: 848-883 (2011).

IUPAC-IUBMB JCBN, "Nomenclature of Carbohydrates", *Carbohydrate Res.*, 297: 1-91 (1997).

IUPAC-IUBMB JCBN, "Nomenclature of glycolipids", *Carbohydrate Research*, 312:167-175 (1998).

IUPAC-IUB JCBN Chester, M., "Nomenclature of glycolipids", *Eur. J. Biochem.*, 257: 293-298 (1998.

Kirsch, P. et al., "Synthesis of N-Acetylglucosarninyl Asparagine-Substituted Puromycin Analogues", *Bioorganic Medicinal Chemistry*, 3(12): 1631-1636 (1995).

Mohammad, R. et al., "A new tubulin polymerization inhibitor, auristatin PE, induces tumor regression in a humb Waldenstroms's macroglobulinemia xenograft model", *Int. J. Oncol.*,15: 367-372 (1999).

(56) References Cited

OTHER PUBLICATIONS

Pettit, G. et al., "Antineoplastic Agents, 592. Highly Effective Cancer Cell Growth Inhibitory Structural Modifications of Dolastatin 10", *J. Nat. Prod.*, 74: 962-968 (2011).
Rillahan, C. et al., "'Click and Pick' Identification of High Affinity Sialoside Ligands for Siglec-based Targeting of Leukocytes", *Agnew. Chem. Int. Ed.*, 51(44): 11014-11018 (2012).
Sammet, B. et al., "Antibody-drug conjugates in tumor therapy", *Pharm. Pat. Analyst*, 1(1): 65-73 (2012).
Staudacher, E. et al., "α1-6(α1-3)-Difucosylation of the asparagine-bound N-acetylglucosamine in honeybee venom phospholipase A$_2$", *Glycoconjugate Journal*, 9:82-85 (1992).
Swarts, B. et al., "Synthesis and DC structural studies of CD53 peptides and glycopeptides", *Carbohydrate Research*, 343(17): 2894-2902 (2008).
Yang, J. et al., "Studies on the Substrate Specificity of *Escherichia coli* Galactokinase", *J. S. Org. Lett.*, 5: 2223-2226 (2003).
Abdu-Allah et al. Design and synthesis of a multivalent hetero-bifunctional CD22 ligand as a potential immunomodulator. Synthesis 18: 2968-2974 (2011).
Chen et al. In vivo targeting of B-cell lymphoma with glycan ligands of CD22. Blood 115(23): 4778-4786 (2010).
Gunther et al., Synthesis of 1,2,3-Triazole-Linked Glycoconjugates of N-(2-Aminoethyl)glycine: Building Blocks for the Construction of Combinatorial Glycopeptide Libraries. Synthesis, 46(17):2362-2370 (2014).
Khedri et al. Chemoenzymic synthesis of sialosides containing C7-modified sialic acids and their application in sialidase substrate specificity studies. Carbohydrate Research 389: 100-111 (2014).
Mbua et al., Selective Exo-Enzymatic Labeling of N-Glycans on the Surface of Living Cells by Recombinant ST6Gal I. Angewandte Chemie, International Edition, 52:13012-13015 (2013).
Mesch et al. From a Library of MAG Antagonists to Nanomolar CD22 Ligands. ChemMedChem, 7(1): 134-143 (2012).
Pynnonen et al. Novel Hydrophilic Glycolinkers for Improved Antibody-Drug Conjugates. Abstract, World ADC San Francisco, Oct. 14-17, 2013.
Saarinen et al. Impact of Different Site-Specific Payload Conjugation Chemistries on Efficacy, Achievable Drug-To-Antibody Ratio and Fc Receptor Affinity of Antibody-Drug Conjugates, Abstract, World ADC San Diego Oct. 26-29, 2014.
Satomaa et al. Hydrophilic Character of Cytotoxic Payloads Affects Functional Properties of Antibody-Drug Conjugates. Abstract, World ADC Frankfurt Feb. 23-25, 2015a.
Satomaa et al. Hydrophilic Character of Cytotoxic Payloads Affects Functional Properties of Antibody-Drug Conjugates. Abstract, PEGS Boston May 4-8, 2015b.
Schweizer et al. Targeting of CD22-positive B-cell lymphoma cells by synthetic divalent sialic acid analogues. European Journal of Immunology, 42(10): 2792-2802 (2012).
ABRF International Symposium of the Association of Biomolecular Resource Facilities (ABRF) conference program and publication policy (2012).
ABRF Meeting Program, extract comprising cover, pp. 1, 10, 62; published Mar. 17, 2012.
Agard et al. A strain-promoted [3+2] azide-alkyne cycloaddition for covalent modification of biomolecules in living systems. J Am Chem Soc. 126(46):15046-7 (2004).
Agard et al. A comparative study of bioorthogonal reactions with azides. ACS Chem Biol. 1(10):644-8 (2006).
Aggeler et al. Site-specific click chemistry-mediated labeling of antibody glycans using metabolic and enzymatic approaches. Poster published at The Essential Protein Engineering Summit, May 9-13, 2011, Boston, MA, USA (2011).
Aggeler et al. Site-specific labelling of antibody N-glycans using a click chemistry-mediated chemoenzymatic approach. Poster published at International Symposium of the Association of Biomolecular Resource Facilities, Mar. 17-20, 2012, Orlando, FL, USA (2012).

Agnew, B. Statement concerning Aggeler et al. PEGS 2011 Poster (2011).
Agnew, B. Statement concerning Aggeler et al. ABRF 2012 Poster (2012).
Agnew et al. Site-specific Labeling of Antibody N-glycans using a Click Chemistry-mediated Chemoenzymatic Approach. J. Biomol. Tech. 23, supplement, S28 (2012).
Allhorn et al. Human IgG/Fc gamma R interactions are modulated by streptococcal IgG glycan hydrolysis. PLoS one. ;3(1):e1413. doi: 10.1371/journal.pone.0001413 (2008).
Anonymous. The Essential Protein Engineering Summit (PEGS) 2011 conference program (2011).
Baruah et al. 2012 Selective deactivation of serum IgG: a general strategy for the enhancement of monoclonal antibody receptor interactions. J Mol Biol. 420(1-2):1-7. doi: 10.1016/j.jmb.2012.04.002 (2012).
Baskin et al. Copper-free click chemistry for dynamic in vivo imaging. Proc Natl Acad Sci U S A. 104(43):16793-7 (2007).
Beck et al. 8(th) Annual European Antibody Congress 2012: Nov. 27-28, 2012, Geneva, Switzerland. MAbs. 5(3)339-57 . doi: 10.4161/mabs.24105 (2013).
Boeggeman et al. Direct Identification of Nonreducing GlcNAc residues on N-glycans of Glycoproteins Using a Novel Chemoenzymatic Method. Bioconjugate Chem. 18, 806-814 (2007).
Boeggeman et al. Site Specific Conjugation of Fluoroprobes to the Remodeled Fc N-Glycan of Monoclonal Antibodies Using Mutant Glycosyltransferases: Application for Cell Surface Antigen Detection. Bioconjugate Chem. 20, 1228-1236 (2009).
Bohle et al. An endo-β-N-acetylglucosaminidase from Enterococcus faecalis V583 responsible for the hydrolysis of high-mannose and hybrid-type N-linked glycans. FEMS Microbiol Lett. 325(2):123-9. doi: 10.1111/i.1574-6968.2011.02419.x (2011).
Chen et al. Strain-Promoted Catalyst-Free Click Chemistry for Rapid Construction of (64)Cu-Labeled PET Imaging Probes. ACS Med Chem Lett. 3(12):1019-23. doi:10.1021/ml300236m (2012).
Clark et al. Direct in-gel fluorescence detection and cellular imaging of O-GlcNAc-modified proteins. J Am Chem Soc. 130(35):11576-7. doi: 10.1021/ja8030467 (2008).
Codelli et al. Second-generation difluorinated cyclooctynes for copper-free click chemistry. J Am Chem Soc. 130(34):11486-93. doi: 10.1021/ja803086r (2008).
Collin et al. EndoS, a novel secreted protein from *Streptococcus pyogenes* with endoglycosidase activity on human IgG. EMBO J. 20(12):3046-55 (2001).
Collin et al. Extracellular enzymes with immunomodulating activities: variations on a theme in *Streptococcus pyogenes*. Infect Immun. 71(6):2983-92 (2003).
De Almeida et al. Thiacycloalkynes for copper-free click chemistry. Angew Chem Int Ed Engl. 51(10):2443-7. doi: 10.1002/anie.201106325 (2012).
Debets et al. Aza-dibenzocyclooctynes for fast and efficient enzyme PEGylation via copper-free (3+2) cycloaddition. Chem Commun (Camb). 46(1):97-9. doi: 10.1039/b917797c (2010a).
Debets et al. Azide: a unique dipole for metal-free bioorthogonal ligations. Chembiochem. 11(9):1168-84. doi: 10.1002/cbic.201000064 (2010b).
Debets et al. Bioconjugation with strained alkenes and alkynes. Acc Chem Res. 44(9):805-15. doi: 10.1021 ar200059z (2013).
Debets MF Dissertation: Dibenzoazacyclooctynes: synthesis and bioconjugation, Radboud Universiteit Nijmegen (2013).
Dommerholt et al. Readily Accessible Bicyclononynes for Bioorthogonal Labeling and Three-Dimensional Imaging of Living Cells. Angew. Chem. 122: 9612-9615 (2010).
Friscourt et al. Polar dibenzocyclooctynes for selective labeling of extracellular glycoconjugates of living cells. J Am Chem Soc. 134(11):5381-9. doi:10.1021/ja3002666 (2012).
Goodfellow et al. An Endoglycosidase with Alternative Glycan Specificity Allows Broadened Glycoprotein Remodelling. J. Am. Chem. Soc. 134, 8080-8033 (2012).
Gordon et al. Reactivity of biarylazacyclooctynones in copper-free click chemistry. J Am Chem Soc. 134(22):9199-208. doi: 10.1021/ja3000936 (2012).

(56) References Cited

OTHER PUBLICATIONS

Gross et al. Activation and transfer of novel synthetic 9-substituted sialic acids. Eur J Biochem. 168(3):595-602 (1987).
Huang et al. Chemoenzymatic glycoengineering of intact IgG antibodies for gain of functions. J Am Chem Soc. 134(29):12308-18. doi: 10.1021/ja3051266 (2012).
Hudak et al. Synthesis of heterobifunctional protein fusions using copper-free click chemistry and the aldehyde tag. Angew Chem Int Ed Engl. 51(17):4161-5. doi:10.1002/anie.201108130 (2012).
Jang et al. Development of a simple method for protein conjugation by copper-free click reaction and its application to antibody-free Western blot analysis. Bioconjug Chem. 23(11):2256-61. doi: 10.1021/bc300364z (2012).
Jewett et al. Rapid Cu-free click chemistry with readily synthesized biarylazacyclooctynones. J Am Chem Soc. 132(11):3688-90. doi: 10.1021/ja100014q (2010).
Junutula et al. Engineered thio-trastuzumab-DM1 conjugate with an improved therapeutic index to target human epidermal growth factor receptor 2-positive breast cancer. Clin Cancer Res. 16(19):4769-78. doi: 10.1158/1078-0432.CCR-10-0987 (2010).
Khidekel et al. A chemoenzymatic approach toward the rapid and sensitive detection of O-GlcNAc posttranslational modifications. J Am Chem Soc. 125(52):16162-3 (2003).
Kim, EJ Chemical arsenal for the study of O-GlcNAc. Molecules. 16(3):1987-2022. doi: 10.3390/molecules16031987 (2011).
Lallana et al. Surpassing the use of copper in the click functionalization of polymeric nanostructures: a strain-promoted approach. J Am Chem Soc. 131(16):5748-50. doi: 10.1021/ja8100243 (2009).
Lallana et al. Reliable and efficient procedures for the conjugation of biomolecules through Huisgen azide-alkyne cycloadditions. Angew Chem Int Ed Engl. 50(38):8794-804. doi: 10.1002/anie.201101019 (2011).
Lugovskoy et al., 7th Annual European Antibody Congress 2011. mAbs 4:2, 134-152 (2012).
Mbua et al. Strain-promoted alkyne-azide cycloadditions (SPAAC) reveal new features of glycoconjugate biosynthesis. Chembiochem. 12(12):1912-21. doi: 10.1002/cbic.201100117 (2011).
Mbua. Dissertation Interrogating the Glycome Using Click Chemistry Athens, Georgia (2012).
Mercer et al. Use of novel mutant galactosyltransferase for the bioconjugation of terminal N-acetylglucosamine (GlcNAc) residues on live cell surface. Bioconjug Chem. 24(1):144-52. doi: 10.1021/bc300542z (2013).
Ning et al. Visualizing Metabolically Labeled Glycoconjugates of Living Cells by Copper-Free and Fast Huisgen Cycloadditions. Angew. Chem. Int. Ed. 47, 2253-225 (2008).
Opposition brief by Genovis against European patent No. EP 2911699 B1, (2018).
Opposition brief by Glykos against European patent No. EP 2911699 B1, (2018).
Opposition brief by HGF against European patent No. EP 2911699 B1, (2018).
Pasek et al. Bioconjugation and detection of lactosamine moiety using alpha1,3-galactosyltransferase mutants that transfer C2-modified galactose with a chemical handle. Bioconjug Chem. 20(3):608-18. doi:10.1021/bc800534r (2009).
Pasek et al. The N-acetyl-binding pocket of N-acetylglucosaminyltransferases also accommodates a sugar analog with a chemical handle at C2. Glycobiology. 22(3):379-88. doi: 10.1093/glycob/cwr110 (2012).
Qasdba et al. Mutant glycosyltransferases assist in the development of a targeted drug delivery system and contrast agents for MRI. AAPS J. 8(1):E190-5 (2006).
Qasdba et al. Structure and function of beta-1,4-galactosyltransferase. Curr Drug Targets. 9(4):292-309 (2008a).
Qasdba et al. Site-specific linking of biomolecules via glycan residues using glycosyltransferases. Biotechnol Prog. 24(3):520-6. doi: 10.1021/bp0704034 (2008b).

Ramakrishnan et al. Structure-based Design of β1,4-Galactosyltransferase I ((β4Gal-T1) with Equally Efficient N-Acetylgalactosaminyltransferase Activity. J. Biol. Chem. 277:23, 20833-20839 (2002).
Ramakrishnan et al. Effect of the Met344His mutation on the conformational dynamics of bovine beta-1,4-galactosyltransferase: crystal structure of the Met344His mutant in complex with chitobiose. Biochemistry. 43(39):12513-22 (2004).
Ramakrishnan et al. Role of a single amino acid in the evolution of glycans of invertebrates and vertebrates. J Mol Biol. 365(3):570-6 (2007).
Ramakrishnan et al. Applications of glycosyltransferases in the site-specific conjugation of biomolecules and the development of a targeted drug delivery system and contrast agents for MRI. Expert Opin Drug Deliv. 5(2):149-53. doi: 10.1517/17425247.5.2.149 (2008).
Ramakrishnan et al. Multiple site-specific in vitro labeling of single-chain antibody. Bioconjug Chem. 20(7):1383-9. doi: 10.1021/bc900149r (2009).
Ramakrishnan et al. Structure-based evolutionary relationship of glycosyltransferases: a case study of vertebrate 31,4-galactosyltransferase, invertebrate β1,4-N-acetylgalactosaminyltransferase and α-polypeptidyl-N-acetylgalactosaminyltransferase. Curr Opin Struct Biol. 20(5):536-42. doi: 10.1016/j.sbi.2010.07.004 (2010).
Ramakrishnan et al. Bioconjugation using mutant glycosyltransferases for the site-specific labeling of biomolecules with sugars carrying chemical handles. Methods Mol Biol. 751:281-96. doi: 10.1007/978-1-61779-151-2_17 (2011).
Sharket et al. Use of antibodies and immunoconjugates for the therapy of more accessible cancers. Adv Drug Deliv Rev. 60(12):1407-20. doi: 10.1016/j.addr.2008.04.011 (2008).
Sjogren et al. EndoS2 is a unique and conserved enzyme of serotype M49 group A *Streptococcus* that hydrolyses N-linked glycans on IgG and α1-acid glycoprotein. Biochem J. 455(1):107-18. doi: 10.1042/BJ20130126 (2013).
Sletten et al. From mechanism to mouse: a tale of two bioorthogonal reactions. Acc Chem Res. 44(9):666-76. doi: 10.1021/ar200148z (2011).
Tarentino et al. Enzymatic Deglycosylation of Asparagine-Linked Glycans: Purification, Properties, and Specificity of Oligosaccharide-Cleaving Enzymes from Flavobacterium meningosepticum. Methods in Enzymology, 230, 44-4 (1994).
Trimble et al. Identification of Distinct Endoglycosidase (Endo) Activities in Flavobacterium meningoseptum: Endo F1, Endo F2, and Endo F3. J. Biol. Chem. 266(3): 1646-1651 (1991).
Van Berkel et al. Metal-free triazole formation as a tool for bioconjugation. Chembiochem. 8(13):1504-8 (2007).
Wang et al. Enrichment and site mapping of O-linked N-acetylglucosamine by a combination of chemical/enzymatic tagging, photochemical cleavage, and electron transfer dissociation mass spectrometry. Mol Cell Proteomics. 9(1):153-60. doi:10.1074/mcp.M900268-MCP200 (2010).
Wei et al. Glycoengineering of human IgG1-Fc through combined yeast expression and in vitro chemoenzymatic glycosylation. Biochemistry. 47(39):10294-304. doi:10.1021/bi800874y (2008).
Zeglis et al. Enzyme-mediated methodology for the site-specific radiolabeling of antibodies based on catalyst-free click chemistry. Bioconjug Chem. 24(6):1057-67. doi: 10.1021/bc400122c (2013).
Saber, "An FDA oncology analysis of antibody-drug conjugates" Regul Toxicol Pharmacol, 2015, 71(3), pp. 444-452.
Sanchez-De Melo et al., "N-glycosylation profile analysis of Trastuzumab biosimilar candidates by Normal Phase Liquid Chromatography and MALDI-TOF MS approaches", J Proteomics, 2015, 127(Pt B), pp. 225-233.
Sazinsky et al., "Aglycosylated immunoglobulin G1 variants productively engage activating Fc receptors", Proc Natl Acad Sci U S A., 2008, 105(51), pp. 20167-20172.
Shen et al., "Conjugation site modulates the in vivo stability and therapeutic activity of antibody-drug conjugates", Nat Biotechnol 2012, 30(2), pp. 184-189.
Shi et al., "Organic nanoscale drug carriers coupled with ligands for targeted drug delivery in cancer", J. Mater. Chem., 19:5485-5498, (2009).

(56) References Cited

OTHER PUBLICATIONS

Sletten, "Bioorthogonal chemistry: fishing for selectivity in a sea of functionality", Angew Chem Int Ed Engl, 2009, 48(38), pp. 6974-6998.
Stefan et al., "Highly Potent, Anthracycline-based Antibody-Drug Conjugates Generated by Enzymatic, Site-specific Conjugation", Mol Cancer Ther, 201716(5), pp. 879-892.
Strop et al., "Location matters: site of conjugation modulates stability and pharmacokinetics of antibody drug conjugates", Chem Biol, 2013, 20(2), pp. 161-167.
Suzuki et al., "Site-specific N-glycosylation of chicken serum IgG", Glycobiology2004, 14(3), pp. 275-792.
Teicher, "Antibody conjugate therapeutics: challenges and potential", Clin Cancer Res, 2011, 17(20), pp. 6389-6397.
Temming et al., "Protein enrichment by capture-release based on strain-promoted cycloaddition of azide with bicyclononyne (BCN)", Bioorg Med Chem, 2012 20(2), pp. 655-661.
Thomas et al., "Application of strain-promoted azide-alkyne cycloaddition and tetrazine ligation to targeted Fc-drug conjugates", Bioconjug Chem, 2012 23(10), pp. 2007-2013.
Tumey et al., "Site Selection: a Case Study in the Identification of Optimal Cysteine Engineered Antibody Drug Conjugates", AAPS J, 2017 19(4) pp. 1123-1135.
Uppal et al., "Potential mechanisms for thrombocytopenia development with trastuzumab emtansine (T-DM1)", Clin Cancer Res, 2014 21(1):123-133.
Van Berkel et al., "Metal-free bioconjugation reactions", Drug Discov Today Technol, 2013, 10(1), pp. 45-51.
Van De Bovenkamp et al., "The Emerging Importance of IgG Fab Glycosylation in Immunity", J Immunol, 2016 196(4), pp. 1435-1441.
Van Geel et al., "Chemoenzymatic Conjugation of Toxic Payloads to the Globally Conserved N-Glycan of Native mAbs Provides Homogeneous and Highly Efficacious Antibody-Drug Conjugates", Bioconjug Chem, 2015, 26(11) pp. 2233-2242.
Wan et al., "Genetically Encoding Bioorthogonal Functional Groups for Site-selective Protein Labeling", Organic Chem Curr Res, 2012 1:3, 1000e111, p. 1.
Wang, "Synthesis of multi-functional dendrimers for targeted delivery of nucleic acids", PhD (Doctor of Philosophy) thesis, University of Aix-Marseille, 2012, p. 1.
Witte et al., "Preparation of unnatural N-to-N and C-to-C protein fusions", Proc Natl Acad Sci U S A, 2012, 109(30), pp. 11993-11998.
Zhao et al., "Inhibition of Megakaryocyte Differentiation by Antibody-Drug Conjugates (ADCs) is Mediated by Macropinocytosis: Implications for ADC-induced Thrombocytopenia", Mol Cancer Ther, 2017 16(9), pp. 1877-1886.
Zhao et al., "A Potential Mechanism for ADC-Induced Neutropenia: Role of Neutrophils in Their Own Demise", Mol Cancer Ther, 2017 16(9), pp. 1866-1876.
Alford R et al., "Toxicity of Organic Fluorophores Used in Molecular Imaging: Literature Review", Mol Imaging. 2009, 8(6), pp. 341-354.
Avital-Shmilovici et al., "Self-immolative dendrimers: A distinctive approach to molecular amplification", Soft Matter, 2010, 6, pp. 1073-1080.
Axup Jy et al., "Synthesis of Site-Specific Antibody-Drug Conjugates Using Unnatural Amino Acids", 2012 Proc Natl Acad Sci U S A. 109(40), pp. 16101-16106.
Beckman, et al. "Azides in Carbohydrate Chemistry, in: Organic Azides: Syntheses and Applications / eds", 2010, Stefan Bräse, Chichester: Wiley, pp. 469-490.
Boeggeman, et al. "Studies on the Metal Binding Sites in the Catalytic Domain of Beta1,4-Galactosyltransferase", Glycobiology, 2002, 12(7), pp. 395-407.
Boeggeman, et al., "The N-Terminal Stem Region of Bovine and Human Beta1,4-Galactosyltransferase I Increases the in Vitro Folding Efficiency of Their Catalytic Domain from Inclusion Bodies", 2003, Protein Expr Purif.30(2), pp. 219-229.
Bojarova et al., Synthesis of LacdiNAc-Terminated Glycoconjugates by Mutant Galactosyltransferase—A Way to New Glycodrugs and Materials. Glycobiology, 2009, 19(5), pp. 509-517.
Bosco et al., 6-Azido D-Galactose Transfer to N-acetyl-d-glucosamine derivative using commercially available 3-1,4-galactosyltransferase. Tetrahedron Letters, 2008, 49(14), pp. 2294-2297.
Bourgeaux et al., "Two-step Enzymatic Synthesis of UDP-N-acetylgalactosamine.",Bioorg Med Chem Lett, 2005, 15(24), pp. 5459-5462.
Bulter et al., "Chemoenzymatic Synthesis of Biotinylated Nucleotide Sugars as Substrates for Glycosyltransferases",Chembiochem, 2001, 2(12), pp. 884-894.
Campbell-Verduyn, "Click for PET", Click Chemistry as a Tool for [18F] Radiolabelling, 2012, Groningen: s.n., p. 1.
Canalle et al., "Polypeptide-Polymer Bioconjugates", Chem Soc Rev, 2010, 39(1): pp. 329-353.
Chaubard et al., Chemoenzymatic Probes for Detecting and Imaging Fucose-α(1-2)-galactose Glycan biomarkers. J Am Chem Soc, 2012, 14;134(10): pp. 4489-4492.
Chen et al., "Enzyme-Catalyzed Synthesis of a Hybrid N-Linked Oligosaccharide using N Acetylglucosaminyltransferase I. Adv", 2008, Synth Catal 350: pp. 1689-1695.
Chuh et al., Changes in Metabolic Chemical Reporter Structure Yield a Selective Probe of O-GlcNAc Modification, J Am Chem Soc, 2014, 136(35), pp. 12283-12295.
Colombo et al., "Site-Specific Conjugation of ScFvs Antibodies to Nanoparticles by Bioorthogonal Strain-Promoted alkyne-nitrone cycloaddition", Angew Chem Int Ed Engl, 2012, 51(2), pp. 496-499.
Dokter et al., "Preclinical Profile of the HER2-targeting ADC SYD983/SYD985: Introduction of a New Duocarmycin-based Linker-Drug Platform", Mol Cancer Ther, 2014 13(11), pp. 2618-2629.
Dommerholt et al., "Strain-Promoted 1,3-Dipolar Cycloaddition of Cycloalkynes and Organic Azides", Top Curr Chem (Cham), 2016, 374(2): p. 16.
Dorywalska et al., "Molecular Basis of Valine-Citrulline-PABC Linker Instability in Site-Specific ADCs and Its Mitigation by Linker Design", Mol Cancer Ther, 2016, 15(5), pp. 958-970.
Ducry, "Antibody-Drug Conjugates: Linking Cytotoxic Payloads to Monoclonal Antibodies", Bioconjug Chem, 2010, 21(1), pp. 5-13.
Elchinger, "Polysaccharides: The "Click" Chemistry Impact", Polymers 3, 2011, pp. 1607-1651.
Ferrara et al., "Unique Carbohydrate-Carbohydrate Interactions are Required for High Affinity Binding Between FcgammaRIII and Antibodies Lacking Core Fucose", Proc Natl Acad Sci U S A, 2011, 108(31), pp. 12669-12674.
Goetze et al., "High-Mannose Glycans on the Fc Region of Therapeutic IgG Antibodies Increase Serum clearance in Humans", Glycobiology, 2011, 21(7), pp. 949-959.
Gorovits, Proposed Mechanism of Off-Target Toxicity for Antibody-Drug Conjugates Driven by Mannose Receptor Uptake, Cancer Immunol Immunother, 2013, 62(2), p. 217-223.
Guan et al., "Highly Efficient Synthesis of UDP-GalNAc/GlcNAc Analogues with Promiscuous Recombinant Human UDP-GalNAc Pyrophosphorylase AGX1", Chemistry, 2010, 16(45), pp. 13343-13345.
Hamann et al., "Gemtuzumab ozogamicin, a potent and selective anti-CD33 antibody-calicheamicin conjugate for treatment of acute myeloid leukemia", Bioconjug Chem, 2002, 13(1), pp. 47-58.
Hein et al., "Click Chemistry, A Powerful Tool for Pharmaceutical Sciences", Pharm Res, 2008, 25(10), pp. 2216-2230.
Huang et al., "Copper-free click conjugation of methotrexate to a PAMAM dendrimer platform", Tetrahedron Lett. 2011, 52(13), pp. 1411-1414.
Jawalekar et al., "Oligonucleotide tagging for copper-free click conjugation", Molecules, 2013, 18(7), pp. 7346-7363.
Jeger et al., "Site-specific and stoichiometric modification of antibodies by bacterial transglutaminase", Angew Chem Int Ed Engl, 2010, 49(51), pp. 9995-9997.
Kalia, "Bioconjugation: Linkage Stability and Novel Methods", 2008, PhD Thesis. p. 1.

(56) References Cited

OTHER PUBLICATIONS

Kanda et al., "Comparison of biological activity among nonfucosylated therapeutic IgG1 antibodies with three lifferent N-linked Fc oligosaccharides: the high-mannose, hybrid, and complex types", Glycobiology., 2007, 17(1), pp. 104-118.
Kim et al., "Drifts in ADCC-related quality attributes of Herceptin®: Impact on development of a trastuzumab biosimilar", MAbs, 2017, 9(4), pp. 704-714.
Li et al, "Preparation of well-defined antibody-drug conjugates through glycan remodeling and strain-promoted azide-alkyne cycloadditions", Angew Chem Int Ed Engl, 2014, 53(28), pp. 7179-7182.
L'Italien et al., "Mechanistic Insights of an Immunological Adverse Event Induced by an Anti-KIT Antibody Drug Conjugate and Mitigation Strategies", Clin Cancer Res, 2018, 24(14), pp. 3465-3474.
Lyon et al., "Reducing hydrophobicity of homogeneous antibody-drug conjugates improves pharmacokinetics and therapeutic index", Nat Biotechnol, 2015, 33(7), pp. 733-735.
Maley et al., "Characterization of glycoproteins and their associated oligosaccharides through the use of endoglycosidases", Anal Biochem, 1989, 180(2), pp. 195-204.
McDonagh et al., "Engineered antibody-drug conjugates with defined sites and stoichiometries of drug attachment", Protein Eng Des Sel, 2006, 19(7), pp. 299-307.
Millward et al., "In situ click chemistry: from small molecule discovery to synthetic antibodies", Integr Biol (Camb), 2013, 5(1), pp. 87-95.
Ning, "Applications of Click Chemistry in Drug Discovery, Bioconjugation and Material Science", A Dissertation Submitted to the Graduate Faculty of the University of Georgia, 2008, Athens, Georgia. p. 1.
Oh-Eda et al., "Overexpression of The Golgi-localized Enzyme Alpha-Mannosidase IIx in Chinese Hamster Ovary Cells Results in the Conversion of Hexamannosyl-N-acetylchitobiose to Tetramannosyl-N-Acetylchitobiose in the N-glycan-Processing Pathway", Eur J Biochem, 2001, 268(5), pp. 1280-1288.
Okeley et al., "Metabolic Engineering of Monoclonal Antibody Carbohydrates for Antibody-Drug Conjugation", Bioconjug Chem, 2013, 24(10), pp. 1650-1655.
Opposition EP 2911699 B1: Glykos reply to observations made by the patent proprietor of patent No. EP 2911699 B1, dated Aug. 9, 2019.
Opposition EP 2911699 B1: HGF reply to observations made by the patent proprietor of patent No. EP 2911699 B1, dated Aug. 8, 2019.
Opposition EP 2911699 B1: Synaffix reply to opposition against European patent No. EP 2911699 B1, dated May 2, 2019.
Opposition EP 2911699 B1: Declarations by Floris Louis van Delft, dated May 2, 2019.
Opposition EP 2911699 B1: Preliminary opinion of European Patent Office, dated Jul. 23, 2019.
Parameswarappa, "Bifunctional cyclooctynes in copper-free click chemistry for applications in radionuclide chemistry nd 4-Alkylpyridine derivatives in intramolecular dearomatization and heterocycle synthesis", PhD (Doctor of Philosophy) thesis, 2011, University of Iowa, (334 pages).
Pouilly et al., "Evaluation of Analogues of GalNAc as Substrates for Enzymes of the Mammalian GalNAc Salvage Pathway", ACS Chem Biol, 2012, 7(4), pp. 753-760.
Raju et al., "Species-specific variation in glycosylation of IgG: evidence for the species-specific sialylation and branch-specific galactosylation and importance for engineering recombinant glycoprotein therapeutics", Glycobiology, 2000, 10(5), pp. 477-486.
Varki, et al., editors. Essentials of Glycobiology. 2nd edition. Cold Spring Harbor (NY): Cold Spring Harbor Laboratory Press; 2009.

* cited by examiner

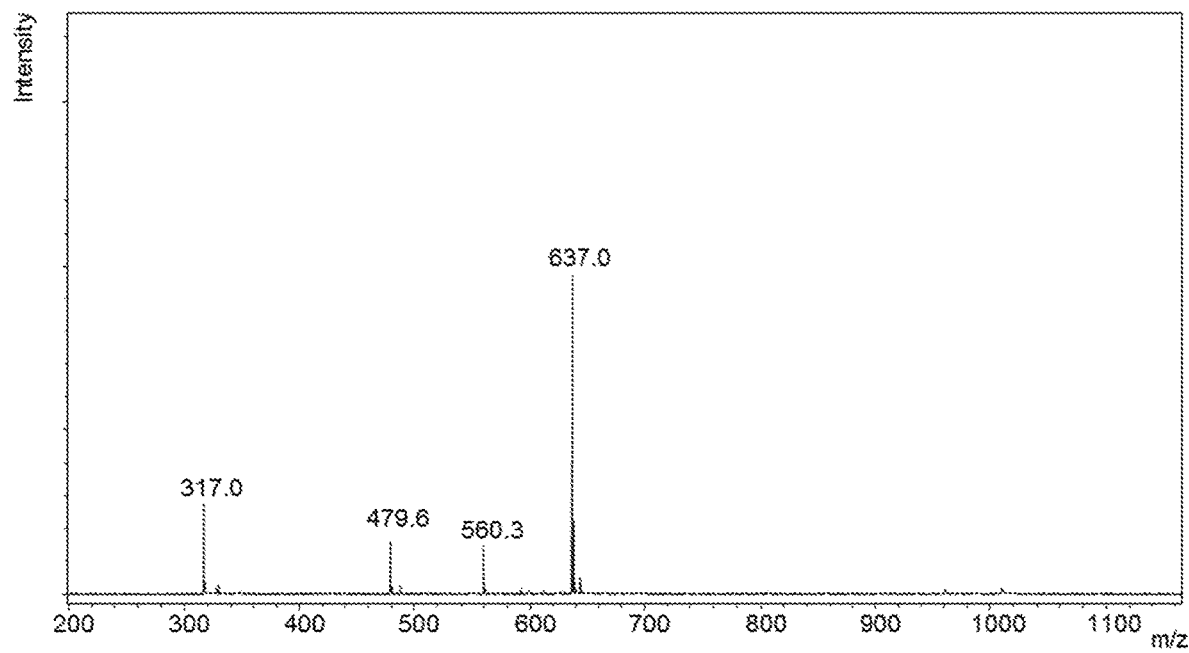
Figure 2
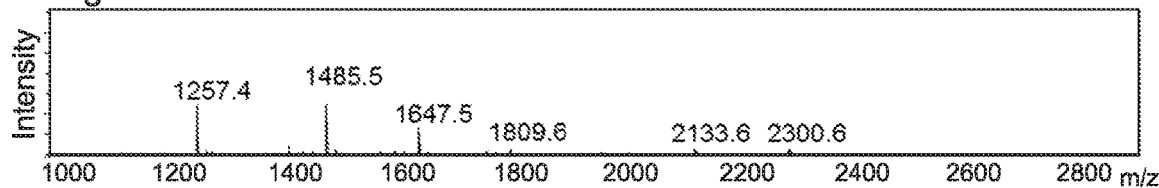
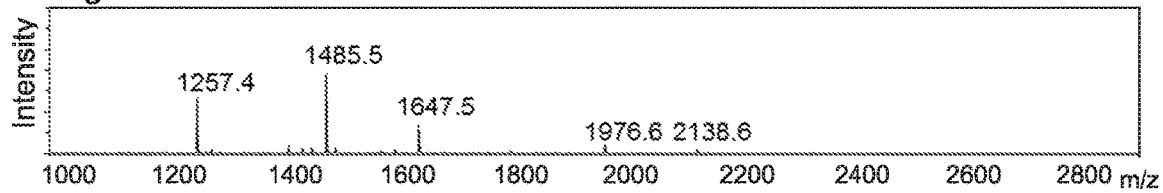
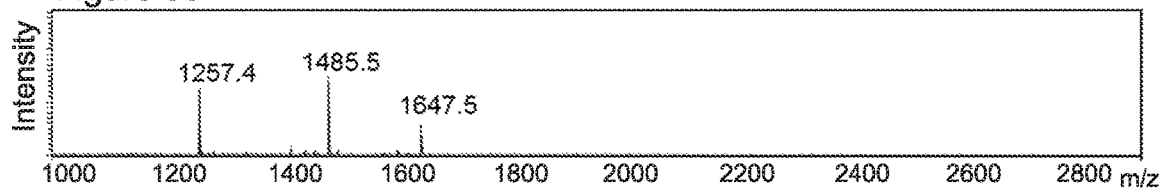
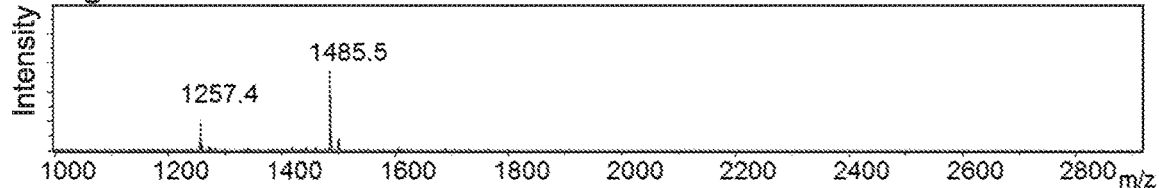

SEQUENCE LISTING

<160> NUMBER OF SEQ ID NOS: 40

<210> SEQ ID NO 1
<211> LENGTH: 1210
<212> TYPE: PRT
<213> ORGANISM: Homo sapiens
<220> FEATURE:
<223> OTHER INFORMATION: EGF receptor, human NP_005219.2

<400> SEQUENCE: 1

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110
```

-continued

```
Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525
```

```
Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
```

```
                         945                 950                 955                 960

Phe Arg Glu Leu Ile Ile Glu Phe Ser Lys Met Ala Arg Asp Pro Gln
                         965                 970                 975

Arg Tyr Leu Val Ile Gln Gly Asp Glu Arg Met His Leu Pro Ser Pro
                         980                 985                 990

Thr Asp Ser Asn Phe Tyr Arg Ala Leu Met Asp Glu Glu Asp Met Asp
                         995                1000                1005

Asp Val Val Asp Ala Asp Glu Tyr Leu Ile Pro Gln Gln Gly Phe Phe
                        1010                1015                1020

Ser Ser Pro Ser Thr Ser Arg Thr Pro Leu Leu Ser Ser Leu Ser Ala
        1025                1030                1035                1040

Thr Ser Asn Asn Ser Thr Val Ala Cys Ile Asp Arg Asn Gly Leu Gln
                        1045                1050                1055

Ser Cys Pro Ile Lys Glu Asp Ser Phe Leu Gln Arg Tyr Ser Ser Asp
                        1060                1065                1070

Pro Thr Gly Ala Leu Thr Glu Asp Ser Ile Asp Asp Thr Phe Leu Pro
                        1075                1080                1085

Val Pro Glu Tyr Ile Asn Gln Ser Val Pro Lys Arg Pro Ala Gly Ser
                        1090                1095                1100

Val Gln Asn Pro Val Tyr His Asn Gln Pro Leu Asn Pro Ala Pro Ser
        1105                1110                1115                1120

Arg Asp Pro His Tyr Gln Asp Pro His Ser Thr Ala Val Gly Asn Pro
                        1125                1130                1135

Glu Tyr Leu Asn Thr Val Gln Pro Thr Cys Val Asn Ser Thr Phe Asp
                        1140                1145                1150

Ser Pro Ala His Trp Ala Gln Lys Gly Ser His Gln Ile Ser Leu Asp
                        1155                1160                1165

Asn Pro Asp Tyr Gln Gln Asp Phe Phe Pro Lys Glu Ala Lys Pro Asn
                        1170                1175                1180

Gly Ile Phe Lys Gly Ser Thr Ala Glu Asn Ala Glu Tyr Leu Arg Val
        1185                1190                1195                1200

Ala Pro Gln Ser Ser Glu Phe Ile Gly Ala
                        1205                1210

<210> SEQ ID NO 2
<211> LENGTH: 1255
<212> TYPE: PRT
<213> ORGANISM: Homo sapiens
<220> FEATURE:
<223> OTHER INFORMATION: HER2 receptor, human NP_004439.2

<400> SEQUENCE: 2

Met Glu Leu Ala Ala Leu Cys Arg Trp Gly Leu Leu Leu Ala Leu Leu
1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
```

```
            100                 105                 110
Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
        130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525
```

```
Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940
```

```
Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255

<210> SEQ ID NO 3
<211> LENGTH: 449
<212> TYPE: PRT
<213> ORGANISM: Artificial Sequence
<220> FEATURE:
<223> OTHER INFORMATION: heavy chain, cetuximab, INN7906H, from IMGT

<400> SEQUENCE: 3

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45
```

-continued

```
Gly Val Ile Trp Ser Gly Gly Asn Thr Asp Tyr Asn Thr Pro Phe Thr
 50                  55                  60
Ser Arg Leu Ser Ile Asn Lys Asp Asn Ser Lys Ser Gln Val Phe Phe
 65                  70                  75                  80
Lys Met Asn Ser Leu Gln Ser Asn Asp Thr Ala Ile Tyr Tyr Cys Ala
                 85                  90                  95
Arg Ala Leu Thr Tyr Tyr Asp Tyr Glu Phe Ala Tyr Trp Gly Gln Gly
                100                 105                 110
Thr Leu Val Thr Val Ser Ala Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 4

<211> LENGTH: 214
<212> TYPE: PRT
<213> ORGANISM: Artificial Sequence
<220> FEATURE:
<223> OTHER INFORMATION: Light chain, cetuximab, INN7906L, from IMGT

<400> SEQUENCE: 4

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 450
<212> TYPE: PRT
<213> ORGANISM: Artificial Sequence
<220> FEATURE:
<223> OTHER INFORMATION: heavy chain, trastuzumab, 7637H, from IMGT

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
```

```
            100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 6
<211> LENGTH: 214
<212> TYPE: PRT
<213> ORGANISM: Artificial Sequence
<220> FEATURE:
<223> OTHER INFORMATION: light chain, trastuzumab, 7637L, from IMGT

<400> SEQUENCE: 6

Asp Ile Gln Met Thr Gln Ser Pro Ser Ser Leu Ser Ala Ser Val Gly
```

```
  1               5                  10                 15
Asp Arg Val Thr Ile Thr Cys Arg Ala Ser Gln Asp Val Asn Thr Ala
                20                  25                 30

Val Ala Trp Tyr Gln Gln Lys Pro Gly Lys Ala Pro Lys Leu Leu Ile
                35                  40                 45

Tyr Ser Ala Ser Phe Leu Tyr Ser Gly Val Pro Ser Arg Phe Ser Gly
                50                  55                 60

Ser Arg Ser Gly Thr Asp Phe Thr Leu Thr Ile Ser Ser Leu Gln Pro
 65                 70                  75                 80

Glu Asp Phe Ala Thr Tyr Tyr Cys Gln Gln His Tyr Thr Thr Pro Pro
                85                  90                 95

Thr Phe Gly Gln Gly Thr Lys Val Glu Ile Lys Arg Thr Val Ala Ala
                100                 105                110

Pro Ser Val Phe Ile Phe Pro Pro Ser Asp Glu Gln Leu Lys Ser Gly
                115                 120                125

Thr Ala Ser Val Val Cys Leu Leu Asn Asn Phe Tyr Pro Arg Glu Ala
                130                 135                140

Lys Val Gln Trp Lys Val Asp Asn Ala Leu Gln Ser Gly Asn Ser Gln
145                 150                 155                160

Glu Ser Val Thr Glu Gln Asp Ser Lys Asp Ser Thr Tyr Ser Leu Ser
                165                 170                175

Ser Thr Leu Thr Leu Ser Lys Ala Asp Tyr Glu Lys His Lys Val Tyr
                180                 185                190

Ala Cys Glu Val Thr His Gln Gly Leu Ser Ser Pro Val Thr Lys Ser
                195                 200                205

Phe Asn Arg Gly Glu Cys
                210

<210> SEQ ID NO 7
<211> LENGTH: 451
<212> TYPE: PRT
<213> ORGANISM: Artificial Sequence
<220> FEATURE:
<223> OTHER INFORMATION: Heavy chain, 7609H, rituximab

<400> SEQUENCE: 7

Gln Val Gln Leu Gln Gln Pro Gly Ala Glu Leu Val Lys Pro Gly Ala
 1               5                  10                 15

Ser Val Lys Met Ser Cys Lys Ala Ser Gly Tyr Thr Phe Thr Ser Tyr
                20                  25                 30

Asn Met His Trp Val Lys Gln Thr Pro Gly Arg Gly Leu Glu Trp Ile
                35                  40                 45

Gly Ala Ile Tyr Pro Gly Asn Gly Asp Thr Ser Tyr Asn Gln Lys Phe
                50                  55                 60

Lys Gly Lys Ala Thr Leu Thr Ala Asp Lys Ser Ser Ser Thr Ala Tyr
 65                 70                  75                 80

Met Gln Leu Ser Ser Leu Thr Ser Glu Asp Ser Ala Val Tyr Tyr Cys
                85                  90                 95

Ala Arg Ser Thr Tyr Tyr Gly Gly Asp Trp Tyr Phe Asn Val Trp Gly
                100                 105                110

Ala Gly Thr Thr Val Thr Val Ser Ala Ala Ser Thr Lys Gly Pro Ser
                115                 120                125

Val Phe Pro Leu Ala Pro Ser Ser Lys Ser Thr Ser Gly Gly Thr Ala
                130                 135                140

Ala Leu Gly Cys Leu Val Lys Asp Tyr Phe Pro Glu Pro Val Thr Val
```

```
                145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 8
<211> LENGTH: 213
<212> TYPE: PRT
<213> ORGANISM: Artificial Sequence
<220> FEATURE:
<223> OTHER INFORMATION: light chain, 7609L, rituximab

<400> SEQUENCE: 8

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
                35                  40                  45

Ala Thr Ser Asn Leu Ala Ser Gly Val Pro Val Arg Phe Ser Gly Ser
```

```
            50                  55                  60
Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 9
<211> LENGTH: 453
<212> TYPE: PRT
<213> ORGANISM: Artificial Sequence
<220> FEATURE:
<223> OTHER INFORMATION: 8017H|bevacizumab|

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asn Tyr
                 20                  25                  30

Gly Met Asn Trp Val Arg Gln Ala Pro Gly Lys Gly Leu Glu Trp Val
             35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
```

```
                195                 200                 205
Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: 8017L|bevacizumab|

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
```

```
              100                 105                 110
Pro Ser Val Phe Ile Phe Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 11
<211> LENGTH: 447
<212> TYPE: PRT
<213> ORGANISM: Artificial Sequence
<220> FEATURE:
<223> OTHER INFORMATION: tositumomab Heavy

<400> SEQUENCE: 11

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                     245                 250                 255
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 12
<211> LENGTH: 210
<212> TYPE: PRT
<213> ORGANISM: Artificial Sequence
<220> FEATURE:
<223> OTHER INFORMATION: tositumomab Light

<400> SEQUENCE: 12

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
            35                  40                  45

Ala Pro Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                    165                 170                 175
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg
    210

<210> SEQ ID NO 13
<211> LENGTH: 467
<212> TYPE: PRT
<213> ORGANISM: Artificial Sequence
<220> FEATURE:
<223> OTHER INFORMATION: 7783M|etanercept

<400> SEQUENCE: 13

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
```

```
                305                 310                 315                 320
Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 14
<211> LENGTH: 121
<212> TYPE: PRT
<213> ORGANISM: Artificial Sequence
<220> FEATURE:
<223> OTHER INFORMATION: 7860H|adalimumab

<400> SEQUENCE: 14

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
                35                  40                  45

Ser Ala Ile Thr Trp Asn Ser Gly His Ile Asp Tyr Ala Asp Ser Val
                50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser
                115                 120

<210> SEQ ID NO 15
<211> LENGTH: 107
<212> TYPE: PRT
<213> ORGANISM: Artificial Sequence
<220> FEATURE:
<223> OTHER INFORMATION: 7860L|adalimumab

<400> SEQUENCE: 15

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

<210> SEQ ID NO 16
<211> LENGTH: 224
<212> TYPE: PRT
<213> ORGANISM: Artificial Sequence
<220> FEATURE:
<223> OTHER INFORMATION: adalimumab Heavy chain, partial

<400> SEQUENCE: 16

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 17
<211> LENGTH: 214
<212> TYPE: PRT
<213> ORGANISM: Artificial Sequence
<220> FEATURE:
<223> OTHER INFORMATION: adalimumab Light chain

<400> SEQUENCE: 17

-continued

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 18
<211> LENGTH: 451
<212> TYPE: PRT
<213> ORGANISM: Artificial Sequence
<220> FEATURE:
<223> OTHER INFORMATION: 8005H|alemtuzumab

<400> SEQUENCE: 18

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Phe Thr Phe Thr Asp Phe
             20                  25                  30

Tyr Met Asn Trp Val Arg Gln Pro Pro Gly Arg Gly Leu Glu Trp Ile
         35                  40                  45

Gly Phe Ile Arg Asp Lys Ala Lys Gly Tyr Thr Thr Glu Tyr Asn Pro
 50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
                 85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 19
<211> LENGTH: 214
<212> TYPE: PRT
<213> ORGANISM: Artificial Sequence
<220> FEATURE:
<223> OTHER INFORMATION: 8005L|alemtuzumab

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45
```

```
Tyr Asn Thr Asn Asn Leu Gln Thr Gly Val Pro Ser Arg Phe Ser Gly
             50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 20
<211> LENGTH: 451
<212> TYPE: PRT
<213> ORGANISM: Artificial Sequence
<220> FEATURE:
<223> OTHER INFORMATION: 8122H|efalizumab

<400> SEQUENCE: 20

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly His
                 20                  25                  30

Trp Met Asn Trp Val Arg Gln Ala Pro Gly Lys Gly Leu Glu Trp Val
             35                  40                  45

Gly Met Ile His Pro Ser Asp Ser Glu Thr Arg Tyr Asn Gln Lys Phe
 50                  55                  60

Lys Asp Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Tyr Phe Tyr Gly Thr Thr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190
```

-continued

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 21
<211> LENGTH: 214
<212> TYPE: PRT
<213> ORGANISM: Artificial Sequence
<220> FEATURE:
<223> OTHER INFORMATION: 8122L|efalizumab

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Leu
                85                  90                  95

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 119
<212> TYPE: PRT
<213> ORGANISM: Artificial Sequence
<220> FEATURE:
<223> OTHER INFORMATION: 7602H|infliximab

<400> SEQUENCE: 22

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser
        115

<210> SEQ ID NO 23
<211> LENGTH: 107
<212> TYPE: PRT
<213> ORGANISM: Artificial Sequence
<220> FEATURE:
<223> OTHER INFORMATION: 7602L|infliximab

<400> SEQUENCE: 23

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
```

```
                    50                  55                  60
Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys
            100                 105
```

<210> SEQ ID NO 24
<211> LENGTH: 215
<212> TYPE: PRT
<213> ORGANISM: Artificial Sequence
<220> FEATURE:
<223> OTHER INFORMATION: 3iu3A|basiliximab Fab|Chimeric||VH-CH1

<400> SEQUENCE: 24

```
Gln Leu Gln Gln Ser Gly Thr Val Leu Ala Arg Pro Gly Ala Ser Val
  1               5                  10                  15

Lys Met Ser Cys Lys Ala Ser Gly Tyr Ser Phe Thr Tyr Trp Met
             20                  25                  30

His Trp Ile Lys Gln Arg Pro Gly Gln Gly Leu Glu Trp Ile Gly Ala
             35                  40                  45

Ile Tyr Pro Gly Asn Ser Asp Thr Ser Tyr Asn Gln Lys Phe Glu Gly
         50                  55                  60

Lys Ala Lys Leu Thr Ala Val Thr Ser Ala Ser Thr Ala Tyr Met Glu
 65                  70                  75                  80

Leu Ser Ser Leu Thr His Glu Asp Ser Ala Val Tyr Tyr Cys Ser Arg
                 85                  90                  95

Asp Tyr Gly Tyr Tyr Phe Asp Phe Trp Gly Gln Gly Thr Thr Leu Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro
        210                 215
```

<210> SEQ ID NO 25
<211> LENGTH: 210
<212> TYPE: PRT
<213> ORGANISM: Artificial Sequence
<220> FEATURE:
<223> OTHER INFORMATION: 3iu3B|basiliximab Fab|Chimeric||L-KAPPA

<400> SEQUENCE: 25

```
Gln Ile Val Ser Thr Gln Ser Pro Ala Ile Met Ser Ala Ser Pro Gly
  1               5                  10                  15

Glu Lys Val Thr Met Thr Cys Ser Ala Ser Ser Ser Arg Ser Tyr Met
             20                  25                  30
```

```
Gln Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Ser Ser Tyr Thr Phe Gly
                 85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu
    210

<210> SEQ ID NO 26
<211> LENGTH: 446
<212> TYPE: PRT
<213> ORGANISM: Artificial Sequence
<220> FEATURE:
<223> OTHER INFORMATION: Basiliximab heavy chain

<400> SEQUENCE: 26

Gln Leu Gln Gln Ser Gly Thr Val Leu Ala Arg Pro Gly Ala Ser Val
 1                   5                  10                  15

Lys Met Ser Cys Lys Ala Ser Gly Tyr Ser Phe Thr Tyr Trp Met
             20                  25                  30

His Trp Ile Lys Gln Arg Pro Gly Gln Gly Leu Glu Trp Ile Gly Ala
            35                  40                  45

Ile Tyr Pro Gly Asn Ser Asp Thr Ser Tyr Asn Gln Lys Phe Glu Gly
 50                  55                  60

Lys Ala Lys Leu Thr Ala Val Thr Ser Ala Ser Thr Ala Tyr Met Glu
 65                  70                  75                  80

Leu Ser Ser Leu Thr His Glu Asp Ser Ala Val Tyr Tyr Cys Ser Arg
                 85                  90                  95

Asp Tyr Gly Tyr Tyr Phe Asp Phe Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 27
<211> LENGTH: 451
<212> TYPE: PRT
<213> ORGANISM: Artificial Sequence
<220> FEATURE:
<223> OTHER INFORMATION: 8039H|omalizumab|Humanized

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95
```

Ala Arg Gly Ser His Tyr Phe Gly His Trp His Phe Ala Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 28
<211> LENGTH: 218
<212> TYPE: PRT
<213> ORGANISM: Artificial Sequence
<220> FEATURE:
<223> OTHER INFORMATION: 8039L|omalizumab

<400> SEQUENCE: 28

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 29
<211> LENGTH: 446
<212> TYPE: PRT
<213> ORGANISM: Artificial Sequence
<220> FEATURE:
<223> OTHER INFORMATION: 7164H|daclizumab

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 30
<211> LENGTH: 213
<212> TYPE: PRT
<213> ORGANISM: Artificial Sequence
<220> FEATURE:
<223> OTHER INFORMATION: 7164L|daclizumab

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60
```

```
Gly Ser Gly Thr Glu Phe Thr Leu Thr Ile Ser Ser Leu Gln Pro Asp
 65                  70                  75                  80

Asp Phe Ala Thr Tyr Tyr Cys His Gln Arg Ser Thr Tyr Pro Leu Thr
                 85                  90                  95

Phe Gly Gln Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 31
<211> LENGTH: 453
<212> TYPE: PRT
<213> ORGANISM: Artificial Sequence
<220> FEATURE:
<223> OTHER INFORMATION: nimotuzumab_HC

<400> SEQUENCE: 31

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Arg Val Glu Pro Lys
    210                 215                 220

Ser Cys Asp Lys Thr His Thr Cys Pro Cys Pro Ala Pro Glu Leu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 32
<211> LENGTH: 219
<212> TYPE: PRT
<213> ORGANISM: Artificial Sequence
<220> FEATURE:
<223> OTHER INFORMATION: nimotuzumab_LC

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110
```

```
Arg Glu Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 33
<211> LENGTH: 219
<212> TYPE: PRT
<213> ORGANISM: Artificial Sequence
<220> FEATURE:
<223> OTHER INFORMATION: GCM012, light chain, anti-EGFR antibody

<400> SEQUENCE: 33

```
Asp Ile Gln Met Thr Gln Ser Pro Ser Ser Leu Ser Ala Ser Val Gly
1               5                   10                  15

Asp Asn Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Glu Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 34
<211> LENGTH: 446
<212> TYPE: PRT
<213> ORGANISM: Artificial Sequence
<220> FEATURE:

<223> OTHER INFORMATION: epratuzumab_HC

<400> SEQUENCE: 34

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Ser Tyr
            20                  25                  30
Trp Leu His Trp Val Arg Gln Ala Pro Gly Gln Gly Leu Glu Trp Ile
        35                  40                  45
Gly Tyr Ile Asn Pro Arg Asn Asp Tyr Thr Glu Tyr Asn Gln Asn Phe
    50                  55                  60
Lys Asp Lys Ala Thr Ile Thr Ala Asp Glu Ser Thr Asn Thr Ala Tyr
65                  70                  75                  80
Met Glu Leu Ser Ser Leu Arg Ser Glu Asp Thr Ala Phe Tyr Phe Cys
                85                  90                  95
Ala Arg Arg Asp Ile Thr Thr Phe Tyr Trp Gly Gln Gly Thr Thr Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445
```

<210> SEQ ID NO 35
<211> LENGTH: 219
<212> TYPE: PRT
<213> ORGANISM: Artificial Sequence
<220> FEATURE:
<223> OTHER INFORMATION: epratuzumab_LC

<400> SEQUENCE: 35

```
Asp Ile Gln Leu Thr Gln Ser Pro Ser Ser Leu Ser Ala Ser Val Gly
1               5                   10                  15

Asp Arg Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 36
<211> LENGTH: 446
<212> TYPE: PRT
<213> ORGANISM: Artificial Sequence
<220> FEATURE:
<223> OTHER INFORMATION: lintuzumab_HC

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45
```

Gly Tyr Ile Tyr Pro Tyr Asn Gly Gly Thr Gly Tyr Asn Gln Lys Phe
         50                  55                  60

Lys Ser Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Pro Ala Met Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445

<210> SEQ ID NO 37
<211> LENGTH: 217

```
<212> TYPE: PRT
<213> ORGANISM: Artificial Sequence
<220> FEATURE:
<223> OTHER INFORMATION: lintuzumab_LC

<400> SEQUENCE: 37
```

| | | | | | | | | | | | | | | |
|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Glu | Ser | Val | Asp | Asn | Tyr |
| | | | 20 | | | | | 25 | | | | | 30 | | |
| Gly | Ile | Ser | Phe | Met | Asn | Trp | Phe | Gln | Gln | Lys | Pro | Gly | Lys | Ala | Pro |
| | | | 35 | | | | | 40 | | | | | 45 | | |
| Lys | Leu | Leu | Ile | Tyr | Ala | Ala | Ser | Asn | Gln | Gly | Ser | Gly | Val | Pro | Ser |
| 50 | | | | | 55 | | | | | 60 | | | | | |
| Arg | Phe | Ser | Gly | Ser | Gly | Ser | Gly | Thr | Asp | Phe | Thr | Leu | Thr | Ile | Ser |
| 65 | | | | | 70 | | | | | 75 | | | | | 80 |
| Ser | Leu | Gln | Pro | Asp | Asp | Phe | Ala | Thr | Tyr | Tyr | Cys | Gln | Gln | Ser | Lys |
| | | | | 85 | | | | | 90 | | | | | 95 | |
| Glu | Val | Pro | Trp | Thr | Phe | Gly | Gln | Gly | Thr | Lys | Val | Glu | Ile | Lys | Thr |
| | | | | 100 | | | | | 105 | | | | | 110 | |
| Val | Ala | Ala | Pro | Ser | Val | Phe | Ile | Phe | Pro | Pro | Ser | Asp | Glu | Gln | Leu |
| | | | | 115 | | | | | 120 | | | | | 125 | |
| Lys | Ser | Gly | Thr | Ala | Ser | Val | Val | Cys | Leu | Leu | Asn | Asn | Phe | Tyr | Pro |
| 130 | | | | | 135 | | | | | 140 | | | | | |
| Arg | Glu | Ala | Lys | Val | Gln | Trp | Lys | Val | Asp | Asn | Ala | Leu | Gln | Ser | Gly |
| 145 | | | | | 150 | | | | | 155 | | | | | 160 |
| Asn | Ser | Gln | Glu | Ser | Val | Thr | Glu | Gln | Asp | Ser | Lys | Asp | Ser | Thr | Tyr |
| | | | | 165 | | | | | 170 | | | | | 175 | |
| Ser | Leu | Ser | Ser | Thr | Leu | Thr | Leu | Ser | Lys | Ala | Asp | Tyr | Glu | Lys | His |
| | | | 180 | | | | | 185 | | | | | 190 | | |
| Lys | Val | Tyr | Ala | Cys | Glu | Val | Thr | His | Gln | Gly | Leu | Ser | Ser | Pro | Val |
| | | | 195 | | | | | 200 | | | | | 205 | | |
| Thr | Lys | Ser | Phe | Asn | Arg | Gly | Glu | Cys | | | | | | | |
| | 210 | | | | | 215 | | | | | | | | | |

```
<210> SEQ ID NO 38
<211> LENGTH: 446
<212> TYPE: PRT
<213> ORGANISM: Artificial Sequence
<220> FEATURE:
<223> OTHER INFORMATION: GCM011, heavy chain, anti-CD33 antibody

<400> SEQUENCE: 38
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asp | Tyr |
| | | | 20 | | | | | 25 | | | | | 30 | | |
| Asn | Met | His | Trp | Val | Arg | Gln | Ala | Pro | Gly | Gln | Gly | Leu | Glu | Trp | Ile |
| | | | 35 | | | | | 40 | | | | | 45 | | |
| Gly | Tyr | Ile | Tyr | Pro | Tyr | Asn | Gly | Gly | Thr | Gly | Tyr | Asn | Gln | Lys | Phe |
| 50 | | | | | 55 | | | | | 60 | | | | | |
| Lys | Ser | Lys | Ala | Thr | Ile | Thr | Ala | Asp | Asn | Ser | Thr | Asn | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Arg | Pro | Ala | Met | Asp | Tyr | Trp | Gly | Gln | Gly | Thr | Leu | Val |
| | | | | 100 | | | | | 105 | | | | | 110 | |

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 39
<211> LENGTH: 214
<212> TYPE: PRT
<213> ORGANISM: Artificial Sequence
<220> FEATURE:
<223> OTHER INFORMATION: 2G12_LC

<400> SEQUENCE: 39

Asp Val Val Met Thr Gln Ser Pro Ser Thr Leu Ser Ala Ser Val Gly
1               5                   10                  15

Asp Thr Ile Thr Ile Thr Cys Arg Ala Ser Gln Ser Ile Glu Thr Trp
            20                  25                  30
```

```
Leu Ala Trp Tyr Gln Gln Lys Pro Gly Lys Ala Pro Lys Leu Leu Ile
         35                  40                  45

Tyr Lys Ala Ser Thr Leu Lys Thr Gly Val Pro Ser Arg Phe Ser Gly
 50                  55                  60

Ser Gly Ser Gly Thr Glu Phe Thr Leu Thr Ile Ser Gly Leu Gln Phe
 65                  70                  75                  80

Asp Asp Phe Ala Thr Tyr His Cys Gln His Tyr Ala Gly Tyr Ser Ala
                 85                  90                  95

Thr Phe Gly Gln Gly Thr Arg Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 453
<212> TYPE: PRT
<213> ORGANISM: Artificial Sequence
<220> FEATURE:
<223> OTHER INFORMATION: 2G12_HC

<400> SEQUENCE: 40

Glu Val Gln Leu Val Glu Ser Gly Gly Gly Leu Val Lys Ala Gly Gly
 1               5                  10                  15

Ser Leu Ile Leu Ser Cys Gly Val Ser Asn Phe Arg Ile Ser Ala His
             20                  25                  30

Thr Met Asn Trp Val Arg Val Pro Gly Gly Gly Leu Glu Trp Val
         35                  40                  45

Ala Ser Ile Ser Thr Ser Ser Thr Tyr Arg Asp Tyr Ala Asp Ala Val
 50                  55                  60

Lys Gly Arg Phe Thr Val Ser Arg Asp Asp Leu Glu Asp Phe Val Tyr
 65                  70                  75                  80

Leu Gln Met His Lys Met Arg Val Glu Asp Thr Ala Ile Tyr Tyr Cys
                 85                  90                  95

Ala Arg Lys Gly Ser Asp Arg Leu Ser Asp Asn Asp Pro Phe Asp Ala
                100                 105                 110

Trp Gly Pro Gly Thr Val Val Thr Val Ser Pro Ala Ser Thr Lys Gly
            115                 120                 125

Pro Ser Val Phe Pro Leu Ala Pro Ser Ser Lys Ser Thr Ser Gly Gly
        130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

US 10,973,922 B2

GLYCOPROTEIN-TOXIC PAYLOAD CONJUGATES

RELATED APPLICATIONS

This application is a continuation of Ser. No. 14/888,545 having a § 371 (c)(1), (2) Date of Nov. 2, 2015, which is the National Stage Application under 35 U.S.C. § 371 of International Application No. PCT/FI2014/050322 filed on May 2, 2014, which claims priority to FI 20136020 filed on Oct. 14, 2013 and FI 20135451 filed on May 2, 2013.

FIELD OF THE INVENTION

The invention relates to a glycoprotein-toxic payload molecule conjugate, a toxic payload molecule-glycan conjugate, a method for preparing the glycoprotein-toxic payload molecule conjugate, a pharmaceutical composition, a method for modulating growth of a cell population and a method of treating and/or modulating the growth and/or prophylaxis of tumour cells.

BACKGROUND OF THE INVENTION

Conjugates of toxic payload molecules such as cytotoxic drugs with proteins, for instance antibodies, may be useful, for instance, in the therapy of cancer. The conjugates currently available utilize various chemistries to conjugate toxic payload molecules to proteins; however, many of them may not be optimal in terms of e.g. activity of the toxic payload molecule, aqueous solubility of the conjugate or the reaction conditions required for conjugation.

For instance, a bulky conjugate or a conjugate having suboptimal solubility may not be efficiently delivered to its target. A toxic payload molecule may not always be efficiently released from the protein and/or delivered into cells or into various parts of cells. The toxicity of the toxic payload molecule may be reduced as a result of the conjugation. In some cases, linkage of the toxic payload molecule may not be stable towards chemical or biochemical degradation during manufacturing or in physiological conditions, e.g. in blood, serum, plasma or tissues. Furthermore, conjugation of the toxic payload molecule to one or more random positions and/or chemical groups of the protein may impair the pharmacokinetic properties of the conjugate or the specificity of the protein, such as an antibody, towards its target.

PURPOSE OF THE INVENTION

The purpose of the present invention is to provide glycoprotein-toxic payload molecule conjugates and toxic payload molecule-glycan conjugates that have improved properties as compared to known conjugates and that retain high activity of the toxic payload molecule. The purpose of the present invention is also to provide methods for preparing the glycoprotein-toxic payload molecule conjugates.

SUMMARY

The glycoprotein-toxic payload molecule conjugate is characterized by what is presented in claim 1.

The toxic payload molecule-glycan conjugate according to the present invention is characterized by what is presented in claim 12.

The pharmaceutical composition is characterized by what is presented in claim 22.

The method for preparing a glycoprotein-toxic payload molecule conjugate according to the present invention is characterized by what is presented in claim 23.

The method for modulating growth of a cell population expressing a target molecule is characterized by what is presented in claim 40.

The method of treating and/or modulating the growth of and/or prophylaxis of tumour cells in humans or animals is characterized by what is presented in claim 43.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings:

FIG. 2 shows MALDI-TOF mass spectrometric analysis of purified CMP-9-deoxy-9-azido-NeuAc. The spectrum shows the product as the major signal at m/z 637 and CTP at m/z 479;

FIG. 3 demonstrates MALDI-TOF MS N-glycan analysis of cetuximab (FIG. 3A), cetuximab digested with α1,3-galactosidase (FIG. 3B), cetuximab digested with α1,3-galactosidase and Sialidase A (FIG. 3C) and cetuximab digested with α1,3-galactosidase, Sialidase A and β1,4-galactosidase (FIG. 3D);

DETAILED DESCRIPTION OF THE INVENTION

Figure 1:
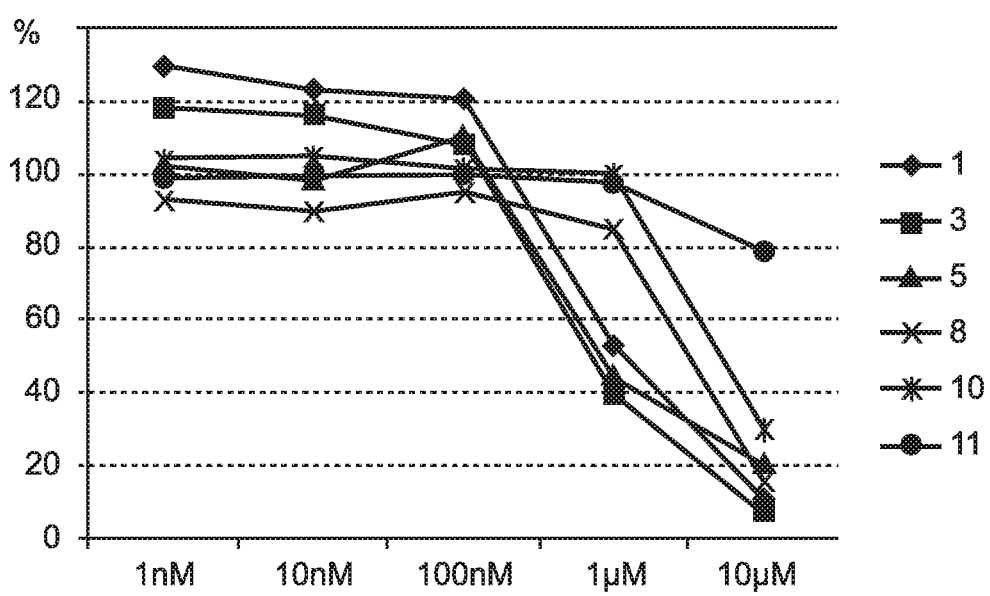
FIG. 1 shows the in vitro cytotoxicity of dolastatin derivatives against ovarian cancer cell line SKOV-3 as viability % compared to control cells (y-axis) measured at different derivative concentrations in the medium (x-axis). Compound numbering is according to Example 1: 1, monomethylauristatin F (MMAF); 3, N-(6-O-propargyl-D-galactosyl)-MMAF; 5, N-(2-deoxy-D-glucosyl)-MMAF; 8, N-[6-O-(β-D-galactopyranosyl)-D-galactosyl]-MMAF; 10, N-{4-O-[4-O-(α-D-galactopyranosyl)-β-D-galactopyranosyl]-D-glucosyl}-MMAF; 11, N-{4-O-[3-O-(α-N-acetylneuraminyl)-β-D-galactopyranosyl]-D-glucosyl}-MMAF (11)

The present invention relates to a glycoprotein-toxic payload molecule conjugate represented by formula I $$[D-L-G]_n-Gp \qquad \text{Formula I}$$

wherein

Gp is a glycoprotein comprising an N-glycan, wherein the N-glycan comprises a GlcNAc residue bound by a β-N linkage to an asparagine;

n is an integer from 1 to about 20;

D is a toxic payload molecule;

L is a linker group covalently joining G to D; and

G is a saccharide structure represented by formula II

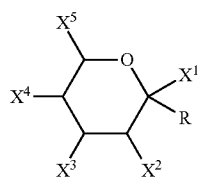

Formula II wherein

R is a glycosidic bond to the N-glycan or a glycosidic bond to the GlcNAc residue bound by a β-N linkage to an asparagine;

$X^1$ is H or carboxyl;

$X^2$, $X^3$ and $X^4$ are each independently OH, H, amino, $C_2$-$C_6$ acylamide, phosphate or sulphate ester, or a bond to L;

$X^5$ is $CH_2OH$, carboxyl, $CH_3$, H, $C_1$-$C_3$ alkyl or substituted $C_1$-$C_3$ alkyl, or a bond to L;

with the proviso that one substituent selected from $X^2$, $X^3$, $X^4$ and $X^5$ is a bond to L or bonded via a bond to L; and with the proviso that when $X^1$ is carboxyl, then $X^2$ is H, $X^3$ is OH, $X^5$ is $C_1$-$C_3$ alkyl or substituted $C_1$-$C_3$ alkyl; R is a glycosidic bond to the N-glycan; and $X^4$ is a bond to L or $X^5$ is bonded via a bond to L; or when $X^1$ is H, then R is a glycosidic bond to the N-glycan or to the GlcNAc residue bound by a β-N linkage to an asparagine.

In this context, the terms "Neu5Ac", "NeuNAc" and "neuraminic acid" refer to N-acetylneuraminic acid; "Gal" refers to D-galactose; "GlcNAc" refers to 2-acetamido-2-deoxy-D-glucose (N-acetyl-D-glucosamine); "Fuc" refers to L-fucose; "Glc" refers to D-glucose; "Man" refers to D-mannose; "Hex" refers to hexose; "NeuGc" refers to N-glycolyl-neuraminic acid; and all monosaccharide residues are in pyranose form and D-sugars except for L-fucose unless otherwise specified.

The notation of saccharide structures and the glycosidic bonds between saccharide residues used herein follows that commonly used in the art, e.g. "Galβ4GlcNAcβ" should be understood as meaning first a Gal residue linked by a covalent linkage between the first carbon atom of the Gal residue to the fourth carbon atom of the N-acetylglucosamine residue linked by an oxygen atom in the beta configuration, and that both monosaccharide residues are in β-anomeric pyranose form.

Carbohydrate nomenclature herein is essentially according to recommendations by the IUPAC-IUB Commission on Biochemical Nomenclature (e.g. Carbohydrate Res. 1998, 312, 167; Carbohydrate Res. 1997, 297, 1; Eur. J. Biochem. 1998, 257, 29).

The glycoprotein may refer to any glycoprotein, provided that it comprises at least one N-glycan comprising a GlcNAc residue bound by a β-N linkage to an asparagine of the glycoprotein. The glycoprotein may be selected based on the selective binding it confers in order to allow for delivering the toxic payload molecule to specific target cells.

In one embodiment, the glycoprotein is an antibody or a fragment thereof. The antibody may be selected based on the selective binding it confers in order to allow for delivering the toxic payload molecule to specific target cells.

In one embodiment, the glycoprotein is capable of binding a target molecule.

In one embodiment, the target molecule is a receptor and the glycoprotein is a ligand for the receptor. In one embodiment, the target molecule is a cancer target molecule.

In one embodiment, the glycoprotein-toxic payload molecule conjugate is internalised by a cell expressing the target molecule after the conjugate is bound to the target molecule. In other words, after binding to its target molecule on the target cell, for example, in a tumor cell, the glycoprotein-toxic payload molecule conjugate is internalized by the target cell as a result of the binding. The effect of this is that the glycoprotein-toxic payload molecule conjugate is taken up by the target cell.

Target molecules or cancer target molecules (antigens) for the glycoprotein-toxic payload molecule conjugate may include CD proteins, such as CD2, CD3, CD4, CD5, CD6, CD11, CD8, CD11a, CD19, CD20, CD22, CD25, CD26, CD30, CD33, CD34, CD37, CD38, CD40, CD44, CD46, CD52, CD56, CD79, CD105, and CD138; members of the ErbB receptor family, such as epidermal growth factor receptor 1 (EGFR), epidermal growth factor receptor 2 (HER2/neu), HER3 or HERO receptor; cell adhesion molecules, such as LFA-1, Mac1, p150.95, VLA-4, ICAM-1, VCAM, EpCAM, alpha$_4$/beta$_7$ integrin, and alpha v/beta3 integrin including either alpha or beta subunits thereof; growth factors, such as VEGF; tissue factor (TF); tumor necrosis factor alpha (TNF-α); human vascular endothelial growth factor (VEGF); glycoprotein IIb/IIIa; TGF-beta; alpha interferon (alpha-IFN); an interleukin, such as IL-8; an interleukin receptor, such as IL-2 receptor; IgE; respiratory syncytial virus (RSV); HIV-1 envelope glycoprotein gp120, cancer-associated high-mannose type N-glycans; blood group antigens Apo2, death receptor; flk2/flt3 receptor; obesity (OB) receptor; mpl receptor; CTLA-4; transferrin receptor; cancer-associated glycan structure, such as Lewis y or GD3; protein C etc.

In one embodiment, the target molecule is selected from the group consisting of CD2, CD3, CD4, CD5, CD6, CD11, CD8, CD11a, CD19, CD20, CD22, CD25, CD26, CD30, CD33, CD34, CD37, CD38, CD40, CD44, CD46, CD52, CD56, CD79, CD105, CD138, epidermal growth factor receptor 1 (EGFR), epidermal growth factor receptor 2 (HER2/neu), HER3 or HERO receptor, LFA-1, Mac1, p150.95, VLA-4, ICAM-1, VCAM, EpCAM, alpha$_4$/beta$_7$ integrin, alpha v/beta3 integrin including either alpha or beta subunits thereof (e.g. anti-CD11a, anti-CD18 or anti-CD11b antibodies), tissue factor (TF), tumor necrosis factor alpha (TNF-α), human vascular endothelial growth factor (VEGF), glycoprotein IIb/IIIa, TGF-beta, alpha interferon (alpha-IFN), IL-8, IL-2 receptor, IgE, respiratory syncytial virus (RSV), HIV-1 envelope glycoprotein gp120, cancer-associated high-mannose type N-glycans, blood group antigen Apo2, death receptor, flk2/flt3 receptor, obesity (OB) receptor, mpl receptor, CTLA-4, transferrin receptor, Lewis y, GD3 and protein C.

Antibodies that may be used are antibodies to CD2, CD3, CD4, CD5, CD6, CD11, CD19, CD20, CD22, CD26, CD30, CD33, CD37, CD38, CD40, CD44, CD52, CD56, CD79, CD105, CD138, EphA receptors (e.g., EphA2 receptor), EphB receptors, EGFr, EGFRvIII, HER2, HER3, trastuzumab, pertuzumab mesothelin, cripto, alpha beta$_6$ integrins, VEGF, VEGFR, folate receptor (for example, FOLR1), transferrin receptor, Lewis y, GD3, or EpCAM.

In one embodiment, the target molecule is EGFR. In other words, the glycoprotein-toxic payload molecule conjugate is an anti-EGFR conjugate.

In one embodiment, the target molecule is epidermal growth factor receptor 1 (EGFR) having a sequence set forth in SEQ ID NO: 1.

In one embodiment, the target molecule is EGFR and the glycoprotein is EGF or an EGF analog capable of binding to EGFR.

Neoplastic diseases or cancers for the treatment of which the anti-EGFR conjugates of the invention can be employed are EGFR-overexpressing tumours, respiratory tract tumours (e.g. parvicellular and non-parvicellular carcinomas, bronchial carcinoma), including preferably non-parvicellular carcinoma of the lung; tumours of the digestive organs (e.g. oesophagus, stomach, gall bladder, small intestine, large intestine, rectum), including especially intestinal tumours; tumours of the endocrine and exocrine glands (e.g. thyroid and parathyroid glands, pancreas and salivary gland), including preferably pancreas; tumours of the head and neck region (e.g. larynx, hypopharynx, nasopharynx, oropharynx, lips, oral cavity, tongue and oesophagus); and/or gliomas.

In one embodiment, the target molecule is HER2 having a sequence set forth in SEQ ID NO: 2.

In one embodiment, the glycoprotein is transferrin and the target molecule is transferrin receptor.

In one embodiment, the glycoprotein is a monoclonal antibody or a fragment thereof.

In one embodiment, the glycoprotein is a recombinant antibody or a fragment thereof.

In one embodiment, the glycoprotein is an IgG antibody or a fragment thereof.

The antibody may also be e.g. an scFv, a single domain antibody, an Fv, a VHH antibody, a diabody, a tandem diabody, a Fab, a Fab', or a F(ab)2. Furthermore, the antibody or a fragment thereof may be present in monovalent monospecific, multivalent monospecific, bivalent monospecific, or multivalent multispecific forms.

In one embodiment, the glycoprotein is an antibody directed against human vascular endothelial growth factor (VEGF), epidermal growth factor receptor 1 (EGFR), tumor necrosis factor alpha (TNF-α), CD20, CD22, epidermal growth factor receptor 2 (HER2/neu), CD52, CD33, CD11a, glycoprotein IIb/IIIa, CD25, IgE, IL-2 receptor, Lewis y, HIV-1 envelope glycoprotein gp120, cancer-associated high-mannose type N-glycans, or respiratory syncytial virus (RSV). However, these antibody targets are provided as examples only, to which the invention is not limited; a skilled person will appreciate that the glycoprotein of the invention is not limited to any particular antibody or form thereof.

In one embodiment, the glycoprotein is the antibody bevacizumab (available e.g. under the trademark AVASTIN®), tositumomab (BEXXAR®), etanercept (ENBREL®), trastuzumab (HERCEPTIN®), adalimumab (HUMIRA®), alemtuzumab (CAMPATH®), gemtuzumab ozogamicin (MYLOTARG®), efalizumab (RAPTIVE®), rituximab (RITUXAN®), infliximab (REMICADE®), abciximab (REOPRO®), basiliximab (SIMULECT®), palivizumab (SYNAGIS®), omalizumab (XOLAIR®), daclizumab (ZENAPAX®), cetuximab (ERBITUX®), panitumumab (VECTIBIX®) or ibritumomab tiuxetan (ZEVALIN®).

In one embodiment, the glycoprotein is the antibody bevacizumab, tositumomab, etanercept, trastuzumab, adalimumab, alemtuzumab, gemtuzumab ozogamicin, efalizumab, rituximab, infliximab, abciximab, basiliximab, palivizumab, omalizumab, daclizumab, cetuximab, panitumumab, epratuzumab, 2G12, lintuzumab, nimotuzumab, GCM011, GCM012 or ibritumomab tiuxetan, or their glycoform antibody wherein the glycoform antibody comprises one or more introduced N-glycosylation sites in the light and/or heavy chain.

In one embodiment, the glycoprotein is the antibody abagovomab, actoxumab, adecatumumab, afutuzumab, altumomab, amatuximab, anifrolumab, apolizumab, atinumab, atlizumab, atorolimumab, bapineuzumab, basiliximab, bavituximab, belimumab, benralizumab, bertilimumab, be-silesomab, bezlotoxumab, bimagrumab, bivatuzumab, blinatumomab, blosozumab, brentuximab, briakinumab, brodalumab, canakinumab, cantuzumab, caplacizumab, capromab, carlumab, catumaxomab, CC49, cedelizumab, cixutumumab, clazakizumab, clenoliximab, clivatuzumab, conatumumab, concizumab, crenezumab, CR6261, dacetuzumab, dalotuzumab, daratumumab, demcizumab, denosumab, detumomab, drozitumab, duligotumab, dupilumab, dusigitumab, ecromeximab, eculizumab, edobacomab, edrecolomab, eldelumab, elotuzumab, elsilimomab, enavatuzumab, enlimomab, enokizumab, enoticumab, ensituximab, epitumomab, epratuzumab, ertumaxomab, etaracizumab, etrolizumab, evolocumab, exbivirumab, fanolesomab, faralimomab, farletuzumab, fasinumab, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gevokizumab, girentuximab, glembatumumab, golimumab, gomiliximab, guselkumab, ibalizumab, icrucumab, imciromab, imgatuzumab, inclacumab, indatuximab, intetumumab, inolimomab, inotuzumab, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, ligelizumab, lintuzumab, lirilumab, lodelcizumab, lorvotuzumab, lucatumumab, lumiliximab, mapatumumab, margetuximab, maslimomab, mavrilimumab, matuzumab, mepolizumab, metelimumab, milatuzumab, minretumomab, mitumomab, mogamulizumab, morolimumab, motavizumab, moxetumomab, muromonab, namilumab, narnatumab, natalizumab, nebacumab, necitumumab, nerelimomab, nesvacumab, nimotuzumab, nivolumab, obinutuzumab, ocaratuzumab, ocrelizumab, odulimomab, ofatumumab, olaratumab, olokizumab, onartuzumab, oregovomab, orticumab, otelixizumab, oxelumab, ozanezumab, ozoralizumab, pagibaximab, panobacumab, parsatuzumab, pascolizumab, pateclizumab, patritumab, pemtumomab, perakizumab, pertuzumab, pi-dilizumab, pinatuzumab, pintumomab, placulumab, polatuzumab, ponezumab, priliximab, pritoxaximab, pritumumab, quilizumab, racotumomab, radretumab, rafivirumab, ramucirumab, raxibacumab, regavirumab, reslizumab, rilotumumab, robatumumab, roledumab, romosozumab, rontalizumab, rovelizumab, ruplizumab, samalizumab, sarilumab, satumomab, secukinumab, seribantumab, setoxaximab, sevirumab, sibrotuzumab, sifalimumab, siltuximab, simtuzumab, siplizumab, sirukumab, solanezumab, solitomab, sonepcizumab, sontuzumab, stamulumab, suvizumab, tabalumab, tacatuzumab, talizumab, tanezumab, taplitumomab, tefiba-zumab, tenatumomab, teneliximab, teplizumab, tepro-tumumab, TGN1412, ticilimumab, tildrakizumab, tiga-tuzumab, tocilizumab, toralizumab, tovetumab, tralokinumab, TRBS07, tregalizumab, tremelimumab, tucotuzumab, tuvirumab, ublituximab, urelumab, urtoxazumab, ustekinumab, vantictumab, vapaliximab, vatelizumab, vedolizumab, veltuzumab, vepalimomab, vesencumab, visilizumab, volociximab, vorsetuzumab, votumumab, zalutumumab, zanolimumab, zatuximab, ziralimumab, 2G12 (anti-HIV-1 envelope glycoprotein gp120), or zolimomab. However, these antibodies are provided as examples only, to which the invention is not limited; a skilled person will appreciate that the antibody of the invention is not limited to any particular antibody or form thereof.

In one embodiment, the glycoprotein is cetuximab.

In one embodiment, cetuximab has a sequence set forth in SEQ ID NO:s 3 and 4. In one embodiment, additional N-glycosylation sites are introduced into the cetuximab heavy chain. In one embodiment, the cetuximab heavy chain comprises one or more substitutions selected from the group consisting of G161S, Q177N, L184N, S192N, and L195N in SEQ ID NO: 3.

In one embodiment, additional N-glycosylation sites are introduced into the cetuximab light chain. In one embodiment, cetuximab light chain comprises one or more substitutions selected from the group consisting of R18N, L154S, Q160N, S174N, and T180N in SEQ ID NO:4.

In some embodiments, an anti-EGFR antibody (or cetuximab glycoform antibody) comprises one or more additional N-glycosylation sites. In some embodiments, an anti-EGFR antibody (or cetuximab glycoform antibody) comprises a heavy chain comprising either SEQ ID NO: 3 or one or more mutations selected from the group of G161S, Q177N, L184N, S192N, and L195N in SEQ ID NO: 3, and a light chain comprising either SEQ ID NO:4 or one or more mutations selected from the group of R18N, L154S, Q160N, S174N, and T180N in SEQ ID NO: 4.

In one embodiment, the glycoprotein is trastuzumab.

In one embodiment, trastuzumab has a sequence set forth in SEQ ID NO:s 5 and 6. In one embodiment, additional N-glycosylation sites are introduced into trastuzumab heavy chain. In one embodiment, trastuzumab heavy chain comprises one or more substitutions selected from the group of: E89N, G162S, Q178N, L185N, S193N, and/or L196N in SEQ ID NO: 5.

In one embodiment, additional N-glycosylation sites are introduced into trastuzumab light chain. In one embodiment, trastuzumab light chain comprises one or more substitutions selected from the group of: R18N, L154S, Q160N, S174N, and/or T180N in SEQ ID NO:6.

In some embodiments, an anti-HER2 antibody (or trastuzumab glycoform antibody) comprises one or more additional N-glycosylation sites. In some embodiments, an anti-HER2 antibody (or trastuzumab glycoform antibody) comprises a heavy chain comprising either SEQ ID NO: 5 or one or more mutations selected from the group of E89N, G162S, Q178N, L185N, S193N, and L196N in SEQ ID NO: 5, and a light chain comprising either SEQ ID NO:6 or one or more mutations selected from the group of R18N, L154S, Q160N, S174N, and T180N in SEQ ID NO:6.

In one embodiment, the antibody is rituximab. In one embodiment, rituximab has a sequence set forth in SEQ ID NO:s 7 and 8. In one embodiment, additional N-glycosylation sites are introduced into rituximab heavy chain. In one embodiment, rituximab heavy chain comprises one or more substitutions selected from the group of: E89N, G163S, Q179N, L186N, S194N, and/or L197N in SEQ ID NO: 7.

In one embodiment, additional N-glycosylation sites are introduced into rituximab light chain. In one embodiment, rituximab light chain comprises one or more substitutions selected from the group of: K18N, L153S, Q159N, S173N, and/or T179N in SEQ ID NO:8.

In some embodiments, an anti-CD20 antibody (or rituximab glycoform antibody) comprises one or more additional N-glycosylation sites. In some embodiments, an anti-CD20 antibody (or rituximab glycoform antibody) comprises a heavy chain comprising either SEQ ID NO: 7 or one or more mutations selected from the group of E89N, G163S, Q179N, L186N, S194N, and L197N in SEQ ID NO: 7, and a light chain comprising either SEQ ID NO:8 or one or more mutations selected from the group of K18N, L153S, Q159N, S173N, and T179N in SEQ ID NO:8.

In one embodiment, the antibody is bevacizumab. In one embodiment, bevacizumab has a sequence set forth in SEQ ID NO:s 9 and 10. In one embodiment, additional N-glycosylation sites are introduced into bevacizumab heavy chain. In one embodiment, bevacizumab heavy chain comprises one or more substitutions selected from the group of: E89N, G165S, Q181N, L188N, S196N, and/or L199N in SEQ ID NO: 9.

In one embodiment, additional N-glycosylation sites are introduced into bevacizumab light chain. In one embodiment, bevacizumab light chain comprises one or more substitutions selected from the group of: R18N, L154S, Q160N, S174N, and/or T180N in SEQ ID NO: 10.

In some embodiments, an anti-VEGF-A antibody (or bevacizumab glycoform antibody) comprises one or more additional N-glycosylation sites. In some embodiments, an anti-VEGF-A antibody (or bevacizumab glycoform antibody) comprises a heavy chain comprising either SEQ ID NO: 9 or one or more mutations selected from the group of E89N, G165S, Q181N, L188N, S196N, and L199N in SEQ ID NO: 9, and a light chain comprising either SEQ ID NO:10 or one or more mutations selected from the group of R18N, L154S, Q160N, S174N, and T180N in SEQ ID NO: 10.

In one embodiment, the antibody is tositumomab. In one embodiment, tositumomab has a sequence set forth in SEQ ID NO:s 11 and 12. In one embodiment, additional N-glycosylation sites are introduced into tositumomab light chain. In one embodiment, additional N-glycosylation sites are introduced into tositumomab heavy chain. In one embodiment, tositumomab heavy chain comprises one or more substitutions selected from the group of: E89N, G159S, Q175N, L182N, S190N, and/or L193N in SEQ ID NO: 11.

In one embodiment, tositumomab light chain comprises one or more substitutions selected from the group of: K18N, L153S, Q159N, S173N, T179N in SEQ ID NO: 12.

In some embodiments, an anti-CD20 antibody (or tositumomab glycoform antibody) comprises one or more additional N-glycosylation sites. In some embodiments, an anti-CD20 antibody (or tositumomab glycoform antibody) comprises a heavy chain comprising either SEQ ID NO: 11 or one or more mutations selected from the group of E89N, G159S, Q175N, L182N, S190N, and L193N in SEQ ID NO:

11, and a light chain comprising either SEQ ID NO:12 or one or more mutations selected from the group of K18N, L153S, Q159N, S173N, and T179N in SEQ ID NO: 12.

In one embodiment, the antibody is etanercept. In one embodiment, etanercept has a sequence set forth in SEQ ID NO: 13. In one embodiment, one or more additional N-glycosylation sites are introduced into etanercept sequence using methods described, for example, in US2013/0084291.

In one embodiment, the antibody is adalimumab. In one embodiment, adalimumab has a sequence set forth in SEQ ID NO:s 14 and 15. In one embodiment, additional N-glycosylation sites are introduced into adalimumab heavy chain. In one embodiment, adalimumab heavy chain comprises one or more substitutions selected from the group of: E89N, G163S, Q179N, L186N, S194N, and/or L197N in SEQ ID NO: 16.

In one embodiment, additional N-glycosylation sites are introduced into adalimumab light chain. In one embodiment, adalimumab light chain comprises one or more substitutions selected from the group of: R18N, L154S, Q160N, S174N, and/or T180N in SEQ ID NO: 17.

In some embodiments, an anti-TNFA antibody (or adalimumab glycoform antibody) comprises one or more additional N-glycosylation sites. In some embodiments, an anti-TNFA antibody (or adalimumab glycoform antibody) comprises a heavy chain comprising either SEQ ID NO: 16 or one or more mutations selected from the group of E89N, G163S, Q179N, L186N, S194N, and L197N in SEQ ID NO: 16, and a light chain comprising either SEQ ID NO:17 or one or more mutations selected from the group of R18N, L154S, Q160N, S174N, and T180N in SEQ ID NO: 17.

In one embodiment, the antibody is alemtuzumab. In one embodiment, alemtuzumab has a sequence set forth in SEQ ID NO:s 18 and 19. In one embodiment, additional N-glycosylation sites are introduced into alemtuzumab heavy chain. In one embodiment, alemtuzumab heavy chain comprises one or more substitutions selected from the group of: A91N, G165S, Q179N, L186N, S194N, L197N, and SEQ ID NO: 18.

In one embodiment, additional N-glycosylation sites are introduced into alemtuzumab light chain. In one embodiment, alemtuzumab light chain comprises one or more substitutions selected from the group of: R18N, L154S, Q160N, S174N, and/or T180N in SEQ ID NO: 19.

In some embodiments, an anti-CD52 antibody (or alemtuzumab glycoform antibody) comprises one ore more additional N-glycosylation sites. In some embodiments, an anti-CD52 antibody (or alemtuzumab glycoform antibody) comprises a heavy chain comprising either SEQ ID NO: 18 or one or more mutations selected from the group of A91N, G165S, Q179N, L186N, S194N, and L197N in SEQ ID NO: 18, and a light chain comprising either SEQ ID NO:19 or one or more mutations selected from the group of R18N, L154S, Q160N, S174N, and T180N in SEQ ID NO: 19.

In one embodiment, the antibody is efalizumab. In one embodiment, efalizumab has a sequence set forth in SEQ ID NO:s 20 and 21. In one embodiment, additional N-glycosylation sites are introduced into efalizumab heavy chain. In one embodiment, efalizumab heavy chain comprises one or more substitutions selected from the group of: E89N, G163S, Q179N, L186N, S194N, and/or L197N in SEQ ID NO: 20.

In one embodiment, additional N-glycosylation sites are introduced into efalizumab light chain. In one embodiment, efalizumab light chain comprises one or more substitutions selected from the group of: R18N, L154S, Q160N, S174N, and/or T180N in SEQ ID NO: 21.

In some embodiments, an anti-CD11a antibody (or efalizumab glycoform antibody) comprises one or more additional N-glycosylation sites. In some embodiments, an anti-CD11a antibody (or efalizumab glycoform antibody) comprises a heavy chain comprising either SEQ ID NO: 20 or one or more mutations selected from the group of E89N, G163S, Q179N, L186N, S194N, L197N, and SEQ ID NO: 20, and a light chain comprising either SEQ ID NO:21 or one or more mutations selected from the group of R18N, L154S, Q160N, S174N, T180N, and SEQ ID NO: 21.

In one embodiment, the antibody is infliximab. In one embodiment, infliximab has a sequence set forth in SEQ ID NO:s 22 and 23. In one embodiment, additional N-glycosylation sites are introduced into infliximab heavy chain. In one embodiment, infliximab heavy chain comprises one or more substitutions selected from the group of: E91N, G to S substitution at about amino acid 161 (in seq NSG), Q to N at about amino acid 177 (in seq QSS), L to N at about amino acid 184 (in seq LSS), S to N at about amino acid 192 (in seq SSS), and/or L to N at about amino acid 195 (in seq LGT) in infliximab heavy chain sequence.

In one embodiment, additional N-glycosylation sites are introduced into infliximab light chain. In one embodiment, infliximab light chain comprises one or more substitutions selected from the group of: R18N, L to S substitution at about amino acid 154 (in sequence NAL), Q to N substitution at about amino acid 160 (in sequence QES), S to N substitution at about amino acid 174 (sequence SLS→NLS), T to N substitution at about amino acid 180 (in sequence TLS) of the infliximab light chain sequence.

In one embodiment, the antibody is basiliximab. In one embodiment, basiliximab has a sequence set forth in SEQ ID NO:s 24 and 25. In one embodiment, additional N-glycosylation sites are introduced into basiliximab heavy chain. In one embodiment, basiliximab heavy chain comprises one or more substitutions selected from the group of: E87N, G157S, Q173N, L180N, S188N, and/or L191N in SEQ ID NO: 24 or SEQ ID NO: 26.

In one embodiment, additional N-glycosylation sites are introduced into basiliximab light chain. In one embodiment, basiliximab light chain comprises one or more substitutions selected from the group of: K18N, L151S, Q157N, S171N, T177N in SEQ ID NO: 25.

In some embodiments, an anti-CD25 antibody (or basiliximab glycoform antibody) comprises one or more additional N-glycosylation sites. In some embodiments, an anti-CD25 antibody (or basiliximab glycoform antibody) comprises a heavy chain comprising either SEQ ID NO:s 24 or 26, or one or more mutations selected from the group of E87N, G157S, Q173N, L180N, S188N, and L191N in SEQ ID NO: 24 or SEQ ID NO: 26, and a light chain comprising either SEQ ID NO:25 or one or more mutations selected from the group of K18N, L151S, Q157N, S171N, and T177N in SEQ ID NO: 25.

In one embodiment, the antibody is omalizumab. In one embodiment, omalizumab has a sequence set forth in SEQ ID NO:s 27 and 28. In one embodiment, additional N-glycosylation sites are introduced into omalizumab heavy chain. In one embodiment, omalizumab heavy chain comprises one or more substitutions selected from the group of: E89N, G163S, Q179N, L186N, S194N, and L197N in SEQ ID NO: 27.

In one embodiment, additional N-glycosylation sites are introduced into omalizumab light chain. In one embodiment, omalizumab light chain comprises one or more substitutions selected from the group of: R18N, L158S, Q164N, S178N, and T184N in SEQ ID NO: 28.

In some embodiments, an anti-IgE antibody (or omalizumab glycoform antibody) comprises one or more additional N-glycosylation sites. In some embodiments, an anti-IgE antibody (or omalizumab glycoform antibody) comprises a heavy chain comprising either SEQ ID NO: 27 or one or more mutations selected from the group of E89N, G163S, Q179N, L186N, S194N, and L197N in SEQ ID NO: 27, and a light chain comprising either SEQ ID NO:28 or one or more mutations selected from the group of R18N, L158S, Q164N, S178N, and T184N in SEQ ID NO: 28.

In one embodiment, the antibody is daclizumab. In one embodiment, daclizumab has a sequence set forth in SEQ ID NO:s 29 and 30. In one embodiment, additional N-glycosylation sites are introduced into daclizumab heavy chain. In one embodiment, daclizumab heavy chain comprises one or more substitutions selected from the group of: E74N, E89N, G158S, Q174N, L181N, S189N, and/or L192N in SEQ ID NO:s 29.

In one embodiment, additional N-glycosylation sites are introduced into daclizumab light chain. In one embodiment, daclizumab light chain comprises one or more substitutions selected from the group of: R18N, L153S, Q159N, S173N, and/or T179N in SEQ ID NO: 30.

In some embodiments, an anti-CD25 antibody (or daclizumab glycoform antibody) comprises one or more additional N-glycosylation sites. In some embodiments, an anti-CD25 antibody (or daclizumab glycoform antibody) comprises a heavy chain comprising either SEQ ID NO: 29 or one or more mutations selected from the group of E74N, E89N, G158S, Q174N, L181N, S189N, and L192N in SEQ ID NO: 29, and a light chain comprising either SEQ ID NO:30 or one or more mutations selected from the group of R18N, L153S, Q159N, S173N, and T179N in SEQ ID NO: 30.

In one embodiment, the antibody is nimotuzumab. In one embodiment, nimotuzumab has a sequence set forth in SEQ ID NO:s 31 and 32. In one embodiment, additional N-glycosylation sites are introduced into nimotuzumab heavy chain to generate a novel anti-EGFR antibody sequence. In one embodiment, the novel anti-EGFR heavy chain comprises one or more substitutions selected from the group of: E74N, E89N, G165S, Q181N, L188N, S196N, and/or L199N in SEQ ID NO: 31.

In one embodiment, additional N-glycosylation sites are introduced into nimotuzumab light chain to generate a novel anti-EGFR antibody sequence. In one embodiment, the novel anti-EGFR light chain comprises one or more substitutions selected from the group of: L159S, Q165N, S179N, and/or T185N in SEQ ID NO: 32. In one embodiment, the novel anti-EGFR light chain comprises R to N substitution at amino acid 18 of SEQ ID NO:32.

In some embodiments, the novel anti-EGFR antibody comprises a heavy chain comprising either SEQ ID NO: 31 or one or more mutations selected from the group of E74N, E89N, G165S, Q181N, L188N, S196N, and L199N in SEQ ID NO: 31, and a light chain comprising either SEQ ID NO:32 or one or more mutations selected from the group of R18N, L159S, Q165N, S179N, and T185N in SEQ ID NO: 32.

In one embodiment, the novel anti-EGFR antibody is GCM012 which comprises sequences set forth in SEQ ID NO: 31 and SEQ ID NO: 33.

In one embodiment, the antibody is epratuzumab. In one embodiment, epratuzumab has a sequence set forth in SEQ ID NO:s 34 and 35. In one embodiment, additional N-glycosylation sites are introduced into epratuzumab heavy chain. In one embodiment, epratuzumab heavy chain comprises one or more substitutions selected from the group of: E74N, E89N, G158S, Q174N, L181N, S189N, and/or L192N in SEQ ID NO: 34.

In one embodiment, additional N-glycosylation sites are introduced into epratuzumab light chain. In one embodiment, epratuzumab light chain comprises one or more substitutions selected from the group of: L159S, Q165N, S179N, and/or T185N in SEQ ID NO: 35.

In some embodiments, an anti-CD22 antibody (or epratuzumab glycoform antibody) comprises one or more additional N-glycosylation sites. In some embodiments, an anti-CD22 antibody (or epratuzumab glycoform antibody) comprises a heavy chain comprising either SEQ ID NO: 34 or one or more mutations selected from the group of E74N, E89N, G158S, Q174N, L181N, S189N, and L192N in SEQ ID NO: 34, and a light chain comprising either SEQ ID NO:35 or one or more mutations selected from the group of L159S, Q165N, S179N, and T185N in SEQ ID NO: 35.

In one embodiment, the antibody is lintuzumab. In one embodiment, lintuzumab has a sequence set forth in SEQ ID NO:s 36 and 37. In one embodiment, additional N-glycosylation sites are introduced into lintuzumab heavy chain. In one embodiment, lintuzumab heavy chain comprises one or more substitutions selected from the group of: E89N, G158S, Q174N, L181N, S189N, and/or L192N in SEQ ID NO: 36.

In one embodiment, additional N-glycosylation sites are introduced into lintuzumab light chain. In one embodiment, lintuzumab light chain comprises one or more substitutions selected from the group of: R18N, L157S, Q163N, S177N, and/or T183N in SEQ ID NO: 37.

In one embodiment, the antibody is an anti-CD33 antibody (or lintuzumab glycoform antibody) which comprises additional N-glycosylation sites. In one embodiment, the antibody is an anti-CD33 antibody which comprises additional N-glycosylation sites as compared to the corresponding human or humanized anti-CD33 antibody. In one embodiment, the anti-CD33 antibody is GCM011 which has a sequence set forth in SEQ ID NO: 38. In some embodiments, an anti-CD33 antibody (or lintuzumab glycoform antibody) comprises a heavy chain comprising either SEQ ID NO: 36 or one or more mutations selected from the group of E89N, G158S, Q174N, L181N, S189N, and L192N in SEQ ID NO: 36, and a light chain comprising either SEQ ID NO:37 or one or more mutations selected from the group of R18N, L157S, Q163N, S177N, and T183N in SEQ ID NO: 37.

In one embodiment, lintuzumab heavy chain comprises E to N substitution at amino acid 74 of SEQ ID NO: 36. In one embodiment, the anti-CD33 antibody is GCM011 which comprises sequences set forth in SEQ ID NO: 38 and SEQ ID NO:37. In one embodiment, an anti-CD33 antibody comprises a sequence set forth in SEQ ID NO: 38 and R to N substitution at amino acid 18 of SEQ ID NO: 37. In one embodiment, the antibody is 2G12. In one embodiment, 2G12 has a sequence set forth in SEQ ID NO:s 39 and 40. In one embodiment, additional N-glycosylation sites are introduced into 2G12 light chain. In one embodiment, 2G12 light chain comprises one or more substitutions selected from the group of: T18N, L154S, Q160N S174N and/or T180N in SEQ ID NO: 39.

In one embodiment, additional N-glycosylation sites are introduced into 2G12 heavy chain. In one embodiment, 2G12 heavy chain comprises one or more substitutions selected from the group of: E89N, G165S, Q181N, L188N, S196N, and/or L199N in SEQ ID NO: 40.

In some embodiments, an anti-mannose antibody (or 2G12 glycoform antibody) comprises one or more additional N-glycosylation sites. In some embodiments, an anti-mannose antibody (or 2G12 glycoform antibody) comprises a heavy chain comprising either SEQ ID NO: 40 or one or more mutations selected from the group of E89N, G165S, Q181N, L188N, S196N, and L199N in SEQ ID NO: 40, and a light chain comprising either SEQ ID NO: 39 or one or more mutations selected from the group of T18N, L154S, Q160N, S174N, and T180N in SEQ ID NO: 39.

In one embodiment, the antibody is ibritumomab tiuxetan. In one embodiment, additional N-glycosylation sites can be introduced into heavy and/or light chains as described above for, e.g. lintuzumab antibody.

In one embodiment, the antibody is panitumumab. In one embodiment, additional N-glycosylation sites can be introduced into heavy and/or light chains as described above for, e.g. lintuzumab antibody.

In one embodiment, the antibody is gemtuzumab ozogamicin. In one embodiment, additional N-glycosylation sites can be introduced into heavy and/or light chains as described above for, e.g. lintuzumab antibody.

In one embodiment, the antibody is abciximab. In one embodiment, additional N-glycosylation sites can be introduced into heavy and/or light chains as described above for, e.g. lintuzumab antibody.

In one embodiment, the antibody is palivizumab. In one embodiment, additional N-glycosylation sites can be introduced into heavy and/or light chains as described above for, e.g. lintuzumab antibody.

The N-glycan may be attached to various positions in the glycoprotein.

In embodiments wherein the glycoprotein is an antibody, the N-glycan may be attached to various positions in the antibody.

In one embodiment, the N-glycan is attached to a site in which the glycoprotein or antibody is naturally glycosylated.

In one embodiment, the N-glycan is attached to the Fc domain of the antibody.

The Fc domain of IgG molecules comprises a single site for N-linked glycosylation within its $C_H2$ domain at an asparagine residue 297 (Asn297) numbered according to the EU index (Kabat et al., Sequences of proteins of immunological interest, 5$^{th}$ ed., US Department of Health and Human Services, NIH Publication No. 91-3242). Typically the oligosaccharide structures attached to the Fc domain comprise biantennary chains with varying galactosylation, sialylation and fucosylation.

In one embodiment, N-glycan is attached to a site in the variable domain of the antibody.

In one embodiment, the antibody is cetuximab and the N-glycan is attached to heavy chain asparagine residue in the variable domain.

In one embodiment, the glycoprotein comprises at least one, or at least 2, or at least 3, or at least 4, or at least 5, or at least 6, or 1-6, or 2-5, or 3-4 N-glycosylation sites.

In one embodiment, the glycoprotein comprises at least one, or at least 2, or at least 3, or at least 4, or at least 5, or at least 6, or 1-6, or 2-5, or 3-4, or 1-2 N-glycans.

In one embodiment, the glycoprotein is genetically engineered to comprise one or more additional N-glycosylation sites. Said additional N-glycosylation sites may be in sites that are accessible to solvent and at a distance from antigen-binding or receptor-binding sites of the glycoprotein or antibody such as a monoclonal antibody. Said sites are genetically engineered to comprise the N-glycosylation consensus sequence Asn-Xaa-Ser/Thr, wherein Xaa is any amino acid encoded in the human genetic code except that Xaa≠Pro.

In one embodiment, the glycoprotein is an antibody genetically engineered to comprise one or more additional N-glycosylation sites in the Fc domain.

In one embodiment, the glycoprotein is an antibody genetically engineered to comprise one or more additional N-glycosylation sites in the variable region.

In one embodiment, the glycoprotein is an antibody genetically engineered to comprise one or more additional N-glycosylation sites in a region other than the Fc domain and the variable region.

In one embodiment, the glycoprotein is an antibody which may be modified by the addition, deletion, or substitution of one or more amino acid residues to introduce one or more N-linked glycosylation site(s), thus resulting a "glycoform antibody". Additional N-glycosylation sites can be engineered into light and heavy chains by methods described in, for example, WO97/34632 and/or WO95/15769. In WO97/34632, additional N-glycosylation sites may be those of depicted in the FIG. 12 and corresponding to HCN1, HCN2, HCN3, HCN4, and/or HCN5 for heavy chain, and KCN1, KCN2, KCN3, and/or KCN4 for kappa light chain. Additional N-glycosylation sites in antibody mean one or more non-Asn297 N-glycosylation sites. The non-Asn297 N-glycosylation sites can exist or be introduced into a heavy and/or a light chain.

In one embodiment, the glycoprotein is an antibody genetically engineered to comprise at least one, or at least 2, or at least 3, or at least 4, or at least 5, or at least 6, or 1-6, or 2-5, or 3-4 additional N-glycosylation sites.

In one embodiment, the glycoprotein is an antibody genetically engineered to comprise at least one, or at least 2, or at least 3, or at least 4, or at least 5, or at least 6, or 1-6, or 2-5, or 3-4 additional non-Asn297 N-glycosylation sites.

In one embodiment, the glycoprotein is an antibody that is genetically engineered to comprise one or more additional N-glycosylation sites than the corresponding human or humanized antibody. In this context, the corresponding human or humanized antibody should be understood as referring to the human or humanized antibody which has not been genetically engineered to comprise one or more additional N-glycosylation sites.

In one embodiment, the glycoprotein is an antibody that comprises one or more additional N-glycans than the corresponding human or humanized antibody. A skilled person will understand that the addition of one or more additional N-glycosylation sites does not necessarily always result in one or more additional N-glycans being incorporated into the glycoprotein. Such one or more additional N-glycosylation sites are not always glycosylated. In other words, if the glycoprotein comprises a number of glycosylation sites, the number of toxic payload molecules or toxic payload molecule loading ("drug/antibody ratio" when glycoprotein is an antibody) (n in formula I) may be equal to or less than the number of glycosylation sites.

Therefore, in one embodiment, the glycoprotein-toxic payload molecule conjugate is represented by formula I, wherein the glycoprotein comprises m glycosylation sites in the glycoprotein, and n≤m.

In one embodiment, the number of glycosylation sites in the glycoprotein is at least one, or at least 2, or at least 3, or at least 4, or at least 5, or at least 6, or 1-6, or 2-5, or 3-4; and n is smaller than or equal to the number of glycosylation sites.

In one embodiment, the number of glycosylation sites in the glycoprotein is at least one, or at least 2, or at least 3, or at least 4, or at least 5, or at least 6, or 1-6, or 2-5, or 3-4; and n is at least one, or at least 2, or at least 3, or at least 4, or at least 5, or at least 6, or 1-6, or 2-5, or 3 4.

In one embodiment, one or more additional N-glycosylation sites, in particular non-Asn297 sites, may all or almost all be glycosylated. In other words, if the glycoprotein comprises a number of glycosylation sites, the number of toxic payload molecules (n in formula I) may be equal to or more than the number of glycosylation sites.

Therefore, in one embodiment, the glycoprotein-toxic payload molecule conjugate is represented by formula I, wherein the glycoprotein comprises m glycosylation sites in the glycoprotein, and $n \geq m$.

In one embodiment, the number of glycosylation sites in the glycoprotein is at least one, or at least 2, or at least 3, or at least 4, or at least 5, or at least 6, or 1-6, or 2-5, or 3-4; and n is higher or equal to the number of glycosylation sites.

In one embodiment, the number of glycosylation sites in the glycoprotein is at least one, or at least 2, or at least 3, or at least 4, or at least 5, or at least 6, or 1-6, or 2-5, or 3-4; and n is at least one, or at least 2, or at least 3, or at least 4, or at least 5, or at least 6, or 1-6, or 2-5, or 3 4.

In one embodiment, the number of non-Asn297 glycosylation sites in the glycoprotein is at least one, or at least 2, or at least 3, or at least 4, or at least 5, or at least 6, or 1-6, or 2-5, or 3-4; and n is at least one, or at least 2, or at least 3, or at least 4, or at least 5, or at least 6, or 1 6, or 2-5, or 3-4. Toxic payload molecule loading, i.e. n, may range from 1 to about 20 payload moieties (D) per glycoprotein or antibody. The average number of toxic payload moieties per glycoprotein or antibody in preparations of ADC from conjugation reactions may be characterized by conventional means such as mass spectroscopy and, ELISA assay. The quantitative distribution of ADC in terms of n may also be determined. In some instances, separation, purification, and characterization of homogeneous ADC where n is a certain value from ADC with other drug loadings may be achieved by means such as electrophoresis.

For glycoprotein-toxic payload molecule conjugates, n is limited by the number of N-glycosylation sites and N-glycan "antennae" per an N-glycan on the glycoprotein or the antibody. For example, where the attachment is a bi-antennary N-glycan on Asn297, the antibody may have one, two, three or four carbohydrate groups through which a linker or saccharide structure may be attached. On the other hand, where an additional N-glycosylation site (non-Asn297 site) is introduced into the antibody (for example, R/K18N in the light chain), the antibody may have three, four, five, six, seven, eight or more carbohydrate groups through which a linker or saccharide structure may be attached in addition to the bi-antennary N-glycan on Asn297. In this embodiment, n is about 8, more than 8, from about 7 to about 8, from about 6 to about 8, from about 5 to about 8, from about 4 to about 8, from about 4 to about 6, or from about 5 to about 6.

In one embodiment, the N-glycan is a multiantennary N-glycan comprising at least three, at least four, at least five or at least six N-glycan antennae. In one embodiment, the N-glycan in a non-Asn297 glycosylation site in the glycoprotein is a multiantennary N-glycan. In one embodiment, the N-glycan is an N-glycan with branched saccharide structure such as branched N-acetyllactosamine structure comprising at least two, at least three, at least four, at least five or at least six branches of the saccharide structure. In one embodiment, the N-glycan in a non-Asn297 glycosylation site in the glycoprotein is an N-glycan with branched saccharide structure. In these embodiments, there are at least three, at least four, at least five or at least six antennae and/or branches to which the payload molecules can be attached per one glycosylation site. In these embodiments, n is about 8, more than 8, from about 8 to about 10, from about 10 to about 12, from about 10 to about 14, more than 14, from about 7 to about 8, from about 6 to about 8, from about 5 to about 8, from about 4 to about 8, from about 4 to about 6, or from about 5 to about 6. These embodiments can be accomplished by methods known in the art, e.g. by expressing the glycoprotein in a suitable cell line capable of producing said multiantennary and/or branched N-glycan structures to the glycoprotein. Suitable such cell lines are for example CHO or HEK-293 cell lines. In one such embodiment, the glycoprotein is an antibody comprising a non-Asn297 glycosylation site that can comprise said multiantennary and/or branched N-glycan structures. In one embodiment, the glycoprotein comprises an N-glycan comprising a sialyltransferase acceptor site selected from the group consisting of Galβ, Galβ4GlcNAc, Galβ3GlcNAc, Galβ3GalNAc, GalNAcβ, GalNAcα, GalNAcβ4GlcNAc and sialic acid.

In one embodiment, the glycoprotein comprises an N-glycan comprising two, three, four, five, six, seven, eight or more sialyltransferase acceptor sites selected from the group consisting of Galβ, Galβ4GlcNAc, Galβ3GlcNAc, Galβ3GalNAc, GalNAcβ, GalNAcα, GalNAcβ4GlcNAc and sialic acid.

In one embodiment, the glycoprotein is a recombinant glycoprotein produced in a cell that is capable of producing glycoproteins in which the sialyltransferase acceptor sites are enriched.

In one embodiment, the glycoprotein is a recombinant glycoprotein produced in a cell that is capable of producing glycoproteins in which N-glycans comprising terminal Galβ residues and/or not comprising terminal sialic acid residues are enriched.

The N-glycan may be any N-glycan, provided that the N-glycan comprises a GlcNAc residue bound by a β-N linkage to an asparagine.

In one embodiment, the N-glycan comprises a terminal Gal residue. In one embodiment, the N-glycan comprises one, two or more terminal Galβ residues.

In one embodiment, the N-glycan is a biantennary complex-type N-glycan.

In one embodiment, the N-glycan is a monoantennary complex-type N-glycan.

In one embodiment, the N-glycan has a structure according to the formula 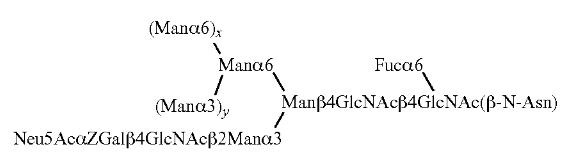 wherein (β-N-Asn)=β-N linkage to Asn;

Z=3 or 6;

x=0 or 1; and y=0 or 1.

In one embodiment, x=1 and y=1.

In this context, the terms "Neu5Ac", "NeuNAc" and "sialic acid" refer to N-acetylneuraminic acid; all monosaccharide residues are in pyranose form; all monosaccharides are in D-sugars except for L-fucose; "HexNAc" refers to an N-acetylhexosamine sugar; and "dHex" refers to a deoxyhexose sugar. In one embodiment of the present invention, "sialic acid" may also refer to other sialic acids in addition to N-acetylneuraminic acid, such as N-glycolylneuraminic acid (Neu5Gc).

In one embodiment, the N-glycan has a structure according to the following formula:

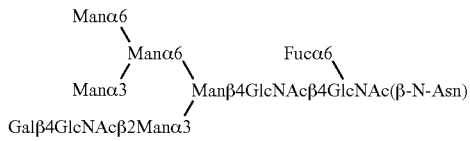

The N-glycan according to the previous two formulae and methods for producing thereof are disclosed in detail in the publication WO 2013/087992. In particular, methods for producing thereof are disclosed on p. 32, line 30—p. 48, line 2 and in Examples 1, 2, 5, 7 and 8 of WO 2013/087992.

In one embodiment, the N-glycan has a structure according to the following formula:

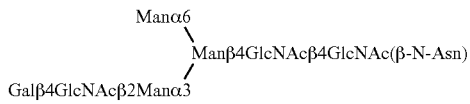

wherein
(β-N-Asn)=β-N linkage to Asn.

The N-glycan according to this formula and methods producing thereof are disclosed in detail in the publication WO 2013/087993. In particular, methods for producing thereof are disclosed on p. 29, line 31—p. 41, line 21 and in Examples 1, 2, 5 and 8 of WO 2013/087993.

In one embodiment, the N-glycan is a hybrid-type N-glycan.

In one embodiment, R is a glycosidic bond to the N-glycan or a glycosidic bond to the GlcNAc residue bound by a β-N linkage to an asparagine;

$X^1$ is H or carboxyl;

$X^2$, $X^3$ and $X^4$ are each independently OH, H, amino, $C_2$-$C_6$ acylamide, phosphate or sulphate ester, or a bond to L;

$X^5$ is $CH_2OH$, carboxyl, $CH_3$, H, $C_1$-$C_3$ alkyl or substituted $C_1$-$C_3$ alkyl, or a bond to L;

with the proviso that one substituent selected from $X^2$, $X^3$, $X^4$ and $X^5$ is a bond to L or bonded via a bond to L; and with the proviso that when $X^1$ is carboxyl, then $X^2$ is H; $X^3$ is OH; $X^4$ is OH, H, amino, $C_2$-$C_6$ acylamide, or a bond to L; $X^5$ is $C_1$-$C_3$ alkyl or substituted $C_1$-$C_3$ alkyl; R is a glycosidic bond to the N-glycan; and either $X^4$ is a bond to L or $X^5$ is bonded via a bond to L; or when $X^1$ is H, then R is a glycosidic bond to the GlcNAc residue bound by a β-N linkage to an asparagine.

In one embodiment, G is a saccharide structure represented by formula III

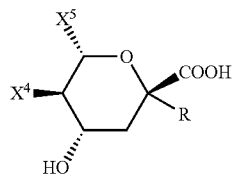

Formula III wherein
R is a glycosidic bond to the N-glycan;
$X^4$ is OH, H, amino, $C_2$-$C_6$ acylamide, phosphate or sulphate ester, or a bond to L;
$X^5$ is $C_1$-$C_3$ alkyl or substituted $C_1$-$C_3$ alkyl;
and $X^4$ is a bond to L or $X^5$ is bonded via a bond to L.

In one embodiment, G is a saccharide structure represented by formula III, wherein
R is a glycosidic bond to the N-glycan;
$X^4$ is OH, H, amino, $C_2$-$C_6$ acylamide or phosphate or sulphate ester;
$X^5$ is $C_1$-$C_3$ alkyl or substituted $C_1$-$C_3$ alkyl;
and $X^5$ is bonded via a bond to L.

In one embodiment, the glycoprotein comprises a sialyltransferase acceptor site and R is a glycosidic bond to the sialyltransferase acceptor site.

In one embodiment, the N-glycan comprises a terminal Galβ residue and R is a glycosidic bond to the terminal Galβ residue.

In one embodiment, the N-glycan comprises a structure according to the following formula

wherein y is 0 or 1.

In one embodiment, the N-glycan consists of a structure according to the following formula

wherein y is 0 or 1.

In one embodiment, the N-glycan consists of the structure represented by formula IV

Formula IV wherein (β-N-Asn) is a β-N linkage to an asparagine and y is 0 or 1.

In one embodiment, n is 2-18. In one embodiment, n is 2-16. In one embodiment, n is 2-10. In other embodiments, n is 2-6; 2-5; 2-4; 2-3; 3-4; or 1, 2, 3 or 4. n, i.e. the number of toxic payload molecules conjugated to a single glycoprotein, may depend e.g. on the glycoprotein, on the number of N-glycans present in the glycoprotein, the structure of the N-glycans present in the glycoprotein, and the method of preparing the glycoprotein-toxic payload molecule conjugate. Typically, a large value of n may lead to higher toxicity of the glycoprotein-toxic payload molecule conjugate; on the other hand, a large value of n may in some cases affect other properties of the glycoprotein-toxic payload molecule conjugate, such as pharmacokinetic properties, adversely.

In one embodiment, the glycoprotein comprises one, two, three, four or more N-glycans comprising a GlcNAc residue bound by a β-N linkage to an asparagine.

In one embodiment, the glycoprotein comprises one, two, three, four or more sialyltransferase acceptor sites.

In one embodiment, the glycoprotein comprises one, two, three, four or more N-glycans comprising a terminal Galβ residue or a GlcNAc residue bound by a β-N linkage to an asparagine.

In one embodiment, G is a saccharide structure represented by formula II

Formula II 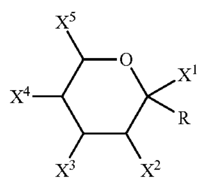 wherein R is a glycosidic bond to the structure represented by formula IV Formula IV wherein (β-N-Asn) is a β-N linkage to an asparagine and y is 0 or 1;

$X^1$ is H;

$X^2$, $X^3$ and $X^4$ are each independently OH, H, amino, $C_2$-$C_6$ acylamide, phosphate or sulphate ester, or a bond to L;

$X^5$ is $CH_2OH$, carboxyl, $CH_3$, H, $C_1$-$C_3$ alkyl or substituted $C_1$-$C_3$ alkyl, or a bond to L;

with the proviso that one substituent selected from $X^2$, $X^3$, $X^4$ and $X^5$ is a bond to L or bonded via a bond to L.

In one embodiment, the N-glycan comprises the saccharide structure G represented by formula II Formula II 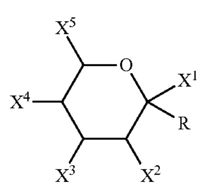 wherein R is a glycosidic bond to the structure represented by formula IV Formula IV wherein (β-N-Asn) is a β-N linkage to an asparagine and y is 0 or 1;

$X^1$ is H;

$X^2$, $X^3$ and $X^4$ are each independently OH, H, amino, $C_2$-$C_6$ acylamide, phosphate or sulphate ester, or a bond to L;

$X^5$ is $CH_2OH$, carboxyl, $CH_3$, H, $C_1$-$C_3$ alkyl or substituted $C_1$-$C_3$ alkyl, or a bond to L;

with the proviso that one substituent selected from $X^2$, $X^3$, $X^4$ and $X^5$ is a bond to L or bonded via a bond to L.

In one embodiment, the anomeric structure of G is selected from the group consisting of β-D-galacto, β-D-gluco and α-L-fuco configuration.

In one embodiment, the anomeric structure of G is in β-D-galacto or β-D-gluco configuration and R is a glycosidic bond to the 4-position of the GlcNAc residue.

In one embodiment, the anomeric structure of G is β-D-galacto configuration.

In one embodiment, R is a glycosidic bond hydrolysable by a lysosomal glycohydrolase.

In one embodiment, G is a saccharide structure represented by formula IIb

Formula IIb 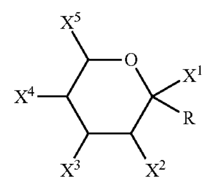 wherein $X^1$ is H or carboxyl;

$X^2$, $X^3$ and $X^4$ are each independently OH, H, amino, $C_2$-$C_6$ acylamide, phosphate or sulphate ester, or a bond to L;

$X^5$ is $CH_2OH$, carboxyl, $CH_3$, H, $C_1$-$C_3$ alkyl or substituted $C_1$-$C_3$ alkyl, or a bond to L;

with the proviso that one substituent selected from $X^2$, $X^3$, $X^4$ and $X^5$ is a bond to L or bonded via a bond to L; and R is a glycosidic bond to the N-glycan hydrolysable by a lysosomal glycohydrolase.

In one embodiment, the N-glycan comprises the saccharide structure G represented by formula IIb Formula IIb 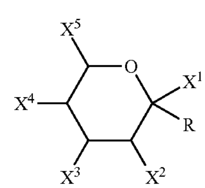 wherein $X^1$ is H or carboxyl;

$X^2$, $X^3$ and $X^4$ are each independently OH, H, amino, $C_2$-$C_6$ acylamide, phosphate or sulphate ester, or a bond to L;

$X^5$ is $CH_2OH$, carboxyl, $CH_3$, H, $C_1$-$C_3$ alkyl or substituted $C_1$-$C_3$ alkyl, or a bond to L;

with the proviso that one substituent selected from $X^2$, $X^3$, $X^4$ and $X^5$ is a bond to L or bonded via a bond to L; and R is a glycosidic bond to the N-glycan hydrolysable by a lysosomal glycohydrolase.

In one embodiment, R is a glycosidic bond hydrolysable by a lysosomal glycohydrolase.

In this context, the term "glycosidic bond hydrolysable by a lysosomal glycohydrolase" should be understood as referring to a glycosidic bond which a lysosomal glycohydrolase is capable of hydrolysing in vitro or in vivo.

In one embodiment, R is an O-glycosidic bond.

In one embodiment, the lysosomal glycohydrolase is a lysosomal β-galactosidase, β-hexosaminidase, β-glucuronidase, α-galactosidase, α-glucosidase, α-mannosidase, β-mannosidase, α-fucosidase or neuraminidase.

In one embodiment, the lysosomal glycohydrolase is a lysosomal β-galactosidase.

In one embodiment, the lysosomal glycohydrolase is a lysosomal β-hexosaminidase.

In one embodiment, the lysosomal glycohydrolase is a lysosomal neuraminidase.

In one embodiment, G is according to Formula IIb, wherein $X^1$ is H and $X^5$ is a bond to L or bonded via a bond to L.

In one embodiment, G is according to Formula IIb, wherein $X^1$ is H, the anomeric structure of G is β-D-galacto configuration and $X^5$ is a bond to L or bonded via a bond to L.

In one embodiment, G is according to Formula IIb, wherein $X^1$ is H, the anomeric structure of G is β-D-gluco configuration and $X^5$ is a bond to L or bonded via a bond to L.

In one embodiment, G is according to Formula IIb, wherein $X^1$ is H, the anomeric structure of G is β-D-galacto configuration, $X^3$ and $X^4$ are OH groups, and $X^5$ is a bond to L or bonded via a bond to L.

In one embodiment, G is according to Formula IIb, wherein $X^1$ is H, the anomeric structure of G is β-D-galacto configuration, $X^2$ and $X^3$ and $X^4$ are OH groups, and $X^5$ is a bond to L or bonded via a bond to L.

In one embodiment, G is according to Formula IIb, wherein $X^1$ is H, the anomeric structure of G is β-D-galacto or β-D-gluco configuration, $X^2$ is an acetamido group, $X^3$ and $X^4$ are OH groups, and $X^5$ is a bond to L or bonded via a bond to L.

In one embodiment, G is according to Formula III, wherein $X^5$ is a bond to L or bonded via a bond to L.

In one embodiment, G is according to Formula III, wherein $X^5$ is $CH(OH)CH(OH)CH_2X^9$, wherein $X^9$ is a bond to L.

In one embodiment, G is according to Formula III, wherein $X^4$ is a $C_2$ acylamido group such as acetamido group, and $X^5$ is $CH(OH)CH(OH)CH_2X^9$, wherein $X^9$ is a bond to L.

In one embodiment, G is according to Formula III, wherein $X^4$ is a $C_2$ acylamido group such as acetamido group, and $X^5$ is $CH(OH)CH(OH)CH_2X^9$, wherein $X^9$ is a bond to L.

In one embodiment, G is according to Formula III, wherein $X^4$ is a bond to L or bonded via a bond to L.

In one embodiment, G is according to Formula III, wherein $X^4$ is a bond to L or bonded via a bond to L, and $X^5$ is $CH(OH)CH(OH)CH_2OH$.

In one embodiment, the anomeric structure of the $X^5$ substituent in structures according to Formula III is as in neuraminic acid and as set forth in the Example 3.

A lysosomal glycohydrolase may release the toxic payload molecule in active form inside a cell. The released toxic payload molecule-glycan conjugate may be more potent and/or active inside a cell than the glycoprotein-toxic payload molecule conjugate.

In one embodiment, the anomeric structure of G and the substituents $X^2$, $X^3$, $X^4$ and $X^5$ are selected according to stability assays in serum or plasma in neutral pH and hydrolysis assays in presence of lysosomal glycohydrolases in acidic pH.

In one embodiment, the anomeric structure of G and the substituents $X^2$, $X^3$, $X^4$ and $X^5$ are selected according to high stability in serum and plasma as set forth in Example 15.

In one embodiment, the anomeric structure of G and the substituents $X^2$, $X^3$, $X^4$ and $X^5$ are selected according to high rate of hydrolysis in presence of lysosomal glycohydrolases in acidic pH as set forth in Example 16.

In one embodiment, the anomeric structure of G and the substituents $X^2$, $X^3$, $X^4$ and $X^5$ are selected according to high stability in serum and plasma as set forth in Example 15 and according to high rate of hydrolysis in presence of lysosomal glycohydrolases in acidic pH as set forth in Example 16.

The present invention further relates to a toxic payload molecule-glycan conjugate represented by formula V

                                            Formula V wherein
D is a toxic payload molecule;
L is a linker group covalently joining G to D; and
G is a saccharide structure represented by formula VI

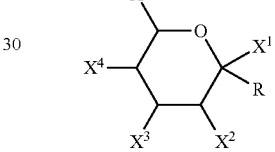
                                            Formula VI wherein
R is OH, N-acetylglucosaminylasparagine or 6-fucosyl-N-acetylglucosaminylasparagine;
$X^1$ is H or carboxyl;
$X^2$, $X^3$ and $X^4$ are each independently OH, H, amino, $C_2$-$C_6$ acylamide, phosphate or sulphate ester, or a bond to L;
$X^5$ is $CH_2OH$, carboxyl, $CH_3$, H, $C_1$-$C_3$ alkyl or substituted $C_1$-$C_3$ alkyl, or a bond to L;
with the proviso that one substituent selected from $X^2$, $X^3$, $X^4$ and $X^5$ is a bond to L or bonded via a bond to L; and
with the proviso that when $X^1$ is carboxyl, then $X^2$ is H, $X^3$ is OH, $X^5$ is $C_1$-$C_3$ alkyl or substituted $C_1$-$C_3$ alkyl; R is OH; and $X^4$ is a bond to L or $X^5$ is bonded via a bond to L; or
when $X^1$ is H, then R is N-acetylglucosaminylasparagine or 6-fucosyl-N-acetylglucosaminylasparagine.

The toxic payload molecule-glycan conjugate may be prepared or formed e.g. by hydrolysing the glycoprotein-toxic payload molecule conjugate according to one or more embodiments of the present invention with a lysosomal hydrolase in vitro e.g. according to Example 15, by contacting the conjugate with cells that internalize the conjugate e.g. according to Example 14, or in vivo by administering the conjugate to an animal that comprises cells capable of internalizing the conjugate (such as cancer cells).

In one embodiment, R is N-acetylglucosaminylasparagine or 6-fucosyl-N-acetylglucosaminylasparagine, and the N-acetylglucosaminylasparagine or 6-fucosyl-N-acetylglucosaminylasparagine is free. In other words, the N-acetylglucosaminylasparagine or 6-fucosyl-N-acetylglucosaminylasparagine is not bound to a glycoprotein.

In one embodiment, G is a saccharide structure represented by formula VII

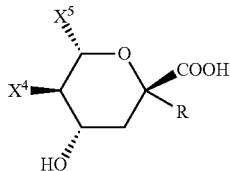

Formula VII wherein
R is OH;
$X^4$ is OH, H, amino, $C_2$-$C_6$ acylamide, phosphate or sulphate ester, or a bond to L;
$X^5$ is $C_1$-$C_3$ alkyl or substituted $C_1$-$C_3$ alkyl;
and $X^4$ is a bond to L or $X^5$ is bonded via a bond to L.

In one embodiment, G is a saccharide structure represented by formula VII wherein
R is OH;
$X^4$ is OH, H, amino, $C_2$-$C_6$ acylamide, phosphate or sulphate ester;
$X^5$ is $C_1$-$C_3$ alkyl or substituted $C_1$-$C_3$ alkyl;
and $X^5$ is bonded via a bond to L.

In one embodiment,
R is N-acetylglucosaminylasparagine or 6-fucosyl-N-acetylglucosaminylasparagine;
$X^1$ is H;
$X^2$, $X^3$ and $X^4$ are each independently OH, H, amino, $C_2$-$C_6$ acylamide, phosphate or sulphate ester, or a bond to L; and
$X^5$ is $CH_2OH$, carboxyl, $CH_3$, H, $C_1$-$C_3$ alkyl or substituted $C_1$-$C_3$ alkyl, or a bond to L;
with the proviso that one substituent selected from $X^2$, $X^3$, $X^4$ and $X^5$ is a bond to L or bonded via a bond to L.

In one embodiment, R is N-acetylglucosaminylasparagine or 6-fucosyl-N-acetylglucosaminylasparagine, and the anomeric structure of G is selected from the group consisting of β-D-galacto, β-D-gluco and α-L-fuco configuration.

In one embodiment, R is N-acetylglucosaminylasparagine or 6-fucosyl-N-acetylglucosaminylasparagine, and the anomeric structure of G is in β-D-galacto configuration.

In one embodiment, R is represented by the formula

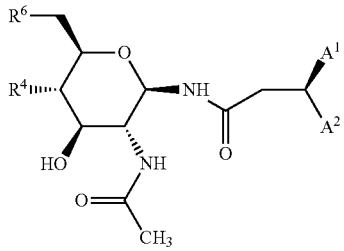

wherein $R^4$ is either OH or a glycosidic bond to G;
$R^6$ is either OH, α-L-fucose or a glycosidic bond to G;
$A^1$ is amino and $A^2$ is carboxyl;
with the proviso that $R^4$ or $R^6$ is a glycosidic bond to G.

In one embodiment, R is represented by the formula

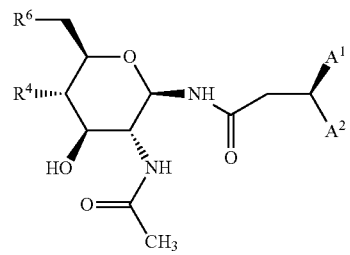

wherein $R^4$ is a glycosidic bond to G;
$R^6$ is either OH or α-L-fucose;
$A^1$ is amino and $A^2$ is carboxyl;
and G is according to Formula II, wherein the pyranose ring is in β-D-galacto or β-D-gluco configuration;
$X^1$ is H;
$X^2$ is OH, acetamido group or a bond to L;
$X^3$ and $X^4$ are each OH; and
$X^5$ is $CH_2OH$ or a bond to L;
with the proviso that one substituent selected from $X^2$ and $X^5$ is a bond to L or bonded via a bond to L.

In one embodiment of the invention, one or more of the substituents $X^2$, $X^3$, $X^4$ and $X^5$ are selected from the group consisting of H, OH, $CH_2OH$, COOH, COOR', $C_1$-$C_8$ alkyl, O($C_1$-$C_8$ alkyl), aryl, COR', OCOR', $CONH_2$, CONHR', $CONR'_2$, NHCOR', SH, $SO_2R'$, SOR', $OSO_2OH$, $OPO(OH)_2$, halogen, $N_3$, $NH_2$, NHR', $NR'_2$, or $NHCO(C_1$-$C_8$ alkyl), wherein each R' is independently either H, $C_1$-$C_8$ alkyl or aryl.

In one embodiment of the invention, one or more of the substituents $X^2$, $X^3$, $X^4$ and $X^5$ are selected from all chemical substituents described in the present invention.

In one embodiment, D is D', wherein D' is the toxic payload molecule comprising an amine moiety, through which the toxic payload molecule may be bound so as to form a secondary or tertiary amine. In formulas VIII, IX, X and XI, D' should thus be understood as referring to the same toxic payload molecule as D shown in formulas I, V and XIV with the proviso that D is D'.

The linker group may be any suitable linker group capable of covalently joining G to D. Linkers that may, in principle, be utilised are described e.g. in Dosio et al., Toxins 2011, 3, 848-883, and Sammet et al., Pharm. Pat. Analyst 2012, 1(1), 2046-8954.

In one embodiment, the linker group is hydrophilic.

In one embodiment, the linker group comprises at least one OH group.

In one embodiment, L is a linker group represented by formula VIII

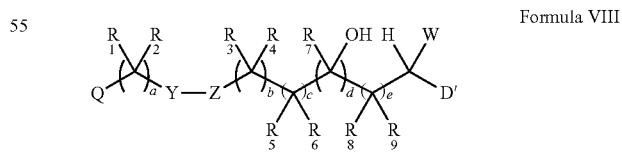

Formula VIII wherein
Y is an oxygen, sulphur, amine, amide, peptide or absent, wherein the peptide is an $E_1$-P-$E_2$ unit in which $E_1$ and $E_2$ are independently C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

D' is the toxic payload molecule, wherein the toxic payload molecule comprises an amine moiety, through which the toxic payload molecule is bound so as to form a secondary or tertiary amine;

$R_1$, $R_2$, $R_3$, $R_4$, $R_5$, $R_6$, $R_7$, $R_8$ and $R_9$ are each independently H, OH, amine, $C_2$-$C_6$ acylamide, carboxyl, substituted carboxyl, $C_1$-$C_6$ alkyl or substituted $C_1$-$C_6$ alkyl;

W is H, $CH_2OH$, $CH_3$, carboxyl, substituted carboxyl, $C_1$-$C_6$ alkyl or substituted $C_1$-$C_6$ alkyl;

a is an integer from 0 to 6;

b is 0 or 1;

c and e are each independently an integer from 0 to 7;

d is an integer from 1 to 7;

Q is E'-F'-E, wherein F' is an amine, amide, disulfide, thioether, thioester, hydrazone, Schiff base, oxime, olefin metathesis reaction product, triazole or phosphine group, or other group generated by the reaction of the functional group F-E and the functional group F', wherein F is a functional group that can react with an amine, thiol, azide, alkene, alkyne, aldehyde, ketone, carboxylic acid or hydroxylamine, and F' is an amine, thiol, azide, alkene, alkyne, aldehyde, ketone, carboxylic acid or hydroxylamine; and E is absent or a polyethyleneoxy unit of formula $(CH_2CH_2O)_p$, wherein p is an integer from 2 to about 20; and E and E' are each independently absent or a polyethyleneoxy unit of formula $(CH_2CH_2O)_p$, wherein p is an integer from 2 to about 20; and Q is bound via a bond to G.

In one embodiment, L is a linker group represented by formula IX

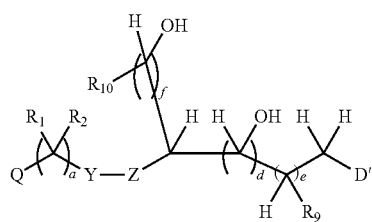

Formula IX wherein

Y is an oxygen, sulphur, amine, amide, peptide or absent, wherein the peptide is an $E_1$-P-$E_2$ unit in which $E_1$ and $E_2$ are independently C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

D' is the toxic payload molecule, wherein the toxic payload molecule comprises an amine moiety, through which the toxic payload molecule is bound so as to form a secondary or tertiary amine;

$R_1$, $R_2$, $R_9$ and $R_{10}$ are each independently H, OH, amine, $C_2$-$C_6$ acylamide, carboxyl, substituted carboxyl, $C_1$-$C_6$ alkyl or substituted $C_1$-$C_6$ alkyl;

a is an integer from 0 to 6;

e is an integer from 0 to 3;

d and f are integers from 0 to 4 with the proviso that their sum is from 1 to 4;

Q is E'-F'-E, wherein F' is an amine, amide, disulfide, thioether, thioester, hydrazone, Schiff base, oxime, olefin metathesis reaction product, triazole or phosphine group, or other group generated by the reaction of the functional group F-E and the functional group F', wherein F is a functional group that can react with an amine, thiol, azide, alkene, alkyne, aldehyde, ketone, carboxylic acid or hydroxylamine, and F' is an amine, thiol, azide, alkene, alkyne, aldehyde, ketone, carboxylic acid or hydroxylamine; and E is absent or a polyethyleneoxy unit of formula $(CH_2CH_2O)_p$, wherein p is an integer from 2 to about 20; and E and E' are each independently absent or a polyethyleneoxy unit of formula $(CH_2CH_2O)_p$, wherein p is an integer from 2 to about 20; and Q is bound via a bond to G.

In one embodiment, L is a linker group represented by formula X

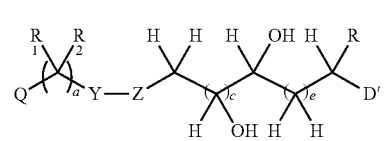

Formula X wherein

Y is an oxygen, sulphur, amine, amide, peptide or absent, wherein the peptide is an $E_1$-P-$E_2$ unit in which $E_1$ and $E_2$ are independently C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

D' is the toxic payload molecule, wherein the toxic payload molecule comprises an amine moiety, through which the toxic payload molecule is bound so as to form a secondary or tertiary amine;

$R_1$ and $R_2$ are each independently H, OH, amine, $C_2$-$C_6$ acylamide, carboxyl, substituted carboxyl, $C_1$-$C_6$ alkyl or substituted $C_1$-$C_6$ alkyl;

a is an integer from 0 to 6;

c and e are each independently an integer from 0 to 3;

Q is E'-F'-E, wherein F' is an amine, amide, disulfide, thioether, thioester, hydrazone, Schiff base, oxime, olefin metathesis reaction product, triazole or phosphine group, or other group generated by the reaction of the functional group F-E and the functional group F', wherein F is a functional group that can react with an amine, thiol, azide, alkene, alkyne, aldehyde, ketone, carboxylic acid or hydroxylamine, and F' is an amine, thiol, azide, alkene, alkyne, aldehyde, ketone, carboxylic acid or hydroxylamine; and E is absent or a polyethyleneoxy unit of formula $(CH_2CH_2O)_p$, wherein p is an integer from 2 to about 20; and E and E' are each independently absent or a polyethyleneoxy unit of formula $(CH_2CH_2O)_p$, wherein p is an integer from 2 to about 20; and Q is bound via a bond to G.

In one embodiment of the invention, F is an amine reacting group, a thiol reactive group, an azide reactive group, an alkyne reactive group, a carbonyl reactive group or a hydroxylamine reactive group.

In one embodiment of the invention, F is an amine reacting group, such as (but not limited) to an N-hydroxysuccinimide ester, p-nitrophenyl ester, dinitrophenyl ester, or pentafluorophenyl ester.

In one embodiment of the invention, F is a thiol reactive group, such as (but not limited to) pyridyldisulfide, nitropyridyldisulfide, maleimide, haloacetate or carboxylic acid chloride.

In one embodiment of the invention, F is an azide reactive group, such as (but not limited to) alkyne.

In one embodiment, F is an alkyne.

In one embodiment, F is CH≡C.

In one embodiment, F is a dibenzocyclooctyl group (DBCO).

In one embodiment of the invention, F is an alkyne reactive group, such as (but not limited to) azide.

In one embodiment, F is azide.

In one embodiment of the invention, F is a carbonyl reactive group, such as (but not limited to) hydroxylamine.

In one embodiment of the invention, F is a hydroxylamine reactive group, such as (but not limited to) aldehyde or ketone.

In one embodiment of the invention, F is isothiocyanate, isocyanate, sulfonyl chloride, glyoxal, epoxide, oxirane, carbonate, aryl halide, imidoester, carbodiimide, or anhydride.

In one embodiment, Z is absent.
In one embodiment, Z is a saccharide.
In one embodiment, Z is an oligosaccharide with a degree of polymerization from 1 to about 20; from 1 to 10; from 1 to 8; from 1 to 6; from 1 to 5; from 1 to 4; from 1 to 3; from 1 to 2; or 1, 2, 3, 4 or 5.
In one embodiment, Z is a monosaccharide, disaccharide or trisaccharide.
In one embodiment, Z is OH.
In one embodiment, Z is H.
In one embodiment, a is 1, 2, 3, 4, 5, or 6.
In one embodiment, a is 1.
In one embodiment, b is 0.
In one embodiment, b is 1.
In one embodiment, c is 0.
In one embodiment, c is 1, 2, 3, 4, 5, 6 or 7.
In one embodiment, d is 1, 2, 3, 4, 5, 6 or 7.
In one embodiment, d is 3, 4 or 5.
In one embodiment, d is 3.
In one embodiment, d is 4.
In one embodiment, d is 5.
In one embodiment, d is 6.
In one embodiment, e is 0.
In one embodiment, e is 1, 2, 3, 4, 5, 6 or 7.
In one embodiment, d is 3; and $R_7$ is H.
In one embodiment, d is 4; and $R_7$ is H.
In one embodiment, b is 1; and $R_3$ and $R_4$ are each H.
In one embodiment, a is 1; and $R_1$ and $R_2$ are each H.
In one embodiment, e is 1; and $R_8$ and $R_9$ are each H.
In one embodiment, a, b, c, or e is 0.
In one embodiment, a, b, c, and/or e is 0.
In one embodiment, W is H.
In one embodiment, a is 2 or 3; and $R_1$ and $R_2$ are each H.
In one embodiment, Y is oxygen.
In one embodiment, Y is sulphur.
In one embodiment, Y is a peptide.
In one embodiment, Y is a peptide that comprises an $E_1$-P-$E_2$ unit in which $E_1$ and $E_2$ are independently either C═O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide.

In one embodiment, Y is a peptide that is an $E_1$-P-$E_2$ unit in which $E_1$ and $E_2$ are independently either C═O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide.

In one embodiment, Y is a peptide from 2 to 5 amino acids in length.

In one embodiment, the peptide is linked to the linker group through the terminal nitrogen i.e. through the amino terminus by an amide bond.

In one embodiment, the peptide is linked to the linker group through the terminal carbon i.e. through the carboxy terminus by an amide bond or an ester bond.

In one embodiment, the peptide is linked to the linker group through a side chain of one of the amino acids of the peptide by an amide, ester, disulfide or thioether bond.

In one embodiment, the peptide comprises an amino acid sequence cleavable by a lysosomal peptidase, e.g. L-Gly-L-Gly, L-Val-L-Cit, L-Phe-L-Leu, L-Leu-L-Ala-L-Leu, L-Leu-L-Ala-L-Ala, L-Ala-L-Leu-L-Ala-L-Leu, and the like.

In one embodiment, Q is E'-F'-E, wherein F' is a triazole group generated by the reaction of the functional group F-E and the functional group F', wherein F is an azide and F' is an alkyne or F' is an azide and F is an alkyne; and E is absent.

In one embodiment, $R_1$, $R_2$, $R_3$, $R_4$ and $R_7$ are each H; W is H; a is 1; b is 1; c and e are each 0; and d is 4.

In one embodiment, $R_3$, $R_4$, and $R_7$ are each H; W is H; b is 1; a, c and e are each 0; and d is 4.

In one embodiment, L is a linker group represented by formula X, wherein Y is an oxygen or absent;
Z is absent;
D' is the toxic payload molecule, wherein the toxic payload molecule comprises an amine moiety, through which the toxic payload molecule is bound so as to form a secondary or tertiary amine;
$R_1$ and $R_2$ are each independently H or OH;
a is 1 or 2;
c is 0, 1, 2 or 3;
e is 0 or 1;
Q is E'-F'-E, wherein F' is a triazole group generated by the reaction of the functional group F-E and the functional group F', wherein F is an azide and F' is an alkyne or F' is an azide and F is an alkyne; E is absent; and
Q is bound via a bond to G.

The term "alkyl" should be understood as referring to a straight or branched chain saturated or unsaturated hydrocarbon having the indicated number of carbon atoms (e.g., "$C_1$-$C_8$ alkyl" refers to an alkyl group having from 1 to 8 carbon atoms). When the number of carbon atoms is not indicated, the alkyl group has from 1 to 8 carbon atoms. Representative "$C_1$-$C_8$ alkyl" groups include (but are not limited to) methyl (Me, $CH_3$), ethyl (Et, $CH_2CH_3$), 1-propyl (n-Pr, n-propyl, $CH_2CH_2CH_3$), 2-propyl (i-Pr, isopropyl, $CH(CH_3)_2$), 1-butyl (n-Bu, n-butyl, $CH_2CH_2CH_2CH_3$), 2-methyl-1-propyl (i-Bu, isobutyl, $CH_2CH(CH_3)_2$), 2-butyl (s-Bu, s-butyl, $CH(CH_3)CH_2CH_3$), 2-methyl-2-propyl (t-Bu, tert-butyl, $C(CH_3)_3$), 1-pentyl (n-pentyl, $CH_2CH_2CH_2CH_2CH_3$), 2-pentyl ($CH(CH_3)CH_2CH_2CH_3$), 3-pentyl ($CH(CH_2CH_3)_2$), 2-methyl-2-butyl ($C(CH_3)_2CH_2CH_3$), 3-methyl-2-butyl ($CH(CH_3)CH(CH_3)_2$), 3-methyl-1-butyl ($CH_2CH_2CH(CH_3)_2$), 2-methyl-1-butyl ($CH_2CH(CH_3)CH_2CH_3$), 1-hexyl ($CH_2CH_2CH_2CH_2CH_2CH_3$), 2-hexyl ($CH(CH_3)CH_2CH_2CH_2CH_3$), 3-hexyl ($CH(CH_2CH_3)(CH_2CH_2CH_3)$), 2-methyl-2-pentyl ($C(CH_3)_2CH_2CH_2CH_3$), 3-methyl-2-pentyl ($CH(CH_3)CH(CH_3)$ $CH_2CH_3$), 4-methyl-2-pentyl ($CH(CH_3)CH_2CH(CH_3)_2$), 3-methyl-3-pentyl ($C(CH_3)$ ($CH_2CH_3)_2$), 2-methyl-3-pentyl ($CH(CH_2CH_3)CH(CH_3)_2$), 2,3-dimethyl-2-butyl ($C(CH_3)_2CH(CH_3)_2$), and 3,3-dimethyl-2-butyl ($CH(CH_3)C(CH_3)_3$). An alkyl group can be unsubstituted or substituted with one or more groups including, but not limited to, OH, $O(C_1$-$C_8$ alkyl), aryl, COR', OCOR', $CONH_2$, CONHR', CONR'$_2$, NHCOR', SH, $SO_2$R', SOR', $OSO_2OH$, $OPO(OH)_2$, halogen, $N_3$, $NH_2$, NHR', NR'$_2$, $NHCO(C_1$-$C_8$ alkyl) or CN, wherein each R' is independently either H, $C_1$-$C_8$ alkyl or aryl. The term "alkyl" should also be understood as referring to an alkylene, a saturated, branched or straight chain or cyclic hydrocarbon radical of 1-18 carbon atoms, and having two monovalent radical centers derived by the removal of two hydrogen atoms from the same or two different carbon atoms of a parent alkane. Typical such alkylenes include (but are not limited to) methylene ($CH_2$) 1,2-ethyl ($CH_2CH_2$), 1,3-propyl ($CH_2CH_2CH_2$), 1,4-butyl ($CH_2CH_2CH_2CH_2$), and the like. The term "alkyl" should also be understood as referring to arylalkyl and heteroarylalkyl radicals as described below.

The term "alkenyl" should be understood as referring to a $C_2$-$C_{18}$ hydrocarbon containing normal, secondary, tertiary or cyclic carbon atoms with at least one site of unsaturation, i.e., a carbon-carbon, $sp^2$ double bond. Examples include, but are not limited to ethylene or vinyl (CH=$CH_2$), allyl ($CH_2CH$=$CH_2$), cyclopentenyl ($C_5H_7$), and 5-hexenyl ($CH_2CH_2CH_2CH_2CH$=$CH_2$). The term "alkenyl" should also be understood as referring to an alkenylene, an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to 1,2-ethylene (CH=CH).

The term "alkynyl" should be understood as referring to a $C_2$-$C_{18}$ hydrocarbon containing normal, secondary, tertiary or cyclic carbon atoms with at least one site of unsaturation, i.e. a carbon-carbon, sp triple bond. Examples include, but are not limited to acetylenic (C≡CH) and propargyl ($CH_2$C≡CH). The term "alkynyl" should also be understood as referring to an alkynylene, an unsaturated, branched or straight chain or cyclic hydrocarbon radical of 2-18 carbon atoms, and having two monovalent radical centers derived by the removal of two hydrogen atoms from carbon atoms of a parent alkyne. Typical alkynylene radicals include (but are not limited to) acetylene (C≡C), propargyl ($CH_2C$≡C), and 4-pentynyl ($CH_2CH_2CH_2C$≡C).

The term "aryl" should be understood as referring to a monovalent aromatic hydrocarbon radical of 6-20 carbon atoms derived by the removal of one hydrogen atom from a single carbon atom of a parent aromatic ring system. An aryl group can be unsubstituted or substituted. Typical aryl groups include (but are not limited to) radicals derived from benzene, substituted benzene, phenyl, naphthalene, anthracene, biphenyl, and the like. An aryl can be substituted with one or more groups including, but not limited to, OH, $O(C_1$-$C_3$ alkyl), aryl, COR', OCOR', $CONH_2$, CONHR', CONR'$_2$, NHCOR', SH, $SO_2$R', SOR', $OSO_2OH$, $OPO(OH)_2$, halogen, $N_3$, $NH_2$, NHR', NR'$_2$, $NHCO(C_1$-$C_8$ alkyl) or CN, wherein each R' is independently either H, $C_1$-$C_8$ alkyl or aryl. The term "aryl" should also be understood as referring to an arylene group which is an aryl group having two covalent bonds and can be in the para, meta, or ortho configurations, in which the phenyl group can be unsubstituted or substituted with up to four groups including but not limited to OH, $O(C_1$-$C_8$ alkyl), aryl, COR', OCOR', $CONH_2$, CONHR', CONR'$_2$, NHCOR', SH, $SO_2$R', SOR', $OSO_2OH$, $OPO(OH)_2$, halogen, $N_3$, $NH_2$, NHR', NR'$_2$, $NHCO(C_1$-$C_8$ alkyl) or CN, wherein each R' is independently either H, $C_1$-$C_8$ alkyl or aryl.

The term "arylalkyl" should be understood as referring to an acyclic alkyl radical in which one of the hydrogen atoms bonded to a carbon atom, typically a terminal or $sp^3$ carbon atom, is replaced with an aryl radical. Typical arylalkyl groups include (but are not limited to) benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "heteroarylalkyl" should be understood as referring to an acyclic alkyl radical in which one of the hydrogen atoms bonded to a carbon atom, typically a terminal or spa carbon atom, is replaced with a heteroaryl radical. Typical heteroarylalkyl groups include (but are not limited to) 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 ring atoms, typically 1 to 3 heteroatoms selected from N, O, P, and S, with the remainder being carbon atoms. The heteroaryl moiety of the heteroarylalkyl group may be a monocycle having 3 to 7 ring members (2 to 6 carbon atoms) or a bicycle having 7 to 10 ring members (4 to 9 carbon atoms) and 1 to 3 heteroatoms selected from N, O, P, and S, for example: a bicyclo [4,5], [5,5], [5,6], or [6,6] system.

The terms "substituted alkyl", "substituted aryl" and "substituted arylalkyl" should be understood as referring to alkyl, aryl, and arylalkyl, respectively, in which one or more hydrogen atoms are each independently replaced with a substituent. Typical substituents include but are not limited to X, R, —O—, OR, SR, —S—, $NR^2$, $NR^3$, =NR, $CX_3$, CN, OCN, SCN, N=C=O, NCS, NO, $NO_2$, =$N_2$, $N_3$, $NRCOR$, COR, $CONR^2$, —$SO_3$—, —$SO_3$H, $SO_2$R, $OSO_2OR$, $SO_2NR$, SOR, $OPO(OR)_2$, $PO(OR)_2$, —$PO_3$—, $PO_3H_2$, COR, COX, C(=S)R, $CO_2R$, —$CO_2$—, C(=S)OR, COSR, C(=S)SR, $CONR^2$, C(=S)$NR^2$, and C(=NR)$NR^2$, where each X is independently a halogen: F, Cl, Br, or I; and each R is independently H, $C_2$-$C_{18}$ alkyl, $C_6$-$C_{20}$ aryl, $C_3$-$C_{14}$ heterocycle or protecting group. Alkylene, alkenylene, and alkynylene groups as described above may also be similarly substituted.

The terms "heteroaryl" and "heterocycle" should be understood as referring to a ring system in which one or more ring atoms is a heteroatom, e.g., nitrogen, oxygen, phosphate and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960).

Examples of heterocycles include, by way of example and not limitation, pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon-bonded heterocycles are bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl and 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole or isoindoline; position 4 of a morpholine; and position 9 of a carbazole or β-carboline. Still more typically, nitrogen bonded heterocycles include 1-aziridyl, 1-azetedyl, 1-pyrrolyl, 1-imidazolyl, 1-pyrazolyl and 1-piperidinyl.

The term "carbocycle" should be understood as referring to a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl and cyclooctyl.

The term "saccharide" should be understood as referring to single simple sugar moieties or monosaccharides or their derivatives, as well as combinations of two or more single sugar moieties or monosaccharides covalently linked to form disaccharides, oligosaccharides, and polysaccharides. A saccharide can be a compound that includes one or more open chain or cyclized monomer units based upon an open chain form of compounds having the chemical structure $H(CHOH)_nC(=O)(CHOH)_mH$, wherein the sum of n+m is an integer in the range of 2 to 8. Thus, the monomer units can include trioses, tetroses, pentoses, hexoses, heptoses, octoses, nonoses, and mixtures thereof. One or several of the hydroxyl groups in the chemical structure can be replaced with other groups such as hydrogen, amino, amine, acylamido, acetylamido, halogen, mercapto, acyl, acetyl, phosphate or sulphate ester, and the like; and the saccharides can also comprise other functional groups such as carboxyl, carbonyl, hemiacetal, acetal and thio groups. Saccharides can include monosaccharides including, but not limited to, simple aldoses such as glyceraldehyde, erythrose, threose, ribose, arabinose, xylose, lyxose, allose, altrose, glucose, mannose, gulose, idose, galactose, talose and mannoheptulose; simple ketoses such as dihydroxyacetone, erythrulose, ribulose, xylulose, psicose, fructose, sorbose, tagatose and sedoheptulose; deoxysugars such as fucose, 2-deoxyglucose, 2-deoxyribose and rhamnose; sialic acids such as ketodeoxynonulosonic acid, N-acetylneuraminic acid and 9-O-acetyl-N-acetylneuraminic acid; uronic acids such as glucuronic acid, galacturonic acid and iduronic acid; amino sugars such as 2-amino-2-deoxygalactose and 2-amino-2-deoxyglucose; acylamino sugars such as 2-acetamido-2-deoxygalactose, 2-acetamido-2-deoxyglucose and N-glycolylneuraminic acid; phosphorylated and sulphated sugars such as 6-phosphomannose, 6-sulpho-N-acetylglucosamine and 3-sulphogalactose; and derivatives and modifications thereof. The term "saccharide" also includes non-reducing carbohydrates such as inositols and alditols and their derivatives. Saccharides according to the present invention may be in D- or L-configuration; in open-chain, pyranose or furanose form; α or β anomer; and any combination thereof.

The term "oligosaccharide" should be understood as referring to saccharides composed of two or several monosaccharides linked together by glycosidic bonds having a degree of polymerization in the range of from 2 to about 20. The term "oligosaccharide" should be understood as referring hetero- and homopolymers that can be either branched or linear and have a reducing end and a non-reducing end, whether or not the saccharide at the reducing end is in fact a reducing sugar. An oligosaccharide described herein may be described with the name or abbreviation for the non-reducing saccharide, followed by the configuration of the glycosidic bond (α or β), the ring bond, the ring position of the reducing saccharide involved in the bond, and then the name or abbreviation of the reducing saccharide, and so on (e.g. Galβ-4Glc for lactose and Galα1-4Galβ1-4Glc for globotriose).

In one embodiment, monosaccharides are in pyranose (P) or furanose (F) cyclized forms according to the formulas:

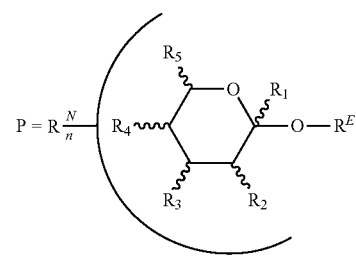

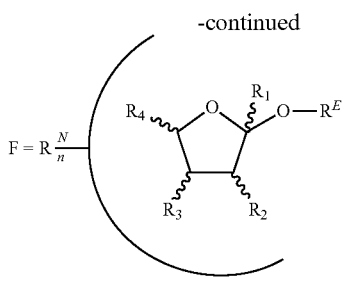

wherein $R^1$, $R^2$, $R^3$, $R^4$ and $R^5$ groups are each independently either H, OH, $CH_2OH$, COOH, COOR', $C_1$-$C_8$ alkyl, O($C_1$-$C_8$ alkyl), aryl, COR', OCOR', $CONH_2$, CONHR', $CONR'_2$, NHCOR', SH, $SO_2R'$, SOR', $OSO_2OH$, $OPO(OH)_2$, halogen, $N_3$, $NH_2$, NHR', $NR'_2$, NHCO($C_1$-$C_8$ alkyl) or $R^N$, wherein each R' is independently either H, $C_1$-$C_8$ alkyl or aryl and each $R^N$ is a non-reducing end saccharide; $R^E$ is either H or reducing end structure such as a saccharide; n is an integer in the range of 0 to 3 in F or in the range of 0 to 4 in P; and the stereochemistry of each $R^1$, $R^2$, $R^3$, $R^4$ and $R^5$ is dependent on the monosaccharide structure and its configuration and anomericity.

The term "disaccharide" should be understood as referring to a saccharide composed of two monosaccharides linked together by a glycosidic bond. Examples of disaccharides include, but are not limited to, lactose, N-acetyllactosamine, galactobiose, maltose, isomaltose and cellobiose.

The term "trisaccharide" should be understood as referring to a saccharide composed of three monosaccharides linked together by glycosidic bonds. Examples of trisaccharides include, but are not limited to, maltotriose, sialyllactose, globotriose, lacto-N-triose and gangliotriose.

The term "toxic payload molecule" should be understood as referring to any toxic molecule suitable for conjugation according to one or more embodiments of invention.

In one embodiment, a toxic payload molecule naturally comprises a primary or secondary amine moiety. In one embodiment, a toxic payload molecule is modified to comprise a primary or secondary amine moiety. In one embodiment, the amine-modified toxic payload molecule essentially retains the activity of the original toxic payload molecule.

The toxic payload molecule may be any compound that results in the death of a cell, or induces cell death, or in some manner decreases cell viability. The toxic payload molecule can be any of many small molecule drugs, including, but not limited to, dolastatins; auristatins; epothilones; daunorubicins and doxorubicins; alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, triethylene-phosphoramide, triethylenethiophosphaoramide and trimethylolomelamine; acetogenins (especially bullatacin and bullatacinone); camptothecins (including the synthetic analogue topotecan); bryostatin; callystatin; CC-1065 (including its adozelesin, carzelesin and bizelesin synthetic analogues); cryptophycins (particularly cryptophycin 1 and cryptophycin 8); duocarmycin (including the synthetic analogues, KW-2189 and CBI-TMI); eleutherobin; pancratistatin; sarcodictyins; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicins, especially calicheamicin γ1; dynemicin, including dynemicin A; esperamicin; as well as neocarzinostatin chromophore and related chromoprotein enediyne antio-biotic chromomophores), aclacinomysins, actinomycin, authramycin, azaserine, bleomycins, cactinomycin, carabicin, caminomycin, carzinophilin; chromomycins, dactinomycin, detorubicin, 6-diazo-5-oxo-L-norleucine, other doxorubicin derivatives including morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-fluorouracil; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; maytansinoids, such as maytansine, ansamitocins, DM-1, DM-4; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; antihormonal agents that act to regulate or inhibit hormone action on tumours, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA; and pharmaceutically acceptable salts, acids or derivatives of any of the above as well as analogues and derivatives thereof, some of which are described below.

In one embodiment, the toxic payload molecule is a dolastatin, auristatin, doxorubicin, DM1, epirubicin, duocarmycin or any analogue or derivative thereof.

In one embodiment, the toxic payload molecule is a dolastatin, auristatin, doxorubicin, or any analogue or derivative thereof.

In one embodiment, the toxic payload molecule is dolastatin 10 or any derivative thereof.

In one embodiment, the toxic payload molecule is dolastatin 15 or any derivative thereof.

In one embodiment, the toxic payload molecule is auristatin F or any derivative thereof.

In one embodiment, the toxic payload molecule is dolastatin 10, dolastatin 15, or auristatin F.

In one embodiment, the toxic payload molecule is dolastatin 10.

In one embodiment, the toxic payload molecule is dolastatin 15.

In one embodiment, the toxic payload molecule is auristatin F.

Dolastatins that can be used in the present invention are well known in the art and can be isolated from natural sources according to known methods or prepared synthetically according to known methods.

Examples of suitable dolastatins include monomethyl and desmethyl dolastatins 10, 15, C, D and H, monomethyl and desmethyl isodolastatin H, and analogues and derivatives thereof. These dolastatins contain a primary or secondary amine at the N-terminus. Dolastatins 10 and 15 are the most potent toxic payload molecules among the naturally occurring dolastatins. Monomethyl and desmethyl dolastatins 10 and 15 can be prepared by chemical synthesis according to standard peptide synthesis chemistry.

Auristatins that can be used in the present invention include (but are not limited to) monomethyl and desmethyl auristatins E, F, EB, EFP, PY, PYE, PE, PHE, TP, 2-AQ and 6-AQ, e.g. described in U.S. Pat. No. 5,635,483; Int. J. Oncol. 15:367-72 (1999); Mol. Cancer Ther. 3:921-32 (2004); U.S. application Ser. No. 11/134,826; U.S. Patent Publication Nos. 20060074008 and 2006022925; and Pettit, G. R., et al. (2011) J. Nat. Prod. 74:962-8.

In one embodiment, monomethyl and desmethyl auristatin and dolastatin 10 derivatives are represented by the formula:

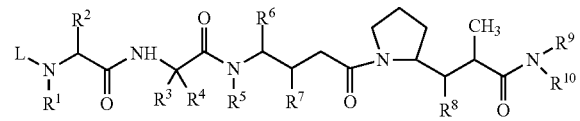

wherein L is either H, or may be understood as referring to the linker group; $R^1$, $R^5$ and $R^9$ are each independently either H or $C_1$-$C_8$ alkyl; $R^2$, $R^3$ and $R^6$ are each independently either H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle or $C_1$-$C_8$ alkyl-($C_3$-$C_8$ heterocycle); $R^4$ is either H or $CH_3$; or $R^3$ and $R^4$ jointly form a carbocyclic ring with the carbon to which they are attached and have the formula $-(CR_aR_b)_n-$, wherein $R_a$ and $R_b$ are independently selected from H, $C_1$-$C_8$ alkyl and $C_3$-$C_8$ carbocycle; and n is selected from 2, 3, 4, 5 and 6; $R^7$ and $R^8$ are each independently selected from H, OH, $C_1$-$C_8$ alkyl, $C_3$-$C_8$ carbocycle and $O(C_1$-$C_8$ alkyl); $R^{10}$ is either $CX_2$—$CX_2$-aryl, $CX_2$—$CX_2$-(substituted aryl), $CX_2$—$CX_2$—($C_3$-$C_8$ heterocycle), $CX_2$—($C_3$-$C_{10}$ heterocycle), $CX_2$—$CX_2$—($C_3$-$C_8$ carbocycle), $C(=O)O(C_1$-$C_4$ alkyl) or $CH(CH_2R^{12})C(=O)ZR^{11}$; each occurrence of X is independently either H, OH, $C_1$-$C_8$ alkyl, $C_3$-$C_8$ carbocycle, $C_3$-$C_{13}$ heterocycle, 2-thiazole or $O(C_1$-$C_8$ alkyl); Z is either O, S, NH or $N(C_1$-$C_8$ alkyl); $R^{11}$ is either H, $C_1$-$C_{20}$ alkyl, aryl, $C_3$-$C_8$ heterocycle, $(R^{13}O)_m$—$R^{14}$ or $(R^{13}O)_m$—$CH(R^{15})_2$; $R^{12}$ is either aryl or $C_3$-$C_8$ heterocycle; m is an integer ranging from 1-1000; $R^{13}$ is $C_2$-$C_8$ alkyl; $R^{14}$ is H or $C_1$-$C_8$ alkyl; each occurrence of $R^{15}$ is independently H, COOH, $(CH_2)_n$—$N(R^{16})_2$, $(CH_2)_n$—$SO_3H$ or $(CH_2)_n$—$SO_3$—$C_1$-$C_8$ alkyl; each occurrence of $R^{16}$ is independently H, $C_1$-$C_8$ alkyl or $(CH_2)_n$—COOH; and n is an integer in the range from 0 to 6.

In one embodiment, monomethyl and desmethyl auristatins and dolastatin 10 derivatives are represented by the formula:

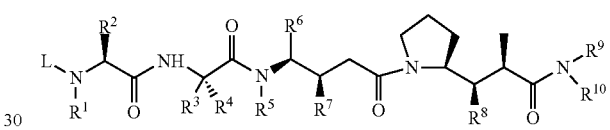

wherein the substituents are as described above.

In one embodiment, monomethyl and desmethyl auristatins and dolastatin 10 derivatives are represented by the formula:

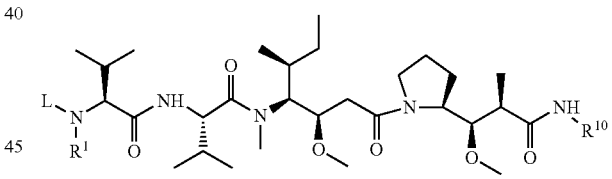

wherein the substituents are as described above.

In one embodiment, monomethyl and desmethyl auristatin F derivatives are represented by the formula:

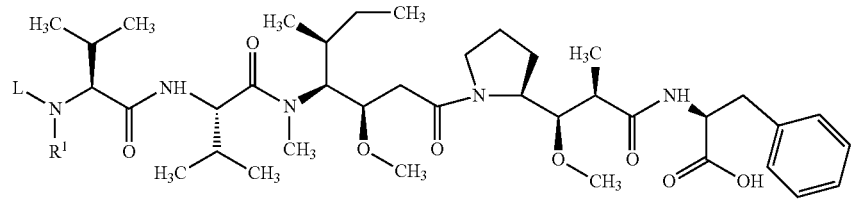

wherein L is either H, or may be understood as referring to the linker group; and R is either H or $CH_3$.

In one embodiment, monomethyl and desmethyl dolastatin 10 derivatives are represented by the formula:

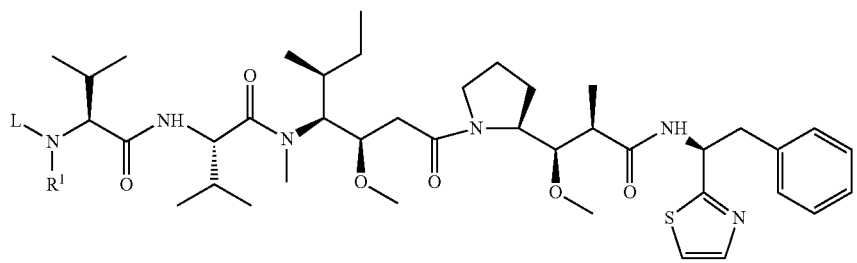

wherein L is either H, or may be understood as referring to the linker group; and $R^1$ is either H or $CH_3$.

In one embodiment, monomethyl and desmethyl dolastatin 15 analogues and derivatives are represented by the formula:

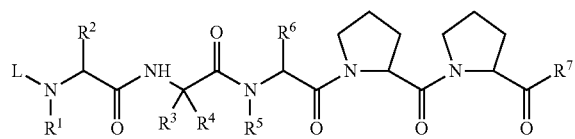

wherein L, $R^1$, $R^2$, $R^3$, $R^4$, $R^5$ and $R^6$ are as described above; $R^7$ is either OH, $NH_2$, $NHR^8$ or $NR^8R^9$; $R^8$ and $R^9$ are each independently either H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, $C_1$-$C_8$ alkyl-($C_3$-$C_8$ heterocycle), benzyl or tert-butyl; or $R^8$ and $R^9$ jointly form a heterocyclic ring with the nitrogen to which they are attached and have the formula $—(CR_aR_b)_n—$, wherein $R_a$ and $R_b$ are independently selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle, $C_1$-$C_8$ alkyl($C_3$-$C_8$ heterocycle), $O(C_1$-$C_8$ alkyl), a double bond with neighboring carbon atom, or they jointly form a carbonyl group; and n is selected from 2, 3, 4, 5 and 6.

In one embodiment, the monomethyl or desmethyl dolastatin 15 analogue or derivative is selected from the group of monomethyl and desmethyl dolastatin 15, monomethyl and desmethyl cemadotin, monomethyl and desmethyl tasidotin, and monomethyl and desmethyl P5 (the corresponding dimethyl compounds are described in Bai et al. 2009. Mol. Pharmacol. 75:218-26).

In one embodiment, monomethyl and desmethyl dolastatin 15 analogues and derivatives are represented by the formula:

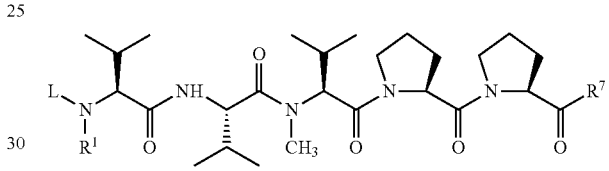

wherein the substituents are as described above.

In one embodiment, monomethyl and desmethyl dolastatin 15 derivatives are represented by the formula:

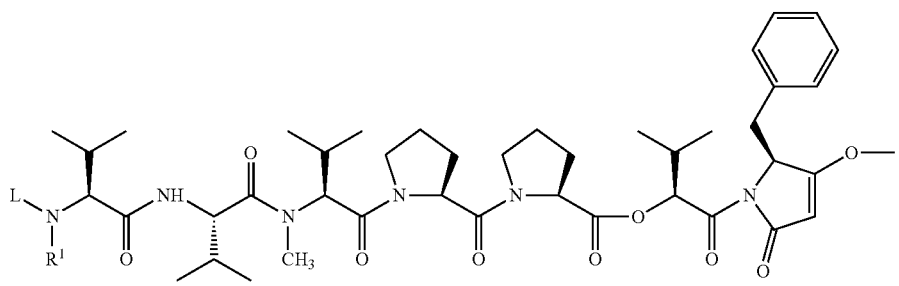

In one embodiment, monomethyl and desmethyl dolastatin 15 analogues and derivatives are represented by the formula:

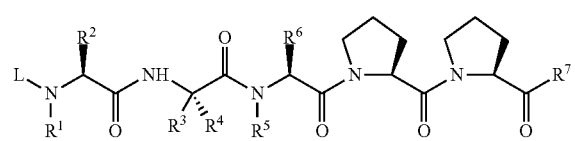

wherein the substituents are as described above.

wherein L is either H, or may be understood as referring to the linker group; and $R^1$ is either H or $CH_3$.

The toxic payload molecule according to the present invention may also be daunorubicin or doxorubicin. The primary amine group of the daunosamine moiety can be used, or daunorubicin or doxorubicin of the present invention can be modified to comprise another primary or secondary amine moiety. Preferred doxorubicin and daunorubicin payload molecules useful in the present invention are according to the formula:

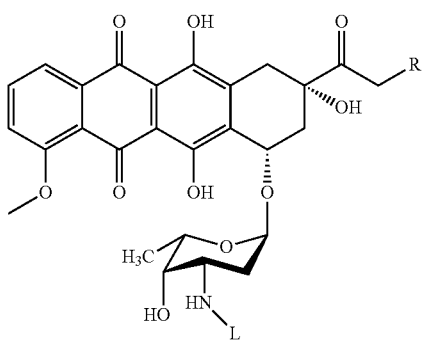

wherein R is either H or OH; and L is either H, or may be understood as referring to the linker group.

In one embodiment, the toxic payload molecule is a maytansinoid.

In one embodiment, the toxic payload molecule is maytansine, an ansamitocin, DM1 or DM4 (also known as DM-4).

In one embodiment, the toxic payload molecule is DM1. DM1 is also known as DM-1 and mertansine.

In one embodiment, the toxic payload molecule is a rubicin. Suitable rubicins may be e.g. daunorubicins, doxorubicins, detorubicin, other doxorubicin derivatives including morpholino-doxorubicin, cyanomorpholino-doxorubicin, 2-pyrrolino-doxorubicin, deoxydoxorubicin, epirubicin, esorubicin, idarubicin, rodorubicin, zorubicin, and pirarubicin.

In one embodiment, the toxic payload molecule is epirubicin.

In one embodiment, the toxic payload molecule is duocarmycin. Suitable duocarmyxins may be e.g. duocarmycin A, duocarmycin B1, duocarmycin B2, duocarmycin C1, duocarmycin C2, duocarmycin D, duocarmycin SA, duocarmycin MA, and CC-1065. The term "duocarmycin" should be understood as referring also to synthetic analogs of duocarmycins, such as adozelesin, bizelesin, carzelesin, KW-2189 and CBI-TMI.

In one embodiment, the duocarmycin is a duocarmycin suitable for conjugating to the linker group L. In one embodiment, the duocarmycin comprises an amino group or another suitable chemical group for conjugating the duocarmycin to the linker group L. In one embodiment, the amino group is a free amino group.

One skilled in the art of toxic payload molecules will readily understand that each of the toxic payload molecules described herein can be modified in such a manner that the resulting compound still retains the specificity and/or activity of the starting compound. The skilled person will also understand that many of these compounds can be used in place of the toxic payload molecules described herein. Thus, the toxic payload molecules of the present invention should be understood as including any analogues and derivatives of the compounds described herein.

In one embodiment, the glycoprotein-toxic payload molecule conjugate is selected from the group consisting of monomethyldolastatin-aminooxyacetic acid-cetuximab conjugate, monomethylauristatin-aminooxyacetic acid-cetuximab conjugate, monomethyldolastatin-aminooxyacetic acid-levulinyl-cetuximab conjugate, N-(6-N$_3$-Gal)-MODO-(triazole)-ABAA-sialic acid oxime-cetuximab conjugate, N-(6-N$_3$-Gal)-MODO-(triazole)-ABAA-sialic acid oxime-Endo S-treated cetuximab conjugate, triazole conjugate of 9-azido-NeuAc-cetuximab and N-(6-O-propargyl-D-galactosyl)-monomethyldolastatin 10, ABAA-MODO-7-aldehydo-NeuNAc-trastuzumab conjugate, ABAA-MODO-7-aldehydo-NeuNAc-anti-CD33 conjugate, ABAA-MODO-7-aldehydo-NeuNAc-afucosyl trastuzumab conjugate, MODO-TREA-DBCO-9-azido-NeuNAc-G2F-trastuzumab conjugate, MODO-TRSLac-Lys-DBCO-9-azido-NeuNAc-G2F-trastuzumab conjugate, DM1-DBCO-9-azido-NeuNAc-G2F-cetuximab conjugate, MODO-Val-Cit-PAB-DBCO-9-azido-NeuAc-cetuximab conjugate, conjugate of N-(6-O-propargyl-D-galactosyl)-epirubicin and 9-azido-NeuAc-cetuximab, conjugate of N-(6-O-propargyl-D-galactosyl)-doxorubicin and 9-azido-NeuAc-cetuximab, conjugate of N-(6-O-propargyl-D-galactosyl)-daunorubicin and 9-azido-NeuAc-cetuximab, conjugate of N-(6-O-propargyl-D-galactosyl)duocarmycin MA and 9-azido-NeuAc-cetuximab, conjugate of N-(6-O-propargyl-D-galactosyl)duocarmycin and 9-azido-NeuAc-cetuximab, ABAA-MODO-7-aldehydo-NeuNAc-cetuximab and ABAA-MODO-7-aldehydo-NeuNAc-GMC012.

Monomethyldolastatin-aminooxyacetic acid-cetuximab conjugate should be understood as referring to MODO-AOAA-cetuximab conjugate, i.e. the conjugate shown in Scheme 12.

Monomethylauristatin-aminooxyacetic acid-cetuximab conjugate should be understood as referring to MMAF-AOAA-cetuximab conjugate, i.e. the conjugate which has the same structure as the conjugate shown in Scheme 12 except wherein monomethyldolastatin has been replaced with monomethylauristatin.

Monomethyldolastatin-aminooxyacetic acid-levulinyl-cetuximab conjugate should be understood as referring to the conjugate shown in Scheme 12 except wherein cetuximab has been conjugated to levulinic acid. Conjugation of levulinic acid to cetuximab may be performed by amidation of levulinic acid to free amino groups in cetuximab, e.g. as described in Example 24.

N-(6-N$_3$-Gal)-MODO-(triazole)-ABAA-sialic acid oxime-cetuximab conjugate should be understood as referring to the conjugate shown in Scheme 15.

N-(6-N$_3$-Gal)-MODO-(triazole)-ABAA-sialic acid oxime-Endo S-treated cetuximab conjugate should be understood as referring to the conjugate shown in Scheme 15, except that cetuximab has been treated with Endo S.

Triazole conjugate of 9-azido-NeuAc-cetuximab and N-(6-O-propargyl-D-galactosyl)-monomethyldolastatin 10 should be understood as referring to the conjugate shown in Scheme 6.

ABAA-MODO-7-aldehydo-NeuNAc-trastuzumab conjugate should be understood as referring to the conjugate shown in Scheme 16.

ABAA-MODO-7-aldehydo-NeuNAc-anti-CD33 conjugate should be understood as referring to the conjugate the preparation of which is described in Example 42. In the context of this molecule, anti-CD33 should be understood as referring to GCM011.

ABAA-MODO-7-aldehydo-NeuNAc-afucosyl trastuzumab conjugate should be understood as referring to the conjugate the preparation of which is described in Example 44, i.e. to the conjugate shown in Scheme 16 in which trastuzumab is afucosylated.

MODO-TREA-DBCO-9-azido-NeuNAc-G2F-trastuzumab conjugate should be understood as referring to the conjugate shown in Scheme 17.

MODO-TRSLac-Lys-DBCO-9-azido-NeuNAc-G2F-trastuzumab conjugate should be understood as referring to the conjugate shown in Scheme 18.

DM1-DBCO-9-azido-NeuNAc-G2F-cetuximab conjugate should be understood as referring to the conjugate shown in Scheme 19.

MODO-Val-Cit-PAB-DBCO-9-azido-NeuAc-cetuximab conjugate should be understood as referring to the conjugate shown in Scheme 20.

The conjugate of N-(6-O-propargyl-D-galactosyl)-epirubicin and 9-azido-NeuAc-cetuximab should be understood as referring to the conjugate shown in Scheme 21.

The conjugate of N-(6-O-propargyl-D-galactosyl)-doxorubicin and 9-azido-NeuAc-cetuximab should be understood as referring to the conjugate of N-(6-O-propargyl-D-galactosyl)-epirubicin and 9-azido-NeuAc-cetuximab, wherein epirubicin is replaced with doxorubicin.

The conjugate of N-(6-O-propargyl-D-galactosyl)-daunorubicin and 9-azido-NeuAc-cetuximab should be understood as referring to the conjugate of N-(6-O-propargyl-D-galactosyl)-epirubicin and 9-azido-NeuAc-cetuximab, wherein epirubicin is replaced with daunorubicin.

The conjugate of N-(6-O-propargyl-D-galactosyl)duocarmycin MA and 9-azido-NeuAc-cetuximab should be understood as referring to the conjugate shown in Scheme 22.

ABAA-MODO-7-aldehydo-NeuNAc-cetuximab should be understood as referring to the conjugate shown in Scheme 16, wherein trastuzumab is replaced with cetuximab.

ABAA-MODO-7-aldehydo-NeuNAc-GMC012 should be understood as referring to the conjugate shown in Scheme 16, wherein trastuzumab is replaced with GMC012.

In one embodiment, D-L-G is selected from the group consisting of D-aminooxyacetic acid-7-aldehydo-NeuAc, D-aminooxyacetic acid-7-aldehydo-NeuAc, N-(6-N$_3$-Gal)-D-(triazole)-ABAA-sialic acid oxime, N-(6-N$_3$-Gal)-D-(triazole)-ABAA-sialic acid oxime, triazole conjugate of 9-azido-NeuAc and N-(6-O-propargyl-D-galactosyl)-D, ABAA-D-7-aldehydo-NeuNAc, D-TREA-DBCO-9-azido-NeuNAc, D-TRSLac-Lys-DBCO-9-azido-NeuNAc, D-DBCO-9-azido-NeuNAc, D-Val-Cit-PAB-DBCO-9-azido-NeuAc, conjugate of N-(6-O-propargyl-D-galactosyl)-D and 9-azido-NeuAc, conjugate of N-(6-O-propargyl-D-galactosyl)-D and 9-azido-NeuAc, conjugate of N-(6-O-propargyl-D-galactosyl)-D and 9-azido-NeuAc, conjugate of N-(6-O-propargyl-D-galactosyl)-D and 9-azido-NeuAc, and conjugate of N-(6-O-propargyl-D-galactosyl)-D and 9-azido-NeuAc, wherein D is a toxic payload molecule. In this embodiment, D may be any toxic payload molecule described in this document.

In one embodiment, D-L-G is selected from the group consisting of monomethyldolastatin-aminooxyacetic acid-7-aldehydo-NeuAc, monomethylauristatin-aminooxyacetic acid-7-aldehydo-NeuAc, N-(6-N$_3$-Gal)-MODO-(triazole)-ABAA-sialic acid oxime, N-(6-N$_3$-Gal)-MODO-(triazole)-ABAA-sialic acid oxime, triazole conjugate of 9-azido-NeuAc and N-(6-O-propargyl-D-galactosyl)-monomethyldolastatin 10, ABAA-MODO-7-aldehydo-NeuNAc, MODO-TREA-DBCO-9-azido-NeuNAc, MODO-TRSLac-Lys-DBCO-9-azido-NeuNAc, DM1-DBCO-9-azido-NeuNAc, MODO-Val-Cit-PAB-DBCO-9-azido-NeuAc, conjugate of N-(6-O-propargyl-D-galactosyl)-epirubicin and 9-azido-NeuAc, conjugate of N-(6-O-propargyl-D-galactosyl)-doxorubicin and 9-azido-NeuAc, conjugate of N-(6-O-propargyl-D-galactosyl)-daunorubicin and 9-azido-NeuAc, conjugate of N-(6-O-propargyl-D-galactosyl)duocarmycin MA and 9-azido-NeuAc, and conjugate of N-(6-O-propargyl-D-galactosyl)duocarmycin and 9-azido-NeuAc.

The present invention further relates to a method for preparing a glycoprotein-toxic payload molecule conjugate according to one or more embodiments of the invention, wherein the method comprises the steps of:

providing a glycoprotein comprising an N-glycan comprising an acceptor site; and reacting a donor molecule with the glycoprotein comprising an N-glycan comprising an acceptor site in the presence of a glycosyltransferase;

wherein the donor molecule is represented by formula XI

L'-G      Formula XI wherein G is a saccharide structure represented by formula XII

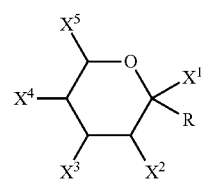

Formula XII wherein
R is CMP, UDP or GDP;
$X^1$ is H or carboxyl;
$X^2$, $X^3$ and $X^4$ are each independently OH, H, amino, $C_2$-$C_6$ acylamide, phosphate or sulphate ester, or a bond to L';
$X^5$ is $CH_2OH$, carboxyl, $CH_3$, H, $C_1$-$C_3$ alkyl or substituted $C_1$-$C_3$ alkyl, or a bond to L';
with the proviso that one substituent selected from $X^2$, $X^3$, $X^4$ and $X^5$ is a bond to L' or bonded via a bond to L';
with the proviso that when $X^1$ is carboxyl, then $X^2$ is H, $X^3$ is OH, $X^5$ is $C_1$-$C_3$ alkyl or substituted $C_1$-$C_3$ alkyl; R is CMP;
and $X^4$ is a bond to L' or $X^5$ is bonded via a bond to L';
or
when $X^1$ is H, then R is UDP or GDP;
and wherein
L' is D-L, wherein D is a toxic payload molecule and L is a linker group covalently joining G to D, or L' comprises F-E, wherein F is a functional group that can react with an amine, thiol, azide, alkene, alkyne, aldehyde, ketone, carboxylic acid or hydroxylamine, and E is absent or a polyethyleneoxy unit of formula $(CH_2CH_2O)_p$, wherein p is an integer from 2 to about 20.

The donor molecule may thus comprise the linker group and the toxic payload molecule, or it may comprise a functional group to which a compound comprising the linker group and the toxic payload molecule may be conjugated at a later step.

The functional group may be selected e.g. so that the product of the method, i.e. a glycoprotein-donor molecule conjugate, may be linked to a molecule comprising the linker group and the toxic payload molecule by utilizing click conjugation such as copper(I)-catalysed azide-alkyne cycloaddition reaction (CuAAC). Click conjugation such as copper-free click chemistry may also be utilized.

In one embodiment, L' is D-L, wherein D is a toxic payload molecule and L is a linker group covalently joining G to D. This embodiment has the added utility that no further steps are necessary for the preparation of the glycoprotein-toxic payload molecule conjugate.

In one embodiment, L' comprises F-E, wherein F is a functional group that can react with an amine, thiol, azide, alkene, alkyne, aldehyde, ketone, carboxylic acid or hydroxylamine, and E is absent or a polyethyleneoxy unit of formula $(CH_2CH_2O)_p$, wherein p is an integer from 2 to about 20. This embodiment has the added utility that the toxic payload molecule may be conjugated in a later step.

In one embodiment, the functional group that can react with an amine, thiol, azide, alkene, alkyne, aldehyde, ketone, carboxylic acid or hydroxylamine is an amine, thiol, azide, alkene, alkyne, aldehyde, ketone, carboxylic acid or hydroxylamine.

In one embodiment, the functional group is a cyclooctyne or a derivative thereof, such as a dibenzocyclooctyl group (DBCO).

In this context, the abbreviation "CMP" should be understood as referring to cytidine monophosphate.

In this context, the abbreviation "UDP" should be understood as referring to uridine diphosphate.

In this context, the abbreviation "GDP" should be understood as referring to guanidine diphosphate.

In one embodiment, the method comprises the following steps in the following order:
  providing a glycoprotein comprising an N-glycan comprising an acceptor site; and
  reacting a donor molecule with the glycoprotein comprising an N-glycan comprising an acceptor site in the presence of a glycosyltransferase;
  wherein the donor molecule is represented by formula XI as described above.

The glycoprotein may, in principle, be any glycoprotein described in this document.

In this context, the term "acceptor site" should be understood as referring to a saccharide residue of the N-glycan to which the donor molecule may be conjugated using a glycosyltransferase.

In principle, the N-glycan may be any N-glycan described in this document, provided it comprises an acceptor site.

In this context, the term "an acceptor site" should be understood as referring to one or more acceptor sites.

In one embodiment, the acceptor site is a sialyltransferase acceptor site or a GlcNAc residue bound by a β-N linkage to an asparagine.

In one embodiment, the acceptor site is a sialyltransferase acceptor site selected from the group consisting of Galβ, Galβ4GlcNAc, Galβ3GlcNAc, Galβ3GalNAc, GalNAcβ, GalNAcα, GalNAcβ4GlcNAc and sialic acid.

In one embodiment, the acceptor site is a terminal Galβ residue.

In one embodiment, the acceptor site is a GlcNAc residue bound by a β-N linkage to an asparagine.

In one embodiment, the glycoprotein comprises one, two, three, four or more N-glycans comprising an acceptor site.

In one embodiment, the glycoprotein comprises one, two, three, four, five, six, seven, eight or more acceptor sites.

In one embodiment, the N-glycan comprises one, two or more acceptor sites.

In one embodiment, the method comprises the step of providing a composition including a glycoprotein comprising an N-glycan comprising an acceptor site.

In one embodiment, at least 50%, or at least 60%, or at least 70%, or at least 80%, or at least 90%, or at least 95%, or at least 98%, or at least 99% of all glycoproteins of the composition comprising an N-glycan comprise an N-glycan comprising at least one acceptor site.

In one embodiment, at least 50%, or at least 60%, or at least 70%, or at least 80%, or at least 90%, or at least 95%, or at least 98%, or at least 99%, or essentially 100% of all glycoproteins of the composition comprising an N-glycan comprise at least one acceptor site.

In one embodiment, at least 50%, or at least 60%, or at least 70%, or at least 80%, or at least 90%, or at least 95%, or at least 98%, or at least 99%, or essentially 100% of all glycoproteins of the composition comprising an N-glycan comprise at least two N-glycans comprising at least one acceptor site.

In one embodiment, at least 50%, or at least 60%, or at least 70%, or at least 80%, or at least 90%, or at least 95%, or at least 98%, or at least 99% of all glycoproteins of the composition comprising an N-glycan comprise two acceptor sites.

In one embodiment, at least 50%, or at least 60%, or at least 70%, or at least 80%, or at least 90%, or at least 95%, or at least 98%, or at least 99% of all glycoproteins of the composition comprising an N-glycan comprise at least one terminal Galβ residue.

In one embodiment, at least 50%, or at least 60%, or at least 70%, or at least 80%, or at least 90%, or at least 95%, or at least 98%, or at least 99% of all glycoproteins of the composition comprising an N-glycan comprise at least two N-glycans comprising at least one terminal Galβ residue.

In one embodiment, at least 50%, or at least 60%, or at least 70%, or at least 80%, or at least 90%, or at least 95%, or at least 98%, or at least 99% of all glycoproteins of the composition comprising an N-glycan comprise two terminal Galβ residues.

In one embodiment, at least 50%, or at least 60%, or at least 70%, or at least 80%, or at least 90%, or at least 95%, or at least 98%, or at least 99% of all glycoproteins of the composition comprising an N-glycan comprise at least one terminal Galβ residue.

In one embodiment, at least 50%, or at least 60%, or at least 70%, or at least 80%, or at least 90%, or at least 95%, or at least 98%, or at least 99% of all glycoproteins of the composition comprising an N-glycan comprise an N-glycan consisting of the structure represented by formula IV.

In this context, the term "glycosyltransferase" should be understood as referring to any enzyme capable of conjugating the donor molecule to the acceptor site.

In one embodiment, the glycosyltransferase is a sialyltransferase, a galactosyltransferase or an N-acetylhexosaminyltransferase.

In one embodiment, the glycosyltransferase is selected from the group consisting of α2,6-sialyltransferases such as human ST6GAL1; α2,3-sialyltransferases such as rat α2,3-N-sialyltransferase; galactosyltransferases such as human β1,4-GalT1, human β1,4-GalT2, bovine milk β1,4-GalT and bovine β1,4-GalT1; and N-acetylhexosaminyltransferases such as human β1,4-GalT1(Y285L) and bovine β1,4-GalT1 (Y289L).

In one embodiment, the glycosyltransferase is selected from the group consisting of human ST6GAL1, rat α2,3-N-sialyltransferase, human β1,4-GalT1, human β1,4-GalT2, bovine milk β1,4-GalT, bovine β1,4-GalT1, human β1,4-GalT1(Y285L) and bovine β1,4-GalT1(Y289L).

In one embodiment, $X^1$ is carboxyl, $X^2$ is H; $X^3$ is OH; $X^4$ is OH, H, amino, $C_2$-$C_6$ acylamide, or a bond to L; $X^5$ is $C_1$-$C_3$ alkyl or substituted $C_1$-$C_3$ alkyl; R is a glycosidic bond to the N-glycan; and either $X^4$ is a bond to L or $X^5$ is bonded via a bond to L.

In one embodiment, $X^1$ is H and $X^5$ is a bond to L' or bonded via a bond to L'.

In one embodiment, $X^1$ is H, the anomeric structure of G is β-D-galacto configuration and $X^5$ is a bond to L' or bonded via a bond to L'.

In one embodiment, $X^1$ is H, the anomeric structure of G is β-D-gluco configuration and $X^5$ is a bond to L' or bonded via a bond to L'.

In one embodiment, $X^1$ is H, the anomeric structure of G is β-D-galacto configuration, $X^3$ and $X^4$ are OH groups, and $X^5$ is a bond to L' or bonded via a bond to L'.

In one embodiment, $X^1$ is H, the anomeric structure of G is β-D-galacto configuration, $X^2$ and $X^3$ and $X^4$ are OH groups, and $X^5$ is a bond to L' or bonded via a bond to L'.

In one embodiment, $X^1$ is H, the anomeric structure of G is β-D-galacto or β-D-gluco configuration, $X^2$ is an acetamido group, $X^3$ and $X^4$ are OH groups, and $X^5$ is a bond to L' or bonded via a bond to L'.

In one embodiment, G is a saccharide structure represented by formula XIII

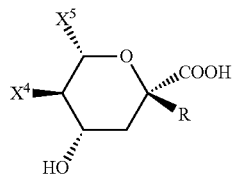

Formula XIII wherein
R is CMP;
$X^4$ is OH, H, amino, $C_2$-$C_6$ acylamide, phosphate or sulphate ester, or a bond to L';
$X^5$ is $C_1$-$C_3$ alkyl or substituted $C_1$-$C_3$ alkyl;
and $X^4$ is a bond to L' or $X^5$ is bonded via a bond to L'; and
the glycosyltransferase is a sialyltransferase.

In one embodiment, G is a saccharide structure represented by formula XIII, wherein $X^5$ is bonded via a bond to L'. In one embodiment, the bond between $X^5$ and L' is an oxime bond. In one embodiment, the bond between $X^5$ and L' is a triazole bond.

A suitable sialyltransferase may be e.g. human ST6Gal1 α2,6-sialyltransferase or rat α2,3-N-sialyltransferase.

In one embodiment, G is a saccharide structure represented by formula XIII

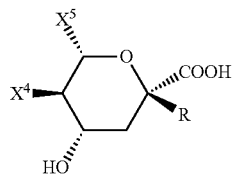

Formula XIII wherein
R is CMP;
$X^4$ is OH, H, amino, $C_2$-$C_6$ acylamide, phosphate or sulphate ester, or a bond to L';
$X^5$ is $C_1$-$C_3$ alkyl or substituted $C_1$-$C_3$ alkyl;
and $X^4$ is a bond to L' or $X^5$ is bonded via a bond to L';
L' is D-L, wherein D is a toxic payload molecule and L is a linker group covalently joining G to D; and
the glycosyltransferase is a sialyltransferase.

In one embodiment, G is a saccharide structure represented by formula XIII, wherein $X^5$ is bonded via a bond to D-L, wherein D is a toxic payload molecule and L is a linker group covalently joining G to D. In one embodiment, the bond between $X^5$ and D-L is an oxime bond. In one embodiment, the bond between $X^5$ and D-L is a triazole bond.

In one embodiment, G is a saccharide structure represented by formula XIII

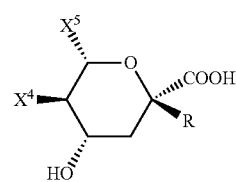

Formula XIII wherein
R is CMP;
$X^4$ is OH, H, amino, $C_2$-$C_6$ acylamide, phosphate or sulphate ester, or a bond to L';
$X^5$ is $C_1$-$C_3$ alkyl or substituted $C_1$-$C_3$ alkyl;
and $X^4$ is a bond to L' or $X^5$ is bonded via a bond to L';
L' comprises F-E, wherein F is a functional group that can react with an amine, thiol, azide, alkene, alkyne, aldehyde, ketone, carboxylic acid or hydroxylamine, and E is absent or a polyethyleneoxy unit of formula $(CH_2CH_2O)_p$, wherein p is an integer from 2 to about 20; and
the glycosyltransferase is a sialyltransferase.

In one embodiment, $X^5$ is a bond to L' or bonded via a bond to L'.

In one embodiment, $X^5$ is $CH(OH)CH(OH)CH_2X^9$, wherein $X^9$ is a bond to L'. In one embodiment, the bond to L' is an oxime bond. In one embodiment, the bond to L' is a triazole bond.

In one embodiment, $X^4$ is a $C_2$ acylamido group such as acetamido group, and $X^5$ is $CH(OH)CH(OH)CH_2X^9$, wherein $X^9$ is a bond to L'. In one embodiment, the bond to L' is an oxime bond. In one embodiment, the bond to L' is a triazole bond.

In one embodiment, $X^4$ is a $C_2$ acylamido group such as acetamido group, and $X^5$ is $CH(OH)CH(OH)CH_2X^9$, wherein $X^9$ is a bond to L'. In one embodiment, the bond to L' is an oxime bond. In one embodiment, the bond to L' is a triazole bond.

In one embodiment, $X^5$ is $CH_2X^7$, wherein $X^7$ is a bond to L'. In one embodiment, the bond to L' is an oxime bond. In one embodiment, the bond to L' is a triazole bond.

In one embodiment, $X^4$ is a $C_2$ acylamido group such as acetamido group, and $X^5$ is $CH_2X^7$, wherein $X^7$ is a bond to L'. In one embodiment, the bond to L' is an oxime bond. In one embodiment, the bond to L' is a triazole bond.

In one embodiment, $X^4$ is a $C_2$ acylamido group such as acetamido group, and $X^5$ is $CH_2X^7$, wherein $X^7$ is a bond to L'. In one embodiment, the bond to L' is an oxime bond. In one embodiment, the bond to L' is a triazole bond.

In one embodiment, structures according to the invention wherein $X^5$ is $CH_2X^7$, wherein $X^7$ is a bond to L', are generated by mild periodate oxidation and specific cleavage of the bond between sialic acid C-7 and C-8. In one embodiment, the mild periodate oxidation and specific cleavage of the bond between sialic acid C-7 and C-8 is performed as set forth in the Examples of the present invention. In one embodiment, the mild periodate oxidation is performed to whole glycoprotein. In one embodiment, the mild periodate oxidation is optimized so that other glycan residues are not oxidized. In one embodiment, the mild periodate oxidation is optimized so that other functional groups in the glycoprotein are not oxidized. In one embodiment, the mild periodate oxidation is optimized so that other functional groups in the glycoprotein are not oxidized.

In one embodiment, $X^4$ is a bond to L' or bonded via a bond to L'.

In one embodiment, $X^4$ is a bond to L' or bonded via a bond to L', and $X^5$ is CH(OH)CH(OH)CH$_2$OH.

In one embodiment, $X^4$ is NH(CO)$_{n1'}$(CH$_2$)$_{n2'}$X$^{4'}$(CH$_3$)$_{n3'}$, wherein $X^{4'}$ is a bond to L', n1' is 0 or 1, n2' is an integer between 1 and about 6, and n3' is 0 or 1. In one embodiment, $X^5$ is CH(OH)CH(OH)CH$_2$OH.

In one embodiment, $X^4$ is NHCOCH$_2$CH$_2$X$^{4'}$CH$_3$, wherein $X^{4'}$ is a bond to L'. In one embodiment, structures according to the invention wherein $X^4$ is NHCOCH$_2$CH$_2$X$^{4'}$CH$_3$, wherein $X^{4'}$ is a bond to L', are generated by reaction with the carbonyl group in NH(C=O)CH$_2$CH$_2$COCH$_3$. In one embodiment, the bond to L' is an oxime bond.

In one embodiment, the anomeric structure of the $X^5$ substituent in structures according to Formula XIII is as in neuraminic acid and as set forth in the Example 3.

In one embodiment, the anomeric structure of G and the substituents $X^2$, $X^3$, $X^4$ and $X^5$ are selected according to stability assays in serum or plasma in neutral pH and hydrolysis assays in presence of lysosomal glycohydrolases in acidic pH.

In one embodiment, the anomeric structure of G and the substituents $X^2$, $X^3$, $X^4$ and $X^5$ are selected according to high stability in serum and plasma as set forth in Example 15.

In one embodiment, the anomeric structure of G and the substituents $X^2$, $X^3$, $X^4$ and $X^5$ are selected according to high rate of hydrolysis in presence of lysosomal glycohydrolases in acidic pH as set forth in Example 16.

In one embodiment, the anomeric structure of G and the substituents $X^2$, $X^3$, $X^4$ and $X^5$ are selected according to high stability in serum and plasma as set forth in Example 15 and according to high rate of hydrolysis in presence of lysosomal glycohydrolases in acidic pH as set forth in Example 16.

In one embodiment, the N-glycan consists of the structure represented by formula IV

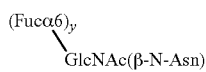

Formula IV wherein (β-N-Asn) is a β-N linkage to an asparagine and y is 0 or 1;
and wherein
$X^1$ is H;
$X^2$, $X^3$ and $X^4$ are each independently OH, H, amino, $C_2$-$C_6$ acylamide, phosphate or sulphate ester, or a bond to L';
$X^5$ is CH$_2$OH, carboxyl, CH$_3$, H, $C_1$-$C_3$ alkyl or substituted $C_1$-$C_3$ alkyl, or a bond to L';
with the proviso that one substituent selected from $X^2$, $X^3$, $X^4$ and $X^5$ is a bond to L' or bonded via a bond to L'; and
R is UDP or GDP.

In one embodiment, the N-glycan consists of the structure represented by formula IV

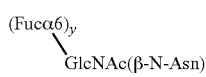

Formula IV wherein (β-N-Asn) is a β-N linkage to an asparagine and y is 0 or 1;
and wherein
$X^1$ is H;
$X^2$, $X^3$ and $X^4$ are each independently OH, H, amino, $C_2$-$C_6$ acylamide, phosphate or sulphate ester, or a bond to L';
$X^5$ is CH$_2$OH, carboxyl, CH$_3$, H, $C_1$-$C_3$ alkyl or substituted $C_1$-$C_3$ alkyl, or a bond to L';
with the proviso that one substituent selected from $X^2$, $X^3$, $X^4$ and $X^5$ is a bond to L' or bonded via a bond to L';
R is UDP; and
the glycosyltransferase is a galactosyltransferase or an N-acetylhexosaminyltransferase.

Suitable galactosyltransferases are e.g. human β1,4-GalT1, human β1,4-GalT2, bovine milk β1,4-GalT or bovine β1,4-GalT1; and suitable N-acetylhexosaminyltransferases are e.g. human β1,4-GalT1(Y285L) and bovine β1,4-GalT1(Y289L).

In one embodiment, the donor molecule is selected from the group consisting of CMP-9-azido-Neu5Ac, UDP-6-propargyl-Gal and UDP-2-(2-azidoacetamido)-2-deoxy-Gal (UDP-GalNAz).

Any glycoprotein comprising an N-glycan comprising one or more acceptor sites may be provided.

In one embodiment, the glycoprotein comprises naturally an N-glycan comprising an acceptor site.

In one embodiment, the glycoprotein comprising an N-glycan comprising an acceptor site is produced in a suitable cell line.

The suitable cell line may be modified so as to produce N-glycans comprising a higher number or proportion of acceptor sites.

Cells or cell lines providing glycoproteins of the invention include but are not limited to mammalian cells, mammalian cell lines modified so as to produce N-glycans comprising a higher number or proportion of terminal Galβ residues as compared to an unmodified cell line (such as galactosylation-optimized CHO cell lines provided by ProBioGen AG, Switzerland), mammalian cell lines modified so as to produce N-glycans comprising a lower number or proportion of terminal Galβ residues as compared to an unmodified cell line (such as antibody producing CHO—S cell lines generated in Example 13), mammalian cell lines modified so as to produce N-glycans comprising lowered amounts of or essentially no fucose, and fungal or yeast or yeast cells which are engineered to express e.g. endoglycosidases (e.g. as disclosed in WO 2010015722).

In one embodiment of the invention, glycosylation in the cell line producing the glycoprotein is modified by use of glycosidase inhibitors. Numerous glycosidase inhibitors useful for the invention and effective concentrations for their application in the culture medium are known to a person skilled in the art. In one embodiment, N-glycan core fucosylation of the glycoprotein is inhibited by a fucosylation inhibitor. In one embodiment, N-glycan core fucosylation is inhibited by addition of about 50 μM peracetylated 2-deoxy-2-fluoro-L-fucose to CHO cell culture medium to produce acceptor sites according to Formula IV wherein y is 0.

All N-glycans do not comprise an acceptor site; furthermore, only a subset of N-glycans present in many glycoproteins comprises one or more suitable acceptor sites. In order to provide a glycoprotein comprising an N-glycan comprising one or more acceptor sites, a glycoprotein comprising an N-glycan may be trimmed or modified to comprise one or more suitable acceptor sites.

In one embodiment, the glycoprotein comprising an N-glycan comprising an acceptor site is prepared by contacting a glycoprotein comprising an N-glycan with a glycosidase.

In one embodiment, the glycosidase is a sialidase, an α-galactosidase, a β-galactosidase, an endoglycosidase, a glycoside hydrolase or a fucosidase.

In one embodiment, the glycosidase is a sialidase such as Sialidase A available from Glyko. This embodiment has the added utility that e.g. terminal NeuAc and NeuGc residues present in many biantennary complex type N-glycans may be removed in order to expose acceptor sites such as terminal Galβ residues.

In one embodiment, the glycosidase is an α-galactosidase such as α-galactosidase from green coffee beans available from e.g. Sigma.

In one embodiment, the glycosidase is a β-galactosidase such as β1,4-galactosidase from S. pneumoniae and β-galactosidase from Jack beans available from Sigma.

In one embodiment, the glycosidase is an endoglycosidase.

This embodiment has the added utility that e.g. the bulk of heterogeneous N-glycan structures may be removed in order to expose an acceptor site such as a GlcNAc residue bound by a β-N linkage to an asparagine. This embodiment also allows for producing a glycoprotein comprising an N-glycan consisting of the structure represented by formula IV.

Figure 15:
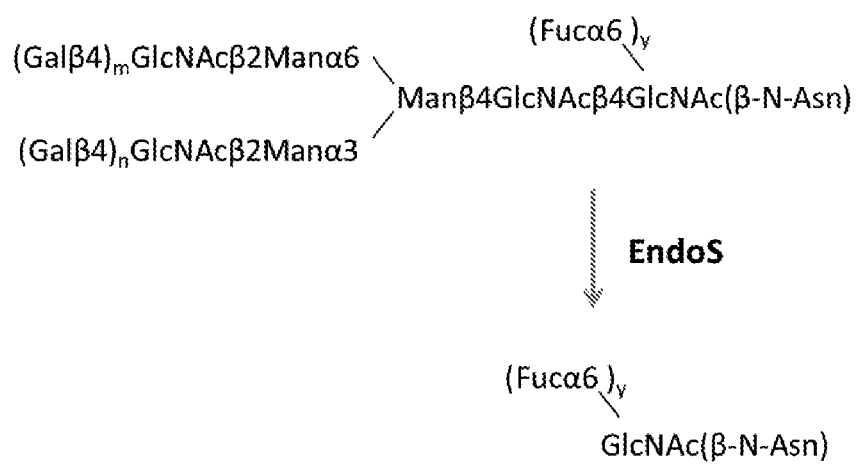
FIG. 15 shows an exemplary reaction.

An exemplary reaction of one such embodiment is shown in FIG. 15 wherein y is 0 or 1; and m and n are each independently 0 or 1.

Suitable endoglycosidases may be e.g. endoS, endoS2, endoT, endoH, endoA, endoB, endoF1, endoF2, endoF3 and endoD. The use of endoS for deglycosylating antibodies is described e.g. in publications WO 2009033670 and WO 2013037824. The use of endoS2 for deglycosylating antibodies can be performed with e.g. GlycINATOR enzyme available from Genovis, Sweden, according to the manufacturer's instructions.

EndoS and endoS2 have specificity to antibody Fc domain N-glycans at the conserved glycosylation site (Asn297). In order to hydrolyse N-glycans in other glycoproteins or other N-glycosylation sites in antibodies, another endoglycosidase may be selected. In order to hydrolyse N-glycans in the Fc domain and other N-glycosylation sites in antibodies simultaneously, a combination of endoS or endoS2 and another endoglycosidase may be selected.

Endoglycosidases are known to have distinct glycan substrate specificities. Based on the known specificities and the N-glycan structures present in the glycoprotein to be modified, a person skilled in the art can select a suitable endoglycosidase or a combination of suitable endoglycosidases to hydrolyse the glycoprotein and to produce a high number of acceptor sites to the glycoprotein.

In one embodiment, the glycosidase is a glycoside hydrolase.

Suitable glycoside hydrolases may be e.g. glycoside hydrolases of family 18 (described e.g. on the web page http://www.cazy.org/GH18_all.html) and 85 (described e.g. on the web page http://www.cazy.org/GH85_all.html).

In one embodiment, the glycosidase is a fucosidase such as fucosidase from almonds.

In one embodiment, the glycoprotein comprising an N-glycan comprising an acceptor site is prepared by contacting a glycoprotein comprising an N-glycan with more than one glycosidase. The glycosidases may be selected so as to obtain an optimal number or proportion of acceptor sites in the N-glycans of the glycoprotein.

In one embodiment, the glycoprotein comprising an N-glycan comprising an acceptor site is prepared by contacting a glycoprotein comprising an N-glycan with a glycosyltransferase and a substrate for the glycosyltransferase.

In one embodiment, the glycosyltransferase is a galactosyltransferase and the substrate for the glycosyltransferase is UDP-Gal. This embodiment has the added utility that a higher number or proportion of terminal Galβ residues in the N-glycans of the glycoprotein may be produced.

Suitable galactosyltransferases are e.g. human β1,4-GalT1, human β1,4-GalT2, bovine milk β1,4-GalT or bovine β1,4-GalT1.

Figure 16:
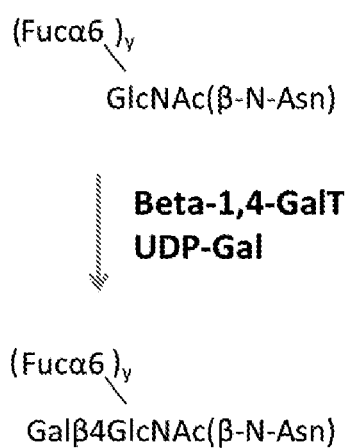
FIG. 16 shows an exemplary reaction.

An exemplary reaction of one such embodiment is shown in FIG. 16 wherein y is 0 or 1.

In one embodiment, the glycoprotein comprising an N-glycan comprising an acceptor site is prepared by contacting a glycoprotein comprising an N-glycan with an endoglycosidase and a glycosyltransferase.

In one embodiment, the glycoprotein comprising an N-glycan comprising an acceptor site is prepared by contacting a glycoprotein comprising an N-glycan with an endoglycosidase such as endoS and a galactosyltransferase.

In one embodiment, the glycoprotein comprising an N-glycan comprising an acceptor site is prepared by contacting a glycoprotein comprising an N-glycan with an endoglycosidase, a galactosyltransferase and a substrate for the galactosyltransferase. In one embodiment, the endoglycosidase is endoS. In one embodiment, the galactosyltransferase is β1,4-GalT. In one embodiment, the substrate for the galactosyltransferase is UDP-Gal.

Figure 17:
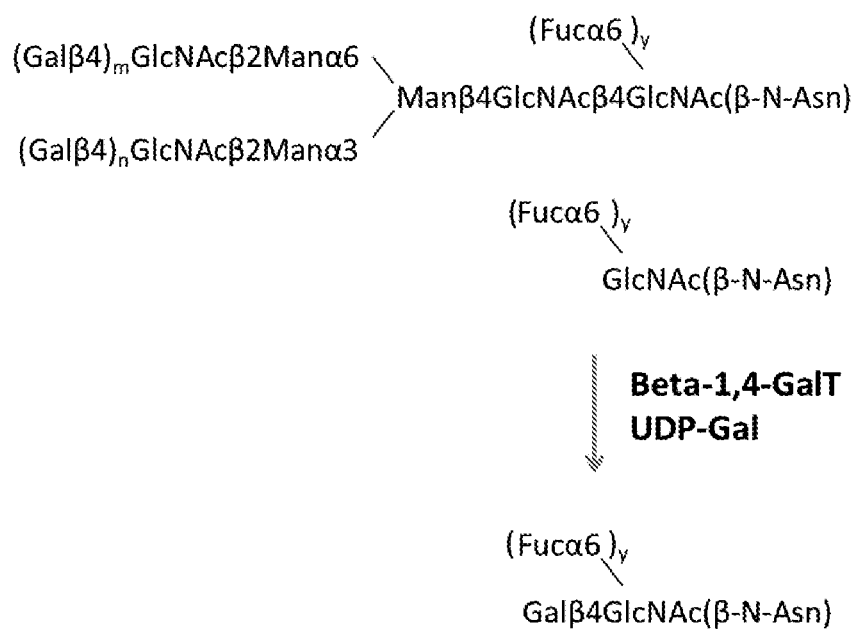
FIG. 17 shows an exemplary reaction.

An exemplary reaction of one such embodiment is shown in FIG. 17 wherein y is 0 or 1; and m and n are each independently 0 or 1.

In one embodiment, L' is F-E, and the method further comprises the step of:

reacting a product obtainable by the method according to one or more embodiments of the method with a compound represented by formula XIV

D-L-L"  Formula XIV wherein D is the toxic payload molecule;

L is the linker group covalently joining L" to D; and

L" is an amine, thiol, azide, alkene, alkyne, aldehyde, ketone, carboxylic acid or hydroxylamine.

A person skilled in the art is capable of selecting each of F and L" so that they are capable of reacting with each other.

In the context of the present method, L should be understood as referring to any linker group as described above.

In the context of the present method, the glycoprotein should be understood as referring to any glycoprotein as described above.

Further, the toxic payload molecule should be understood as referring to any toxic payload molecule as defined above.

The method may further comprise e.g. a step of purifying the glycoprotein-toxic payload molecule conjugate obtained.

The present invention also relates to a pharmaceutical composition comprising the glycoprotein-toxic payload molecule conjugate or toxic payload molecule-glycan conjugate according to one or more embodiments of the invention.

The pharmaceutical composition of the present invention may further comprise a pharmaceutically acceptable carrier. Examples of suitable pharmaceutically acceptable carriers are well known in the art and include e.g. phosphate buffered saline solutions, water, oil/water emulsions, wetting agents, and liposomes. Compositions comprising such carriers may be formulated by methods well known in the art. The pharmaceutical composition may further comprise other components such as vehicles, additives, preservatives, other pharmaceutical compositions administrated concurrently, and the like.

In one embodiment, the pharmaceutical composition comprises an effective amount of the glycoprotein-toxic payload molecule conjugate or toxic payload molecule-glycan conjugate according to one or more embodiments of the invention.

In one embodiment, the pharmaceutical composition comprises a therapeutically effective amount of the glycoprotein-toxic payload molecule conjugate or toxic payload molecule-glycan conjugate according to one or more embodiments of the invention.

The term "therapeutically effective amount" or "effective amount" of the glycoprotein-toxic payload molecule conjugate or the toxic payload molecule-glycan conjugate should be understood as referring to the dosage regimen for modulating the growth of cancer cells and/or treating a patient's disease. The therapeutically effective amount may be selected in accordance with a variety of factors, including the age, weight, sex, diet and medical condition of the patient, the severity of the disease, the route of administration, and pharmacological considerations, such as the activity, efficacy, pharmacokinetic and toxicology profiles of the particular conjugate used. The therapeutically effective amount can also be determined by reference to standard medical texts, such as the Physicians Desk Reference 2004. The patient may be an animal, a mammal, or a human. The patient may also be male or female, and may be an infant, child or adult.

In the context of this invention the term "treatment" or "treat" is used in the conventional sense and means attending to, caring for and nursing a patient with the aim of combating, reducing, attenuating or alleviating an illness or health abnormality and improving the living conditions impaired by this illness, such as, for example, with a cancer disease.

In one embodiment, the pharmaceutical composition comprises a composition for e.g. oral, parenteral, transdermal, intraluminal, intraarterial, intrathecal and/or intranasal administration or for direct injection into tissue. Administration of the pharmaceutical composition may be effected in different ways, e.g. by intravenous, intraperitoneal, subcutaneous, intramuscular, topical or intradermal administration.

The present invention also relates to a method for modulating the growth of a cell population expressing a target molecule, wherein the method comprises the step of contacting the glycoprotein-toxic payload molecule conjugate or the toxic payload molecule-glycan conjugate according to one or more embodiments of the invention or the pharmaceutical composition according to the invention with the cell population.

In this context, the term "a cell population" should be understood as referring to one or more cell populations.

In this context, the term "a target molecule" should be understood as any target molecule as defined above.

The glycoprotein-toxic payload molecule conjugate or the toxic payload molecule-glycan conjugate may be contacted in vitro, in vivo and/or ex vivo to with the cell population, for example, cancer cells, including, for example, cancer of the blood, plasma, lung, breast, colon, prostate, kidney, pancreas, brain, bones, ovary, testes, and lymphatic organs; more preferably lung, colon prostate, plasma, blood or colon cancer; or in autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like; or, for example, low density lipoprotein receptor-related protein-1 LRP-1 expressing cells such as fibrosarcoma cells. "Modulating the growth of cell populations" includes inhibiting the proliferation of cell populations, for example, tumour cell populations (e.g., multiple myeloma cell populations, such as MOLP-8 cells, OPM2 cells, H929 cells, and the like) from dividing to produce more cells; reducing the rate of increase in cell division as compared, for example, to untreated cells; killing cell populations; and/or preventing cell populations (such as cancer cells) from metastasizing. The growth of cell populations may be modulated in vitro, in vivo or ex vivo.

In one embodiment, the cell population is a cancer cell population.

The present invention further relates to the glycoprotein-toxic payload molecule conjugate or the toxic payload molecule-glycan conjugate according to one or more embodiments of the invention for use as a medicament.

The present invention further relates to the glycoprotein-toxic payload molecule conjugate or the toxic payload molecule-glycan conjugate according to one or more embodiments of the invention for use in therapy.

The present invention further relates to the glycoprotein-toxic payload molecule conjugate or the toxic payload molecule-glycan conjugate according to one or more embodiments of the invention for use in the treatment of cancer.

The present invention further relates to the use of the glycoprotein-toxic payload molecule conjugate or the toxic payload molecule-glycan conjugate according to one or more embodiments of the invention for the manufacture of a medicament.

The present invention further relates to the use of the glycoprotein-toxic payload molecule conjugate or the toxic payload molecule-glycan conjugate according to one or more embodiments of the invention for the manufacture of a medicament for the treatment of cancer.

In one embodiment, the cancer is selected from the group consisting of leukemia, lymphoma, breast cancer, prostate cancer, ovarian cancer, colorectal cancer, gastric cancer, squamous cancer, small-cell lung cancer, head-and-neck cancer, multidrug resistant cancer and testicular cancer.

The present invention further relates to a method of treating and/or modulating the growth of and/or prophylaxis of tumour cells in humans or animals, wherein the glycoprotein-toxic payload molecule conjugate, the toxic payload molecule-glycan conjugate or the pharmaceutical composition according to one or more embodiments of the invention is administered to a human or animal in an effective amount.

In one embodiment, the tumour cells are selected from the group consisting of leukemia cells, lymphoma cells, breast cancer cells, prostate cancer cells, ovarian cancer cells, colorectal cancer cells, gastric cancer cells, squamous cancer cells, small-cell lung cancer cells, head-and-neck cancer cells, multidrug resistant cancer cells, and testicular cancer cells, or metastatic, advanced, drug- or hormone-resistant, or multidrug resistant cancer cells, or versions thereof.

The present invention further relates to a method of treating cancer in humans or animals, wherein the glycoprotein-toxic payload molecule conjugate or the toxic payload molecule-glycan conjugate according to one or more embodiments of the invention is administered to a human or animal in an effective amount.

In one embodiment, a glycoprotein-toxic payload molecule conjugate, a toxic payload molecule-glycan conjugate or a pharmaceutical composition according to one or more embodiments of the invention can also be used to effectively treat drug resistant cancers, including multidrug resistant cancers, "multidrug resistance" meaning the resistance of cancer cells to more than one chemotherapeutic agent. Multidrug resistance may be aided e.g. by a P-glycoprotein transmembrane pump that lowers the concentration of drugs in the cell. As is known in the art, the resistance of cancer cells to chemotherapy is one of the central problems in the management of cancer. Certain cancers, such as prostate and breast cancer can be treated by hormone therapy, i.e. with hormones or anti-hormone drugs that slow or stop the growth of certain cancers by blocking the body's natural hormones. Such cancers may develop resistance, or be intrinsically resistant, to hormone therapy. The present invention further contemplates the use of a glycoprotein-toxic payload molecule conjugate, a toxic payload molecule-glycan conjugate or a pharmaceutical composition according to one or more embodiments of the invention in the treatment of these "hormone-resistant" or "hormone-refractory" cancers.

In one embodiment, a glycoprotein-toxic payload molecule conjugate, a toxic payload molecule-glycan conjugate or a pharmaceutical composition according to one or more embodiments of the invention, is used in the treatment of metastatic, advanced, drug- or hormone-resistant, or multidrug resistant, versions of solid tumours. In one embodiment, a glycoprotein-toxic payload molecule conjugate, a toxic payload molecule-glycan conjugate or a pharmaceutical composition according to one or more embodiments of the invention is used in the treatment of a leukaemia, including a metastatic, advanced or drug-resistant, or multidrug resistant leukaemia, or version thereof.

The embodiments of the invention described hereinbefore may be used in any combination with each other. Several of the embodiments may be combined together to form a further embodiment of the invention. A method, or a product to which the invention is related, may comprise at least one of the embodiments of the invention described hereinbefore.

The glycoprotein-toxic payload molecule conjugate according to one or more embodiments of the invention has a number of advantageous properties.

The conjugate is highly cytotoxic.

The glycoprotein-toxic payload molecule conjugate according to one or more embodiments of the invention comprises a relatively small toxic payload molecule-glycan moiety that is efficiently released inside cells. Further, the moiety released is relatively small; small toxin payload molecule conjugates tend to be more toxic than large toxic payload molecule conjugates e.g. comprising a complex-type N-glycan core structure. The toxic payload molecule-glycan conjugate released from the glycoprotein-toxic payload molecule conjugate in cells is capable of delivering the toxic payload molecule into cells and further into the cytosol, the nucleus or the endoplasmic reticulum.

Various embodiments of the glycoprotein-toxic payload molecule conjugate comprise a hydrophilic linker group that comprises one or more hydroxyl groups. Said linker group conveys good solubility in aqueous solutions. The glycan moiety of the glycoprotein-toxic payload molecule conjugate is also relatively well soluble in aqueous solutions.

The glycoprotein-toxic payload molecule conjugate according to one or more embodiments of the invention is sufficiently stable towards chemical or biochemical degradation during manufacturing or in physiological conditions, e.g. in blood, serum, plasma or tissues.

The toxic payload molecule conjugate according to one or more embodiments of the invention is also relatively stable e.g. in reducing conditions, in low pH and inside cells, cellular organelles, endosomes and lysosomes.

The glycoprotein-toxic payload molecule conjugate according to one or more embodiments of the invention may, however, be cleaved e.g. in reducing conditions, in low pH, or inside cells, cellular organelles, endosomes and lysosomes. Subsequently, the toxic payload molecule may be released in selected conditions or in selected locations such as target cancer cells. The glycoprotein-toxic payload molecule conjugate according to one or more embodiments of the invention may e.g. be cleaved by a lysosomal hydrolase present at relatively high levels in cancer cells.

The method according to one or more embodiments of the present invention allows for conjugating toxic payload molecules into specific acceptor sites in a glycoprotein. The glycoprotein-toxic payload molecule conjugate according to one or more embodiments of the present invention has improved pharmacokinetic properties as compared to a conjugate to which a toxic payload molecule is conjugated randomly, e.g. due to conjugation of the toxic payload molecule to random amino acid side chains.

EXAMPLES

In the following, the present invention will be described in more detail. Reference will now be made in detail to the embodiments of the present invention, examples of which are illustrated in the accompanying drawings. The description below discloses some embodiments of the invention in such detail that a person skilled in the art is able to utilize the invention based on the disclosure. Not all steps of the embodiments are discussed in detail, as many of the steps will be obvious for the person skilled in the art based on this specification.

Example 1. Synthesis of Dolastatin Derivatives

Unless otherwise noted, materials were obtained from commercial suppliers in the highest purity grade available and used without further purifications. Reaction solvents were dried and distilled prior to use when necessary. All reactions containing moisture- or air-sensitive reagents were carried out under an argon atmosphere. Monomethylauristatin F (MMAF) and monomethyldolastatin 10 were purchased from Concortis (San Diego, Calif., USA). Sodium cyanoborohydride, sodium hydride (NaH), methanol, 4-bromo-1-butyne, 5-iodo-1-pentyne, 2-deoxy-D-glucose, 6-O-(β-D-galacto-pyranosyl)-D-galactose, diisopropylethylamine and 2,5-dihydroxybenzoic acid were purchased from Sigma-Aldrich. Dimethylsuphoxide (DMSO) and N,N-dimethylformamide (DMF) were purchased from VWR. 2-acetamido-2-deoxy-4-O-(β-D-galactopyranosyl)-D-glucose, N-{4-O-[4-O-(α-D-galactopyranosyl)-β-D-galactopyranosyl]-D-glucose and 4-O-[3-O-(α-N-acetylneuraminyl)-β-D-galactopyranosyl]-D-glucose were from Kyowa Hakko Kogyo. Trifluoroacetic acid and ammonium hydrogen carbonate were purchased from Fluka, acetonitrile (ACN) from J.T.Baker and disuccinimidyl glutarate from Pierce.

The NMR spectra were recorded with a Bruker Avance spectrometer operating at 600.13 MHz ($^1$H: 600.13 MHz, $^{13}$C: 150.90 MHz). Pulse sequences provided by the manufacturer were utilized. The probe temperature during the experiments was kept at 22° C. unless otherwise mentioned. Chemical shifts are expressed on the δ scale (in ppm) using TMS (tetramethylsilane), residual chloroform, acetone, H$_2$O or methanol as internal standards. Coupling constants are given in Hz and provided only once when first encountered. Coupling patterns are given as s, singlet, d, doublet, t, triplet etc.

TLC was performed on aluminium sheets precoated with silica gel 60 F$_{254}$ (Merck). Flash chromatography was carried out on silica gel 60 (0.040-0.060 mm, Aldrich). Spots were visualized by UV followed by charring with 1:8 H$_2$SO$_4$/MeOH and heating.

Scheme 1. Synthesis of 6-azido-6-deoxy-D-galactose.

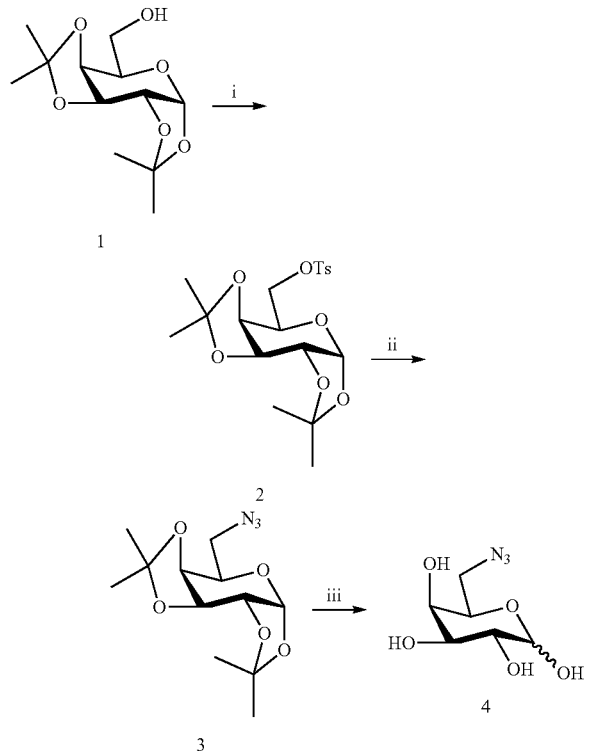

i) TsCl, pyridine, RT, 22 h, 81%; ii) NaN$_3$, DMF, 120° C., 68%; iii) 60% TFA, 50° C., 1 h, quantitative.

Synthesis of 1,2;3,4-di-O-isopropylidene-6-O-tosyl-α-D-galactopyranose (Scheme 1.2): 0.39 g (1.5 mmol) of (Scheme 1.1) was dissolved in 5 ml of dry pyridine under an argon atmosphere. The reaction mixture was cooled on an ice bath and 0.88 g (3.1 equiv.) of TsCl was added. The reaction was slowly warmed to RT and stirred overnight. After 22 hours the reaction was diluted with 30 ml of CH$_2$Cl$_2$ and washed with 30 ml of ice-cold water. The organic phase was washed with 20 ml of 10% (w/v) aqueous CuSO$_4$-solution, 20 ml of saturated NaHCO$_3$-solution and 20 ml H$_2$O. The organic phase was separated, dried over Na$_2$SO$_4$, filtered and concentrated. The crude product was purified by column chromatography (Hexane:EtOAc 1:1) to give (Scheme 1.2) as a yellowish oil (0.49 g, 81%). TLC: R$_f$=0.74 (Hexane:EtOAc 1:1). $^1$H NMR (600 MHz, CDCl$_3$, 22° C.): δ=7.81-7.32 (m, 4H, CH$_3$C$_6$H$_4$SO$_2$), 5.45 (d, 1H, J$_{1,2}$=4.9 Hz, H-1), 4.59 (dd, 1H, J$_{3,2}$=2.5, J$_{3,4}$=7.9 Hz, H-3), 4.29 (dd, 1H, H-2), 4.22-4.18 (m, 2H, H-6a, H-4), 4.09 (dd, 1H, J$_{6b,5}$=6.9, J$_{6b,6a}$=−10.3 Hz, H-6b), 4.05 (ddd, 1H, J$_{5,4}$=1.9, J$_{5,6a}$=6.2 Hz, H-5), 2.44 (s, 3H, CH$_3$C$_6$H$_4$SO$_2$), 1.50, 1.34, 1.31 and 1.28 (each s, each 3H, O$_2$C(CH$_3$)$_2$) ppm.

Synthesis of 1,2;3,4-di-O-isopropylidene-6-deoxy-6-azido-α-D-galactopyranose (Scheme 1.3). To a solution containing 1.5 g (3.7 mmol) of (Scheme 1.2) in 20 ml dry DMF (under an argon atmosphere) was added 1.7 g (7 equiv.) NaN$_3$ and the resulting mixture was stirred at 120° C. overnight. After 18 hours, the reaction mixture was brought to RT, diluted with 20 ml CHCl$_3$, filtered and concentrated. The crude product was purified by column chromatography (Hexane:EtOAc 3:1) to give (Scheme 1.3) as a colorless oil (0.7 g, 68%). TLC: R$_f$=0.52 (Hexane:EtOAc 3:1). $^1$H NMR (600 MHz, CDCl$_3$, 22° C.): δ=5.55 (d, 1H, J$_{1,2}$=5.1 Hz, H-1), 4.63 (dd, 1H, J$_{3,2}$=2.5, J$_{3,4}$=8.1 Hz, H-3), 4.33 (dd, 1H, H-2), 4.19 (dd, 1H, J$_{4,5}$=2.0 Hz, H-4), 3.92 (ddd, 1H, J$_{5,6b}$=5.3, J$_{5,6a}$=7.8 Hz, H-5), 3.51 (dd, 1H, J$_{6a,6b}$=−12.9 Hz, H-6a), 3.36 (dd, 1H, H-6b), 1.55, 1.46, 1.35 and 1.34 (each s, each 3H, O$_2$C(CH$_3$)$_2$) ppm.

Synthesis of 6-azido-6-deoxy-D-galactose (Scheme 1.4). 80 mg (0.3 mmol) of (Scheme 1.3) was dissolved in 3 ml 60% TFA and the resulting mixture was stirred at 50° C. for 1 hour. The mixture was then diluted with water and concentrated to give (Scheme 1.4) as a colorless oil (60 mg, quantitative, furanose:pyranose 3:97, alpha$_{pyranose}$: beta$_{pyranose}$ 35:65). Selected NMR-data: $^1$H NMR (600 MHz, D$_2$O, 22° C.): δ=5.28 (d, 1H, J$_{1,2}$=4.7 Hz, H-1 furanose) 5.26 (d, 1H, J$_{1,2}$=3.9 Hz, H-1α$_{pyranose}$), 5.22 (d, 1H, J$_{1,2}$=3.4 HZ, H-1$_{furanose}$) 4.60 (d, 1H, J$_{1,2}$=7.8 Hz, H-1β$_{pyranose}$).

Scheme 2. Synthesis of 6-O-propargyl-D-galactose.

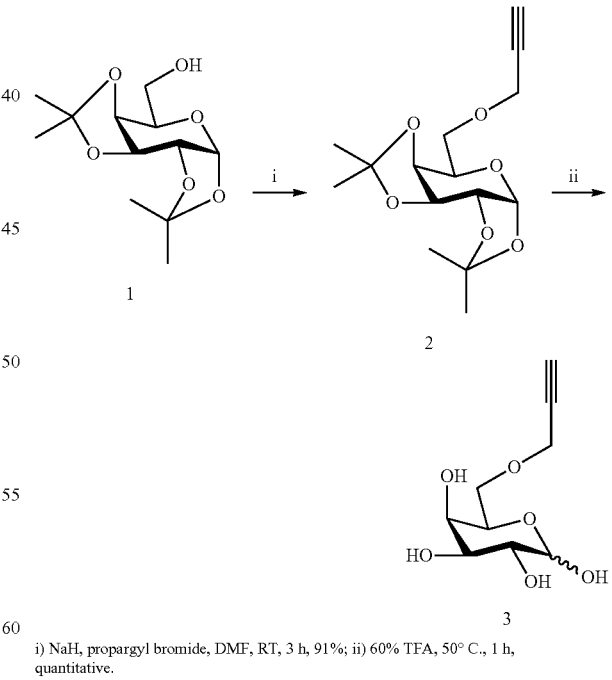

i) NaH, propargyl bromide, DMF, RT, 3 h, 91%; ii) 60% TFA, 50° C., 1 h, quantitative.

1,2;3,4-di-O-isopropylidene-6-O-propargyl-α-D-galactopyranose (Scheme 2.2). To a solution containing 0.27 g (1.0 mmol) 1 in 5 ml dry DMF (under an argon atmosphere) was added 75 mg (2.0 equiv.) NaH at 0° C. The resulting mixture was stirred for 20 min. and 171 µl (1.5 equiv.) of propargyl bromide was added. After 20 min. the mixture was brought to RT and stirred for an additional 2.5 hours. The mixture was cooled on an ice bath and quenched by the addition of MeOH (0.5 ml). The reaction mixture was brought to RT, diluted with 20 ml $CH_2Cl_2$ and washed with 20 ml saturated $NaHCO_3$-solution. The water phase was extracted with 20 ml $CH_2Cl_2$. The combined organic phase was washed with 20 ml $H_2O$, dried over $Na_2SO_4$, filtered and concentrated. The crude product was purified by column chromatography (Hexane:EtOAc 2:1) to give (Scheme 2.2) as a white solid (0.27 g, 91%). TLC: $R_f$=0.77 (Hexane:EtOAc 1:1). $^1H$ NMR (600 MHz, $CDCl_3$, 22° C.): δ=5.54 (d, 1H, $J_{1,\,2}$=5.1 Hz, H-1), 4.61 (dd, 1H, $J_{3,\,2}$=2.5, $J_{3,\,4}$=8.0 Hz, H-3), 4.32 (dd, 1H, H-2), 4.26 (dd, 1H, $J_{4,\,5}$=1.9 Hz, H-4), 4.25 (dd, 1H, $J_{CH2a,\,\equiv CH}$=2.4, $J_{CH2a,\,CH2b}$=15.9 Hz, $CH_{2a}C\equiv CH$), 4.20 (dd, 1H, $J_{CH2b,\,\equiv CH}$=2.4 Hz, $CH_2bC\equiv CH$), 4.00 (ddd, 1H, $J_{5,\,6a}$=5.4, $J_{5,\,6b}$=7.1 Hz, H-5), 3.78 (dd, 1H, $J_{6a,\,6b}$=−10.1 Hz, H-6a), 3.67 (dd, 1H, H-6b), 2.43 (dd, 1H, $CH_2C\equiv CH$), 1.55, 1.45, 1.34 and 1.33 (each s, each 3H, $O_2C(CH_3)_2$) ppm.

Synthesis of 6-O-propargyl-D-galactose (Scheme 2.3). 25 mg (0.08 mmol) of (Scheme 2.3) was dissolved in 3 ml 60% TFA and the resulting mixture was stirred at 50° C. for 1 hour. The mixture was then diluted with water and concentrated to give (Scheme 2.3) as a colorless oil (18 mg, quantitative, furanose:pyranose 3:97, $alpha_{pyranose}$:$beta_{pyranose}$ 35:65). Selected NMR-data: $^1H$ NMR (600 MHz, $D_2O$, 22° C.): δ=5.26 (d, 1H, $J_{1,\,2}$=4.7 Hz, H-1$_{furanose}$) 5.23 (d, 1H, $J_{1,\,2}$=3.8 Hz, H-1$α_{pyranose}$), 5.20 (d, 1H, $J_{1,\,2}$=3.5 Hz, H-1$_{furanose}$) 4.55 (d, 1H, $J_{1,\,2}$=7.9 Hz, H-1$β_{pyranose}$).

The following MMAF (1) and monomethyldolastatin 10 (2) derivatives (3-14) were prepared:

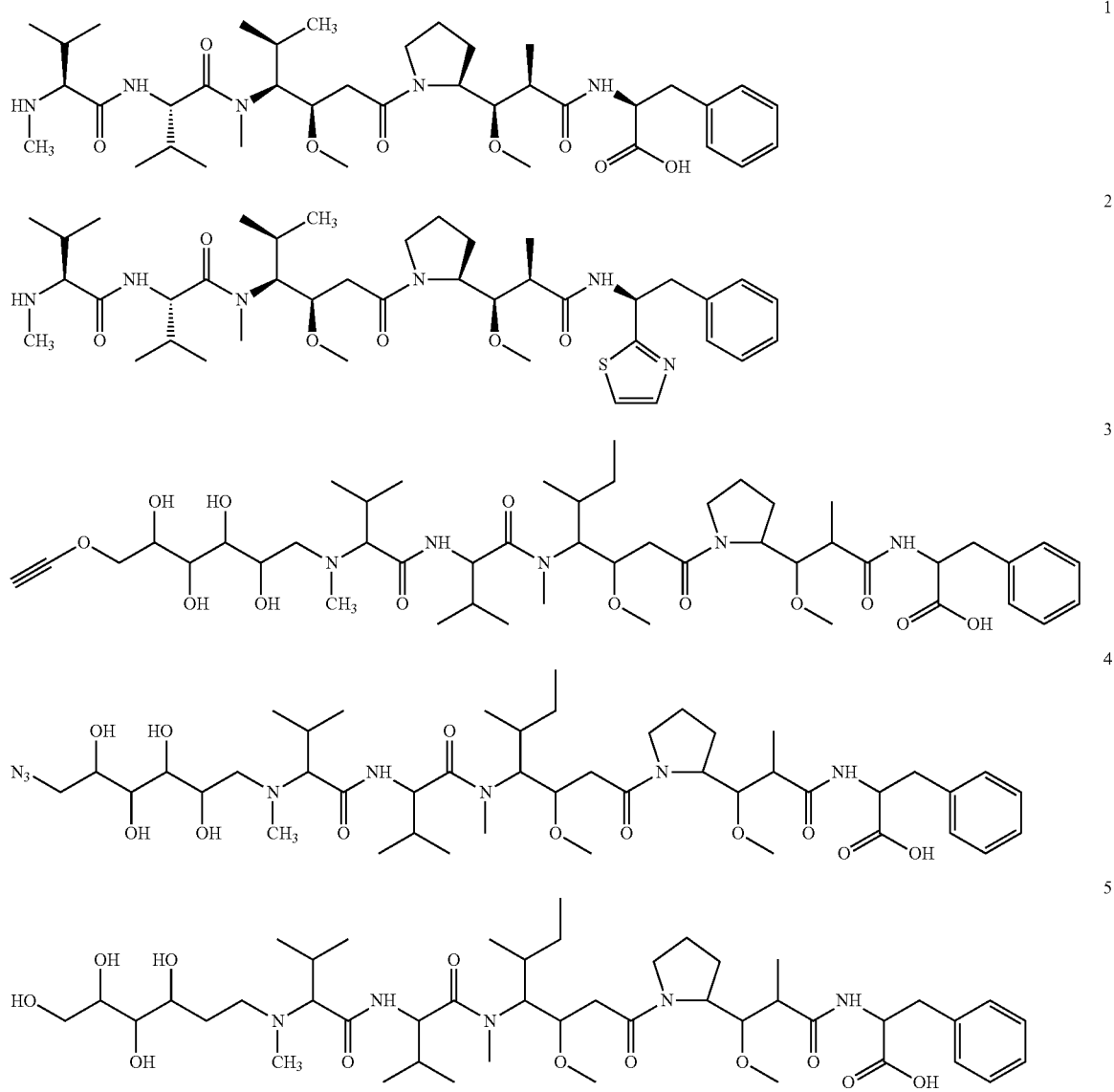

6
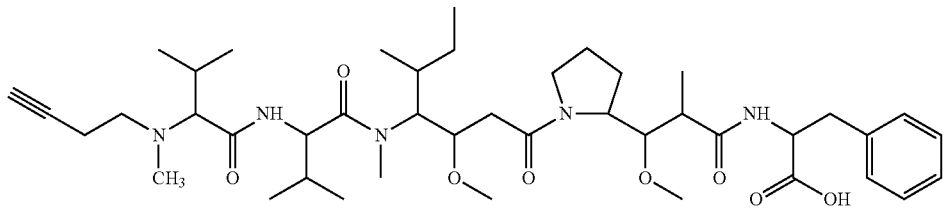
7
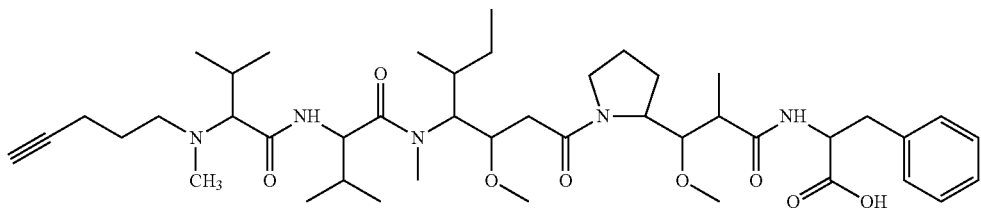
8
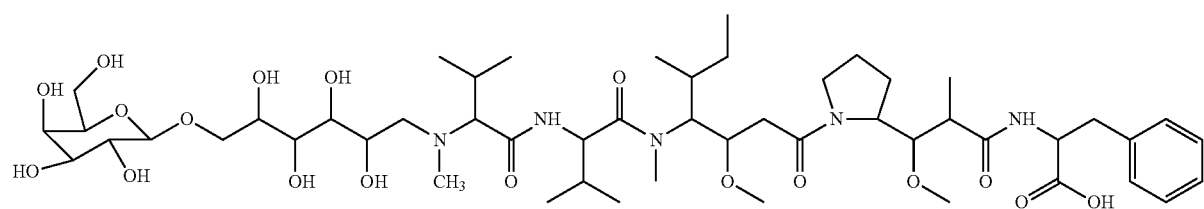
9
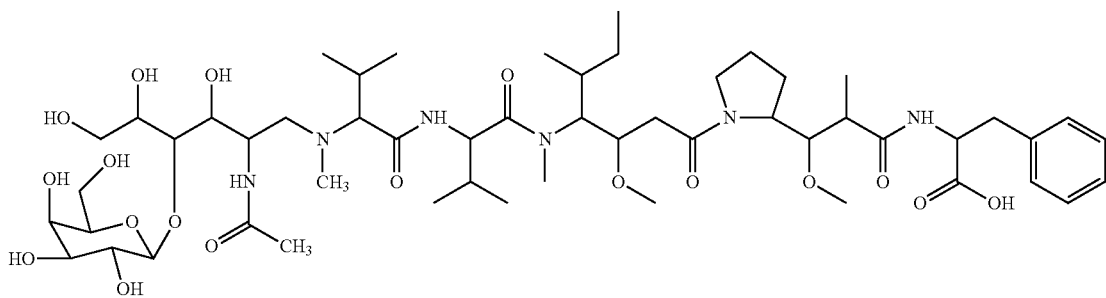
10
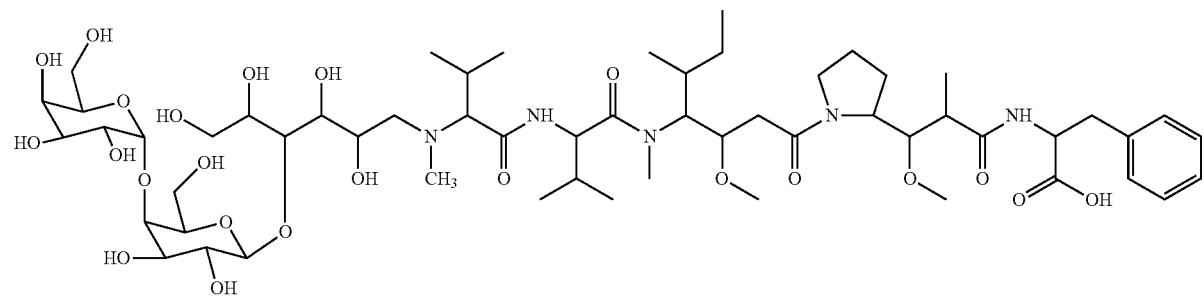
11
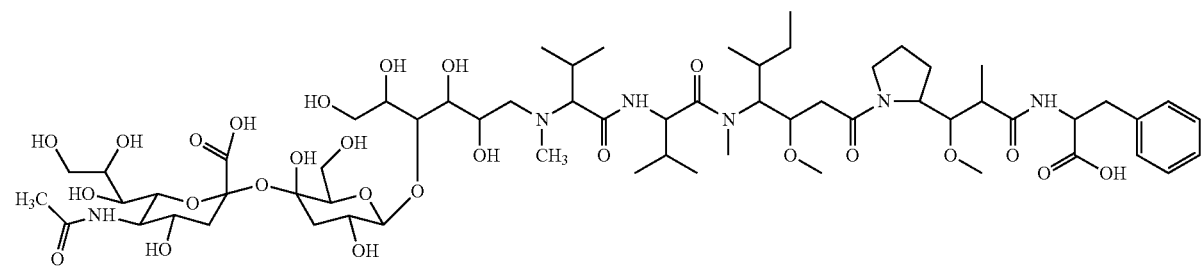

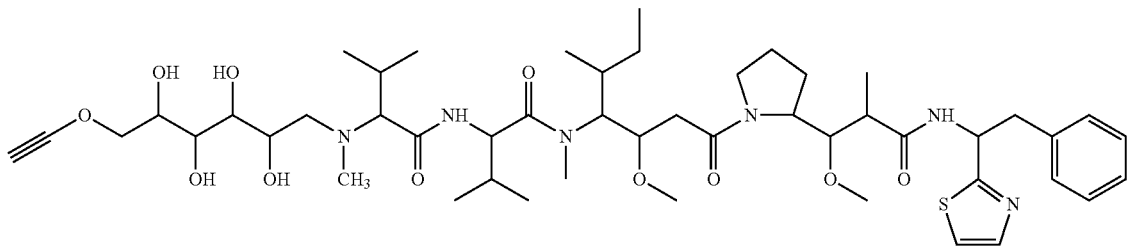

12

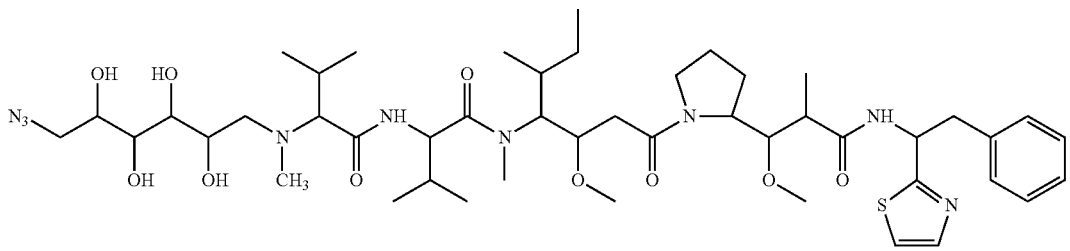

13

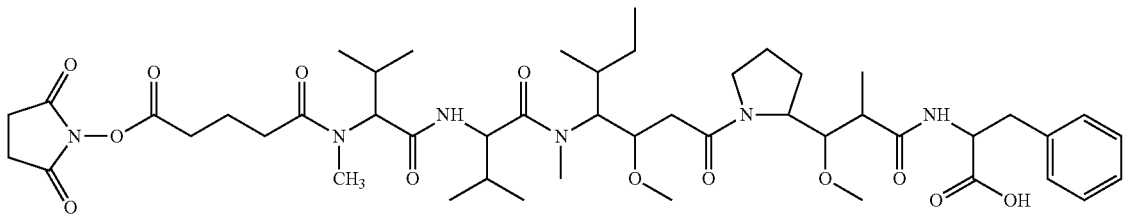

14

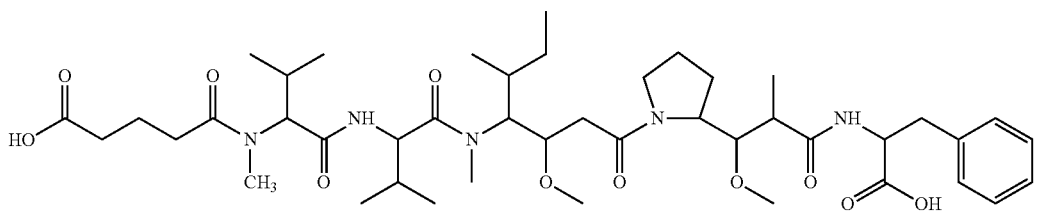

14b

N-(6-O-propargyl-D-galactosyl)-MMAF (3): sodium cyanoborohydride (200 µmol) and 6-O-propargyl-D-galactose (45 µmol) were added to the solution of MMAF (2.7 µmol) in dimethylsulphoxide (0.7 ml). The mixture was stirred at 60° C. for three days.

N-(6-azido-6-deoxy-D-galactosyl)-MMAF (4): sodium cyanoborohydride (160 µmol) and 6-azido-6-deoxy-D-galactose (95 µmol) were added to the solution of MMAF (2.7 µmol) in DMSO (0.6 ml). The mixture was stirred at 60° C. for three days.

N-(2-deoxy-D-glucosyl)-MMAF (5): sodium cyanoborohydride (28 µmol) and 2-deoxy-D-glucose (21 µmol) were added to the solution of MMAF (1.4 µmol) in DMSO (0.6 ml). The mixture was stirred at 60° C. for three days.

N-(3-butynyl)-MMAF (6): to the solution of MMAF (2.7 µmol) in dry DMF (0.6 ml) was added NaH (54 µmol) and 4-bromo-1-butyne (27 µmol). The mixture was stirred at 60° C. for 4 hours. Reaction was quenched by adding dry methanol (0.2 ml).

N-(4-pentynyl)-MMAF (7): to the solution of MMAF (1.4 µmol) in dry DMF (0.4 ml) was added NaH (7 µmol) and 5-iodo-1-pentyne (7 µmol). The mixture was stirred at room temperature for 3 hours. Reaction was quenched by adding dry methanol (0.2 ml).

N-[6-O-(β-D-galactopyranosyl)-D-galactosyl]-MMAF (8): sodium cyanoborohydride (25 µmol) and 6-O-(β-D-galactopyranosyl)-D-galactose (5.3 µmol) were added to the solution of MMAF (0.7 µmol) in DMSO (0.25 ml). The mixture was stirred at 60° C. for five days.

N-[2-acetamido-2-deoxy-4-O-(β-D-galacto-pyranosyl)-D-glucosyl)-MMAF (9): sodium cyanoborohydride (50 µmol) and 2-acetamido-2-deoxy-4-O-(β-D-galactopyranosyl)-D-glucose (11 µmol) were added to the solution of MMAF (1.4 µmol) in DMSO (0.4 ml). The mixture was stirred at 60° C. for five days.

N-{4-O-[4-O-(α-D-galactopyranosyl)-β-D-galactopyranosyl]-D-glucosyl}-MMAF (10): sodium cyanoborohydride (50 µmol) and 4-O-[4-O-(α-D-galactopyranosyl)-β-D-galactopyranosyl]-D-glucose (11 µmol) were added to the solution of MMAF (1.4 µmol) in DMSO (0.4 ml). The mixture was stirred at 60° C. for five days.

N-{4-O-[3-O-(α-N-acetylneuraminyl)-β-D-galactopyranosyl]-D-glucosyl}-MMAF (11): sodium cyanoborohydride (50 µmol) and 4-O-[3-O-(α-N-acetyl-neuraminyl)-β-D-galactopyranosyl]-D-glucose (11 µmol) were added to the solution of MMAF (1.4 µmol) in DMSO (0.4 ml). The mixture was stirred at 60° C. for five days.

N-(6-O-propargyl-D-galactosyl)-dolastatin 10 (12): sodium cyanoborohydride (200 µmol) and 6-O-propargyl- D-galactose (45 µmol) were added to the solution of momomethyldolastatin 10 (2.5 µmol) in DMSO (0.7 ml). The mixture was stirred at 60° C. for three days.

N-(6-azido-6-deoxy-D-galactosyl)-dolastatin 10 (13): sodium cyanoborohydride (160 µmol) and 6-azido-6-deoxy-D-galactose (95 µmol) were added to the solution of momomethyldolastatin 10 (2.5 µmol) in DMSO (0.6 ml). The mixture was stirred at 60° C. for three days.

N—(N-hydroxysuccinimidylglutaryl)-MMAF (14): disuccinimidyl glutarate (20 µmol) and diisopropylethylamine (20 µmol) were added to the solution of MMAF (1.4 µmol) in ACN (0.4 ml). The mixture was stirred at room temperature overnight. To produce N-glutaryl-MMAF (14b), an aliquot of (14) was hydrolyzed in aqueous solution.

The products were purified by Äkta purifier 10 (GE Healthcare) HPLC instrument with Gemini-NX-5u C-18 reverse-phase column (4.6×250 mm, 110 Å (Phenomenex)) eluted with ACN gradient in aqueous ammonium hydrogen carbonate or aqueous trifluoroacetic acid.

For example N-(2-deoxy-D-glucosyl)-MMAF (5) eluted with lower ACN concentration at 19.6 min (about 37% ACN) before both the original MMAF (1) at 21.7 min (about 40% ACN) and N-(3-butynyl)-MMAF (6) at 26.0 min (about 45% ACN), showing that it was more hydrophilic.

Matrix-assisted laser desorption-ionization time-of-flight (MALDI-TOF) mass spectra were recorded on a Bruker Ultraflex III TOF/TOF mass spectrometer (Bruker Daltonics, Bremen, Germany) using 2,5-dihydroxybenzoic acid matrix: (3) m/z=956 [M+Na], (4) m/z=943 [M+Na], (5) m/z=902 [M+Na], (6) m/z=806 [M+Na], (7) m/z=820 [M+Na], (8) m/z=1080 [M+Na], (9) m/z=1121 [M+Na], (10) m/z=1242 [M+Na], (11) m/z=1371 [M+Na], (12) m/z=995 [M+Na], (13) m/z=982 [M+Na], (14) m/z=868 for hydrolyzed NHS [M+Na].

Example 2. In Vitro Cytotoxicity of Dolastatin Derivatives

Human ovarian cancer cell line SKOV-3 was from the ATCC (Manassas, Va., USA). The cells were grown according to the manufacturer's recommendations. Log phase cultures were collected and 5000 cells/well were seeded onto 96-well plates and incubated for 24 h. Serial dilutions of test molecules from a stock solution of 100 µM in 10% DMSO were made in cell culture medium, added to cells (maximum concentration of dimethylsulphoxide was 1%) and cultures were incubated further for 96 h. Cell viability was evaluated using PrestoBlue cell viability reagent (Life Technologies, Carlsbad, Calif., USA) according to the manufacturer's instructions. Cells were incubated for 2 h, and dye reduction was measured by absorbance at 570 nm. The compounds were assayed 1-2 times in triplicate.

Results of an exemplary assay are shown in FIG. 1, in which compound numbering is according to Example 1. The results are expressed in Table 1 as IC50 values of the analyzed derivatives. In conclusion, 1) all the analyzed alkyl derivatives of MMAF and dolastatin 10 were cytotoxic against SKOV-3 ovarian cancer cells; 2) monosaccharide derivatives 3, 4 and 5 were equally or only slightly less cytotoxic as 1, and monosaccharide derivatives 13 and 14b were equally or only slightly less cytotoxic as 2, showing that the amine conjugates of saccharides and MMAF or monomethyldolastatin 10 have preserved capability to bind to tubulin; 3) oligosaccharide derivatives 8, 11 and 12 were less cytotoxic than 1 when applied to the cell culture medium, reflecting their high hydrophilicity and lowered ability to pass through cellular membranes; and 4) the hydrophobic alkyl derivative 6 was more cytotoxic than 1, showing that a hydrophobic linker increases the ability of the conjugate to pass through cellular membranes.

TABLE 1

| Cytotoxicity of dolastatin derivatives. | |
|---|---|
| Compound | IC50[1] |
| 1 | 0.1-1 µM |
| 14b | 0.1-1 µM |
| 3 | 0.1-10 µM |
| 4 | 0.1-1 µM |
| 5 | 1 µM |
| 6 | <1 nM[2] |
| 8 | 1-10 µM |
| 10 | 1-10 µM |
| 11 | >10 µM[2] |
| 2 | <1 nM[2] |
| 12 | 1 nM |
| 13 | <1 nM[2] |

[1]IC50 values were determined as the concentration range wherein SKOV-3 ovarian cancer cell viability falls to 50%.
[2]The measured range was between 1 nM-10 µM.

Example 3. Synthesis of CMP-9-deoxy-9-azido-NeuNAc

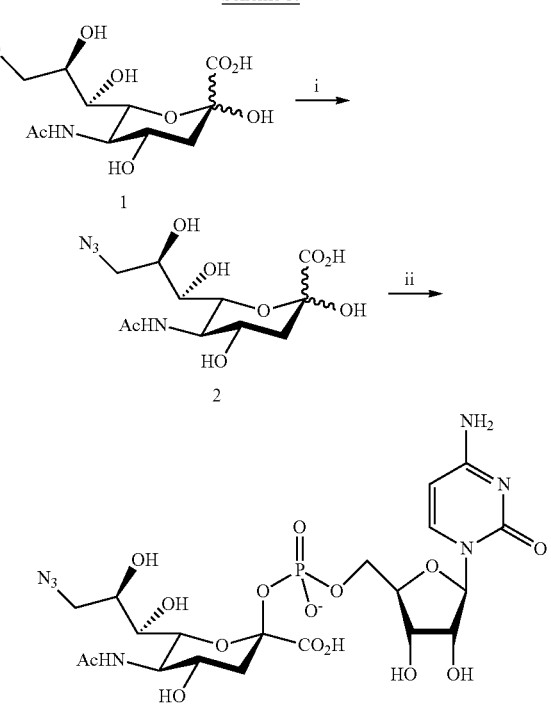

Scheme 3.

i) 1) MeOH, AG 50W-X8 (H+-form), 45° C., o/n, quantitative; 2) TsCl, pyridine, 0° C.→RT, o/n, 67%; 3) NaN3, Acetone:H2O 3:1, 75° C., o/n, 52%; ii) CMP-sialic acid synthetase, CTP.

5-acetamido-9-azido-3,5,9-trideoxy-D-glycero-D-galacto-2-nonulosonic acid (2): To a solution containing 63 mg of 1 (0.2 mmol) in 5 ml dry MeOH (under argon) was added 127 mg AG 50 W-×8 (2 weight equiv.) and the resulting mixture was stirred at 45° C. o/n. The mixture was then filtered and concentrated to give methyl N-acetyl neuraminate as a white solid (65 mg, quantitative). TLC: $R_f$=0.43 (DCM:MeOH 3:1)

157 mg of methyl N-acetyl neuraminate (0.49 mmol) was dissolved in 5 ml of dry pyridine (under argon) and the reaction mixture was cooled to 0° C. 135 mg TsCl (0.7 mmol, 1.4 equiv.) was added and the reaction mixture was slowly warmed to RT and left to stir o/n. After 23 hours 134 mg TsCl (0.7 mmol, 1.4 equiv.) was added to the reaction mixture and it was stirred for an additional 2 hours at RT. The mixture was then cooled to 0° C. and the reaction quenched with MeOH. The mixture was concentrated and the crude product was purified by column chromatography (MeOH:DCM 1:9) to give methyl 9-O-tosyl-N-acetyl-neuraminate as a yellowish oil (159 mg, 67%). TLC: $R_f$=0.29 (DCM:MeOH 9:1). $^1$H NMR (600 MHz, CD$_3$OD, 22° C.): δ Selected NMR-data; 7.80-7.43 (m, 4H, CH$_3$C$_6$H$_4$SO$_2$), 4.28 (dd, 1H, J=2.2, 10.1 Hz), 4.06-3.99 (m, 2H), 3.93 (dd, 1H, J=1.5, 10.6 Hz), 3.85 (ddd, 1H, J=2.0, 5.7, 8.5 Hz), 3.77 (s, 3H, CO$_2$CH$_3$), 3.43 (dd, 1H, J=1.5, 9.0 Hz), 2.46 (s, 3H, CH$_3$C$_6$H$_4$SO$_2$), 2.19 (dd, 1H, J=4.9, 12.9 Hz, H-3eq), 2.00 (s, 3H, NHCOCH$_3$), 1.86 (dd, 1H, J=11.5, 12.9 Hz, H-3ax). HRMS: calcd. for C$_{19}$H$_{27}$O$_{11}$NNaS [M+Na]$^+$ 500.12. found 500.20.

110 mg of methyl 9-O-tosyl-N-acetyl-neuraminate (0.23 mmol) was dissolved in 2 ml acetone: H$_2$O 3:1 and 70 mg NaN$_3$ (1.1 mmol, 4.3 equiv.) was added. The resulting mixture was heated to 75° C. and stirred o/n. The reaction mixture was then concentrated and the crude product purified by gel filtration chromatography to give 2 as a yellowish foam (40 mg, 52%). Selected NMR-data; $^1$H NMR (600 MHz, D$_2$O, 22° C.): δ 4.03 (ddd, 1H, J=5.1, 10.1, 10.3 Hz), 3.99 (dd, 1H, J=0.9, 10.6 Hz), 3.94-3.89 (m, 2H), 3.61 (dd, 1H, J=2.8, 13.1 Hz), 3.53 (ap d, 1H, J=9.4 Hz), 3.49 (dd, 1H, J=6.0, 13.1 Hz), 2.22 (dd, 1H, J=4.9, 12.9 Hz, H-3eq), 2.07 (s, 3H, NHCOCH$_3$), 1.83 (dd, 1H, J=11.7, 12.9 Hz, H-3ax). HRMS: calcd. for C$_{11}$H$_{18}$O$_8$N$_4$Na [M+Na]$^+$ 357.10. found 357.12; calcd. for C$_{11}$H$_{17}$O$_8$N$_4$Na$_2$ [M+2Na—H]$^+$ 379.08. found 379.10.

Cytidine-5'-monophospho-5-acetamido-9-azido-3,5,9-trideoxy-D-glycero-D-galacto-2-nonulosonic acid (CMP-9'-azido-NeuAc) (3): Enzymatic synthesis of CMP-9'-azido-NeuAc was carried out in 2 ml of 100 mM Tris-HCl buffer pH 8.5 containing 20 mM MgCl$_2$, 15 mM CTP, 10 mg (15 mM) of 9'-azido-NeuAc and 100 mU of CMP-sialic acid synthetase (Sigma Aldrich). All reagents except 9'-azido-NeuAc were of commercial origin. Reaction was allowed to proceed for 2.5 hours at +37° C. After 1 hour CTP was added to reach final CTP-concentration of 30 mM and pH was adjusted to 8.5 with NaOH. The reaction was monitored at time points 1 h and 2.5 h by taking samples to MALDI-TOF MS analysis. MALDI-TOF MS analyses were performed using 2',4',6'-trihydroxyacetophenone (THAP) as the matrix in reflector negative ion mode with Bruker Ultraflex III instrument (Bruker Daltonics, Germany). After 2.5 hours the enzyme was removed from the mixture by running the reaction mixture through Bond Elute C$_{18}$-column (Varian Inc.). CMP-9'-azido-NeuAc-sample eluted from Bond Elute-column was purified by gel filtration chromatography with Superdex peptide column (GE Healthcare) using 0.1 M ammonium bicarbonate as eluent. Two consecutive chromatographic runs resulted in sample containing mainly CMP-9'-azido-NeuAc with minor proportion of CTP as exemplified by MALDI-spectrum in FIG. 2: CMP-9'-azido-NeuAc, m/z 637; CTP, m/z 479. Final yield of CMP-9'-azido-NeuAc based on absorbance at 280 nm (against CTP-standard) was 5.7 mg.

Example 4. Synthesis of UDP-6-O-Propargyl-Galactose

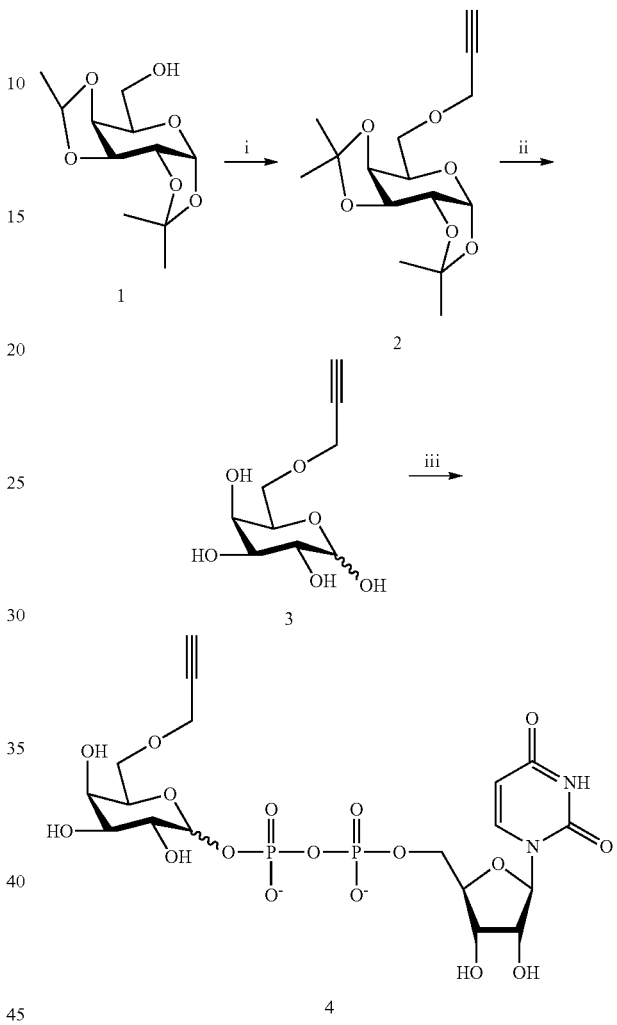

Scheme 4.

i) NaH, propargyl bromide, DMF, RT, 3 h, 91%; ii) 60% TFA, 50° C., 1 h, quantitative, iii) 1) TMSCl, pyridine, 0° C. → RT, 2 h, 54%; 2) a) TMSI, DCM, 0° C., 1 h; b) UDP, -30° C., 1 h, then 0° C., 2 h, then Bu$_4$NF, THF, RT, 1 h, 33%.

1,2;3,4-di-O-isopropylidene-6-O-propargyl-α-D-galactopyranose (2): To a solution containing 0.27 g (1.0 mmol) 1 in 5 ml dry DMF (under an argon atmosphere) was added 75 mg (2.0 equiv.) NaH at 0° C. The resulting mixture was stirred for 20 min. and 171 μl (1.5 equiv.) of propargyl bromide was added. After 20 min. the mixture was brought to RT and stirred for an additional 2.5 hours. The mixture was cooled on an ice bath and quenched by the addition of MeOH (0.5 ml). The reaction mixture was brought to RT, diluted with 20 ml CH$_2$Cl$_2$ and washed with 20 ml saturated NaHCO$_3$-solution. The water phase was extracted with 20 ml CH$_2$Cl$_2$. The combined organic phase was washed with 20 ml H$_2$O, dried over Na$_2$SO$_4$, filtered and concentrated. The crude product was purified by column chromatography (Hexane:EtOAc 2:1) to give the title compound as a white solid (0.27 g, 91%). TLC: $R_f$=0.77 (Hexane:EtOAc 1:1). $^1$H NMR (600 MHz, CDCl$_3$, 22° C.): δ=5.54 (d, 1H, J$_{1,2}$=5.1

Hz, H-1), 4.61 (dd, 1H, $J_{3,2}$=2.5, $J_{3,4}$=8.0 Hz, H-3), 4.32 (dd, 1H, H-2), 4.26 (dd, 1H, $J_{4,5}$=1.9 Hz, H-4), 4.25 (dd, 1H, $J_{CH2a,=CH}$=2.4, $J_{CH2a,CH2b}$=−15.9 Hz, $CH_{2a}C$≡CH), 4.20 (dd, 1H, $J_{CH2b,=CH}$=2.4 Hz, CH2bC≡CH), 4.00 (ddd, 1H, $J_{5,6a}$=5.4, $J_{5,6b}$=7.1 Hz, H-5), 3.78 (dd, 1H, $J_{6a,6b}$=−10.1 Hz, H-6a), 3.67 (dd, 1H, H-6b), 2.43 (dd, 1H, CH2C≡CH), 1.55, 1.45, 1.34 and 1.33 (each s, each 3H, $O_2C(CH_3)_2$) ppm.

6-O-propargyl-D-galactose (3): 25 mg (0.08 mmol) of 2 was dissolved in 3 ml 60% TFA and the resulting mixture was stirred at 50° C. for 1 hour. The mixture was then diluted with water and concentrated to give the title compound as a colorless oil (18 mg, quant., furanose:pyranose 3:97, $\alpha_{pyranose}:\beta_{pyranose}$ 35:65). Selected NMR-data: $^1$H NMR (600 MHz, $D_2O$, 22° C.): δ=5.26 (d, 1H, $J_{1,2}$=4.7 Hz, H-1$_{furanose}$), 5.23 (d, 1H, $J_{1,2}$=3.8 Hz, H-1$\alpha_{pyranose}$) 5.20 (d, 1H, $J_{1,2}$=3.5 Hz, H-1$_{furanose}$), 4.55 (d, 1H, $J_{1,2}$=7.9 Hz, H-1$\beta_{pyranose}$).

6-O-propargyl-D-galactopyranosyl-1-uridinyldiphosphate (4): To a solution containing 73 mg (0.33 mmol) 3 in 4 ml dry pyridine (under argon atmosphere) was added 0.25 ml (2.0 mmol, 6 equiv.) TMSCl at 0° C. The resulting mixture was slowly brought to RT and stirred for 1.5 hours. The mixture was diluted with 20 ml pentane and washed with 6 ml (5×) $H_2O$. The organic phase was dried with $Na_2SO_4$, filtered and concentrated to give 6-O-propargyl-1,2,3,4-tetra-O-trimethylsilyl-D-galactopyranose (TLC: $R_f$=0.80 [Hexane:EtOAc 6:1]) as a colorless oil (92 mg, 54%). 92 mg (0.18 mmol) 6-O-propargyl-1,2,3,4-tetra-O-trimethylsilyl-D-galactopyranose was dissolved in 2 ml dry DCM (under an argon atmosphere) and 26 µl (0.18 mmol, 1 equiv.) TMSI was added at 0° C. The resulting mixture was stirred for 1 hour and half of the amount (1 ml) was transferred to a separate flask. The remaining solution was cooled to −30° C., stirred for 15 minutes and 80 mg (0.09 mmol, 1 equiv.) UDP (as its $Bu_4N^+$-salt) dissolved in 1 ml DCM was added. The resulting mixture was stirred for 1 hour at −30° C., then slowly brought to 0° C. and stirred for an additional 3 hours. The product was then deprotected by the addition of 0.15 ml $Bu_4NF$ (1 M solution in THF). The resulting mixture was stirred for 1 hour at RT and concentrated to give the crude product. The crude product was purified by gel filtration chromatography to give title compound (18 mg, 33%, alpha:beta 30:70). Selected NMR-data: $^1$H NMR (600 MHz, $D_2O$, 22° C.): δ=5.64 (dd, 1H, $J_{1,2}$=3.0, $^3J_{1,P}$=6.9 Hz, H-1α), 4.97 (t, 1H, $J_{1,2}$=8.0, $^3J_{1,P}$=8.0 Hz, H-1β). HRMS: calcd. for $C_{18}H_{25}N_2O_{17}P_2$ [M–H]$^−$ 603.06. found 603.07.

Example 5. Enzymatic Synthesis of Azido- and Propargyl-Modified Saccharides

The hexasaccharide GalNAzβ4GlcNAcβ3Galβ4GlcNAcβ3Galβ4Glc (GalNAz, N-(2-azido)acetyl-D-galactosamine) was prepared with an enzymatic reaction using UDP-GalNAz (Invitrogen) and pentasaccharide GlcNAcβ3Galβ4GlcNAcβ3Galβ4Glc (GNLNLac) as follows: UDP-GalNAz and GNLNLac were mixed with MOPS pH 7.2 buffer and $MnCl_2$. Bovine GalT1 (Y289L) enzyme (Invitrogen) was added to the reaction mixture and it was mixed gently. Enzyme amount and final concentrations of components are as follows:

10 µl Bovine GalT1 (Y289L)
50 mM MOPS, pH 7.2
20 mM $MnCl_2$
0.15 mM GNLNLac
10 µg UDP-GalNaz Total volume 20 µl The samples were incubated at +37° C. overnight.

Reaction mixture was purified with 150 mg/4 ml Carbograph Extract-Clean columns (Grace Davison Discovery Sciences) and eluted with 25% ACN in aqueous 0.05% TFA. Eluted samples were dried in centrifugal evaporator before storage.

Samples were analysed with MALDI-TOF positive mode using DHB (2,5-dihydroxybenzoic acid) as matrix. The mass spectrum showed that no acceptor pentasaccaharide GNLNLac (933.4 m/z) was present and the reaction thus proceeded to completion. Product peaks at m/z 1177.549 and m/z 1421.623 indicated addition of one and two GalNAz units to the acceptor glycan, respectively, showing that the acceptor saccharide was effectively modified by azido groups.

The hexasaccharide 6-propargylgalactose-GNLNLac was prepared with an enzymatic reaction using UDP-6-propargylgalactose (UDP-PrGal) and pentasaccharide GNLNLac as follows: GNLNLac and UDP-PrGal were mixed with MOPS pH 7.2 buffer and $MnCl_2$. Bovine milk GalT (Calbiochem) or human GalT1 (Y285L) (R&D Systems) enzyme was added to the reaction mixture and it was mixed gently. Enzyme amounts and final concentrations of components were as follows:

| 100 mU Bovine milk GalT | 0.2 µg Human GalT1 (Y285L) |
| 50 mM MOPS, pH 7.2 | 50 mM MOPS, pH 7.2 |
| 20 mM $MnCl_2$ | 20 mM $MnCl_2$ |
| 0.3 mM GNLNLac | 0.3 mM GNLNLac |
| 10 mM UDP-PrGal | 10 mM UDP-PrGal |
| Total volume 20 µl | Total volume 10 µl |

The samples were incubated at +37° C. overnight.

Reaction products were purified with 150 mg/4 ml Carbograph Extract-Clean columns (Grace Davison Discovery Sciences) and eluted with 25% ACN in aqueous 0.05% TFA. Eluted samples were dried in centrifugal evaporator before storage.

Samples were analysed with MALDI-TOF MS in positive mode using DHB (2,5-dihydroxybenzoic acid) as matrix. The mass spectrum of the purified reaction products from reaction with Bovine milk GalT showed major signals at m/z 1133.549, m/z 1333.627 and m/z 1533.688, which represent products with one, two and three propargylgalactose units attached to the acceptor pentasaccaride, respectively, showing that the acceptor saccharide was effectively modified by propargyl groups.

Example 6. Generation of GlcNAc(β-N-Asn) Units in Glycoproteins Transferrin

The biantennary complex N-glycans of bovine transferrin (Sigma) were truncated to single GlcNAc units by digestion with endo-β-N-acetylglucosaminidase F2 as instructed by the enzyme supplier (Endo F2 from *Elizabethkingia miricola*, Calbiochem). In brief, 300 µg of bovine transferrin was incubated with 30 mU of Endo F2 in 50 µl of 50 mM sodium acetate, pH 4.5, for ca. 24 h at 37° C. MALDI-TOF MS analysis of the reaction product implied that ca. 40% of the N-glycans were converted to single GlcNAc(β-N-Asn) units.

RNAse B

The high-mannose N-glycans of bovine RNAse B (Sigma) were truncated to single GlcNAc units by digestion with endo-β-N-acetylglucosaminidase H as instructed by the enzyme supplier (Endoglycosidase H from *Streptomyces plicatus*, Calbiochem). In brief, 200 μg of bovine RNAse B was incubated with 20 mU of Endo H in 50 μl of 50 mM sodium acetate, pH 5.5, for ca. 24 h at 37° C. MALDI-TOF MS analysis of the reaction product showed full conversion of N-glycans to single GlcNAc(β-N-Asn) units.

Trastuzumab

The Fc-domain complex N-glycans of trastuzumab antibody (Roche) were truncated to single GlcNAc units by digestion with endo-β-N-acetylglucosaminidase S as instructed by the enzyme supplier (IgGZERO, Genovis). In brief, 8 mg antibody was incubated with 1000 U of Endo H in 1050 μl of 10 mM sodium phosphate, 150 mM NaCl, pH 7.4, for 4 h at 37° C. SDS-PAGE analysis of the reaction product showed clear reduction of molecular weight, implying efficient cleavage of the N-glycan. Furthermore, N-glycan analysis of the Endo S treated antibody showed that virtually all complex-type N-glycans had been cleaved.

Example 7. Modification of GlcNAc(β-N-Asn) Units in Glycoproteins

Galactosylation of GlcNAc(β-N-Asn) units in glycoproteins is carried out by incubating the acceptor glycoprotein with β1,4-galactosyltransferase enzyme and UDP-galactose. For example, 1 mg glycoprotein, 30 mM UDP-Gal, 20 mM MnCl$_2$ and 3.2 mU/μl β1,4-galactosyltransferase are mixed in 100 μl of appropriate buffer (e.g. 50 mM MOPS-buffer, pH 7.0), and incubated for 24-48 h at +37° C.

6-propargylgalactose is added to GlcNAc(β-N-Asn) units in glycoproteins by incubating the acceptor glycoprotein with appropriate β1,4-galactosyltransferase enzyme, for example bovine milk galactosyltransferase (Sigma) or mutant human galactosyltransferase 1 (Y285L; R&D Systems) and the donor UDP-PrGal. For example, 1 mg glycoprotein, 30 mM UDP-PrGal, 20 mM MnCl$_2$ and 3.2 mU/μl galactosyltransferase are mixed in 100 μl of appropriate buffer (e.g. 50 mM MOPS-buffer, pH 7.0), and incubated for 24-48 h at +37° C. for production of 6-propargyl-Galβ4GlcNAc(β-N-Asn) units in glycoproteins.

GalNAz is added to GlcNAc(β-N-Asn) units in glycoproteins by incubating the acceptor glycoprotein with appropriate β1,4-galactosyltransferase enzyme, for example mutant bovine galactosyltransferase 1 (Y289L; Invitrogen) or mutant human galactosyltransferase 1 (Y285L; R&D Systems) and the donor UDP-GalNAz. For example, 1 mg glycoprotein, 30 mM UDP-GalNAz, 20 mM MnCl$_2$ and 3.2 mU/μl galactosyltransferase are mixed in 100 μl of appropriate buffer (e.g. 50 mM MOPS-buffer, pH 7.0), and incubated for 24-48 h at +37° C. for production of GalNAzβ4GlcNAc(β-N-Asn) units in glycoproteins.

MODO-TREA-DBCO was prepared as described in Example 34, and it was then conjugated to GalNAz units in GalNAz-trastuzumab (see above) in a copper-free click reaction according to manufacturer's instructions. Fc-analysis after conjugation revealed complete reaction with major signal at m/z 25695 corresponding to MODO-TREA-DBCO-GalNAZ-β4(Fucα6)GlcNAc-trastuzumab.

9-azido-N-acetylneuraminic acid is transferred to GalNAzβ4GlcNAc(β-N-Asn) units in glycoproteins by incubating the acceptor glycoprotein with appropriate sialyltransferase, for example recombinant human ST6Gal1 α2,6-sialyltransferase, and the donor CMP-9-deoxy-9-azido-NeuNAc. The glycoprotein acceptor can be modified with either Galβ4GlcNAc(β-N-Asn) or GalNAzβ4GlcNAc(β-N-Asn) structures as described above. For example, 0.5-10 μg human α-2,6-sialyltransferase ST6Gal1 (R&D Systems), 0.5 mg glycoprotein acceptor and 30 mM CMP-9'-azido-NeuAc are mixed in 75 μl of appropriate buffer (e.g. 50 mM Tris-HCl, 50 mM NaCl, pH 7.5), and incubated for 24-48 h at +37° C.

Example 8. Enzymatic Modification of Cetuximab

Cetuximab (Merck Serono) was digested with either 1) α1,3-galactosidase (Sigma Aldrich), 2) α1,3-galactosidase and Sialidase A (Glyko) or 3) α1,3-galactosidase, Sialidase A and β1,4-galactosidase (Calbiochem). Reactions were carried out over night at +37° C. in 50 mM Na-acetate pH 5.5 containing 5 mg of cetuximab. Enzyme concentrations in reactions were 10 mU/μl α1,3-galactosidase, 0.4 mU/μl Sialidase A and 0.19 mU/μl β1,4-galactosidase. After o/n reactions the progress of digestions was confirmed by N-glycan isolation followed by MALDI-TOF MS analysis: 10-20 μg of antibody was precipitated with ice-cold 67% (v/v) ethanol. Precipitate was pelleted by centrifugation and N-glycans were released by o/n incubation with N-glycosidase F (Glyko). Reaction mixtures were purified successively on Hypersep C-18 and Hypersep Hypercarb 50 mg 96-well plates (Thermo Scientific). The neutral and acidic glycans were eluted together from Hypercarb with 25% acetonitrile in aqueous 0.05% trifluoroacetic acid. MALDI-TOF MS analyses were carried out in reflector positive ion mode using 2,5-dihydroxybenzoic acid (DHB, Aldrich) as the matrix.

MALDI TOF MS analysis of isolated N-glycans of the original cetuximab revealed major signals fr Hex5HexNac2 at m/z 1257, Hex3HexNAc4dHex at m/z 1485 and Hex4HexNAc4dHex at m/z 1647 corresponding to N-linked glycans Man5GlcNAc2, GlcNAcMan(GlcNAcMan)Man-GlcNAcGlcNAc (G0F) and GalGlcNAcMan(GlcNAcMan) ManGlcNAcGlcNAc (G1F) (FIG. 3). Minor signals for Hex5HexNAc4dHex at m/z 1809, Hex7HexNAc4dHex at m/z 2133 and Hex6HexNAc4dHexNeuGcNa2OH at m/z 2300 corresponded to N-linked glycans GalGlcNAcNan (GalGlcNAcMan)ManGlcNAcGlcNAc (G2F), di-α-1,3-galactosylated G2F and NeuGc-containing mono-α-1,3-galactosylated G2F.

MALDI TOF MS analysis of α1,3-galactosidase-digested Cetuximab revealed major signals for Hex5HexNac2 at m/z 1257, Hex3HexNAc4dHex at m/z 1485 and Hex4HexNAc4dHex at m/z 1647 corresponding to N-linked glycans Man5GlcNAc2, G0F and G1F. Minor signals for Hex4HexNAc4dHexNeuGcNa2OH at m/z 1976 and Hex5HexNAc4dHexNeuGcNa2OH at m/z 2138 corresponded to NeuGc-containing G1F and G2F.

MALDI TOF MS analysis of α1,3-galactosidase- and Sialidase A-digested cetuximab revealed major signals for Hex5HexNac2 at m/z 1257, Hex3HexNAc4dHex at m/z 1485 and Hex4HexNAc4dHex at m/z 1647 corresponding to N-linked glycans Man5GlcNAc2, G0F and G1F.

MALDI-analysis of α1,3-galactosidase-, Sialidase A and and β1,4-galactosidase-digested cetuximab revealed major signals for Hex5HexNac2 at m/z 1257 and Hex3HexNAc4dHex at m/z 1485 corresponding to N-linked glycans Man5GlcNAc and G0F.

MALDI-TOF MS N-glycan analysis of A) cetuximab, B) cetuximab digested with α1,3-galactosidase, C) cetuximab digested with α1,3-galactosidase and Sialidase A and D) cetuximab digested with α1,3-galactosidase, Sialidase A and β1,4-galactosidase is shown in FIG. 3.

Reaction mixtures were stored frozen until purified with HiTrap Protein G column (GE Healthcare) using 0.02 M Na-phosphate pH 7 as the binding buffer and 0.1 M citric acid pH 2.6 as the elution buffer. Fractions containing IgG were pooled and neutralized with 1 M Na$_2$HPO$_4$.

Example 9. β1,4-Galactosylation of Modified Cetuximab

Cetuximab treated with α1,3-galactosidase or with α1,3-galactosidase and Sialidase A was galactosylated with β1,4-galactosyltransferase (Calbiochem). Reactions were carried out in 100 μl of 50 mM MOPS-buffer pH 7.0 containing 5 mg modified cetuximab, 30 mM UDP-Gal, 20 mM MnCl$_2$ and 3.2 mU/μl β1,4-galactosyltransferase for 48 h at +37° C. Completion of reaction was confirmed by N-glycan analysis followed by MALDI-TOF MS analysis as described above.

Reaction mixtures were stored frozen until purified with HiTrap Protein G column as described above.

MALDI TOF MS analysis of β1,4-galactosyltransferase treated α1,3-galactosidase-digested cetuximab revealed major signals for Hex5HexNAc2 at m/z 1257 and Hex5HexNAc4dHex at m/z 1809, corresponding to N-linked glycans Man5GlcNAc2 and G2F, respectively, thus confirming successful galactosylation. Minor signal for Hex5HexNAc4dHexNeuGcNa2-H at m/z 2138 corresponded to NeuGc-containing G2F.

Figure 4:
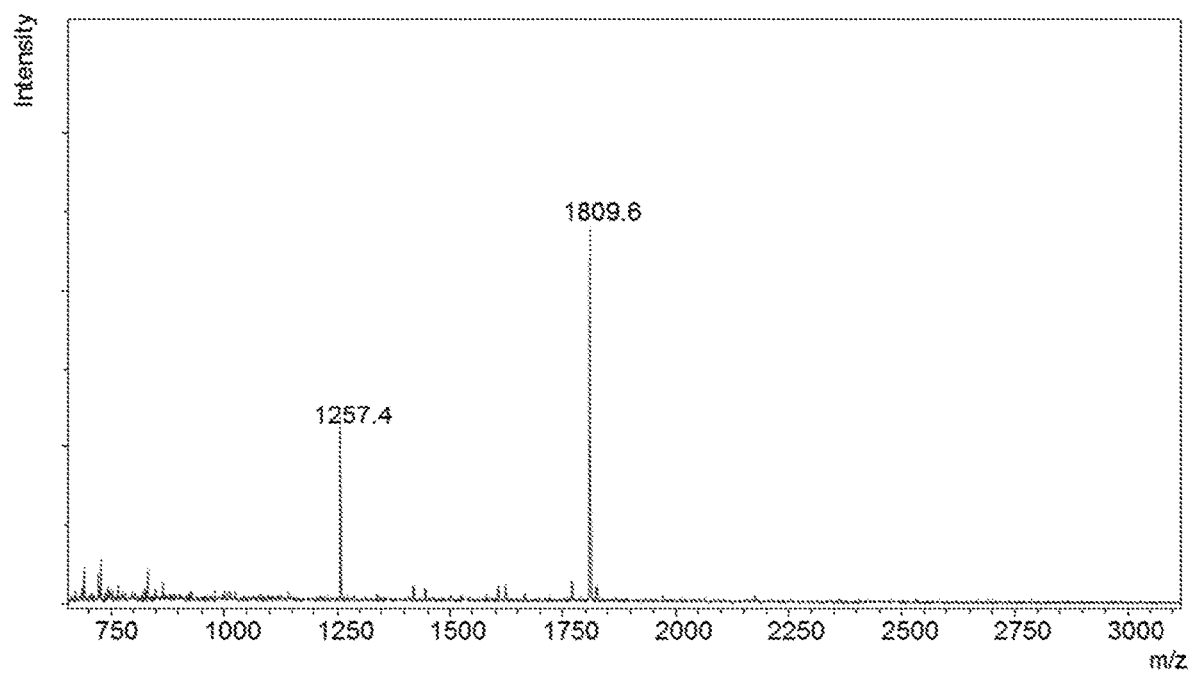
FIG. 4 shows MALDI-TOF MS analysis of N-glycans of cetuximab digested with α1,3-galactosidase and Sialidase A and galactosylated with β1,4-galactosyltransferase.

MALDI TOF MS analysis of β1,4-galactosyltransferase treated α1,3-galactosidase- and Sialidase A-digested cetuximab revealed major signals for Hex5HexNAc2 at m/z 1257 and Hex5HexNAc4dHex at m/z 1809 corresponding to N-linked glycans Man5GlcNAc2 and G2F (FIG. 4). This result confirmed successful galactosylation.

Example 10. α2,6-Sialylation of Enzymatically Modified Cetuximab with CMP-9-Deoxy-9-Azido-NeuNAc Donor Protein G purified cetuximab digested with α1,3-galactosidase and Sialidase A and galactosylated with β1,4-galactosyltransferase was sialylated with human α2,6-Sialyltransferase (ST6Gal1, R&D Systems) and CMP-9-deoxy-9-azido-NeuNAc (above). Reaction was carried out for 2× overnight at +37° C. in 50 mM Tris-HCl, 50 mM NaCl pH 7.5 containing 0.5 mg modified cetuximab and 30 mM CMP-9'-azido-NeuAc in 75 μl volume. Reaction was monitored by N-glycan isolation followed by MALDI-TOF MS analysis as described above. Reaction mixtures were stored frozen until purified with HiTrap Protein G column as described above.

Figure 5:
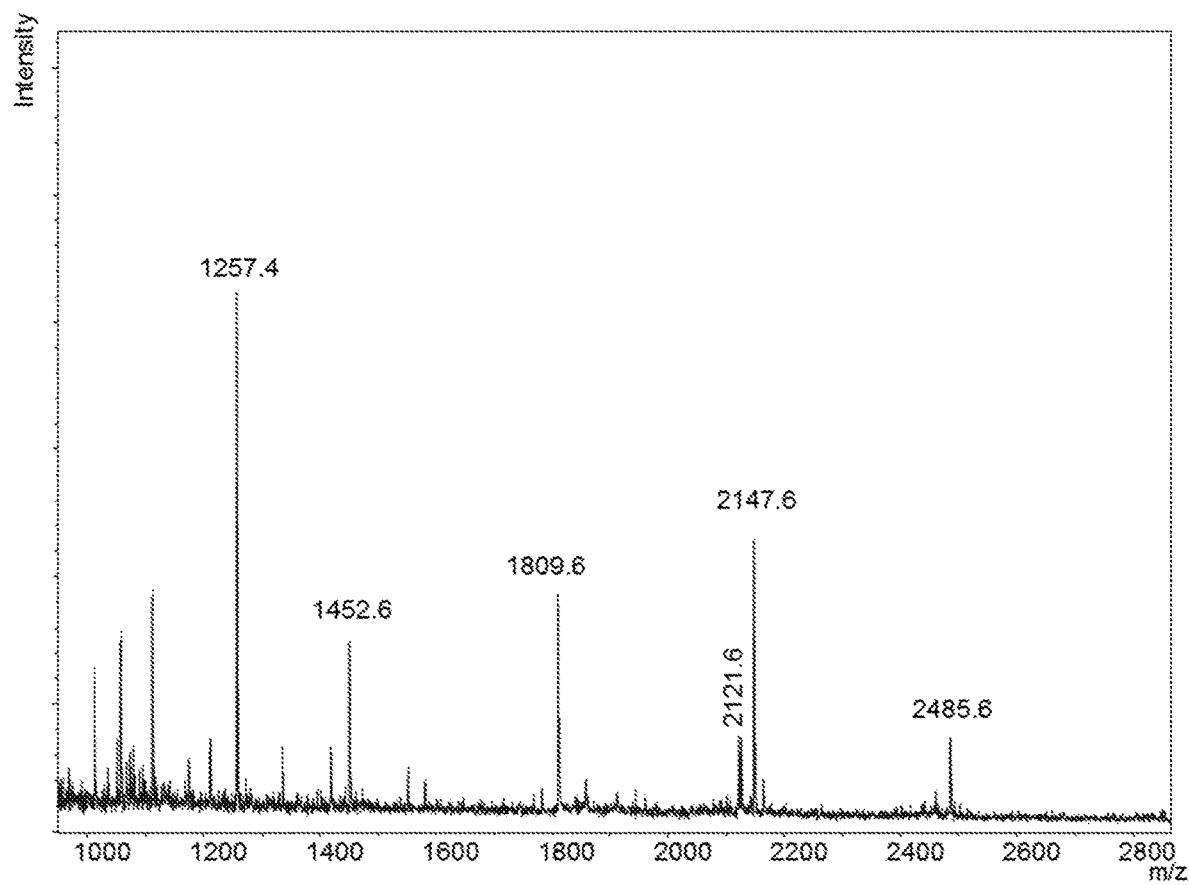
FIG. 5 demonstrates MALDI-TOF MS analysis of ST6Gal1-reaction of α1,3-galactosidase- and Sialidase A-digested and galactosylated cetuximab.

MALDI-analysis of ST6Gal1-treated cetuximab revealed signals for Hex5HexNac2 at m/z 1257 and Hex5HexNAc4dHex at m/z 1809 corresponding to N-linked glycans Man5GlcNAc2 and G2F, respectively, and sialylated glycans at m/z 2147 and m/z 2485, corresponding to G2F carrying one and two 9-azido-NeuNAc units, respectively (FIG. 5). This sample was named 9-azido-NeuAc-cetuximab.

Example 11. Synthesis of TGTA (tris{[1-(6-D-galactosyl)-1H-1,2,3-triazol-4-yl]methyl}amine)

General experimental details: Reagents and solvents were purchased from commercial sources. Reaction solvents were dried and distilled prior to use when necessary. All reactions containing moisture- or air-sensitive reagents were carried out under an argon atmosphere. The preparation of 1 has been described previously and similar routes were employed in the current synthesis (see for example Yang, J., et al., 2003. J. S. Org. Lett. 5:2223-6).

The NMR spectra were recorded with a Bruker Avance spectrometer operating at 600 MHz ($^1$H: 600 MHz, $^{13}$C: 150 MHz). Pulse sequences provided by the manufacturer were utilized. The probe temperature during the experiments was kept at 22° C. unless otherwise mentioned. Chemical shifts are expressed on the δ scale (in ppm) using TMS (tetramethylsilane), residual chloroform, acetone, H$_2$O or methanol as internal standards. Coupling constants are given in Hz and provided only once when first encountered. Coupling patterns are given as s, singlet, d, doublet, t, triplet etc. Mass spectra were obtained with a Bruker Ultraflex III MALDI-TOF mass spectrometer operated in positive/negative mode. TLC was performed on aluminium sheets precoated with silica gel 60 F254 (Merck). Flash chromatography was carried out on silica gel 60 (0.040-0.060 mm, Aldrich). Spots were visualized by UV followed by charring with 1:5 H$_2$SO$_4$/MeOH and heating.

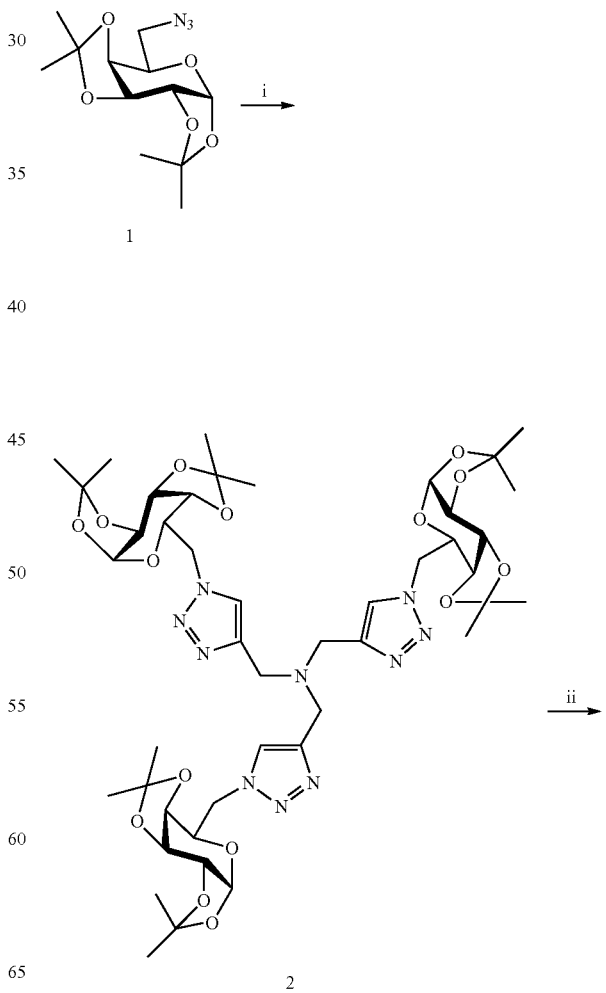

Scheme 5

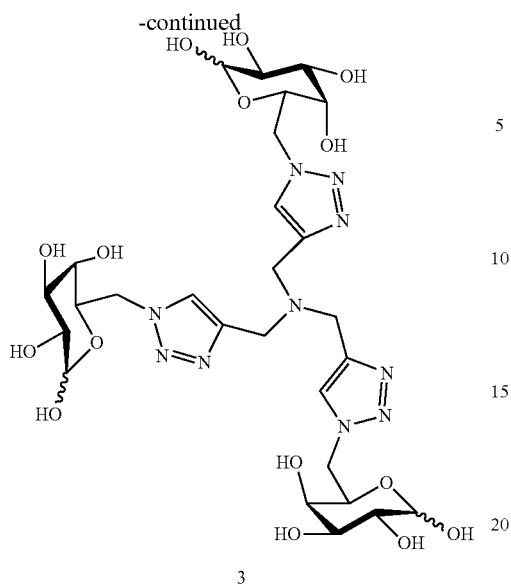

3 i) Tripropargylamine, CuSO$_4$, sodium L-ascorbate, DMF:H$_2$O 3:1, RT, 40 h, quantitative; ii) 60% TFA (in H$_2$O), 60° C., 2.5 h, quantitative.

Protected TGTA (2): To a solution containing 43 mg of 1 (0.15 mmol, 5 equiv.) and 4.3 µl tripropargylamine (0.03 mmol, 1 equiv.) in 2 ml of DMF:H$_2$O (3:1) was added 2.4 mg CuSO$_4$ (0.015 mmol, 0.5 equiv.) and 6.4 mg sodium L-ascorbate (0.03 mmol, 1 equiv.). The resulting mixture was stirred at RT for 40 h (during this time a white solid precipitated from the reaction mixture). After 40 h, the reaction mixture was diluted with 20 ml EtOAc transferred to a separatory funnel and washed with 5 ml NH$_4$Cl-solution (prepared by dissolving a saturated NH$_4$Cl-solution with equal amount of water 1:1 v/v) and 15 ml brine. The organic phase was dried with Na$_2$SO$_4$, filtered and concentrated to give the crude product. The crude product was purified by column chromatography (EtOAc→EtOAc:MeOH 3:1) to give 2 as a colorless oil (30 mg, quantitative). TLC: R$_f$=0.22 (EtOAc). $^1$H NMR (600 MHz, CDCl$_3$, 25° C.): δ=8.56 (s, 3H, triazole-H), 5.48 (d, 3H, J$_{1,2}$=5.0 Hz, H-1), 4.67 (dd, 3H, J$_{6a,5}$=3.1, J$_{6a,6b}$=14.1 Hz, H-6a), 4.65 (dd, 3H, J$_{3,2}$=2.5, J$_{3,4}$=8.1, H-3), 4.58 (dd, 3H, J$_{6b,5}$=9.0 Hz, H-6b), 4.41 and 4.33 (each d, each 3H. J$_{NCH2a, NCH2b}$=14.1 Hz, N(CH$_2$)$_3$), 4.32 (dd, 3H, H-2), 4.25 (dd, 3H, J$_{4,5}$=1.4 Hz, H-4), 4.17 (ddd, 3H, H-5), 1.50, 1.39, 1.37 and 1.25 (each s, each 9H, O$_2$C(CH$_3$)$_2$) ppm. HRMS: calcd. for C$_{45}$H$_{66}$N$_{10}$O$_{15}$Na [M+Na]$^+$ 1009.46. found 1009.40.

TGTA (3): 33 mg of 2 (0.034 mmol) was dissolved in 3 ml 60% TFA (in H$_2$O) and stirred at 50° C. for 1.5 hours. The reaction mixture was then diluted with water, concentrated and dried under vacuum to give 3 as a white solid (25 mg, quantitative, α:β 2:3). Selected NMR-data; $^1$H NMR (600 MHz, D$_2$O, 25° C.): δ=8.32 (s, 6H (α and β, 3H each), triazole-H), 5.21 (d, 3H, J$_{1,2}$=3.9 Hz, H-1α), 4.59 (s, 12H (α and β, 6H each), N(CH$_2$)$_3$), 4.50 (d, 3H, J$_{1,2}$=8.1 Hz, H-1β). HRMS: calcd. for C$_{27}$H$_{42}$N$_{10}$O$_{15}$Na [M+Na]$^+$ 769.27. found 769.23.

The structure of TGTA and its proposed copper(I) chelating mode:

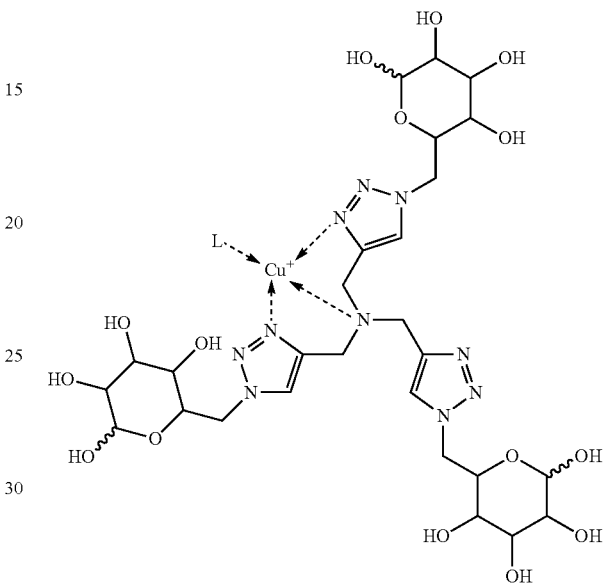

Example 12. Conjugation of 9-azido-NeuAc-cetuximab with N-(6-propargyl-D-galactose)-monomethyldolastatin 10

N-(6-propargyl-D-galactose)-monomethyldolastatin 10 (MODO-Gal) was conjugated to 9-azido-NeuAc-cetuximab N-glycans via the 9-azido-modified sialic acids. Reaction was carried out for 3.5 hours at RT in diluted PBS containing 75 µg 9-azido-NeuAc-cetuximab (above), 13 nmol MODO-Gal, 25 nmol of TGTA, 25 nmol Na-ascorbate and 5 nmol of CuSO$_4$. Reaction product was purified in Amicon Ultracel 30 K concentrator (Millipore) by several additions of PBS and subsequent centrifugations. Reducing SDS-PAGE of the reaction product revealed IgG light (≈30 kDa) and heavy chains (≈55 kDa). No protein cleavage products could be detected.

Scheme 6: Structure of the antibody-drug conjugate of cetuximab and dolastatin 10.

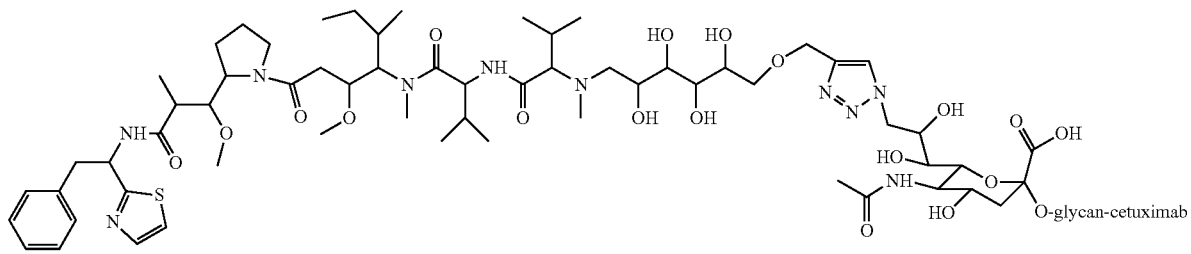

Example 13. Production of Monoclonal Antibody Glycoforms in CHO Cells

Trastuzumab was produced transiently with FreeStyle™ Max Expression System (Life Technologies) according to manufacturer's instructions. The trastuzumab amino acid sequences were according to the IMGT database (http://www.imgt.org) for the light chain (7637_L) and heavy chain (7367_H) sequences. Optimized nucleotide sequences encoding the heavy and light chain sequences were purchased from GeneArt (Life Technologies) and cloned separately into pCEP4 expression vectors (Life Technologies). For antibody expression, the FreeStyle™ CHO—S cells were transfected 1:1 with light chain and heavy chain vectors.

N-glycan analysis was done to the produced Trastuzumab antibodies as described above. Analysis revealed the following N-glycan profile: 1.2% Hex3HexNAc3, 9.6% Hex5HexNAc2 (Man5), 2.2% Hex3HexNAc3dHex, 2.5% Hex3HexNAc4 (G0), 3.3% Hex6HexNAc2, 56.7% Hex3HexNAc4dHex (G0F), 1.8% Hex4HexNAc4 (G1), 1.6% Hex7HexNAc2, 7.4% Hex4HexNAc4dHex (G1F), 1.1% Hex5HexNAc4 (G2), 5.6% Hex3HexNAc5dHex, 1.5% Hex8HexNAc2, 1.9% Hex5HexNAc4dHex (G2F) and 1.2% Hex9HexNAc2. Thus the major N-glycan types were G0(F) (59%), G1(F) (9%) and Man5 (10%).

Freedom CHO—S Kit (Life Technologies) was used for the development of stable cell lines producing cetuximab. The work was done according to manufacturer's instructions. Cetuximab amino acid sequences were according to IMGT database (http://www.imgt.org) for the light chain and heavy chain sequences. Optimized nucleotide sequences encoding the heavy and light chain sequences were purchased from GeneArt (Life Technologies) and cloned separately into pCEP4 expression vectors (Life Technologies). For stable expression, the FreeStyle™ CHO—S cells were transfected with linearized 1:1 light chain and heavy chain vectors. Transfectants were selected with puromycin and methotrexate after which clone isolation was done by limited dilution cloning. Cloned cell lines were scaled up and assessed for productivity.

N-glycan analysis was done to the produced cetuximab antibodies as described above. Analysis of a selected antibody-producing cell clone revealed the following N-glycan profile: 1.7% Hex3HexNAc3, 5.7% Hex5HexNAc2, 4.8% Hex3HexNAc3dHex, 2.8% Hex3HexNAc4 (G0), 1.6% Hex6HexNAc2, 75.3% Hex3HexNAc4dHex (G0F), 4.3% Hex4HexNAc4dHex (G1F) and 2.8% Hex3HexNAc5dHex. Thus N-glycans were mainly G0(F)-type (>78%) with only minor proportions of high-mannose (Hex5HexNAc2, Hex6HexNAc2), galactosylated (G1F) or afucosylated (G0) glycans. Other analyzed cell clones were also similarly mainly G0(F)-type. Analysis of isolated Fab heavy chains showed that the variable domain N-glycosylation sites of the produced cetuximab antibodies were glycosylated. Thus the generated cell lines had unexpectedly low galactosylation level and high proportion of accessible GlcNAc residues also in the variable domain N-glycans.

Example 14. In Vitro Cytotoxicity of Antibody Conjugates

Human ovarian cancer cell line SKOV-3 and head-and-neck cancer cell line HSC-2 were from the ATCC (Manassas, Va., USA). The cells were grown according to the manufacturer's recommendations. Log phase cultures were collected and 5000 cells/well were seeded onto 96-well plates and incubated for 24 h. Serial dilutions of test molecules were made in cell culture medium, added to cells and cultures were incubated further for 96 h. Cell viability was evaluated using PrestoBlue cell viability reagent (Life Technologies, Carlsbad, Calif., USA) according to the manufacturer's instructions. Cells were incubated for 2 h, and dye reduction was measured by absorbance at 570 nm. The compounds were assayed 1-2 times in triplicate.

The results are expressed as 1050 values of the analyzed derivatives as the concentration range in dolastatin equivalents wherein cancer cell viability falls to 50%. The triazole conjugate of 9-azido-NeuAc-cetuximab and N-(6-O-propargyl-D-galactosyl)-monomethyldolastatin 10 was cytotoxic to both cell lines SKOV-3 and HSC-2 with IC50 at or below 1 nM, while the unconjugated derivative N-(6-O-propargyl-D-galactosyl)-monomethyldolastatin 10 was at least 100 times less toxic to the cells than the antibody conjugate in the same experiments.

Example 15. Stability Assays of Saccharide Conjugates

Stability of saccharide conjugate is evaluated by incubation at +37° C. for varying periods of time from about 1 hour to about 1 week in human or animal serum prepared by incubating blood in room temperature and centrifugation to remote the clot, or similarly incubating in human or animal plasma prepared by collection of fresh blood in heparinized tubes. The conjugate is isolated and analysed as described above to detect proportion of intact conjugate.

Example 16. Hydrolysis Assays of Saccharide Conjugates

Hydrolysis rate of saccharide conjugate is evaluated by incubation at +37° C. for varying periods of time from about 1 minute to about 1 day in presence of enzyme source at acidic pH, preferably at pH 4.5. The enzyme source is e.g. recombinant peptidase or glycohydrolase enzyme such as human lysosomal β-galactosidase or β-hexosaminidase available from R&D Systems, or a human or animal cell lysate as a source of all lysosomal enzymes, or human red blood cell membrane preparate as a source of lysosomal sialidase. The conjugate is isolated and analysed as described above to detect proportion of intact conjugate.

Example 17. Synthesis of Aminooxy-Linker

Scheme 7. Synthesis of compounds 2 and 3: i) N-methylmorpholine (NMM), isobutylchloroformatem (IBCF), 1-amino-3-butyne, tetrahydrofuran (THF), RT, 1.5 h; ii) DCM:TFA (1:1), RT, 1 h.

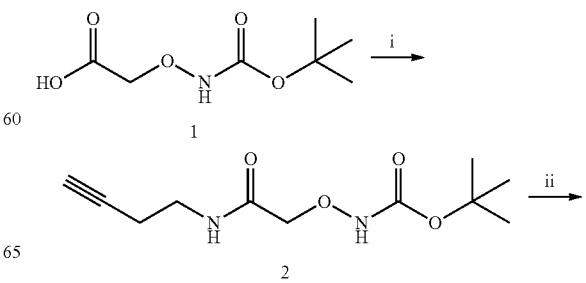

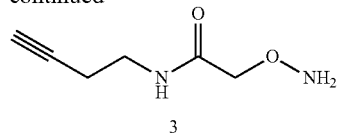

2-[N-(tert-butoxycarbonyl)aminooxy]-N-(butynyl) acetamide (2)

0.41 g (2.1 mmol) of 1 was dissolved in 7 ml dry THF (under argon atmosphere) and the mixture was cooled on an ice bath. 0.24 ml (2.1 mmol, 1 equiv.) NMM and 0.28 ml (2.1 mmol, 1 equiv.) IBCF were added and the reaction mixture was stirred for 0.5 h at 0° C. 0.18 ml (2.1 mmol, 1 equiv.) of 1-amino-3-butyne was added and the resulting mixture was brought to RT and stirred for an additional 1.5 h. The mixture was then filtered and concentrated and the crude product was dissolved in 20 ml Et$_2$O and washed with 10 ml 0.1 M NaOH, 10 ml 1 M HCl and 10 ml brine. The organic phase was dried with Na$_2$SO$_4$, filtered and concentrated. The crude product was purified by column chromatography (hexane:EtOAc 1:2) to give the title compound as a white solid. TLC: R$_f$=0.34 (in hexane:EtOAc 1:2). $^1$H NMR (600 MHz, CDCl3, 22° C.): δ 8.25 (br s, 1H, NH), 7.48 (s, 1H, NH), 4.33 (s, 2H, OCH$_2$CO), 3.49 (ap q, 2H, J=6.8 Hz, NHCH$_2$CH$_2$C≡CH), 2.44 (ap td, 2H, J=2.6, 6.8 Hz, NHCH$_2$CH$_2$C≡CH) 1.99 (ap t, 1H, J=2.6 Hz, NHCH$_2$CH$_2$C≡CH) and 1.49 (s, 9H, OC(CH$_3$)$_3$) ppm.

2-[N-aminooxy]-N-(butynyl) acetamide (3)

0.13 g (0.5 mmol) of 2 was dissolved in 2 ml DCM, cooled on an ice bath and 2 ml of TFA was slowly added to the mixture. The mixture was stirred for 1 h at RT (TLC monitoring) and concentrated to give the title compound as a colorless oil. $^1$H NMR (600 MHz, D$_2$O, 22° C.): δ 4.62 (s, 2H, OCH$_2$CO), 3.40 (ap t, 2H, J=6.7 Hz, NHCH$_2$CH$_2$C≡CH), 2.43 (ap td, 2H, J=2.6, 6.7 Hz, NHCH$_2$CH$_2$C≡CH) and 2.34 (ap t, 1H, J=2.6 Hz, NHCH$_2$CH$_2$C≡CH) ppm.

Example 18. Synthesis of 9-Modified NeuNAc

Scheme 8. Synthesis of compound 3: 1) MeOH, AG 50 W-X8 (H$^+$-form), 45° C., o/n; 2) TsCl, pyridine, 0° C.,→ RT, o/n; 3) NaN$_3$, Acetone:H$_2$O (3:1), 75° C., o/n; ii) 1) Pd/C, H$_2$ (40 psi), H$_2$O:AcOH, o/n: 2) Levulinic acid NHS ester, NaHCO$_3$, dioxane:H$_2$O (4:3), RT, o/n.

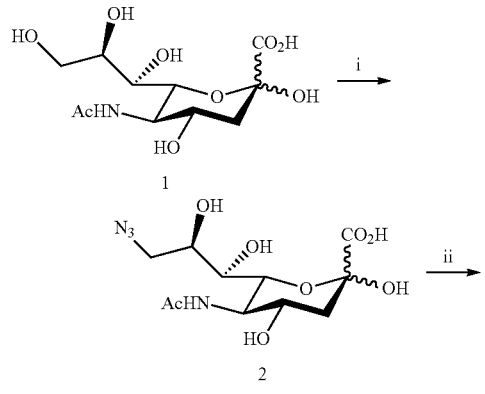

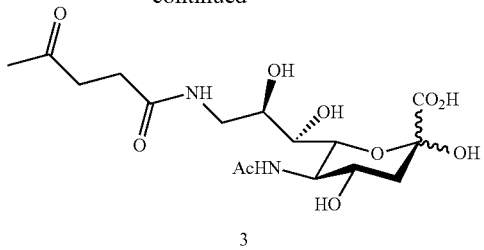

Levulinic Acid NHS Ester 0.3 ml (2.93 mmol) Levulinic acid was dissolved in 7 ml dry DMF (under argon atmosphere) and 0.84 g (4.4 mmol, 1.5 equiv.) EDC×HCl and 0.41 g (3.5 mmol, 1.2 equiv.) NHS were added. The resulting mixture was stirred o/n at RT, then diluted with 20 ml EtOAc and washed with 20 ml of a satd. ammonium chloride solution, 20 ml H$_2$O and 20 ml brine. The organic phase was separated and dried with Na$_2$SO$_4$, filtered and concentrated to give the crude product as a white powder (0.45 g, 71%). The crude product was utilized as such in the following step.

5-acetamido-9-azido-3,5,9-trideoxy-D-glycero-D-galacto-2-nonulosonic Acid (2)

To a solution containing 63 mg of 1 (0.2 mmol) in 5 ml dry MeOH (under argon) was added 127 mg AG 50 W×8 (H$^+$-form, 2 weight equiv.) and the resulting mixture was stirred at 45° C. o/n. The mixture was then filtered and concentrated to give methyl N-acetyl neuraminate as a white solid (65 mg, quantitative). TLC: R$_f$=0.43 (DCM:MeOH 3:1)

157 mg of methyl N-acetyl neuraminate (0.49 mmol) was dissolved in 5 ml of dry pyridine (under argon) and the reaction mixture was cooled to 0° C. 135 mg TsCl (0.7 mmol, 1.4 equiv.) was added and the reaction mixture was slowly warmed to RT and left to stir o/n. After 23 hours 134 mg TsCl (0.7 mmol, 1.4 equiv.) was added to the reaction mixture and it was stirred for an additional 2 hours at RT. The mixture was then cooled to 0° C. and the reaction quenched with MeOH. The mixture was concentrated and the crude product was purified by column chromatography (MeOH:DCM 1:9) to give methyl 9-O-tosyl-N-acetyl-neuraminate as a yellowish oil (159 mg, 67%). TLC: R$_f$=0.29 (DCM:MeOH 9:1). Selected NMR-data; $^1$H NMR (600 MHz, CD$_3$OD, 22° C.): δ 7.80-7.43 (m, 4H, CH$_3$C$_6$H$_4$SO$_2$), 4.28 (dd, 1H, J=2.2, 10.1 Hz), 4.06-3.99 (m, 2H), 3.93 (dd, 1H, J=1.5, 10.6 Hz), 3.85 (ddd, 1H, J=2.0, 5.7, 8.5 Hz), 3.77 (s, 3H, CO$_2$CH$_3$), 3.43 (dd, 1H, J=1.5, 9.0 Hz), 2.46 (s, 3H, CH$_3$C$_6$H$_4$SO$_2$), 2.19 (dd, 1H, J=4.9, 12.9 Hz, H-3eq), 2.00 (s, 3H, NHCOCH$_3$) and 1.86 (dd, 1H, J=11.5, 12.9 Hz, H-3ax) ppm. HRMS: calcd. for C$_{19}$H$_{27}$O$_{11}$NNaS [M+Na]$^+$ 500.12. found 500.20.

110 mg of methyl 9-O-tosyl-N-acetyl-neuraminate (0.23 mmol) was dissolved in 2 ml acetone:H$_2$O (3:1) and 70 mg NaN$_3$ (1.1 mmol, 4.3 equiv.) was added. The resulting mixture was heated to 75° C. and stirred o/n. The reaction mixture was then concentrated and the crude product purified by gel filtration chromatography to give 2 as a yellowish foam (40 mg, 52%). Selected NMR-data; $^1$H NMR (600 MHz, D$_2$O, 22° C.): δ 4.03 (ddd, 1H, J=5.1, 10.1, 10.3 Hz), 3.99 (dd, 1H, J=0.9, 10.6 Hz), 3.94-3.89 (m, 2H), 3.61 (dd, 1H, J=2.8, 13.1 Hz), 3.53 (ap d, 1H, J=9.4 Hz), 3.49 (dd, 1H, J=6.0, 13.1 Hz), 2.22 (dd, 1H, J=4.9, 12.9 Hz, H-3eq), 2.07 (s, 3H, NHCOCH$_3$) and 1.83 (dd, 1H, J=11.7, 12.9 Hz, H-3ax) ppm. HRMS: calcd. for $C_{11}H_{18}O_8N_4Na$ [M+Na]$^+$ 357.10. found 357.12; calcd. for $C_{11}H_{17}O_8N_4Na_2$ [M+2Na—H]$^+$ 379.08. found 379.10.

5-Acetamido-3,5,9-trideoxy-9-[(1,4-dioxopentyl)amino]-D-glycero-D-galacto-2-nonulosonic Acid (3)

26 mg (0.08 mmol) of 2 was dissolved in 2.5 ml $H_2O$ and the pH was adjusted to ⅓ with AcOH. 7.9 mg (0.3 weight equiv.) Pd/C (10% Pd) was added and the resulting mixture was placed inside a hydrogenation reactor. The hydrogen pressure was set to 40 psi (~2.7 bar) and the mixture was stirred o/n, then filtered through celite and concentrated to give the crude product 5-acetamido-3,5,9-trideoxy-9-amino-D-glycero-D-galacto-2-nonulosonic acid as a yellowish oil. This product was utilized as such in the following step.

22 mg (0.07 mmol) of 5-acetamido-3,5,9-trideoxy-9-amino-D-glycero-D-galacto-2-nonulosonic acid was dissolved in 3 ml $H_2O$ and the pH was adjusted to ⅜ with a satd. $NaHCO_3$-solution. 23 mg (0.11 mmol, 1.5 equiv.) levulinic acid NHS ester was dissolved in 4 ml dioxane and slowly added to the solution containing the sialic acid in $H_2O$. The reaction mixture was then stirred at RT o/n in the dark and concentrated. The crude product was purified by gel filtration chromatography to give the title compound. HRMS: calcd. for $C_{16}H_{26}O_{10}N_2Na$ [M+Na]$^+$ 429.15. found 429.19; calcd. for $C_{16}H_{25}O_{10}N_2Na_2$ [M+2Na—H]$^+$ 451.13. found 451.17.

Synthesis of Other 9-Modified NeuNAc Analogues

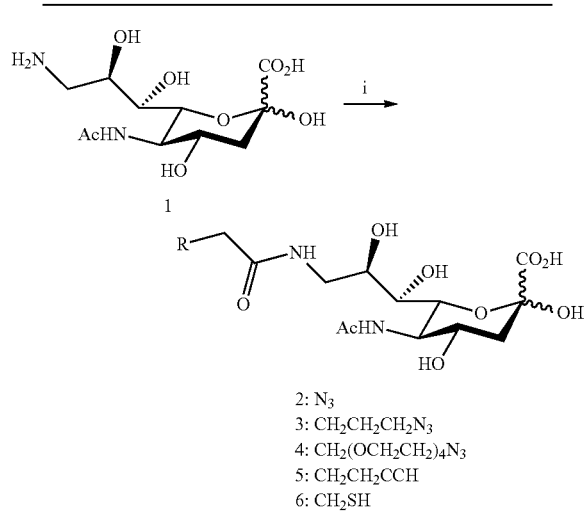

Scheme 9. Synthesis of compound 2-6: i) corresponding NHS ester, NaHCO$_3$, dioxane:H$_2$O (4:3), RT, o/n.

2: $N_3$
3: $CH_2CH_2CH_2N_3$
4: $CH_2(OCH_2CH_2)_4N_3$
5: $CH_2CH_2CCH$
6: $CH_2SH$

General Procedure for Synthesis of Carboxylic Acid NHS Esters

The corresponding carboxylic acid was dissolved in 2 ml dry DMF/mmol acid (under argon atmosphere) and 1.5 equiv. EDC×HCl and 1.2 equiv. NHS were added. The resulting mixture was stirred o/n at RT, then diluted with 7 ml EtOAc/mmol acid and washed with 7 ml of a satd. ammonium chloride solution/mmol acid, 7 ml $H_2O$/mmol acid and 7 ml brine/mmol acid. The organic phase was separated and dried with $Na_2SO_4$, filtered and concentrated to give the crude product. The crude product was utilized as such in the following step.

General Procedure for Synthesis of 9-Amido Modified NeuNAc 5-acetamido-3,5,9-trideoxy-9-amino-D-glycero-D-galacto-2-nonulosonic acid was dissolved in 2 ml $H_2O$/30 mg 1 and the pH was adjusted to ⅜ with a satd. $NaHCO_3$-solution. 1.5 equiv. of the corresponding carboxylic acid NHS ester was dissolved in 2 ml dioxane/30 mg of NHS ester and slowly added to the solution containing the sialic acid in $H_2O$. The reaction mixture was then stirred at RT o/n in the dark and concentrated. The crude product was purified by gel filtration chromatography to give the corresponding 9-amido NeuNAc.

Hexynoic Acid NHS Ester

The synthesis commenced according to the general procedure for synthesis of carboxylic acid NHS esters to give the title compound as a yellowish oil in quantitative yield.

5-Azidopentanoic Acid NHS Ester

The synthesis commenced according to the general procedure for synthesis of carboxylic acid NHS esters to give the title compound as a colorless oil in quantitative yield.

Compound 2

The synthesis commenced according to the general procedure for synthesis of 9-amido modified NeuNAc. HRMS: calcd. for $C_{13}H_{21}O_9N_5Na$ [M+Na]$^+$ 414.12. found 413.97; calcd. for $C_{13}H_{20}O_9N_5Na_2$ [M+2Na—H]$^+$ 436.11. found 435.97. NMR in agreement with the data published by J. C. Paulson et. al. in Angew. Chem. Int. Ed. 2012, 51, 11014.

Compound 3

The synthesis commenced according to the general procedure for synthesis of 9-amido modified NeuNAc. Selected NMR-data; $^1$H NMR (600 MHz, D$_2$O, 22° C.) δ 3.56 (dd, 1H, J=3.0, 14.1 Hz), 3.40 (dd, 1H, J=1.0, 9.0 Hz), 3.25 (dd, 1H, J=7.8, 14.1 Hz), 2.03 (s, 3H, NHCOCH$_3$) and 1.68-1.55 (m, 4H, NHCOCH$_2$CH$_2$CH$_2$CH$_2$N$_3$) ppm. HRMS: calcd. for $C_{16}H_{27}O_9N_5Na$ [M+Na]$^+$ 456.17. found 456.21; calcd. for $C_{16}H_{26}O_9N_5Na_2$ [M+2Na—H]$^+$ 478.15. found 478.17.

Compound 4

The synthesis commenced according to the general procedure for synthesis of 9-amido modified NeuNAc. HRMS: calcd. for $C_{22}H_{39}O_{13}N_5Na$ [M+Na]$^+$ 604.22. found 604.23; calcd. for $C_{22}H_{38}O_{13}N_5Na_2$ [M+2Na—H]$^+$ 626.23. found 626.21.

Compound 5

The synthesis commenced according to the general procedure for synthesis of 9-amido modified NeuNAc. Selected NMR-data; $^1$H NMR (600 MHz, D$_2$O, 22° C.): δ 3.55 (dd, 1H, J=2.9, 14.2 Hz), 3.40 (dd, 1H, J=1.0, 9.1 Hz), 3.27 (dd, 1H, J=7.6, 14.2 Hz), 2.03 (s, 3H, NHCOCH$_3$) and 1.83-1.76 (m, 2H) ppm. HRMS: calcd. for $C_{17}H_{26}O_9N_2Na$ [M+Na]$^+$ 425.15. found 425.11; calcd. for $C_{17}H_{25}O_9N_2Na_2$ [M+2Na—H]$^+$ 447.14. found 447.10.

Compound 6

The synthesis commenced according to the general procedure for synthesis of 9-amido modified NeuNAc starting from 1 and SPDP (pyridyldithiol protective group is partially cleaved under the reaction conditions to give 6). HRMS: calcd. for $C_{14}H_{24}O_9N_2SNa$ [M+Na]$^+$ 419.11. found 419.16; calcd. for $C_{14}H_{23}O_9N_2SNa_2$ [M+2Na—H]$^+$ 441.09. found 441.13.

Example 19. Synthesis of 5-Modified NeuNAc

Scheme 10. Synthesis of compound 4: i) MeSO$_3$H, MeOH, 60° C., o/n; ii) Levulinic acid NHS ester, NaHCO$_3$, dioxane:H$_2$O (4:3), RT, o/n; iii) 1) NBS, acetone:H$_2$O (9:1), 0° C. → RT, 2 h; 2) Na—OMe, MeOH:H$_2$O, RT, o/n.

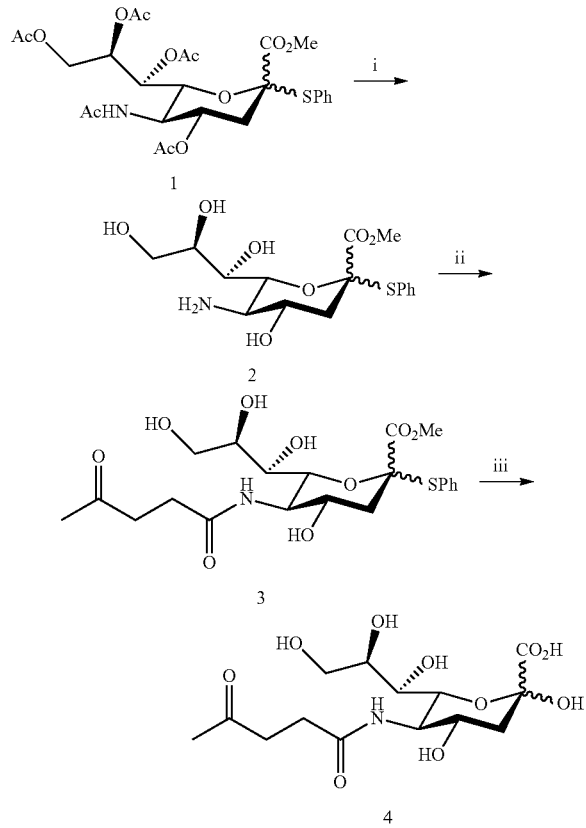

Phenyl 5-amino-2-thio-D-neuraminic Acid Methyl Ester (2)

96.3 mg (0.17 mmol) of 1 was dissolved in 7 ml dry MeOH (under argon atmosphere) and 0.45 ml MeSO$_3$H was added. The resulting mixture was stirred at 60° C. o/n and concentrated to give the crude product. This product was utilized as such in the following step. Selected analytical data; HRMS: calcd. for C$_{16}$H$_{24}$O$_7$NS [M+H]$^+$ 374.13. found 374.15; calcd. for C$_{16}$H$_{23}$O$_7$NSNa$_2$ [M+Na]$^+$ 396.11; found 396.13.

Phenyl 5-[(1,4-dioxopentyl)amino]-2-thio-D-neuraminic Acid Methyl Ester (3)

The crude product from the previous step (63 mg, 0.17 mmol) was dissolved in 3 ml H$_2$O and the pH was adjusted to 8/9 with a satd. NaHCO$_3$-solution. 0.1 g (0.51 mmol, 3 equiv.) of levulinic acid NHS ester dissolved in 4 ml dioxane was slowly added to the reaction mixture. The resulting mixture was stirred o/n at RT in the dark and then concentrated. The crude product was purified by column chromatography (MeOH:DCM 1:5→1:3) to give the title compound as a colorless oil (80 mg, quant.). TLC: R$_f$=0.43 (DCM: MeOH 5:1). Selected NMR-data; $^1$H NMR (600 MHz, CD$_3$OD, 22° C.): δ 7.62-7.32 (m, 5H, arom. H), 4.53 (dd, 1H, J=0.7, 10.6 Hz), 4.13 (m, 1H, H-4), 3.87 (t, 1H, J=10.2 Hz), 3.82 (dd, 1H, J=2.9, 11.3 Hz), 3.78 (m, 1H), 3.67 (dd, 1H, J=5.5, 11.3 Hz), 3.57 (d, 1H, 9.4 Hz), 3.50 (s, 3H, CO$_2$CH$_3$) and 2.19 (s, 3H, NHCOCH$_2$CH$_2$COCH$_3$) ppm.

HRMS: calcd. for C$_{21}$H$_{29}$O$_9$NSNa [M+Na]$^+$ 494.15. found 494.16.

5-[(1,4-dioxopentyl)amino]-D-neuraminic Acid (4)

80 mg (0.17 mmol) of 3 was dissolved in 5 ml acetone: H$_2$O (9:1) and cooled on an ice bath. 127 mg (0.72 mmol, 4.2 equiv.) NBS was added and the resulting mixture was stirred for 2 h (0° C.→RT; TLC monitoring) and concentrated. The crude product was purified by column chromatography (MeOH:DCM 1:5→MeOH:EtOAc 1:3) to give 5-[(1,4-dioxopentyl)amino]-D-neuraminic acid methyl ester as a colorless oil (36 mg, 56%). TLC: R$_f$=0.17 (DCM:MeOH 5:1). HRMS: calcd. for C$_{15}$H$_{25}$O$_{10}$NNa [M+Na]$^+$ 402.14. found 402.16.

36 mg (0.096 mmol) 5-[(1,4-dioxopentyl)amino]-D-neuraminic acid methyl ester was dissolved in 4 ml dry MeOH (under argon atmosphere) and 70 µl of a 5 M solution of NaOMe in MeOH was added. A few drops of H$_2$O was added and the resulting mixture was left to stir o/n at RT. The reaction mixture was then neutralized with AG 50 W×8 (H$^+$-form), filtered and concentrated to give the crude product. The crude product was purified by gel filtration chromatography to give the title compound. HRMS: calcd. for C$_{14}$H$_{23}$O$_{10}$NNa [M+Na]$^+$ 388.12. found 388.17; calcd. for C$_{14}$H$_{22}$O$_{10}$NNa$_2$ [M+2Na—H]$^+$ 410.10. found 410.15.

Example 20. Generation of Fucα1-6GlcNAc(β-N-Asn) Units in Cetuximab

Figure 6:
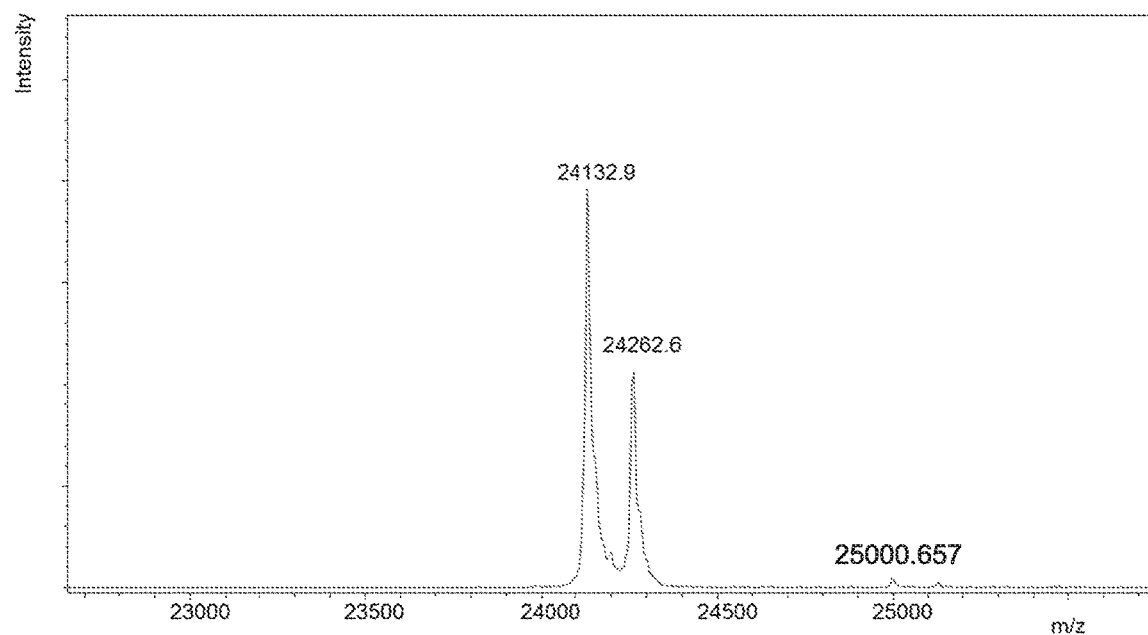
FIG. 6 shows MALDI-TOF MS analysis of Endo S-digested cetuximab Fc-region N-glycans.

The Fc-domain complex N-glycans of cetuximab antibody were truncated to Fucα1-6GlcNAc units by digestion with endo-β-N-acetylglucosaminidase S (Endo S) according to manufacturer's instructions (IgGZERO, Genovis). In brief, 13 mg antibody was incubated with 1500 U of Endo S in 1375 µl of 10 mM sodium phosphate, 150 mM NaCl, pH 7.4, at 37° C. overnight. Fc-analysis of the Endo S treated antibody showed that all complex-type N-glycans had been cleaved (FIG. 6). Fabricator-enzyme used in the Fc-analysis cleaved some of the lysine residues at the cleavage site. Accordingly, signals m/z 24132 and 24262 correspond to Fucα1-6GlcNAc-Fc without lysine and Fucα1-6GlcNAc-Fc with lysine. No sign of heavy chain Fab-region N-glycan cleavage was seen.

Reaction mixture was purified with HiTrap Protein G column (GE Healthcare) using 0.02 M Na-phosphate pH 7 as the binding buffer and 0.1 M citric acid pH 2.6 as the elution buffer. Fractions containing IgG were pooled and neutralized with 1 M Na$_2$HPO$_4$.

FIG. 6 shows MALDI-TOF of Endo S-digested cetuximab Fc-region N-glycans.

Example 21. Galactosylation and Sialylation of GlcNAc(β-N-Asn) Units in Endo S Treated Cetuximab Galactosylation of Fucα1-6GlcNAc(β-N-Asn) units in cetuximab was carried out by incubating the antibody with β1,4-galactosyltransferase enzyme and UDP-galactose. 12 mg antibody, 30 mM UDP-Gal, 20 mM MnCl$_2$ and 3.2 mU/µl β1,4-galactosyltransferase were mixed in 400 µl of 50 mM MOPS-buffer, pH 7.2, and incubated for 24 h at +37° C. Sample was taken to Fc-analysis. After that α-2,6-Sialyltransferase enzyme and CMP-NeuNAc were added to reaction mixture to final concentrations of 0.03 μg/μl and 30 mM, respectively, and incubation was continued 3 days.

Figure 7:
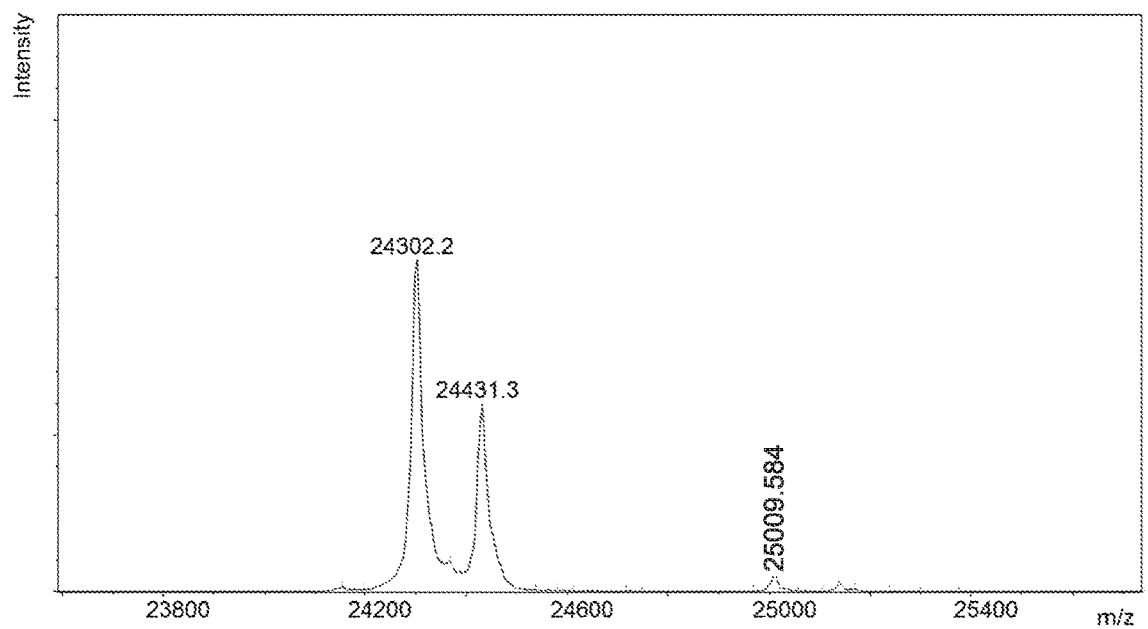
FIG. 7 shows MALDI-TOF of β1-4-galactosylated Endo S-treated Fc-glycans of cetuximab.

Fc-analysis of the β1,4-galactosyltransferase treated sample revealed complete galactosylation of N-acetylglucosamines (FIG. 7). Signals m/z 24302 and 24431 correspond to Galβ1-4(Fucα1-6)GlcNAc-Fc without lysine and Galβ1-4(Fucα1-6)GlcNAc-Fc with lysine.

Figure 8:
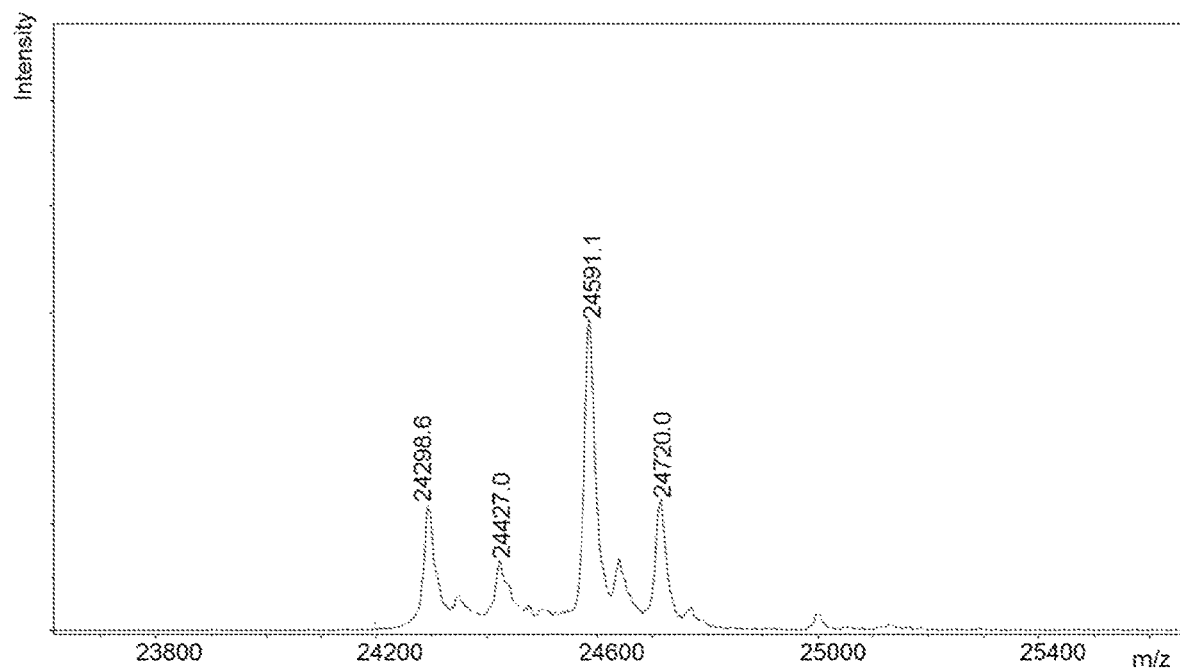
FIG. 8 shows MALDI-TOF of β-1,4-galactosylated and α-2,6-sialylated Endo S-treated Fc-glycans of cetuximab.

Fc-analysis of the β1,4-galactosyltransferase and α-2,6-sialyltransferase treated sample revealed major signals at m/z 24298, 24591 and 24720 corresponding to Galβ1-4 (Fucα1-6)GlcNAc-Fc without lysine, NeuNacα2-6Galβ1-4 (Fucα1-6)GlcNAc-Fc without lysine and NeuNacα2-6Galβ1-4(Fucα1-6)GlcNAc-Fc with lysine (FIG. 8). Approximately 65% of the galactoses were sialylated.

FIG. 7 shows MALDI-TOF of β1-4-galactosylated Endo S-treated Fc-glycans of cetuximab.

FIG. 8 shows MALDI-TOF of β-1,4-galactosylated and α-2,6-sialylated Endo S-treated Fc-glycans of cetuximab.

The reaction mixture was purified with HiTrap Protein G column (GE Healthcare) using 0.02 M Na-phosphate pH 7 as the binding buffer and 0.1 M citric acid pH 2.6 as the elution buffer. Fractions containing IgG were pooled and neutralized with 1 M $Na_2HPO_4$.

Example 22. Galactosylation and Sialylation of Cetuximab

Galactosylation of terminal GlcNAc's in cetuximab complex N-Glycans was carried out by incubating the antibody with β-1,4-galactosyltransferase enzyme and UDP-galactose. 13 mg antibody, 30 mM UDP-Gal, 20 mM $MnCl_2$ and 2.5 mU/μl β1,4-galactosyltransferase were mixed in 400 μl of 50 mM MOPS-buffer, pH 7.2, and incubated for 48 h at +37° C. After that α-2,6-Sialyltransferase enzyme and CMP-NeuNac were added to final concentrations of 0.03 μg/μl and 30 mM, respectively, and incubation was continued 4 days.

Figure 9A:
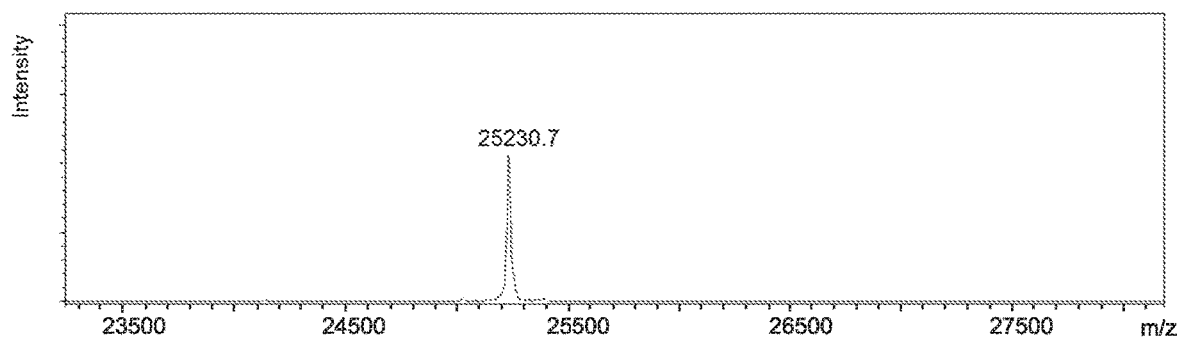
FIG. 9 demonstrates MALDI-TOF of cetuximab Fc-glycans (FIG. 9A) and β-1,4-galactosylated and α-2,6-sialylated cetuximab Fc-glycans (FIG. 9B)
Figure 9B:
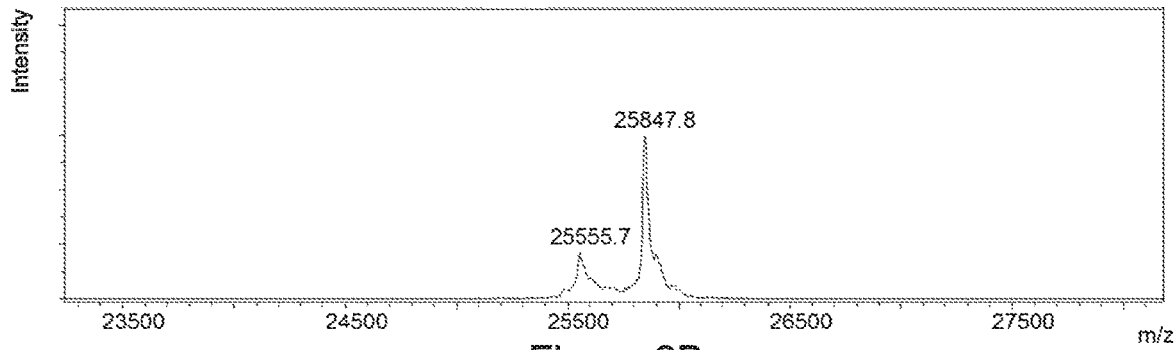

Fc-analysis of cetuximab before galactosylation and sialylation revealed major signal at m/z 25230 corresponding to G0F-Fc. Fc-analysis of the β1,4-galactosyltransferase and α-2,6-sialyltransferase treated sample revealed major signals at m/z 25555 and 25847 corresponding to G2F-Fc and mono-sialylated G2F-Fc, respectively (FIG. 9B). Absence of signal G0F-Fc at m/z 25230 revealed complete galactosylation in the β-1,4-galactosyltransferase reaction.

Example 23. Oxidation of Sialic Acids in Galactosylated and Sialylated Cetuximab (Endo S Treated/Non-Endo S Treated)

Sialic acids in N-glycans of galactosylated and sialylated cetuximab samples were selectively oxidized with periodate. 5-10 mg of antibody was mixed with 1 mM sodium metaperiodate in 1 ml of 0.1 M Na-acetate buffer pH 5.5 and incubated 0.5 h RT in dark. Unreacted sodium meta-periodate was removed by repeated PBS additions and centrifugations in an Amicon Ultracel 30 K 0.5 ml centrifugal filter unit (Millipore).

Figure 10:
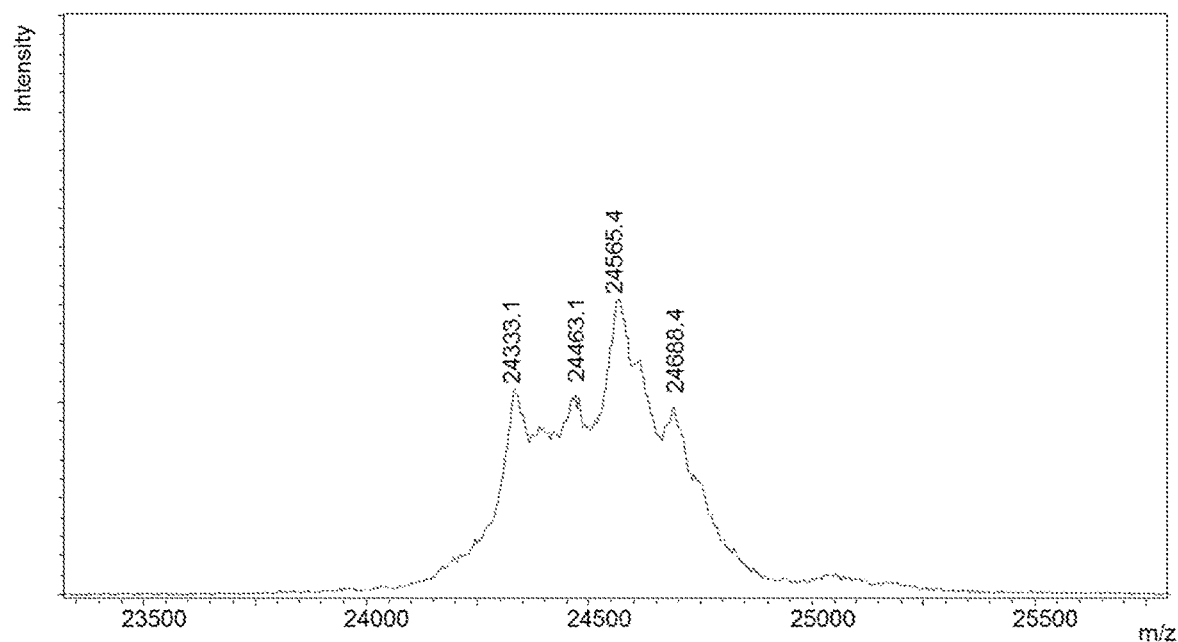
FIG. 10 shows MALDI-TOF of oxidized β-1,4-galactosylated and α-2,6-sialylated Endo S-treated Fc-glycans of cetuximab.

Fc-analysis of the Endo S treated, galactosylated, sialylated and oxidized cetuximab revealed major signals at m/z 24333, 24463, 24565 and 24688 corresponding to Galβ-4 (Fucα1-6)GlcNAc-Fc without lysine and with lysine and ox-NeuNacα2-6Galβ1-4(Fucα1-6)GlcNAc-Fc without lysine and with lysine, respectively (FIG. 10).

Figure 11A:
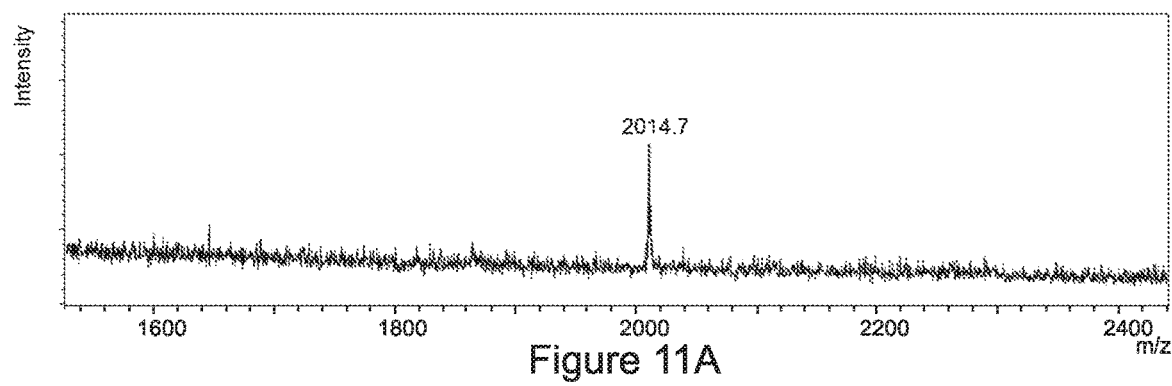
FIG. 11 shows MALDI-TOF of oxidized β-1,4-galactosylated and α-2,6-sialylated N-glycans of cetuximab: Reflector negative MALDI (FIG. 11A), Reflector positive (FIG. 11B)
Figure 11B:
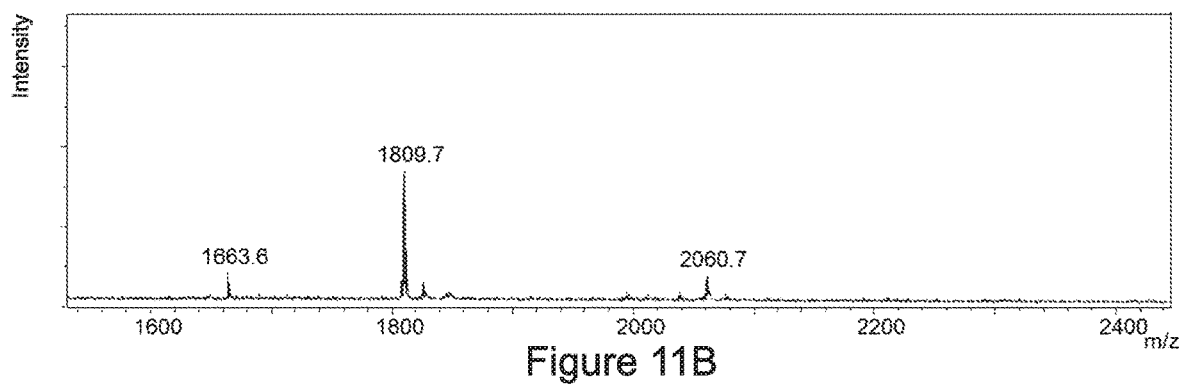

MALDI-TOF in reflector negative mode after N-glycan analysis of the galactosylated, sialylated and oxidized cetuximab revealed major signal at m/z 2104 corresponding to mono-sialylated G2F containing oxidized sialic acid (FIG. 11A). The same sample in reflector positive mode revealed major signals at m/z 1663, 1809 and 2060 corresponding to G2, G2F and mono-sialylated G2F containing oxidized sialic acid. i.e. 7-aldehydo-NeuAc.

Example 24. Conjugation of Levulinic Acid to Cetuximab

Amidation of levulinic acid to free amino groups in cetuximab was carried out as follows: to 5 mg (33 nmol) of cetuximab in PBS (200 μl) was added 10-30 molar excess of levulinic acid succinimidyl ester (prepared as described in Example 18) in ACN (8-25 μl) and the mixture was allowed to react for 4 hours at room temperature. Low molecular weight reagents were removed by Amicon centrifugal filter unit, 30K, according to manufacturer's instructions using PBS as washing eluent.

In order to analyse the success of levulinate amidation, antibody light chains were released by denaturating the antibodies with 6M guanidine-HCl at 60° C. for 0.5 hour. Disulfide bonds were then reduced with 0.1 M dithiothreitol at 60° C. for 0.5 hour. Light chains were purified from reaction mixture with self-manufactured miniaturized Poros R1 columns by eluting them with 60% ACN in 0.1% TFA (5 μl). Light chain analysis was performed by MALDI-TOF mass spectra using sinapinic acid matrix. The analysis showed that 1-4 levulinate groups were bound to antibody light chain.

Example 25. Conjugation of Monomethyldolastatin (MODO) by Val-Cit-PAB Linker to Cetuximab Val-Cit-PAB-MODO 6.5 mg (8 μmol) MODO in DMF (200 μl), 2 molar excess of Fmoc-Val-Cit-PAB-pnp, 0.3 mg (2 μmol) HoBt in DMF (28 μl), 7 μl (40 μmol) diisopropylethylamine and 65 μl DMF were stirred for two days at room temperature. The crude reaction mixture was analysed by MALDI-TOF mass spectra using 2,5-dihydroxybenzoic acid matrix, showing expected mass for Fmoc-Val-Cit-PAB-MODO (m/z 1420 [M+Na]).

Fmoc was removed by adding 150 μl of diethylamine and by stirring at room temperature overnight. MALDI-TOF mass analysis using 2,5-dihydroxybenzoic acid matrix showed the generation of expected deprotected product (m/z 1198 [M+Na]).

Val-Cit-PAB-MODO was purified by Äkta purifier (GE Healthcare) HPLC instrument with Gemini 5 μm NX-C18 reverse phase column (21.1×250 mm, 110 Å, AXIA (Phenomenex)) eluted with ACN gradient in aqueous ammonium acetate.

Alkyne-Val-Cit-PAB-MODO 15 mg (67 μmol) of 3-propargyloxypropionic acide NHS-ester (Cambio, Dry Drayton, Cambs, UK) and 2 mg (24 μmol) sodium hydrogen carbonate were added to the solution of Val-Cit-PAB-MODO (6.4 μmol) in 75% DMSO (1 ml). The mixture was stirred at room temperature for two days. The product was analysed by MALDI-TOF MS, showing the expected product (m/z 1308 [M+Na]).

Alkyne-Val-Cit-PAB-MODO was purified by Äkta purifier (GE Healthcare) HPLC instrument with Gemini 5 μm NX-C18 reverse phase column (4.6×250 mm, 110 Å (Phenomenex)) eluted with ACN gradient in aqueous ammonium acetate.

PEG-N$_3$-Cetuximab 1 mg (6.7 nmol) of cetuximab in PBS (150 µl) was incubated with 10 molar excess of N$_3$-PEG-NHS (Pierce) in DMSO (9 µl) for 2 hours at room temperature. Non-reacted N$_3$-PEG-NHS was separated by Amicon centrifugal filter unit, 30K.

To verify the PEG-azide attachment, antibody light chains were released by denaturating the antibodies with 6M guanidine-HCl at 60° C. for 0.5 hours, followed by disulfide reduction with 0.1 M dithiothreitol at 60° C. for 0.5 hour. Light chains were purified from reaction mixture with self-manufactured miniaturized Poros R1 columns by eluting them with 60% ACN in 0.1% TFA (5 µl). Light chain analysis was performed by MALDI-TOF MS, which confirmed the presence of PEG-azide units (+273 Da).

Val-Cit-PAB-MODO-Cetuximab

The title drug-antibody conjugate (Scheme 11) was generated by a copper(I) catalyzed click reaction containing 3.2 nmol PEG-N$_3$-Cetuximab in PBS (90 µl), 32 nmol Alkyne-Val-Cit-PAB-MODO in DMSO (125 µl), 1250 nmol TGTA in MQ (90 µl), 1250 nmol Na-ascorbate in MQ (12.6 µl), 250 nmol of CuSO$_4$ in MQ (5 µl) and PBS (reaction volume 0.5 ml). The mixture was allowed to react for 1 hour at RT. Antibody conjugate was purified in Amicon centrifugal filter unit, 30K.

To estimate the drug-antibody-ratio (DAR), the conjugate was subjected to Fc-fragment and light chain isolation. Fc-fragments were released by FabRICATOR enzyme (Genovis AB, Lund, Sweden) overnight at 37° C. and purified with Poros R1 tips. Fc-fragments were eluted with 60% ACN, 0.1% TFA (5 µl). Light chains were released by 6M guanidine-HCl and dithiothreitol as above, and recovered using Poros R1 tips. Based on MALDI-TOF MS analysis of these protein domains, the drug-antibody-ratio was on average 1.5.

Example 26. Synthesis of Hydroxylamine Derivatives of Monomethyldolastatin 10 and Monomethylauristatin F 10 mg of monomethyldolastatin (11.3 µmol) or 10 mg monomethylauristatin (11.8 µmol) were dissolved in acetonitrile (2.5 ml). 10× molar excess of Boc-aminooxyacetic acid and DMT-MM were added. 25 µl of diisopropylethylamine was added and the reaction mixtures were stirred overnight at room temperature. MALDI-TOF MS analysis showed the formation of expected products, monomethyldolastatin-boc-aminooxyacetic acid amide, m/z=966 [M+Na], and monomethylauristatin-boc-aminooxyacetic acid amide, m/z=927 [M+Na]. The reaction mixtures were dried by a flow of nitrogen gas. Boc-protecting group were removed by dissolving the reaction mixtures in 2 ml of dichloromethane:trifluoroacetic acid (12.5:1) on ice and the reaction was allowed to proceed for 4 hours. Samples were analysed by MALDI: monomethyldolastatin-aminooxyacetic acid (MODO-AOAA), [M+Na]$^+$ m/z 866 and monomethylauristatin-aminooxyacetic acid (MMAF-AOAA) [M+Na]$^+$ m/z 827. The products were dried and purified by HPLC on Gemini-NX-5u C-18 reverse-phase column eluted with acetonitrile gradient in ammonium acetate buffer pH 5.6.

Scheme 11. Structure of Val-Cit-PAB-MODO-Cetuximab conjugate.

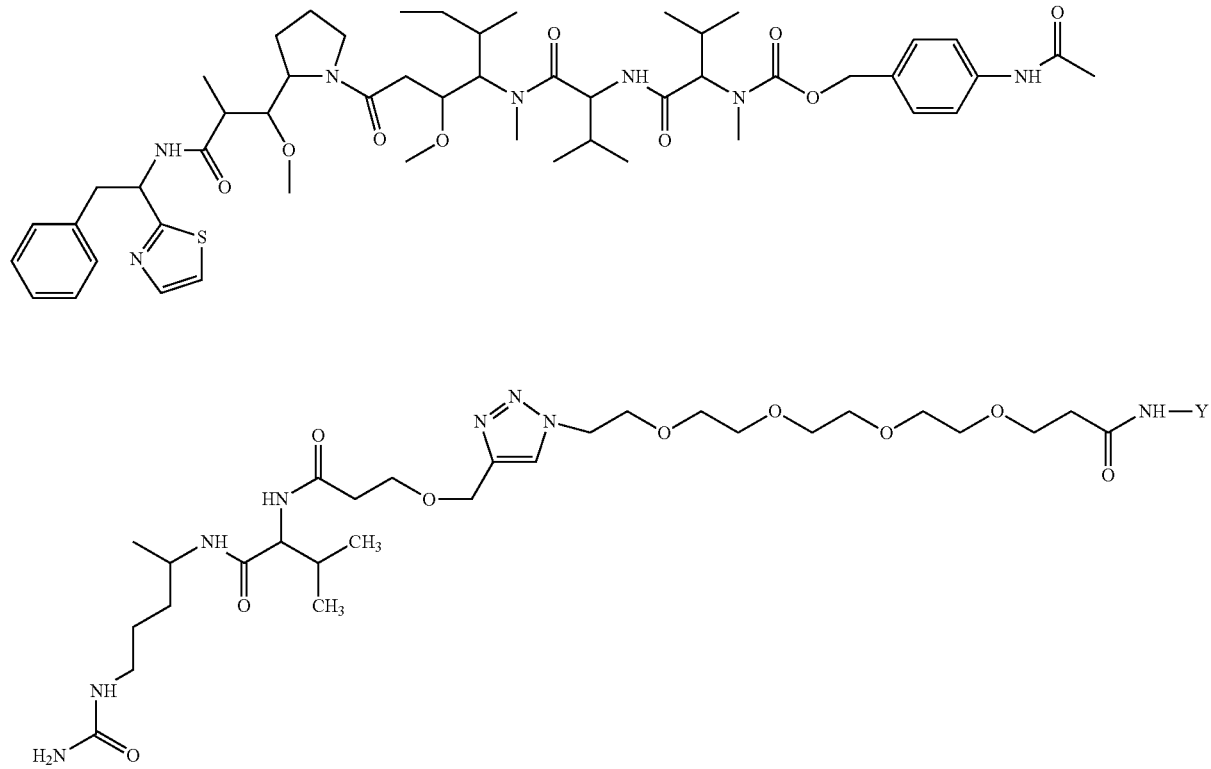

Example 27. Conjugation of MODO-AOAA and MMAF-AOAA to 7-Aldehydo-NeuAc-Cetuximab 200 μg of 7-aldehydo-NeuAc-cetuximab (prepared as described in Example 23) in 0.1 M sodium acetate buffer pH 5.5 (90 μl) was mixed with 100 molar excess of MODO-AOAA or 300 molar excess of MMAF-AOAA in DMSO (10 μl). Reactions were allowed to proceed for 18-120 h at room temperature.

The Fc-fragment of MODO-AOAA-Cetuximab conjugate was isolated as described in Example 25 and analyzed by MALDI-TOF MS. The spectrum of Fc-fragment showed a major signal at m/z 26637, corresponding to expected oxime product (Scheme 12).

Figure 12:
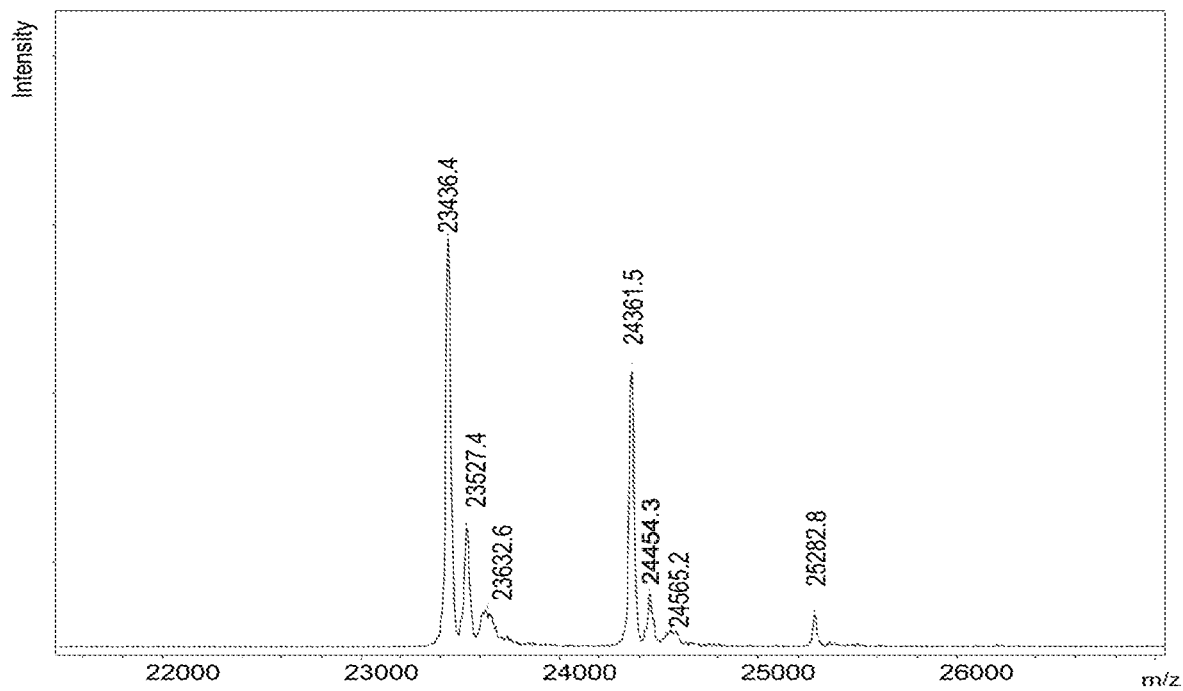
FIG. 12 demonstrates MALDI-TOF MS of light chains isolated from MODO-AOAA-levulinyl-cetuximab.

24 and analyzed by MALDI-TOF MS (FIG. 12). The spectrum shows two signals corresponding to drug-conjugates: m/z 24361 and m/z 25282, corresponding to one and two linked MODO-AOAA units in light chains, respectively.

Example 29. Conjugation of Boc-Aminooxybutynylacetamide (Boc-ABAA) with N-(6-azido-6-deoxy-D-galactosyl)-monomethyldolastatin 10 (N-(6-$N_3$-Gal)-MODO)

Boc-ABAA was conjugated to N-(6-$N_3$-Gal)-MODO by copper(I) catalyzed azide-alkyne cycloaddition reaction.

The reaction contained 2.5 μmol N-(6-$N_3$-Gal)-MODO, 6.3 μmol Boc-ABAA (2.5× molar excess to N-(6-$N_3$-Gal)-

Scheme 12. Structure of MODO-AOAA-Cetuximab conjugate. For clarity, only sialic acid and galactose residues are shown.

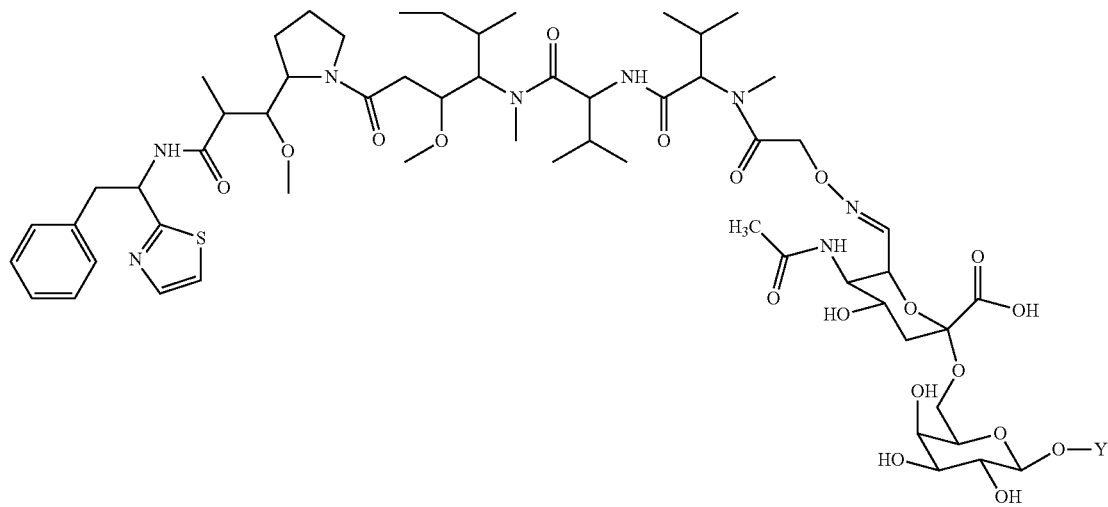

The Fc-fragment of MMAF-AOAA-Cetuximab conjugate was isolated as described in Example 25 and analyzed by MALDI-TOF MS. The spectrum of Fc-fragment showed a major signal at m/z 26614, corresponding to expected oxime product.

Example 28. Conjugation of MODO-AOAA to Levulinyl-Cetuximab 2.7 nmol of levulinyl-cetuximab (prepared as in EXAMPLE 24) in 0.1 M sodium acetate buffer pH 5.5 (100 μl) was mixed with 100 molar excess of MODO-AOAA in DMSO (10 μl). Reaction was allowed to proceed 2 d at room temperature and 4 d at +37° C. For MALDI analysis, the conjugate light chains were isolated as described in Example MODO), 25 μmol Na-ascorbate (10× molar excess to N-(6-$N_3$-Gal)-MODO) and 5 μmol of $CuSO_4$ (2× molar excess to N-(6-$N_3$-Gal)-MODO). Boc-ABAA and N-(6-$N_3$-Gal)-MODO were dissolved in DMSO and Na-ascorbate and $CuSO_4$ in MilliQ-$H_2O$ before adding to the reaction. Total volume of the reaction was 117 μl containing 64% DMSO. Reaction was carried out for 1.5 hours at RT. The conjugation was stopped with 40 μl of 0.5M EDTA pH 8 (20 μmol EDTA).

Progress of the reaction was analyzed with MALDI-TOF MS using 2,5-dihydroxybenzoic acid matrix in the positive ion reflector mode. Major signal was observed at m/z 1224.6, which corresponds to [M+Na]$^+$ ion of the expected click-reaction product (Scheme 13).

Scheme 13.

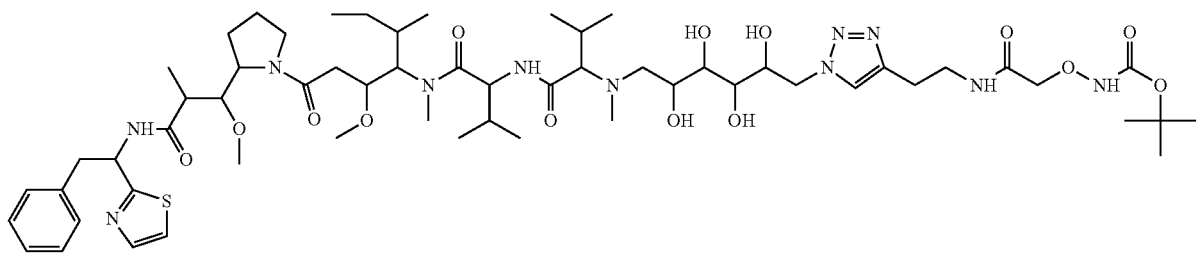

Example 30. Conjugation of Aminooxybutynylacetamide (ABAA) to 7-Aldehydo-NeuAc-Cetuximab Using Oxime Ligation 2.67 mg (17.8 nmol) of 7-aldehydo-NeuAc-cetuximab (Example 23) was incubated with 100× molar excess of ABAA (1.78 µmol; obtained as shown in Example 17) in 0.2 M sodium acetate buffer pH 5.5 (650 µl) overnight at room temperature. Non-reacted ABAA was removed and the buffer exchanged to PBS by several PBS additions in Amicon Ultracel 30 K concentrator (Millipore).

The Fc-fragments of the conjugate obtained were isolated as described in Example 25, and subjected to MALDI-TOF MS analysis in 2.5-dihydroxyacetophenone matrix. Major signal was observed at m/z 25955, corresponding to ABAA-sialic acid oxime in the Fc-fragment. (Scheme 14).

Scheme 14. Structure of cetuximab-ABAA. For clarity, only sialic acid and galactose residues are shown.

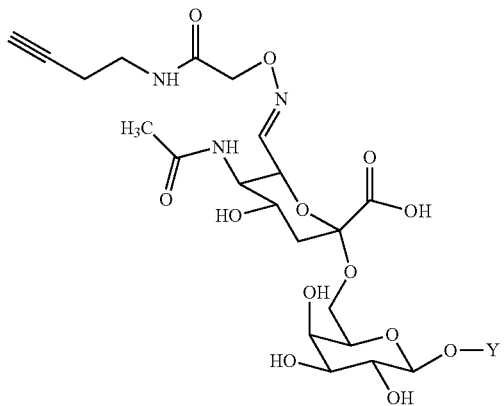

In a similar reaction, ABAA was linked to Endo S treated, then galactosylated, sialylated and oxidized cetuximab (Example 23).

The Fc-fragment analysis of the oxime ligation product revealed a major signal at m/z 24703, corresponding to ABAA-sialic acid oxime in the Fc-fragment.

Example 31. Conjugation of Cetuximab-ABAA with N-(6-$N_3$-Gal)-MODO

Cetuximab-ABAA obtained as shown above was conjugated with N-(6-$N_3$-Gal)-MODO using an azide-alkyne cycloaddition reaction.

The reaction contained 1 mg (6.6 nmol) of antibody-ABAA (in 195 µl PBS), 660 nmol N-(6-$N_3$-Gal)-MODO (100× molar excess to antibody-ABAA), 330 nmol Na-ascorbate (50× molar excess to antibody-ABAA), 66 nmol of $CuSO_4$ (10× molar excess to antibody-ABAA) and 330 nmol TGTA (50× molar excess to antibody-ABAA). Na-ascorbate, $CuSO_4$ and TGTA were dissolved to MilliQ-$H_2O$ and N-(6-$N_3$-Gal)-MODO to DMSO before adding to the reaction. Total volume of the reaction was 250 µl containing 195 µl PBS and 6% DMSO. Reaction was carried out for two hours at RT.

The resulting antibody-drug conjugates (ADC) were purified and the buffer exchanged to PBS by several PBS additions with Amicon Ultracel 30 K concentrator (Millipore).

The Fc-fragments of the ADC thus obtained were isolated as described in Example 25, and subjected to MALDI-TOF MS analysis in 2,5-dihydroxyacetophenone matrix. Major conjugation product was observed at m/z 26902, corresponding to N-(6-$N_3$-Gal)-MODO-(triazole)-ABAA-sialic acid oxime in the Fc-fragment (see Scheme 15).

Scheme 15. Structure of N-(6-$N_3$-Gal)-MODO- (triazole)-ABAA-sialic acid oxime ADC (MODO-ABAA-cetuximab). For clarity, only sialic acid and galactose residues of the the N-glycan are shown.

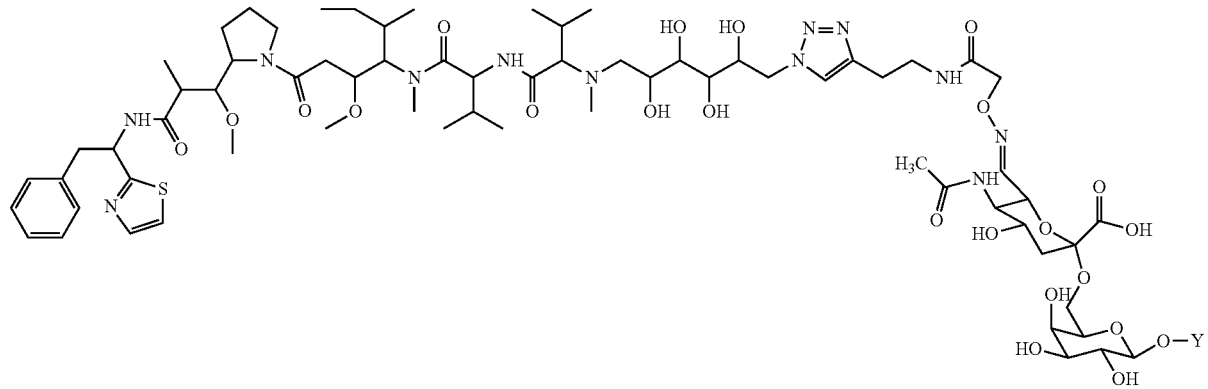

In a similar click reaction, N-(6-N$_3$-Gal)-MODO was linked to Endo S treated ABAA-cetuximab (MODO-ABAA-cetuximab-S; Example 30).

Figure 13A:
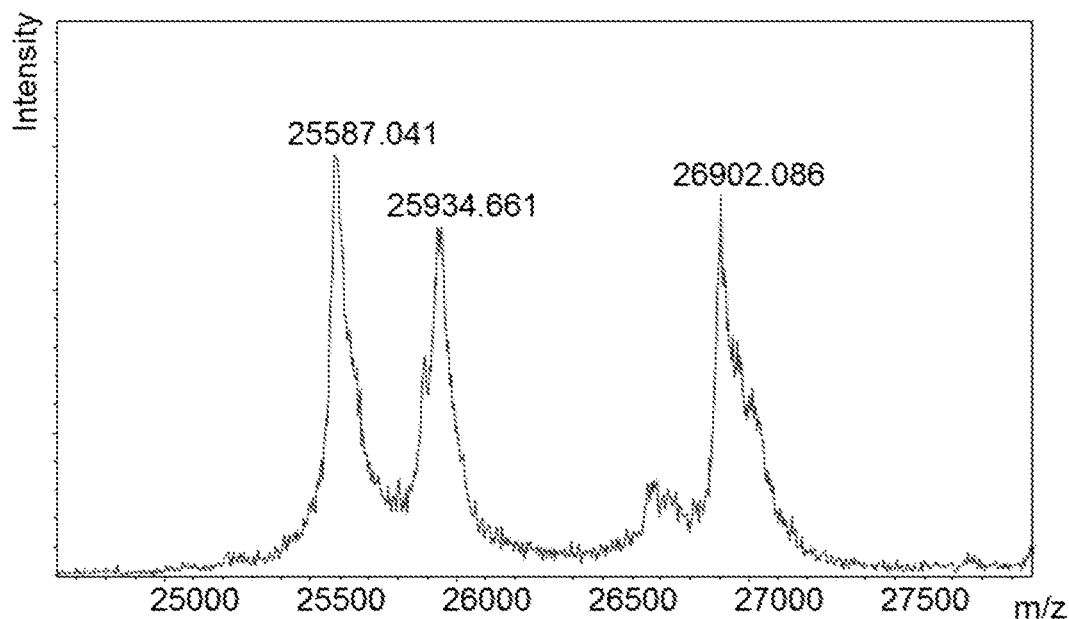
FIG. 13 shows MALDI-TOF mass spectra of Fc-fragments obtained from MODO-ABAA-cetuximab (FIG. 13A) and MODO-ABAA-cetuximab-S (FIG. 13B)
Figure 13B:
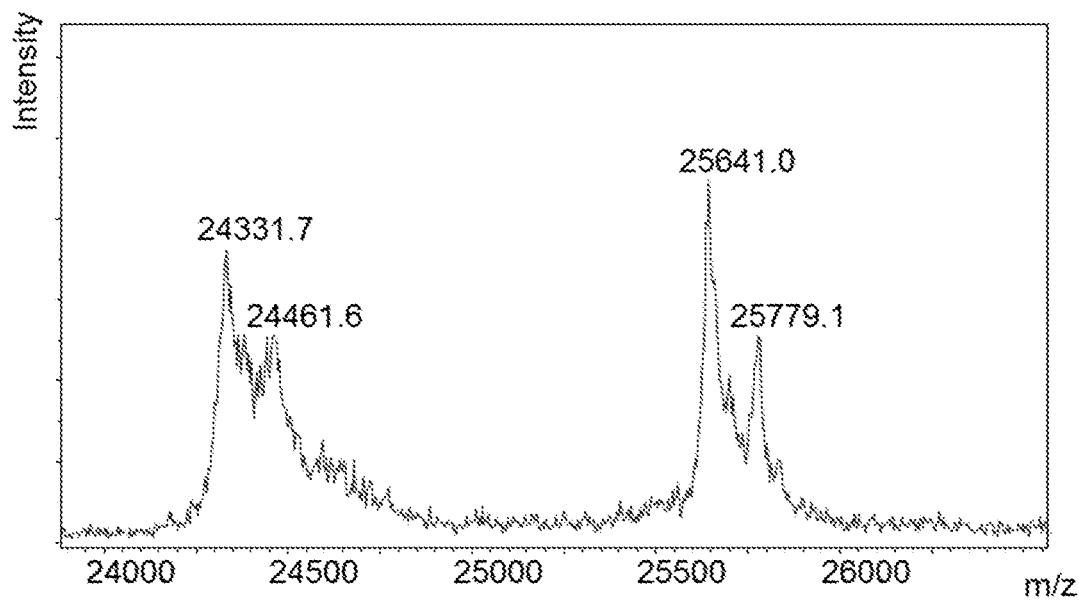

The Fc-fragment MS analysis of the click reaction product revealed a major signal at m/z 25641, corresponding to N-(6-N$_3$-Gal)-MODO-(triazole)-ABAA-sialic acid oxime in the Fc-fragment (FIG. 13).

Example 32. In Vitro Cytotoxicity of Antibody-Drug Conjugates

Figure 14A:
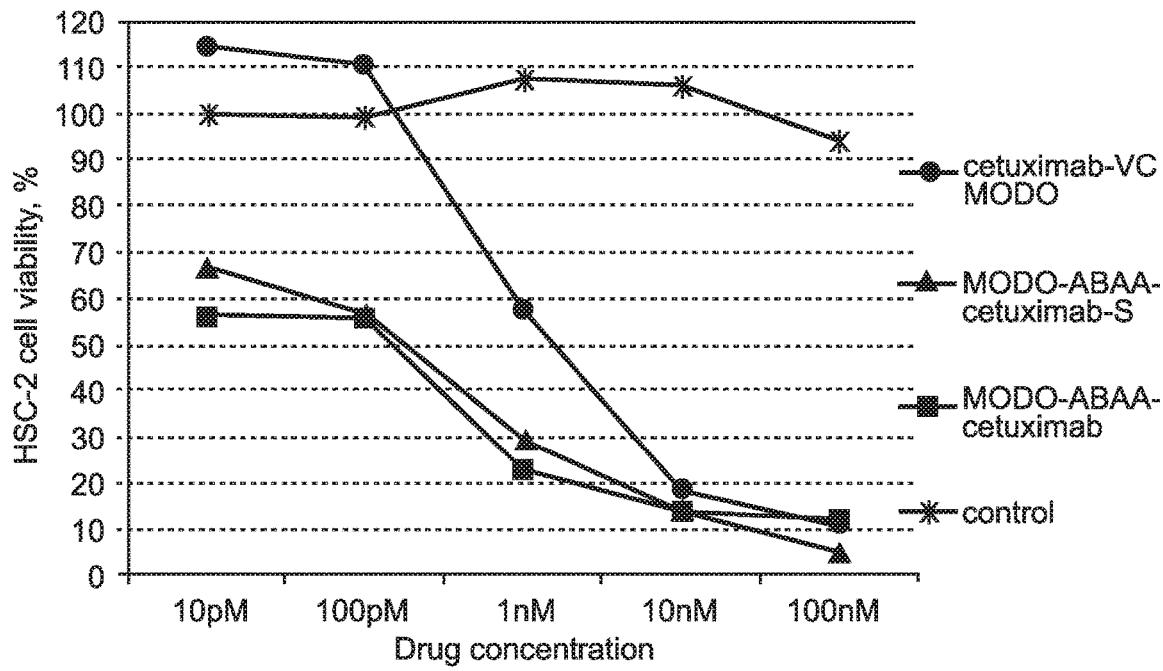
FIG. 14 shows in vitro cytotoxicity of antibody-drug conjugates to cancer cells: HSC-2 cell viability, % (FIG. 14A); LS513 cell viability, % (FIG. 14B).

Human ovarian cancer cell line SKOV-3 (EGFR$^+$HER2$^+$), head-and-neck squamous cell carcinoma cell line HSC-2 (EGFR$^+$) and multidrug-resistant colorectal carcinoma cell line LS513 (EGFR$^+$) were from the ATCC (Manassas, Va., USA). The cells were grown according to the manufacturer's recommendations. In vitro cytotoxicity assays with the cells were performed as above. Results of an exemplary assay are shown in FIG. 14A, in which cytotoxicities of MODO-ABAA-cetuximab and MODO-ABAA-cetuximab-S glycoconjugated monomethyldolastatin 10 (MODO) conjugates were compared to cetuximab-VC-MODO (Val-Cit-PAB-MODO-cetuximab) that contains valine-citrulline peptidase sensitive linker to antibody lysines in contrast to the hydrophilic linker moiety to glycan residues. Both MODO-ABAA-cetuximab and MODO-ABAA-cetuximab-S were more effective against the HSC-2 head-and-neck cancer cells than cetuximab-VC-MODO.

FIG. 14 shows in vitro cytotoxicity of antibody-drug conjugates to cancer cells. All drug concentrations in the y-axis were normalized to actual monomethyldolastatin 10 drug content in each conjugate. A) Cytotoxicities of MODO-ABAA-cetuximab and MODO-ABAA-cetuximab-S (glycoconjugated monomethyldolastatin 10 (MODO) conjugates) and cetuximab-VC-MODO (Val-Cit-PAB-MODO-cetuximab) were compared to control (PBS) in HSC-2 head-and-neck cancer cells. B) Cytotoxicities of MODO-ABAA-cetuximab and MODO-ABAA-cetuximab-S were compared to cetuximab-VC-MODO in multidrug-resistant LS513 colorectal cancer cells.

In other experiments, IC50 values were established for prepared antibody-drug conjugate of cetuximab and dolastatin 10 according to Scheme 6 against cancer cells as described above: IC50 against SKOV-3 cells was from 1 nM to 10 nM and IC50 against HSC-2 cells was from 1 nM to 10 nM in the experiments.

Figure 14B:
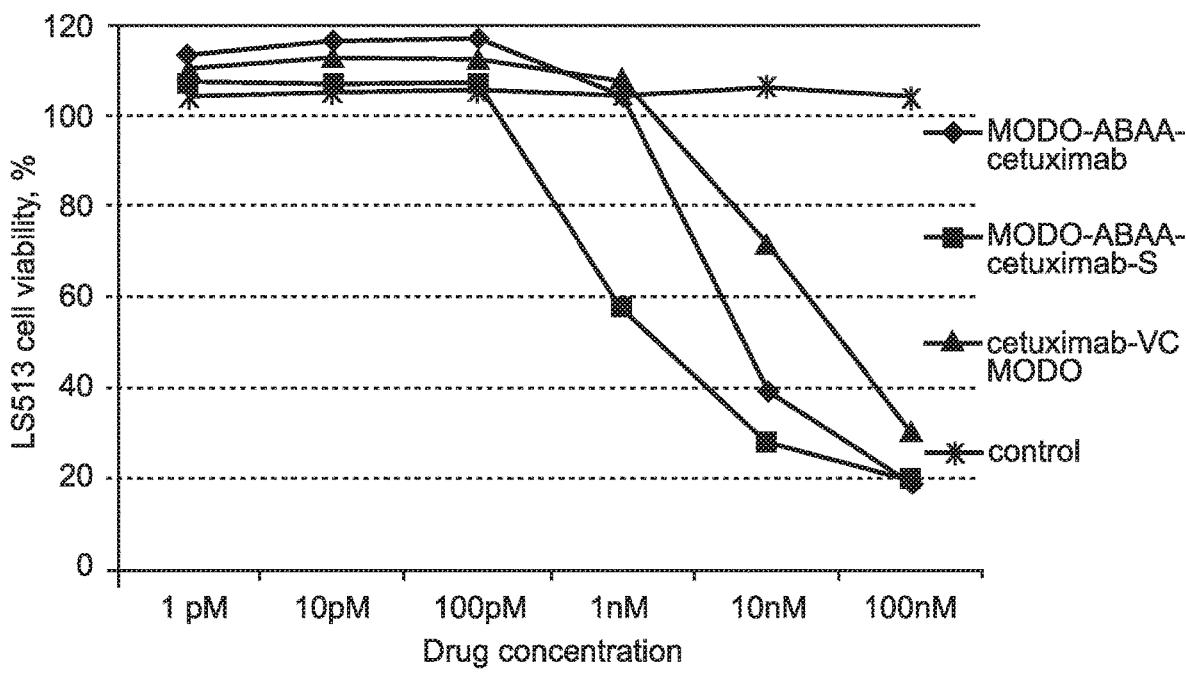

In the experiment described in FIG. 14B, cytotoxicities of MODO-ABAA-cetuximab and MODO-ABAA-cetuximab-S were compared to cetuximab-VC-MODO in multidrug-resistant LS513 colorectal cancer cells. Both MODO-ABAA-cetuximab and MODO-ABAA-cetuximab-S (containing linker that releases drug with hydrophilic linker moiety by action of glycohydrolase inside cells) were more effective than cetuximab-VC-MODO (containing linker that releases free unconjugated drug inside cells).

Example 33. Synthesis of MODO-TREA (1-[MODO-Gal]-1,2,3-triazol-4-ethylamine)

12 µmol N$_3$-Gal-MODO (Example 1) in DMSO (40 µl), 2× molar excess of 1-amino-3-butyne in DMSO (20 µl), 3.1 mg (19 mmol) CuSO$_4$ in MQ (50 µl), 19.2 mg Na-ascorbate in MQ (50 µl), 90 µl DMSO and 400 µl MQ were stirred at RT for 2.5 hours. The crude reaction mixture was analysed by MALDI-TOF mass spectra using 2,5-dihydroxybenzoic acid matrix, showing expected mass for MODO-TREA (m/z 1051 [M+Na]).

MODO-TREA was purified by Äkta purifier (GE Healthcare) HPLC instrument with Gemini 5 µm NX-AXIA-C18 reversed phase column (21.2×250 mm, 110 Å (Phenomenex)) eluted with ACN gradient in aqueous ammonium acetate.

Example 34. Synthesis of MODO-TREA-DBCO

8 µmol MODO-TREA, 5× molar excess of DBCO-NHS ester (Jena Bioscience) in DMF (1 ml) and 16 µl diisopropylethylamine were stirred at RT for three hours. The crude reaction mixture was analysed by MALDI-TOF mass spectra using 2,5-dihydroxybenzoic acid matrix, showing expected mass for MODO-TREA-DBCO (m/z 1338 [M+Na]).

MODO-TREA-DBCO was purified by Äkta purifier (GE Healthcare) HPLC instrument with Gemini 5 µm NX-AXIA-C18 reversed phase column (21.2×250 mm, 110 Å (Phenomenex)) eluted with ACN gradient in aqueous ammonium acetate.

Example 35. Synthesis of MODO-TRSLac (1-(MODO-Gal)-1,2,3-triazol-4-[9-sialyllactose])

N$_3$-NeuNAcα2,6lactose was obtained by enzymatic α2,6-sialylation of lactose using CMP-9-deoxy-9-azido-NeuNAc (Example 3) and *P. damsela* α2,6-sialyltransferase (Sigma). The product trisaccharide was purified by ion-exchange chromatography on DEAE Sepharose Fast Flow (GE Healthcare) using an ammonium bicarbonate gradient.

9 µmol N$_3$-NeuNAcα2,6lactose in MQ (100 µl), 1.5× molar excess of propargyl-Gal-MODO in DMSO (300 µl), 4 mg (25 µmol) CuSO$_4$ in MQ (50 µl), 32.8 mg (44 µmol) TGTA in MQ (50 µl) 8.9 mg Na-ascorbate (45 µmol) in MQ (50 µl) and 50 µl MQ were stirred at RT for 4 hours. The crude reaction mixture was analysed by MALDI-TOF mass spectra using 2,5-dihydroxybenzoic acid matrix, showing expected mass for MODO-TRSLac (m/z 1653 [M+Na]).

MODO-TRSLac was purified by Äkta purifier (GE Healthcare) HPLC instrument with Gemini 5 µm NX-AXIA-C18 reverse phase column (21.2×250 mm, 110 Å (Phenomenex)) eluted with ACN gradient in aqueous ammonium acetate.

Example 36. Synthesis of MODO-TRSLac-Lys

~8 µmol MODO-TRSLac in DMSO (1.6 ml), ~50 molar excess of lysine in MQ (150 µl), 44 mg (707 µmol) NaCNBH3 in MQ (174 µl) and 76 µl diisopropylethylamine were stirred at 60° C. for two days.

MODO-TRSLac-Lys was purified by Äkta purifier (GE Healthcare) HPLC instrument with Gemini 5 µm NX-AXIA-C18 reverse phase column (21.2×250 mm, 110 Å (Phenomenex)) eluted with ACN gradient in aqueous ammonium acetate.

Example 37. Synthesis of MODO-TRSLac-Lys-DBCO

~6 µmol MODO-TRSLac-Lys, ~5 molar excess of DBCO-NHS ester in DMF (72 µl), 10 µl diisopropylethylamine and 450 µl DMF were stirred at RT for overnight. The crude reaction mixture was analysed by MALDI-TOF mass spectra using 2,5-dihydroxybenzoic acid matrix, showing expected mass for MODO-TRSLac-Lys-DBCO (m/z 2093 [M−H+2Na]$^+$).

MODO-TRSLac-Lys-DBCO was purified by Äkta purifier (GE Healthcare) HPLC instrument with Gemini 5 μm NX-AXIA-C18 reverse phase column (21.2×250 mm, 110 Å (Phenomenex)) eluted with ACN gradient in aqueous ammonium acetate.

Example 38. Synthesis of Carboxymethylated DM1 (DM1-S—CH$_2$COOH)

3.9 μmol DM1, 2.5 molar excess of iodoacetic acid in DMF (33 μl), 67 μl DMF and 90 μl 200 mM NH$_4$HCO$_3$ were stirred at RT for one hour. The crude reaction mixture was analysed by MALDI-TOF mass spectra using 2,5-dihydroxybenzoic acid matrix, showing expected mass for DM1-S—CH$_2$COOH (m/z 818 [M+Na]).

Example 39. Synthesis of DM1-DBCO

~3.9 μmol DM1-S—CH$_2$COOH, 3.5 molar excess of DBCO-NH$_2$ (Sigma) in DMF (200 μl) and 26 mg (95 μmol) DMT-MM in DMF (500 μl) were stirred at RT for overnight. The crude reaction mixture was analysed by MALDI-TOF mass spectra using 2,5-dihydroxybenzoic acid matrix, showing expected mass for DM1-DBCO (m/z 1076 [M+Na]). DM1-DBCO was purified by reversed-phase chromatography as described in Example 25.

Example 40. Synthesis of MODO-Val-Cit-PAB-DBCO

~2 μmol MODO-Val-Cit-PAB (Example 25), ~5 molar excess of DBCO-NHS ester in DMF (126 μl) and 3.5 μl diisopropylethylamine were stirred at RT for three hours. The crude reaction mixture was analysed by MALDI-TOF mass spectra using 2,5-dihydroxybenzoic acid matrix, showing expected mass for MODO-Val-Cit-PAB-DBCO (m/z 1485 [M+Na]).

29, and it was purified by solid-phase extraction on Bond-Elut C18 extraction cartridge. Boc-protecting group was removed by incubating in dichloromethane-TFA (12.5:1), and the product MODO-ABAA was isolated by reversed-phase chromatography using Gemini NX C18 column (Phenomenex) using a acetonitrile gradient in 20 mM ammonium acetate, pH 5.6.

Fc N-glycans of trastuzumab were galactosylated and sialylated essentially as in Example 21. Fc-analysis of the β1,4-galactosyltransferase and α2,6-sialyltransferase treated sample revealed major signal at m/z 25846 corresponding to NeuNAc-G2F-Fc without C-terminal lysine. Approximately 95% of the galactoses were sialylated. Sialic acids were then selectively oxidized to 7-aldehydo-NeuNAc with 1 mM periodate as in Example 23. Fc-analysis of the galactosylated, sialylated and oxidized trastuzumab revealed major signal at m/z 25821 corresponding to 7-aldehydo-NeuAc-G2F-Fc.

ABAA-MODO conjugation to oxidized sialic acids of tratuzumab was performed by oxime ligation with minor modifications as in example 30. Briefly, 180 μg (1.2 nmol) of 7-aldehydo-NeuNAc-trastuzumab was incubated with 75× molar excess of ABAA-MODO in 10% DMSO, 0.2 M sodium acetate buffer pH 4.5 (300 μl) overnight at room temperature. Non-reacted ABAA was removed and the buffer exchanged to PBS by several PBS additions in Amicon Ultracel 30 K concentrator (Millipore).

Fc-analysis of ABAA-MODO-7-aldehydo-NeuNAc-trastuzumab (see Scheme 16) revealed major signal at m/z 26908 corresponding to ABAA-MODO-7-aldehydo-NeuAc-G2F-Fc and minor signal at m/z 27990 corresponding to 7-aldehydo-NeuAc-G2F-Fc with two ABAA-MODOs attacked. Almost complete disappearance of the 7-aldehydo-NeuAc-G2F-Fc signal was seen.

Scheme 16. Structure of N-(6-N$_3$-Gal)-MODO- (triazole)-ABAA-sialic acid oxime ADC (MODO-ABAA-trastuzumab). For clarity, only sialic acid and galactose residues of the N-glycan are shown.

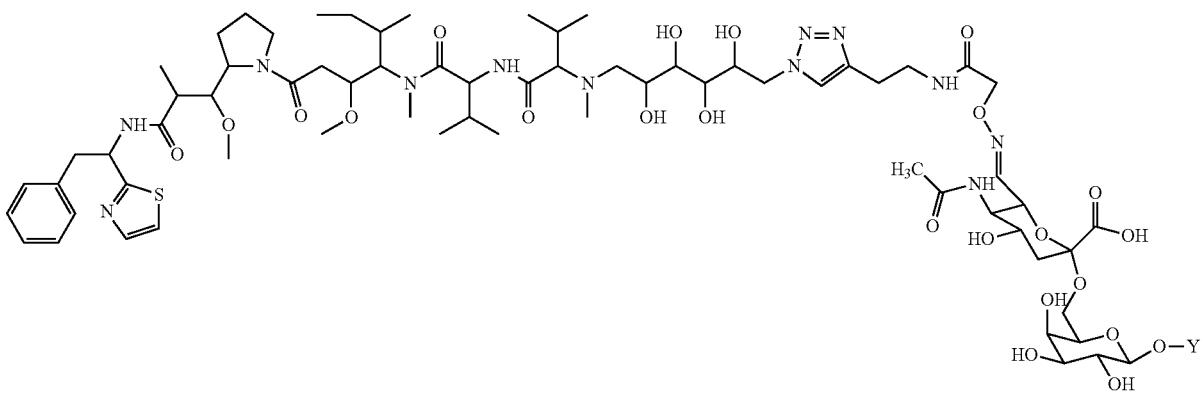

MODO-Val-Cit-PAB-DBCO was purified by reversed-phase chromatography as described in Example 25.

Example 41. Conjugation of Aminooxybutynylacetamide-Monomethyldolastatin 10 (ABAA-MODO) to 7-Aldehydo-NeuNAc-Trastuzumab Modo-Boc-aminooxybutynylacetamide (Boc-ABAA-MODO, scheme 13) was prepared as described in Example Example 42. Conjugation of Aminooxybutynylacetamide-Monomethyldolastatin 10 (ABAA-MODO) to 7-Aldehydo-NeuNAc-Anti-CD33

GCM011, a humanized anti-CD33 antibody with an additional N-glycosylation site in the heavy chain variable region sequence, was produced as follows. Synthetic DNA sequences optimized for CHO cell expression were ordered from GeneArt (Life Technologies) encoding both 1) heavy chain and 2) light chain of the antibody and these sequences were cloned into pCHO1.0 vector with N-terminal signal peptides and E74N mutation in the heavy chain sequence (Glu-74 changed to Asn):
1) DNA sequence encoding the amino acid sequence of signal peptide MAVLGLLFCLVTFPSCVLS fused to SEQ ID NO: 38, and
2) DNA sequence encoding the amino acid sequence of the signal peptide MVSTPQFLVFLLFWIPASRS fused to SEQ ID NO: 37.

For antibody expression, FreeStyle™ CHO—S cells were transfected with the vectors using FreeStyle™ Max Expression System (Life Technologies) according to manufacturer's instructions. Supernatant was harvested from the cells at day 10 and antibodies were purified with protein G affinity chromatography. MALDI-TOF MS analysis of the FabRICATOR digested reaction products as well as N-glycosidase liberated N-glycans demonstrated that the additional N-glycosylation site at heavy chain Asn-74 was 100% glycosylated with complex-type N-glycans and the expressed antibody thus contained four N-glycans/antibody molecule.

N-glycan galactosylation and sialylation was done to anti-CD33 GCM011 essentially as in Example 21. Fc-fragments were released from small aliquot of sample with Fabricator enzyme as in example 25. Variable heavy chains were released by 6M guanidine-HCl and dithiothreitol, and recovered using Poros R1 tips. MALDI-TOF MS analysis of purified Fc revealed major signal at m/z 25865 corresponding to NeuNAc-G2F-Fc without lysine. MALDI-TOF MS analysis of purified variable heavy chain revealed major signal at m/z 27359 corresponding to NeuNAc2-G2F-Fab HC.

Sialic acids in galactosylated and sialylated GCM011 were oxidized as in Example 23 and ABAA-MODO conjugation to 7-aldehydo-sialic acids was done via oxime-ligation as in Example 41. Fc-fragments were analysed as in Example 25 and it revealed signal at m/z 26889 corresponding to ABAA-MODO-7-aldehydo-NeuNAc-G2F-Fc and minor signal at m/z 27965 corresponding to 7-aldehydo-NeuAc-G2F-Fc with two ABAA-MODOs attached.

In another experiment selective periodate oxidation and ABAA-MODO-conjugation to 7-aldehydo-sialic acids was done to unmodified GCM011 anti-CD33 (i.e. no galactosylation or sialylation was done prior oxidation). Periodate oxidation was done as in Example 23 except 3 mM periodate was used. ABAA-MODO conjugation was done as in Example 41 except 18× molar excess of ABAA-MODO to antibody was used. Fab HC N-glycans were analysed as in Example 41 and it revealed signals at m/z 28543 and 28667 corresponding to ABAA-MODO-7-aldehydo-NeuAc-G2F-Fab HC and ABAA-MODO-7-aldehydo-NeuAc-2-G2F-Fab HC. Minor signals were detected at m/z 26292 and 26757 corresponding to 7-aldehydo-NeuAc-G2F-Fc with two ABAA-MODOs attached and 7-aldehydo-NeuAc2-G2F-Fab HC with two ABAA-MODOs attached.

Example 43. Production of Afucosylated Trastuzumab

Afucosylated trastuzumab was produced in CHO—S cells (Invitrogen) by transiently transfecting the cells with trastuzumab heavy and light chain DNA according to Invitrogen CHO—S instructions. Prior transfection and during antibody production AV39 (a GDP-fucose synthesis inhibitor; Glykos Finland Ltd., Helsinki, Finland) was added to cells to prevent N-glycan fucosylation. In day 5 after transfection supernatants were collected and antibody purified with HiTrap Protein G column (GE Healthcare) using 0.02 M Na-phosphate pH 7 as the binding buffer and 0.1 M citric acid pH 2.6 as the elution buffer. Fractions containing IgG were pooled and neutralized with 1 M $Na_2HPO_4$. Inhibition of fucosylation was confirmed by N-glycan analysis as in Example 8.

Example 44. Conjugation of MODO-ABAA to Afucosylated 7-Aldehydo-NeuNAc-Trastuzumab Afucosylated trastuzumab was galactosylated and sialylated as in Example 21. Fc-analysis of the β1,4-galactosyltransferase and α-2,6-sialyltransferase treated sample revealed major signal at m/z 25700 corresponding to NeuNAc-G2-Fc without lysine. 85% of N-glycans were monosialylated. Selective oxidation of sialic acids was done as in Example 23 and MODO-ABAA conjugated to 7-aldehydo-sialic acids as is Example 41. Fc-analysis of ABAA-MODO-7-aldehydo-NeuNAc-afucosyl trastuzumab revealed major signal at m/z 26754 corresponding to ABAA-MODO-7-aldehydo-NeuAc-G2-Fc without lysine. Complete disappearance of the 7-aldehydo-NeuAc-G2F-Fc signal was seen.

Example 45. Enzymatic Linking of CMP-9-Deoxy-9-Azido-NeuNAc to Fc N-Glycans of Trastuzumab Fc N-glycans of trastuzumab (Herceptin) were galactosylated with β1,4-galactosyltransferase as in Example 21. α2,6-sialyltransferase was then used to sialylate terminal galactoses with 9-azido-NeuNAc using CMP-9-deoxy-9-azido-NeuNAc (Example 3) as the donor substrate. Sialylation reaction was accomplished as in Example 21. Fc-analysis of the β1,4-galactosyltransferase and α2,6-sialyltransferase treated sample revealed major signal at m/z 25872 corresponding to G2F-Fc with one attached 9-deoxy-9-azido-NeuNAc residue. Proportion of this signal was >90% of all signals.

Example 46. Conjugation of MODO-TREA-DBCO to Modified Fc N-Glycans of Trastuzumab 20 μM galactosylated and 9-azido-sialylated trastuzumab (Example 45) was incubated with 400 μM MODO-TREA-DBCO (Example 34) in PBS, 2.5% DMSO. Reaction was allowed to proceed 16 h at room temperature after which unconjugated MODO-TREA-DBCO was removed by repeated additions of PBS and centrifugations through Amicon Ultracel 30 k centrifugal filter. A sample was taken to Fc-analysis, which revealed major signal at m/z 27189 corresponding to MODO-TREA-DBCO-9-azido-NeuNAc-G2F-trastuzumab (see Scheme 17). Conjugation degree was over 95%.

Scheme 17. Structure of MODO-TREA-DBCO ADC (MODO-TREA-DBCO-9-azido-NeuNAc-G2F-trastuzumab). For clarity, only sialic acid and galactose residues of the N-glycan are shown.

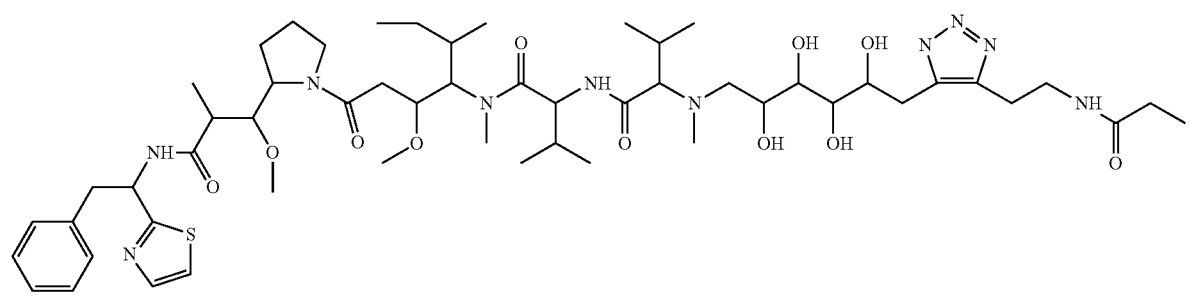

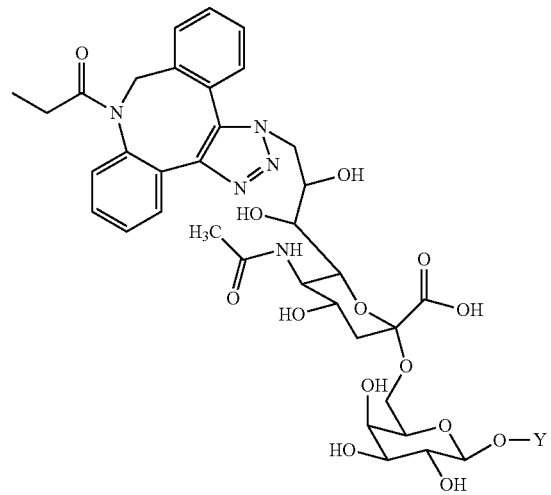

Example 47. Conjugation of MODO-TRSLac-Lys-DBCO to Modified Fc N-Glycans of Trastuzumab 20 μM galactosylated and sialylated trastuzumab carrying 9-deoxy-9-azido-NeuNAc at Fc-N-glycan termini (Example 45) was incubated with 400 μM MODO-TRSLac-Lys-DBCO (Example 37) in PBS. 8% DMSO and 20% propylene glycol were present in the reaction in order to prevent toxin precipitation. Reaction was allowed to proceed 16 h at room temperature after which unconjugated MODO-TRSLac-Lys-DBCO was removed by repeated additions of PBS and centrifugations through Amicon Ultracel 30 k centrifugal filter. A sample was taken to Fc-analysis, which revealed major signal at m/z 27923 corresponding to MODO-TRSLac-Lys-DBCO-9-azido-NeuNAc-G2F-trastuzumab. Signals at m/z 25559 and 25871 revealed presence of minor amounts of G2F-trastuzumab and azido-NeuNAc-G2F-trastuzumab.

Scheme 18. Structure of MODO-TRSLac-Lys-DBCO ADC (MODO-TRSLac-Lys-DBCO-9-azido-NeuNAc-G2F-trastuzumab). For clarity, only sialic acid and galactose residues of the N-glycan are shown.

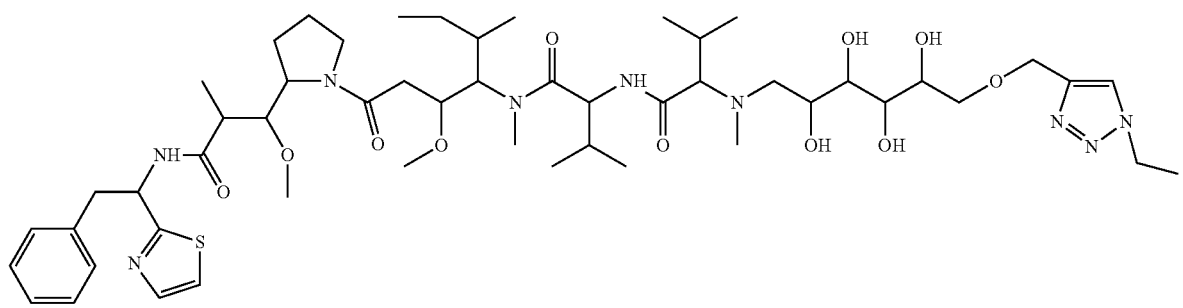

-continued

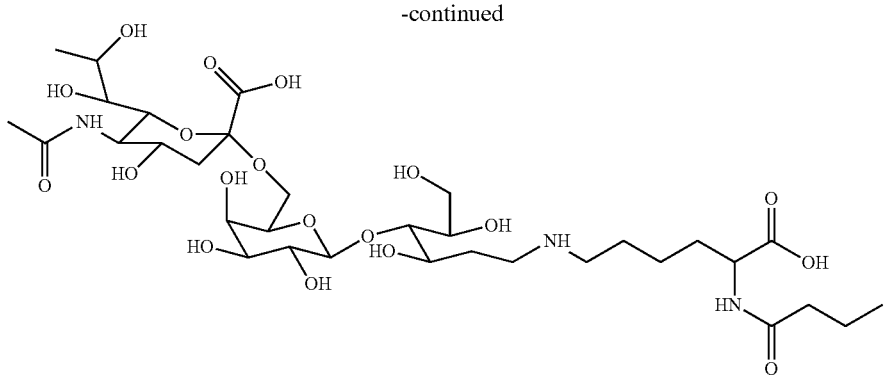

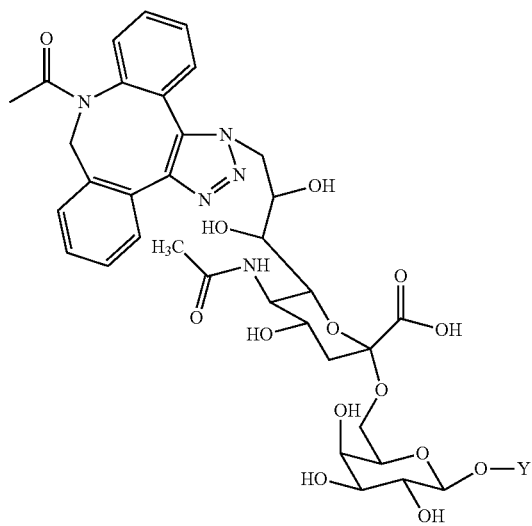

Example 48. Conjugation of DM1-DBCO to Modified Fc N-Glycans of Cetuximab

Cetuximab was galactosylated and sialylated with 9-azido-N-acetylneuraminic acid essentially as described in Examples 9 and 10.

MALDI-TOF MS analysis of the FabRICATOR digested reaction product implied that ca. 74% of the N-glycans were converted to G2F with one azido-NeuAc, remaining portion being G2F glycoform.

DM1-DBCO (Example 39) was conjugated to 9-azido-NeuAc-cetuximab N-glycans in a copper-free click reaction as described in Example 46. Reaction products were purified in Amicon Ultracel 30 K concentrators (Millipore) by several additions of 5% mannitol, 0.1% Tween 20 in PBS and subsequent centrifugations. MALDI-TOF MS analysis of the FabRICATOR digested ADCs revealed complete reaction on the azido N-glycans (see Scheme 19).

Scheme 19. Structure of DM1-DBCO ADC (DM1-DBCO-9-azido-NeuNAc-G2F-cetuximab). For clarity, only sialic acid and galactose residues of the N-glycan are shown.

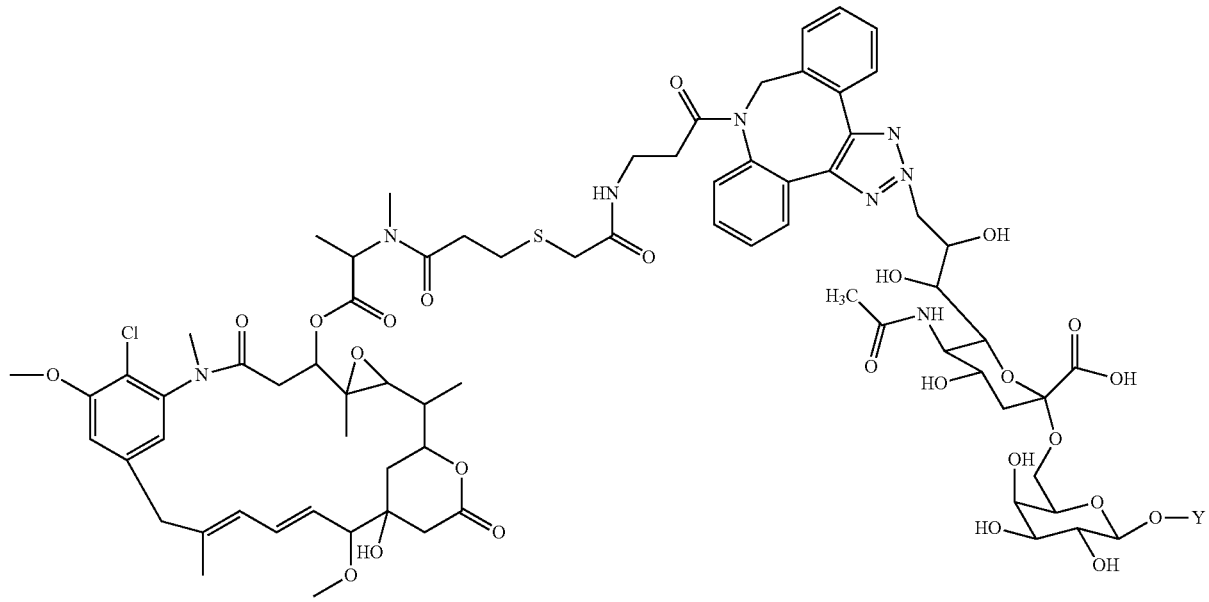

Example 49. Conjugation of MODO-Val-Cit-PAB-DBCO to Modified Fc N-Glycans of Cetuximab Cetuximab was galactosylated and sialylated with 9-azido-N-acetylneuraminic acid essentially as described in Examples 9 and 10. MALDI-TOF MS analysis of the FabRICATOR digested reaction product implied that ca. 74% of the N-glycans were converted to G2F with one azido-NeuAc, remaining portion being G2F glycoform.

MODO-Val-Cit-PAB-DBCO (Example 40) was conjugated to 9-azido-NeuAc-cetuximab N-glycans in a copper-free click reaction as described in Example 46 (see Scheme 20). Reaction products were purified as described above in Example 48. Majority of azido groups were reacted as analyzed by MALDI-TOF MS analysis of the Fc part.

Example 50. Synthesis of N-(6-O-propargyl-D-galactosyl)epirubicin and Conjugation to 9-azido-NeuAc-cetuximab Epirubicin is N-alkylated by reductive amination in alkaline aqueous solution using 6-propargyl-6-deoxy-D-galactose (Example 1) and sodium cyanoborohydride. The product N-(6-O-propargyl-D-galactosyl)-epirubicin is isolated with reversed-phase chromatography using method described in Example 1. N-(6-O-propargyl-D-galactosyl)-epirubicin is conjugated to 9-azido-NeuAc-cetuximab (Example 10) in a copper catalyzed click reaction as described in Example 12 (see Scheme 21).

Scheme 20. Structure of MODO-VC-DBCO ADC (MODO-Val-Cit-PAB-DBCO-9-azido-NeuNAc-G2F-cetuximab). For clarity, only sialic acid and galatose residues of the N-glycan are shown.

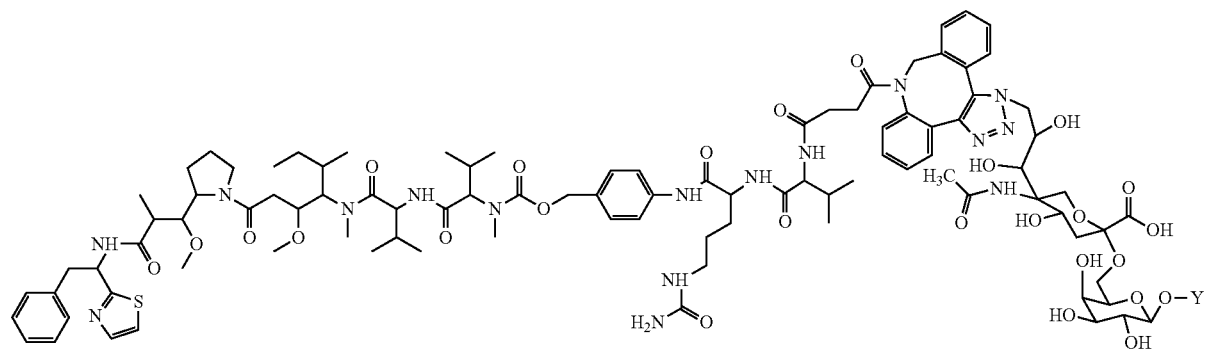

Scheme 21. Structure of epirubicin ADC (Epirubicin-N (Gal-triazol-NeuNAc-G2F-cetuximab). For clarity, only sialic acid and galactose residues of the N-glycan are shown.

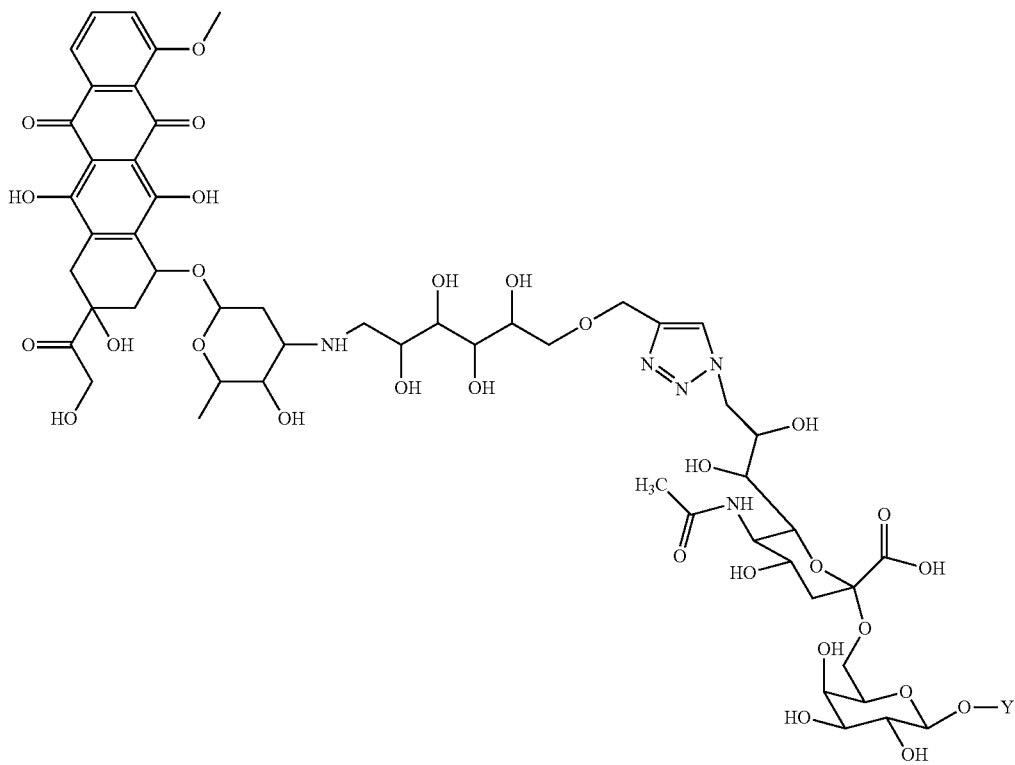

Example 51. Synthesis of N-(6-O-propargyl-D-galactosyl)duocarmycin MA and Conjugation to 9-azido-NeuAc-cetuximab Duocarmycin MA (ALB Technology Limited) is treated with dry trifluoroacetic acid in DCM to remove Boc-group, and the unprotected duocarmycin derivative is N-alkylated by reductive amination in alkaline aqueous solution using 6-propargyl-6-deoxy-D-galactose (Example 1) and sodium cyanoborohydride. The product N-(6-O-propargyl-D-galactosyl)-duocarmycin MA is isolated with reversed-phase chromatography using e.g. method described in Example 1. N-(6-O-propargyl-D-galactosyl)-duocarmycin MA is conjugated to 9-azido-NeuAc-cetuximab (Example 10) in a copper catalyzed click reaction as described in Example 12 (see Scheme 22).

As is evident to a person skilled in the art, other similar toxins, e.g. doxorubicin and daunorubicin, can be derivatized and conjugated similarly.

Scheme 22. Structure of duocarmycin ADC (Duocarmycin MA-N (Gal-triazol-NeuNAc-G2F-cetuximab). For clarity, only sialic acid and galactose residues of the N-glycan are shown.

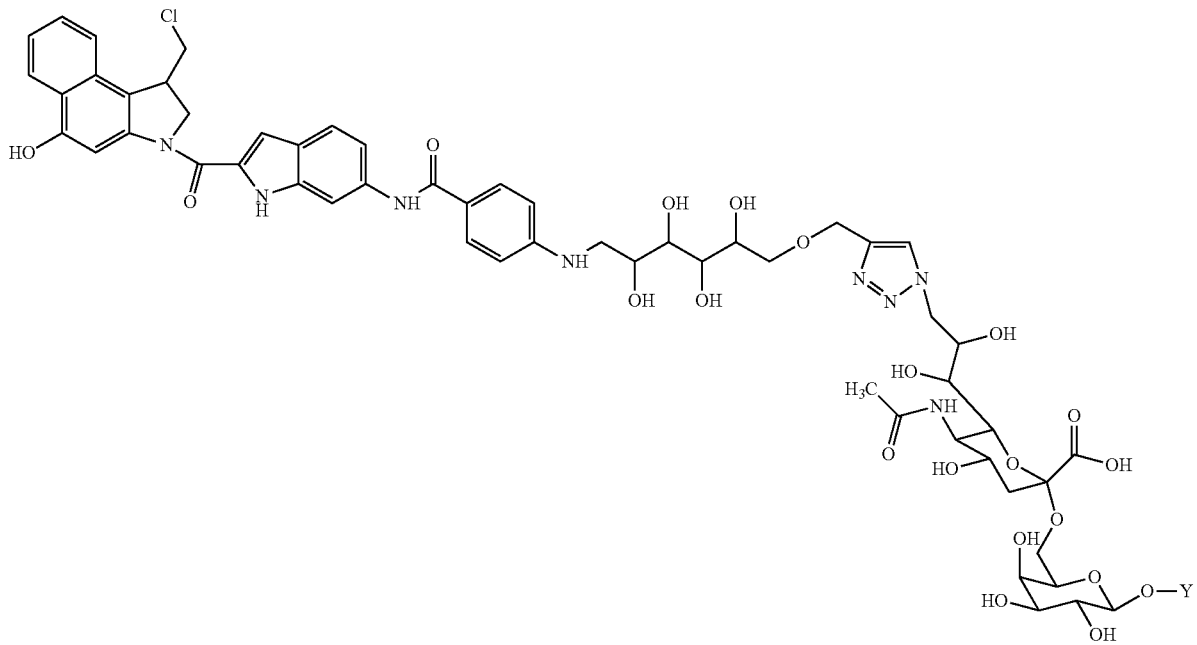

Example 52. In Vivo Experiment

A non-randomized study of anti-EGFR IgG1 antibody-drug conjugates (ADCs; test substances prepared by conjugating monomethyldolastatin 10 to N-glycans of CHO-expressed cetuximab antibody to form MODO-abaa-cetuximab as described in the preceding Examples) and control (phosphate buffered saline, PBS) was carried out in a xenograft nude mouse model to evaluate in vivo efficacy of the ADCs. The study was conducted according to standard guidelines of the test facility and was approved by appropriate ethical committee (University of Turku and Turku University Hospital, Turku, Finland).

Human cancer cell line LS531 (EGFR+, colorectal carcinoma with multi-drug resistant phenotype) was implanted s.c. in one flank of female, adult Harlan HSD:athymic nude Foxn1$^{nu}$ mice. The first dose of the test or control substances was administered when the tumors had grown above average volume of 100 mm$^3$ (4-8 mm diameter). Tumor length (L) and width (W) were recorded in mm. Tumor volumes (V) in mm$^3$ were calculated according to the formula V=½ L×W$^2$. Mice with different sized tumors were equally divided into study groups to obtain homogenous groups (four or five mice in each group).

Test substance was administered i.v. 10 mg/kg ADC in PBS three times at seven days' intervals and control animals were given PBS. Tumor volume, animal weight and clinical signs and general behavior of the animals were followed twice weekly. Any unusual signs or behavior were recorded. End-point of the study was at eight weeks after first dosing.

MODO-abaa-cetuximab showed anti-tumor activity and inhibited tumor growth compared to control treatment. Average tumor volume in the end of the experiment was 189% compared to the average volume at the time of the first ADC injection (100%) in MODO-abaa-cetuximab treated mice, while in the control mice receiving only PBS the average tumor volume in the end of the experiment was 375% compared to the average volume at the time of the first ADC injection.

Another non-randomized study of anti-EGFR IgG1 antibody-drug conjugates was carried out in a xenograft nude mouse model to evaluate in vivo efficacy of ADCs. Test substances were prepared by conjugating monomethyldolastatin 10 to N-glycans of CHO-expressed cetuximab and Endo S-treated CHO-expressed cetuximab to form MODO-abaa-cetuximab and N-(6-N$_3$-Gal)-MODO-(triazole)-ABAA-sialic acid oxime-Endo S-treated cetuximab conjugate (MODO-abaa-Endo-S-cetuximab), respectively, as described in the preceding Examples. Control treatment was PBS without ADC. The study was conducted according to standard guidelines of the test facility and was approved by appropriate ethical committee (University of Turku and Turku University Hospital, Turku, Finland).

Human cancer cell line HSC-2 (EGFR+, squamous cell head-and-neck carcinoma) was implanted s.c. in one flank of female, adult Harlan HSD:athymic nude Foxn1$^{nu}$ mice. The first dose of the test or control substances was administered when the tumors had grown above average volume of 100 mm$^3$ (4-8 mm diameter). Tumor length (L) and width (W) were recorded in mm. Tumor volumes (V) in mm$^3$ were calculated according to the formula V=½ L×W$^2$. Mice with different sized tumors were equally divided into study groups (five mice in each group) to obtain homogenous groups.

Test substance was administered i.v. 10 mg/kg ADC in PBS three times at seven days' intervals and control animals were given PBS. Tumor volume, animal weight and clinical signs and general behavior of the animals were followed twice weekly. Any unusual signs or behavior were recorded. End-point of the study was at eight weeks after first dosing.

Both MODO-abaa-cetuximab and MODO-abaa-EndoS-cetuximab showed anti-tumor activity and inhibited tumor growth compared to control treatment. Average tumor volume in the end of the experiment was 220% and 175% in the ADCs compared to the average volume at the time of the first ADC injection (100%) in MODO-abaa-cetuximab and MODO-abaa-EndoS-cetuximab treated mice, respectively, while in the control mice receiving only PBS the average tumor volume in the end of the experiment was over 600% compared to the average volume at the time of the first ADC injection.

Example 53. Plasma Clearance in Mouse

Plasma clearance pharmacokinetics of antibody drug conjugates and total antibody is studied in Sprague-Dawley rats. Animals are dosed by bolus tail vein injection (IV Push). Approximately 300 µl whole blood is collected through jugular cannula, or by tail stick, into lithium/heparin anticoagulant vessels at each timepoint: 0 (predose), 10, and 30 minutes; 1, 2, 4, 8, 24 and 36 hours; and 2, 3, 4, 7, 14, 21, and 28 days post dose. Total antibody is measured by ELISA, for example, by coating with the extracellular domain of the target protein and detecting with an antihuman Fc-HRP antibody conjugate (ECD/GxhuFc-HRP). Antibody drug conjugate is measured by ELISA, for example, by coating with an anti-drug or antiFc antibody and detecting with an extracellular domain-biotin conjugate and a streptavidin-horse radish peroxidase conjugate.

Example 54. Conjugation of Aminooxybutynylacetamide-Monomethyldolastatin 10 (ABAA-MODO) to 7-aldehydo-NeuNAc-cetuximab Sialylated cetuximab was prepared as described in Example 10. Periodate oxidized cetuximab was prepared as described in Example 23, and the 7-aldehydo-NeuNAc-cetuximab thus obtained was conjugated by oxime ligation with ABAA-MODO (Example 41). MS analysis of HC-glycans revealed that of the N-glycans in the HC Asn-88 ca. 50% carried one ABAA-MODO oxime and ca. 50% carried two ABAA-MODO oximes, and of the Fc domain N-glycans ca. 80% carried one ABAA-MODO oxime while 20% had not reacted. Thus the reaction product composed of antibody-drug conjugates with between 2 to 6 drug molecules per antibody, in other words either 2, 3, 4, 5 or 6 drug molecules per antibody, with average drug-to-antibody ratio of 4.6.

Example 55. Conjugation of Aminooxybutynylacetamide-Monomethyldolastatin 10 (ABAA-MODO) to 7-aldehydo-NeuNAc-GCM012

Sialylated GCM012 was prepared as described in Example 10. Periodate oxidized GCM012 was prepared as described in Example 23, and the 7-aldehydo-NeuNAc-GCM012 thus obtained was conjugated by oxime ligation with ABAA-MODO (Example 41). MS analysis of LC-glycans revealed that of the N-glycans in the Asn-18 >90% carried two ABAA-MODO oximes and <10% carried one ABAA-MODO oxime. The drug-to-antibody ratio was thus higher than in the antibody-drug conjugate of the previous Example 54. According to the MS analysis the reaction product composed of antibody-drug conjugates with between 2 to 6 drug molecules per antibody, in other words either 2, 3, 4, 5 or 6 drug molecules per antibody.

The in vitro cytotoxicity of MODO-ABAA-GCM012 conjugate was established with human ovarian cancer cell line SKOV-3 as described in Example 14. The IC50 against SKOV-3 cells was found to be between 1 nM to 10 nM.

As is clear for a person skilled in the art, the invention is not limited to the examples and embodiments described above, but the embodiments can freely vary within the scope of the claims.

The invention claimed is:

1. A method for preparing a glycoprotein-toxic payload molecule conjugate of Formula I:

[D-L-G]$_n$-Gp                                   Formula (I)

wherein:
Gp is a glycoprotein comprising an N-glycan, wherein the N-glycan comprises a GlcNAc residue bound by a β-N linkage to an asparagine;
the glycoprotein is an antibody;
n is 2;
D is a toxic payload molecule;
L is a linker group covalently joining G to D; and
G is a saccharide structure of Formula II

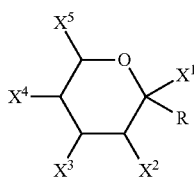                             Formula (II)

and wherein:
R is a glycosidic bond to the 4-position of the GlcNAc residue bound by a β-N linkage to an asparagine;
$X^1$ is H;
$X^2$ is NHCOCH$_2$-triazole, wherein the triazole comprises a bond to L;
$X^3$ and $X^4$ are each OH;
$X^5$ is CH$_2$OH; and,
the anomeric structure of G is in β-D-galacto configuration;
and wherein the method consists of the steps of:
providing Gp which is an antibody comprising an N-glycan with an acceptor site;
reacting a donor molecule with the acceptor site in the presence of a glycosyltransferase;
reacting the G component with a compound of Formula XIV D-L-L"                                            Formula (XIV)

wherein:
D is the toxic payload molecule;
L is the linker group covalently joining L" to D; and
L" is an alkyne;
and,
purifying the glycoprotein-toxic payload molecule conjugate using Protein G;
wherein the antibody comprising the N-glycan with the acceptor site is prepared by contacting the antibody comprising the N-glycan with endoglycosidase EndoS49;
wherein the N-glycan is a hybrid-type N-glycan;
and wherein the N-glycan after the contacting with the endoglycosidase EndoS49 consists of the structure of Formula IV:

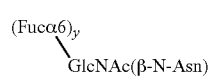                             Formula IV wherein ((β-N-Asn) is a β-N linkage to an asparagine and y is 0 or 1;
wherein:
100% of the antibodies comprising the N-glycan comprises two N-glycans that each comprises one acceptor site;
the glycosyltransferase is a human β1,4-GalT1(Y285L) or a bovine β1,4-GalT1(Y289L);
the antibody and the toxic payload molecule are linked using click conjugation;
the antibody is an IgG antibody; and,
the donor molecule is UDP-2-(2-azidoacetamido)-2-deoxy-Gal (UDP-GalNAz).

2. The method of claim 1, wherein the antibody is capable of binding a target molecule selected from the group consisting of CD2, CD3, CD4, CD5, CD6, CD11, CD8, CD11a, CD19, CD20, CD22, CD25, CD26, CD30, CD33, CD34, CD37, CD38, CD40, CD44, CD46, CD52, CD56, CD79, CD105, CD138, epidermal growth factor receptor 1 (EGFR), epidermal growth factor receptor 2 (HER2/neu), HER3 or HER4 receptor, LFA-1, Mac1, p150.95, VLA-4, ICAM-1, VCAM, EpCAM, alpha4/beta7 integrin, alpha v/beta3 integrin, tissue factor (TF), tumor necrosis factor alpha (TNF-α), human vascular endothelial growth factor (VEGF), glycoprotein IIb/IIIa, TGF-beta, alpha interferon (alpha-IFN), IL-8, IL-2 receptor, IgE, respiratory syncytial virus (RSV), HIV-1 envelope glycoprotein gp120, cancer-associated high mannose type N-glycans, blood group antigen Apo2, death receptor, flk2/flt3 receptor, obesity (OB) receptor, mpl receptor, CTLA-4, transferrin receptor and protein C.

3. The method of claim 1, wherein the linker group L is hydrophilic.

4. The method of claim 3, wherein the linker group L comprises a Val-Cit-PAB group.

5. The method of claim 1, wherein the toxic payload molecule is selected from the group consisting of dolastatin, auristatin, doxorubicin, mertansine (DM1), epirubicin, and duocarmycin.

* * * * *